US008021848B2

(12) United States Patent
Straus

(10) Patent No.: US 8,021,848 B2
(45) Date of Patent: Sep. 20, 2011

(54) RAPID AND SENSITIVE DETECTION OF CELLS AND VIRUSES

(75) Inventor: Don Straus, Cambridge, MA (US)

(73) Assignee: Straus Holdings Inc., Bedford, MA (US)

( * ) Notice: Subject to any disclaimer, the term of this patent is extended or adjusted under 35 U.S.C. 154(b) by 1714 days.

(21) Appl. No.: 10/237,010

(22) Filed: Sep. 6, 2002

(65) Prior Publication Data

US 2003/0170613 A1 Sep. 11, 2003

Related U.S. Application Data

(60) Provisional application No. 60/317,658, filed on Sep. 6, 2001.

(51) Int. Cl.
  *G01N 33/53* (2006.01)
(52) U.S. Cl. ............................ 435/7.1; 435/7.2; 436/518
(58) Field of Classification Search .................... 435/7.2, 435/7.21, 29, 40.5, 288.3, 7.1
See application file for complete search history.

(56) References Cited

U.S. PATENT DOCUMENTS

| | | | |
|---|---|---|---|
| 2,761,813 A | 9/1956 | Goetz | |
| 3,694,317 A | 9/1972 | Scher | |
| 3,981,776 A | 9/1976 | Saxholm | |
| 4,097,586 A | 6/1978 | Gross | |
| 4,098,876 A | 7/1978 | Piasio et al. | |
| 4,115,535 A | 9/1978 | Giaever | |
| 4,125,375 A | 11/1978 | Hunter | |
| 4,129,419 A | 12/1978 | Hermann, Jr. | |
| 4,141,687 A | 2/1979 | Forrest et al. | |
| 4,157,323 A | 6/1979 | Yen et al. | |
| 4,177,253 A | 12/1979 | Davies et al. | |
| 4,222,744 A | 9/1980 | McConnell | |
| 4,436,826 A | 3/1984 | Wang | |
| 4,438,068 A | 3/1984 | Forrest | |
| 4,454,233 A | 6/1984 | Wang | |
| 4,455,370 A | 6/1984 | Bartelsman et al. | |
| 4,477,578 A | 10/1984 | Miles et al. | |
| 4,537,861 A | 8/1985 | Elings et al. | |
| 4,562,157 A | 12/1985 | Lowe et al. | |
| 4,565,783 A | 1/1986 | Hansen et al. | |
| 4,582,810 A | 4/1986 | Rosenstein | |
| 4,587,213 A | 5/1986 | Malecki | |
| 4,614,585 A | 9/1986 | Mehra et al. | |
| 4,693,972 A | 9/1987 | Mansour et al. | |
| 4,731,337 A | 3/1988 | Luotola et al. | |
| 4,745,077 A | 5/1988 | Holian et al. | |
| 4,777,137 A | 10/1988 | Lemonnier | |
| 4,777,145 A | 10/1988 | Luotola et al. | |
| 4,912,037 A | 3/1990 | Lemonnier et al. | |
| 4,959,301 A | 9/1990 | Weaver et al. | |
| 4,988,302 A | 1/1991 | Smith et al. | |
| 4,988,618 A | 1/1991 | Li et al. | |
| 5,073,497 A | 12/1991 | Schwartz | |
| 5,089,413 A | 2/1992 | Nelson et al. | |
| 5,137,812 A | 8/1992 | Matner | |
| 5,190,666 A | 3/1993 | Bisconte | |
| 5,232,838 A | 8/1993 | Nelson et al. | |
| 5,238,810 A | 8/1993 | Fujiwara et al. | |
| 5,258,284 A | 11/1993 | Morris, Jr. et al. | |
| 5,262,526 A | 11/1993 | Sasamoto et al. | |
| 5,292,644 A | 3/1994 | Berg | |
| 5,306,420 A | 4/1994 | Bisconte | |
| 5,321,545 A | 6/1994 | Bisconte | |
| 5,366,867 A | 11/1994 | Kawakami et al. | |
| 5,464,749 A | 11/1995 | Schwarzberg et al. | |
| 5,474,910 A | 12/1995 | Alfano | |
| 5,510,246 A | 4/1996 | Morgan | |
| 5,538,857 A | 7/1996 | Rosenthal et al. | |
| 5,541,069 A | 7/1996 | Mortensen et al. | |
| 5,552,272 A | 9/1996 | Bogart | |
| 5,558,839 A | 9/1996 | Matte et al. | |
| 5,585,241 A | 12/1996 | Lindmo | |
| 5,604,351 A | 2/1997 | Bisconte | |
| 5,606,413 A | 2/1997 | Bellus et al. | |
| 5,653,939 A | 8/1997 | Hollis et al. | |
| 5,663,057 A | 9/1997 | Drocourt et al. | |
| 5,672,880 A | 9/1997 | Kain | |
| 5,681,530 A | 10/1997 | Kuster et al. | |
| 5,681,712 A | 10/1997 | Nelson | |
| 5,705,402 A | 1/1998 | Leland et al. | |

(Continued)

FOREIGN PATENT DOCUMENTS

DE  19631997  2/1998

(Continued)

OTHER PUBLICATIONS

Journal of Immunology, 1998, vol. 160, p. 316-321.*
Corkidi et al. (Appl Environ. Microbiol. 1998 vol. 64, p. 1400-1404.*
Moore et al. (1998) J. Biochem. Biopjys. Methods vol. 37, p. 11-33.*
Kamentsky, L., "Laser Scanning Cytometry," *In Cytometry*, Z. Darzynkiewicz, H. Crissman, and J. Robinsnon, eds. (San Diego: Academic Press), (2001) pp. 51-87.
Logtenberg, T. et al., "Enumeration of (auto)antibody producing cells in human using the "spot-ELISA"," *Immunol Lett* 9, (1985) pp. 343-347.
Masuko, M. et al., "A novel method for detection and counting of single bacteria in a wide field using an ultra-high-sensitivity TV camera without a microscope," *FEMS Microbiol Lett* 81, (1991) pp. 287-290.

(Continued)

*Primary Examiner* — Jacob Cheu
(74) *Attorney, Agent, or Firm* — Clark & Elbing LLP

(57) ABSTRACT

The invention provides efficient methods for rapidly and sensitively identifying cellular and viral targets in medical, industrial, and environmental samples. The invention labels targets and then detects them using large area imaging. Diagnostic tests based on the invention can be rapid, ultrasensitive, quantitative, multiplexed, and automated. The tests minimize sample preparation and do not require nucleic acid amplification or cell culture. A broad range of cells and viruses can be detected by the tests. Tests based on the invention can deliver the high level sensitivity of nucleic acid amplification tests, the user-friendliness, and speed of immunoassays, as well as the cost effectiveness and quantification offered by microbiological tests. The invention embodies the best attributes of the current diagnostic technologies, while addressing gaps in the diagnostic repertoire.

96 Claims, 43 Drawing Sheets

U.S. PATENT DOCUMENTS

| | | | |
|---|---|---|---|
| 5,736,405 | A | 4/1998 | Alfano et al. |
| 5,744,322 | A | 4/1998 | Krejcarek et al. |
| 5,792,617 | A | 8/1998 | Rotman |
| 5,814,454 | A | 9/1998 | Ju |
| 5,821,066 | A | 10/1998 | Pyle |
| 5,828,716 | A | 10/1998 | Bisconte de Saint Julien |
| 5,852,498 | A | 12/1998 | Youvan et al. |
| 5,861,270 | A | 1/1999 | Nelis |
| 5,891,394 | A | 4/1999 | Drocourt et al. |
| 5,914,245 | A | 6/1999 | Bylina et al. |
| 5,958,790 | A * | 9/1999 | Cerny .......................... 436/501 |
| 5,968,766 | A | 10/1999 | Powers |
| 5,976,892 | A | 11/1999 | Bisconte |
| 5,981,180 | A | 11/1999 | Chandler et al. |
| 5,985,675 | A * | 11/1999 | Charm et al. ................. 436/514 |
| 5,993,740 | A | 11/1999 | Niiyama et al. |
| 6,051,395 | A | 4/2000 | Rocco |
| 6,121,055 | A | 9/2000 | Hargreaves |
| 6,122,396 | A | 9/2000 | King et al. |
| 6,130,931 | A | 10/2000 | Laurila et al. |
| 6,140,653 | A | 10/2000 | Che |
| 6,165,742 | A | 12/2000 | Ofjord et al. |
| 6,171,180 | B1 | 1/2001 | Koutny, Jr. et al. |
| 6,171,780 | B1 | 1/2001 | Pham et al. |
| 6,200,762 | B1 | 3/2001 | Zlokarnik et al. |
| 6,214,560 | B1 | 4/2001 | Yguerabide et al. |
| 6,258,326 | B1 | 7/2001 | Modlin |
| 6,259,807 | B1 | 7/2001 | Ravkin |
| 6,268,222 | B1 | 7/2001 | Chandler et al. |
| 6,274,384 | B1 | 8/2001 | Starzl et al. |
| 6,306,589 | B1 | 10/2001 | Muller et al. |
| 6,309,822 | B1 | 10/2001 | Fodor et al. |
| 6,358,730 | B1 | 3/2002 | Kane |
| 6,472,166 | B1 | 10/2002 | Wardlaw et al. |
| 6,623,983 | B1 | 9/2003 | Terstappen et al. |
| 6,664,528 | B1 | 12/2003 | Cartlidge et al. |
| 6,710,879 | B1 | 3/2004 | Hansen et al. |
| 6,727,071 | B1 * | 4/2004 | Dunlay et al. ................ 435/7.21 |
| 6,764,648 | B1 | 7/2004 | Roach et al. |
| 6,919,960 | B2 | 7/2005 | Hansen et al. |
| 7,068,365 | B2 | 6/2006 | Hansen et al. |
| 7,582,415 | B2 | 9/2009 | Straus |
| 2001/0039060 | A1* | 11/2001 | Siiman et al. ................. 436/525 |
| 2002/0028471 | A1 | 3/2002 | Oberhardt |
| 2002/0055092 | A1 | 5/2002 | Hochman |
| 2002/0137106 | A1* | 9/2002 | Leung et al. .................... 435/7.9 |
| 2003/0143580 | A1 | 7/2003 | Straus |
| 2004/0048395 | A1 | 3/2004 | Lee et al. |
| 2004/0171121 | A1 | 9/2004 | Leppla et al. |
| 2004/0172000 | A1* | 9/2004 | Roe et al. ....................... 604/361 |
| 2004/0246483 | A1 | 12/2004 | Hansen et al. |
| 2005/0013737 | A1 | 1/2005 | Chow et al. |
| 2005/0148085 | A1 | 7/2005 | Larsen |
| 2005/0191687 | A1 | 9/2005 | Wang et al. |
| 2005/0220670 | A1 | 10/2005 | Palmieri et al. |
| 2005/0221403 | A1 | 10/2005 | Gazenko |
| 2005/0225766 | A1 | 10/2005 | Hansen et al. |
| 2005/0226779 | A1 | 10/2005 | Oldham et al. |
| 2006/0129327 | A1 | 6/2006 | Kim et al. |
| 2006/0188967 | A1 | 8/2006 | Nalin et al. |
| 2006/0210435 | A1 | 9/2006 | Alavie et al. |
| 2006/0216696 | A1 | 9/2006 | Goguen |
| 2006/0256340 | A1 | 11/2006 | Hansen et al. |
| 2006/0292552 | A1 | 12/2006 | Haquette et al. |
| 2007/0184546 | A1 | 8/2007 | Farrelly et al. |
| 2007/0212681 | A1 | 9/2007 | Shapiro et al. |
| 2007/0212747 | A1 | 9/2007 | Browne et al. |
| 2008/0003571 | A1 | 1/2008 | McKernan et al. |
| 2008/0014576 | A1 | 1/2008 | Jovanovich et al. |
| 2008/0032328 | A1 | 2/2008 | Cline et al. |
| 2008/0038738 | A1 | 2/2008 | Weigum et al. |
| 2008/0206099 | A1 | 8/2008 | Aruga et al. |
| 2009/0315987 | A1 | 12/2009 | Straus |
| 2010/0248281 | A1 | 9/2010 | Straus |

FOREIGN PATENT DOCUMENTS

| | | |
|---|---|---|
| DE | 19940810 A1 | 5/2000 |
| EP | 171174 A2 | 2/1986 |
| EP | 0574977 | 12/1993 |
| EP | 1207394 | 5/2002 |
| JP | 3102240 | 4/1991 |
| JP | H3-83598 | 4/1991 |
| JP | H11-346795 | 12/1999 |
| JP | 2000-509827 | 8/2000 |
| JP | 2001-224355 | 8/2001 |
| JP | 2001-512875 | 8/2001 |
| WO | WO 83/01581 | 5/1983 |
| WO | WO 97/44664 | 11/1997 |
| WO | WO98/38490 | 9/1998 |
| WO | WO 98/50577 | 11/1998 |
| WO | WO99/08233 | 2/1999 |
| WO | WO 99/20789 | 4/1999 |
| WO | WO 99/35483 | 7/1999 |
| WO | WO99/36577 | 7/1999 |
| WO | WO 99/58948 | 11/1999 |
| WO | WO 9958948 * | 11/1999 |
| WO | WO 00/04382 | 1/2000 |
| WO | WO 00/47766 | 8/2000 |
| WO | WO 01/57522 | 8/2001 |
| WO | WO 01/61348 | 8/2001 |

OTHER PUBLICATIONS

Masuko, M. et al., "Rapid detection and counting of single bacteria in a wide field using a photon-counting TV camera," *FEMS Microblol Lett* 83, (1991) pp. 231-238.

Mignon-Godefroy, K. et al., "Solid phase cytometry for detection of rare events," *Cytometry* 27, (1997) pp. 336-344.

Miraglia, S., "Homogeneous cell-and bead-based assays for high throughput screening using fluorometric microvolume assay technology," *Journal of Biomolecular Screening* 4, (1999) pp. 193-204.

Tibbe, A., "Optical tracking and detection of immunomagnetically selected and aligned cells," *Nature Biotechnology* 17, (1999) pp. 1210-1213.

Yasui, T. et al., "Imaging of Lactobacillus brevis single cells and microcolonies without a microscope by an ultrasensitive chemiluminescent enzyme immunoassay with a photon-counting television camera," *Appl. Environ. Microbiol.* 63, (1997) pp. 4528-4533.

Al-Hakiem et al., "Development of Fluoroimmunassays for the Determination of Individual or Combined Levels of Procainamide and N-Acetylprocainamide in Serum," *J. Immunoassay* 3(1):91-110, 1982.

Allman et al., "Fluoroimmunoassay of Progesterone in Human Serum or Plasma," *Clin. Chem.* 27(7):1176-1179, 1981.

Anonymous, The Brain, Enchanted Learning.com, http://www.enchantedlearning.com/subjects/anatomy/brain.neuron.html copyright 2001-2007, printed Nov. 4, 2007, pp. 1-4.

Clean Technology, vol. 5, p. 60-61 (1995) [in Japanese].

Colony Counter (http://www.topac.com/acolyte.html), downloaded Apr. 12, 2005; p. 1-3.

Colony Counter Models and Specifications (http://biologics-inc.com/cc-models.htm), downloaded Apr. 15, 2005; p. 1-3.

Definition and Procedure for the Determination of the Method Detection Limit, Appendix B to 40 C.F.R. § 136, available at http://www.access.gpo.gov, pp. 343-346, downloaded Nov. 20, 2007.

Digital Multi-Purpose High-Resolution Colony and Plaque Counter (http://www.loats.com/mla.html), downloaded Apr. 12, 2005; p. 1-3.

Esteban et al., "Improved Direct Epifluorescent Filter Technique for Rapid Bioburden Control in Intravenous Solutions," *J. Parenter. Sci. Technol.* 46:146-149, 1992.

Frost, "Improved Technic for the Micro or Little Plate Method of Counting Bacteria in Milk," 1920; p. 177-184.

Lamture et al., "Direct Detection of Nucleic Acid Hybridization on the Surface of a Charge Coupled Device," *Nucleic Acid Res.* 22:2121-2125, 1994.

Loats et al., "LAI High-Resolution Automated Copy Colony Counting System—Mouse Lymphoma Assay: Performance Analysis," (http://loats.com/docs/HRCCval/HRCCval/HRCCval/HRCCval.html), 1999; p. 1-11.

Nargessi et al., "Magnetizable Solid-Phase Fluoroimmunoassay of Thyroxine by a Sequential Addition Technique," Clin. Chem. 26(12):1701-1703, 1980.

Nargessi et al., "Immunoassays for Serum C-Reactive Protein Employing Fluorophore-Labelled Reactants," J. Immunol. Methods 71(1):17-24, 1984.

Perkin Elmer, Inc., Gene Screen™ Hybridization Technique Transfer Membranes, Application Notes, available at http://las.perkinelmer.com/, downloaded on Feb. 27, 2007; p. 1-17.

Rousseau, "New Minaturized Highly Sensitive Immunoassay Device for Quantitative Measurement of Soluble or Particular Antigen or Antibodies in a Liquid Sample," Clin. Chem. 45:1685-1687, 1999.

Schultz, "Single Target Molecule Detection with Nonbleaching Multicolor Optical Immunolabels," Proc. Natl. Acad. Sci. U.S.A. 97:996-1001, 2000.

System Specifications (http://www.loats.com/order_info.html), 1999; p. 1-7.

Technical Specification (http://www.perceptive.co.uk/products/scc/techspec.html), downloaded Apr. 12, 2005; p. 1-2.

Thomas et al., "Making Gold Nanoparticles Glow: Enhanced Emission from a Surface-Bound Fluoroprobe," J. Am. Chem. Soc. 122:2655-2656, 2000.

Wilson et al., "Use of the IUL Countermat Automatic Colony Counter for Spiral Plated Total Viable Counts," Appl. Environ. Microbiol. 61:3158-3160, 1995.

Viinikka L. et al., "A Two-Site Immunofluorometric Assay for Human Placental Lactogen," Clin. Chim. Acta 114(1):1-9, 1981.

Wellman et al., "Magnetically-Assisted Transport Evanescent Field Fluoroimmunoassay," Anal. Chem. 78(13):4450-4456, 2006.

Wolniak et al., 2004. BSCI 427 Principles of Microscopy Fall 2004 Syllabus, (http://www.life.umd.edu/cbmg/faculty/wolniak/wolniac/micro.html), printed Nov. 8, 2007; p. 1-8.

Yasui et al., "Imaging of Lactobacillus brevis Single Cells and Microcolonies without a Microscope by an Ultrasensitive Chemiluminescent Enzyme Immunoassay with a Photon-Counting Television Camera," Appl. Environ. Microbiol. 63:4528-4533, 1997.

Zhao et al., "Competitive Immunoassay for Microliter Protein Samples with Magnetic Beads and Near-Infrared Fluorescence Detection," Anal. Chem. 76(7):1871-1876, 2004.

International Search Report for PCT/US02/28434, completed Sep. 26, 2004, mailed Oct. 6, 2004.

International Preliminary Examination Report for PCT/US02/28434, completed Jan. 3, 2006.

"Innovative Plate Holder for Colony Counter," downloaded from http://www.laboratorytalk.com on Oct. 16, 2002 (2 pages).

"Innovative Plate Holder for ProtoCOL," downloaded from http://www.synbiosis.com on Oct. 16, 2002 (2 pages).

Sorcerer Automated Colony Counting, Perceptive Instruments, 2 pages, 2002.

Vidon et al. "A simple chemiluminescence-based method for rapid enumeration of Listeri spp. microcolonies", Journal of Applied Microbiology, 90:988-993 (2001).

Nelis et al. "Enzymatic detection of 1-15 coliforms and Escherichia coli within 4 hours II" Water Air and Soil Pollution, 123:43-52 (2000).

Van Poucke et al. "Rapid detection of 1-15 fluorescent and chemiluminescent total coliforms and Escherichia coli on membrane filters" Journal of Microbiological Methods, 42:233-244 (2000).

Van Poucke et al.. "A 210-min solid 1-15 phase cytometry test for the enumeration of Escherichia coli in drinking water", Journal of Applied Microbiology, 89:390-396 (2000).

Kroll et al. "A Laser-Light Pulse Counting Method for Automatic and Sensitive Counting of Bacteria Stained with Acridine Orange", Journal of Applied Bacteriology, 66:161-167 (1989).

Van Poucke et al. "Solid phase cytometry-based enzymatic detection of coliforms in drinking water within 4 h", Water Supply 17:67-72 (1999).

English translation of Japanese Patent Application No. H11-346795, filed Feb. 28, 1985.

English translation of Japanese Patent Application No. H3-83598, filed Aug. 29, 1989.

* cited by examiner

FIG. 1. Detecting individual labeling particles using a CCD array.

Non-magnified large area imaging of *Mycobacterium tuberculosis* in a sputum sample using CCD imaging FIG. 3. A CCD imaging device for large area imaging.

FIG. 4. A CCD imaging system for non-magnified large area imaging.

Distinct labeling of different pathogens using combinatorial labeling

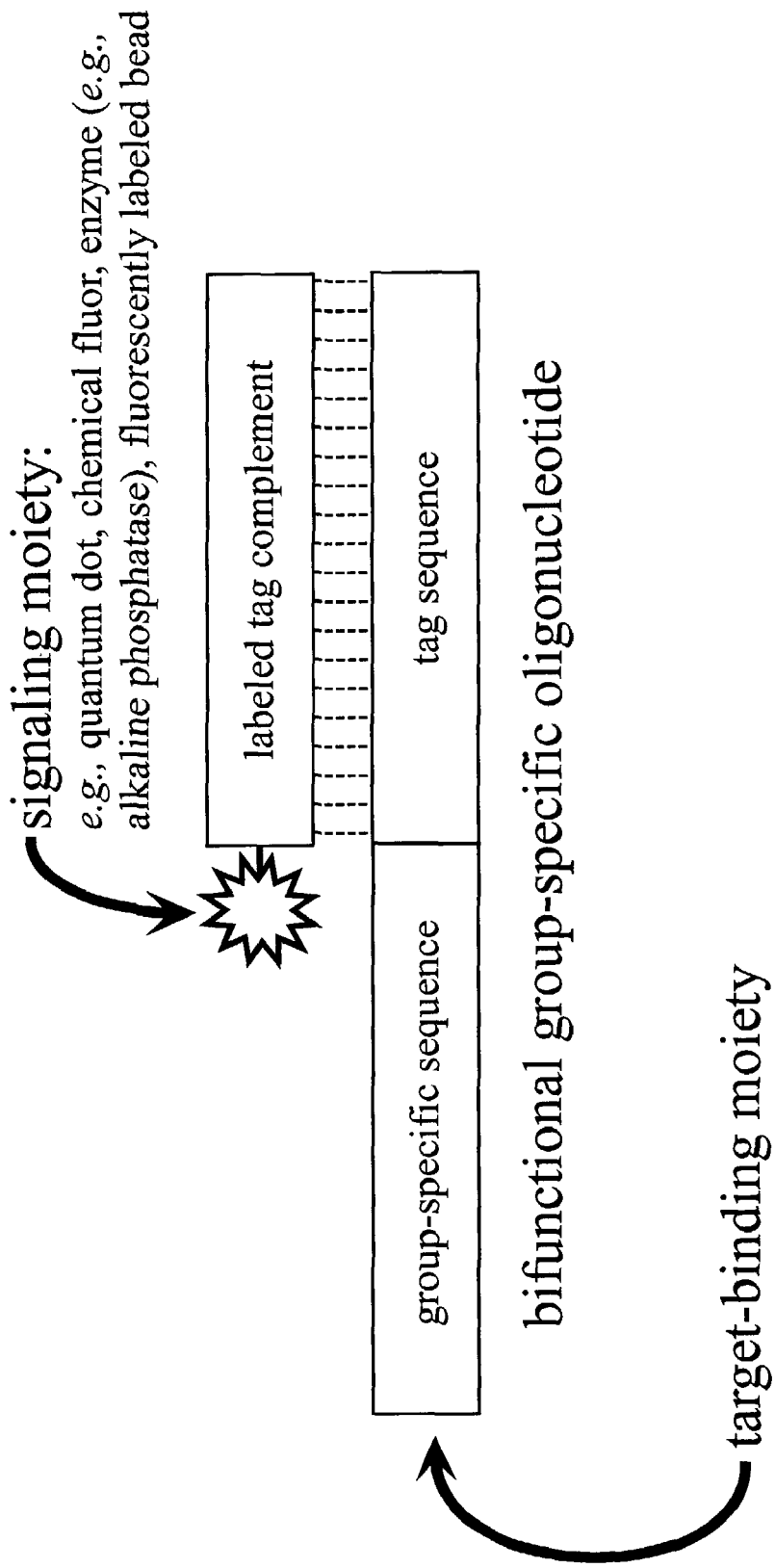
FIG. 6. Indirect labeling of an oligonucleotide target-binding molecule using a tag sequence and labeled tag complement

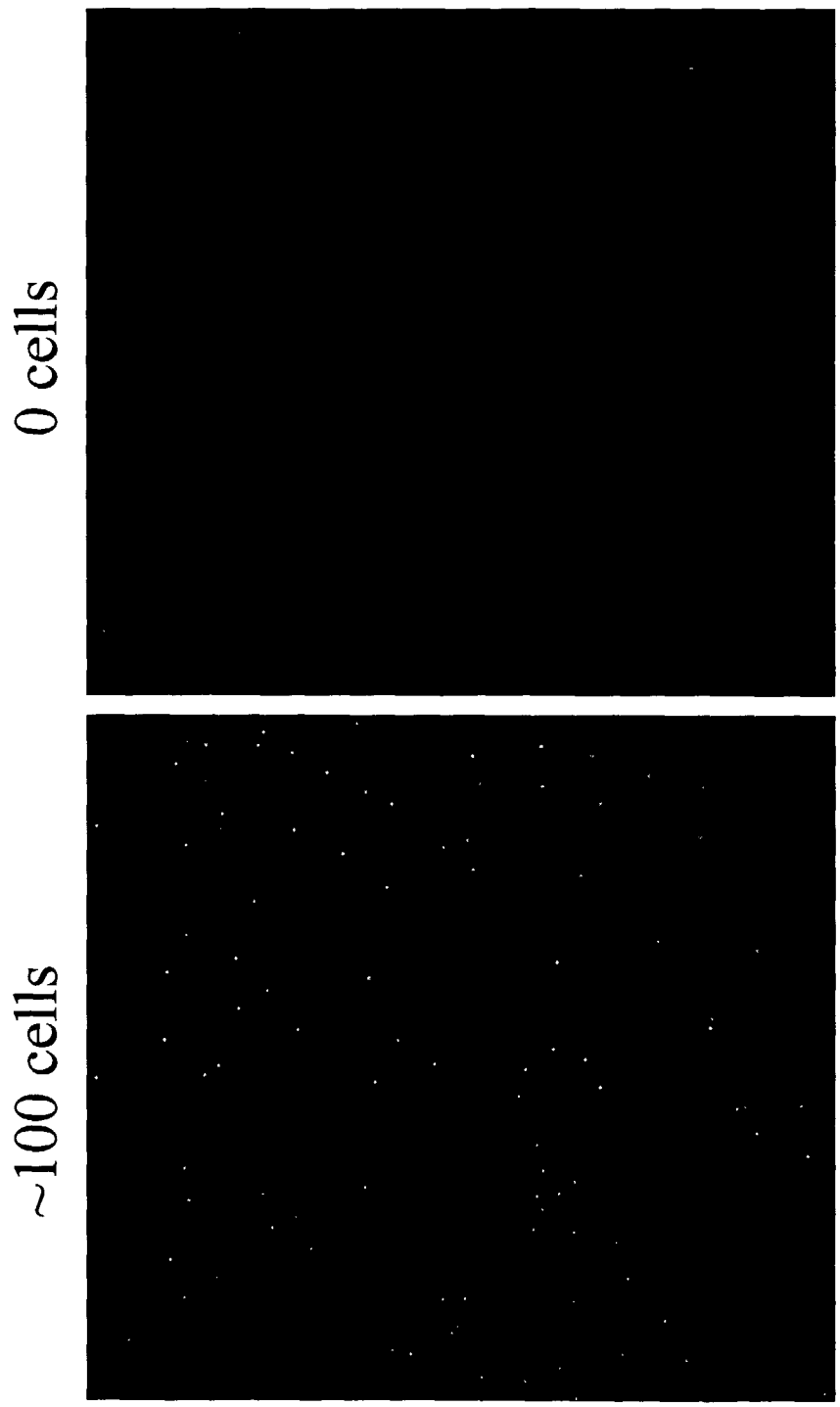
FIG. 7. Large area imaging of individual bacteria labeled with a fluorescent DNA-binding stain (Example 1).

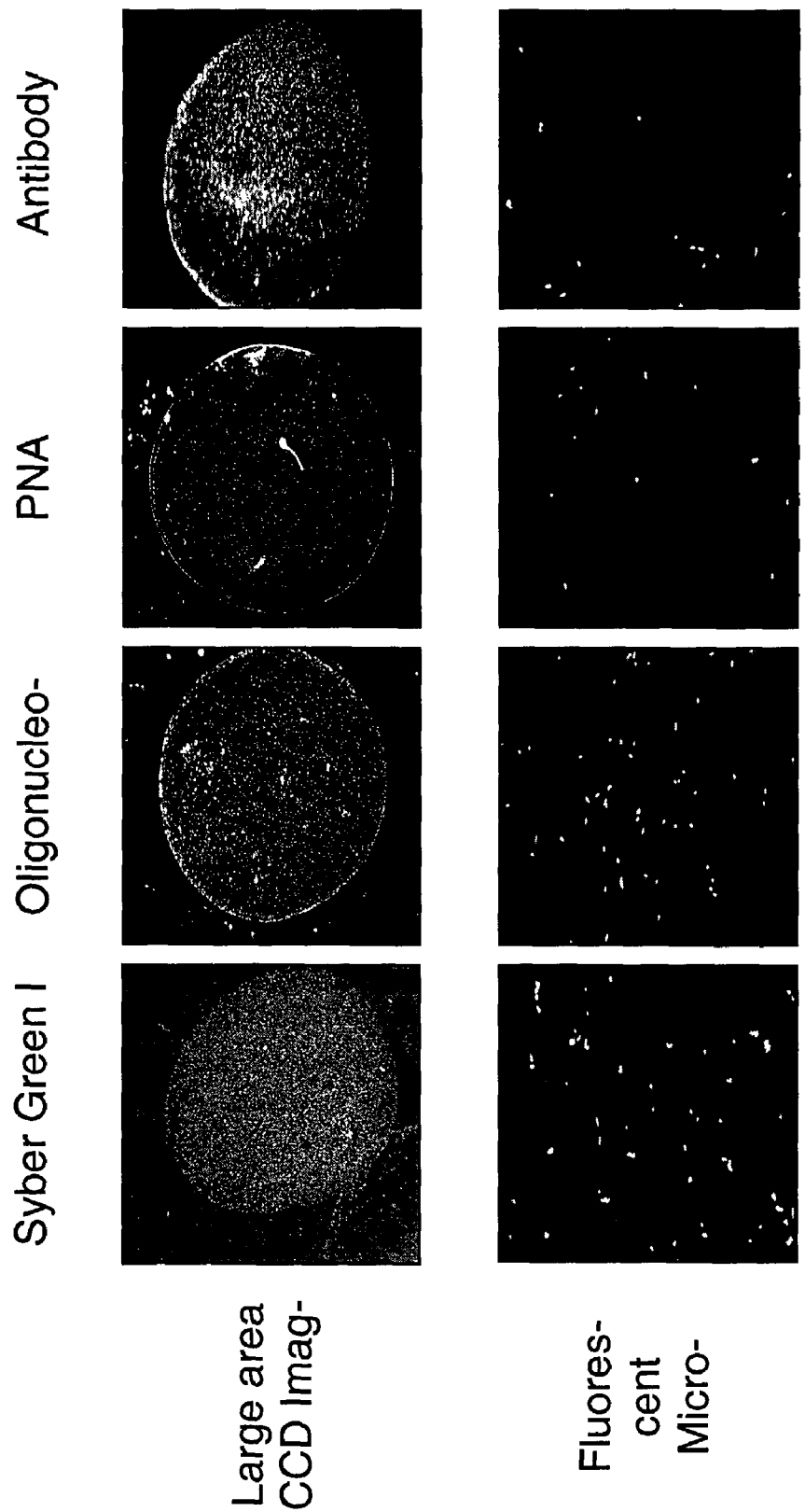
FIG. 8. Large area non-magnified imaging of single *E.coli* cells using various signaling moieties (Examples 2-5).

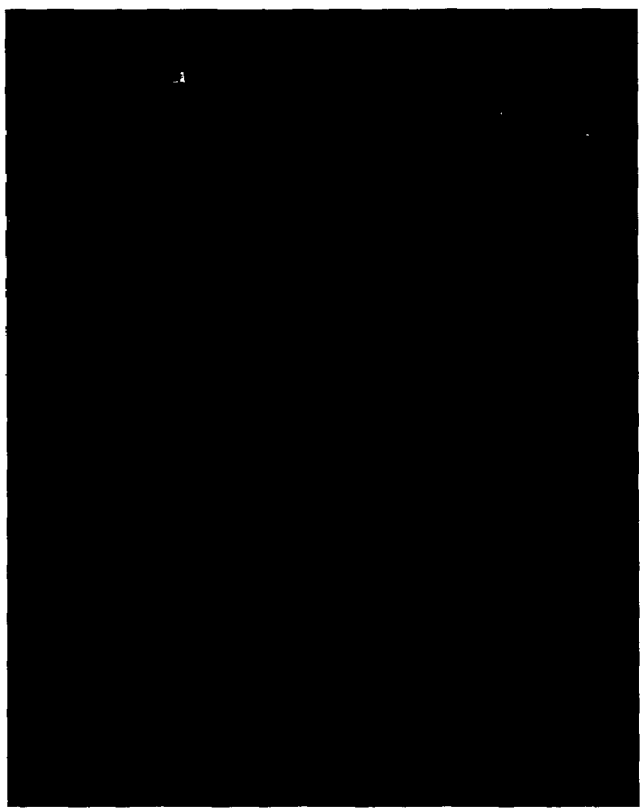
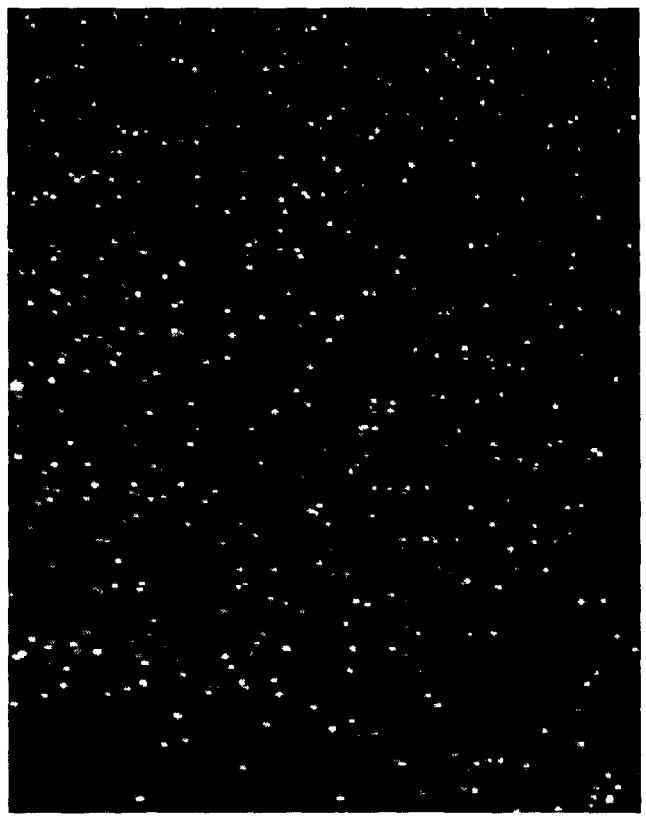
FIG. 9. Large area imaging of individual live bacteria stained with a fluoro-genic esterase substrate (Example 6).

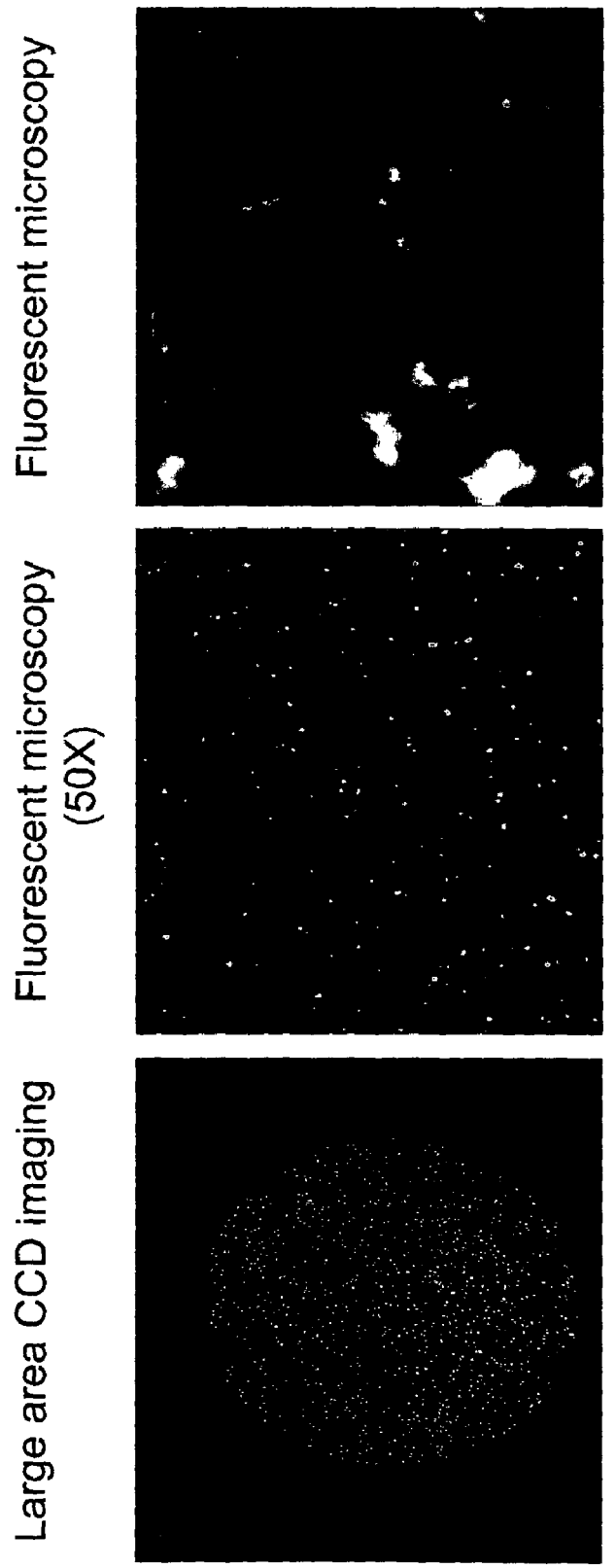
FIG. 10. Large area non-magnified imaging of single bacteria labeled with highly fluorescent beads (Example 7).

Homogenous immunoassay for a virus (HCV) using liquid-phase magnetic selection of fluorescent bead:virus:magnetic bead complexes followed by non-magnified large area imaging.

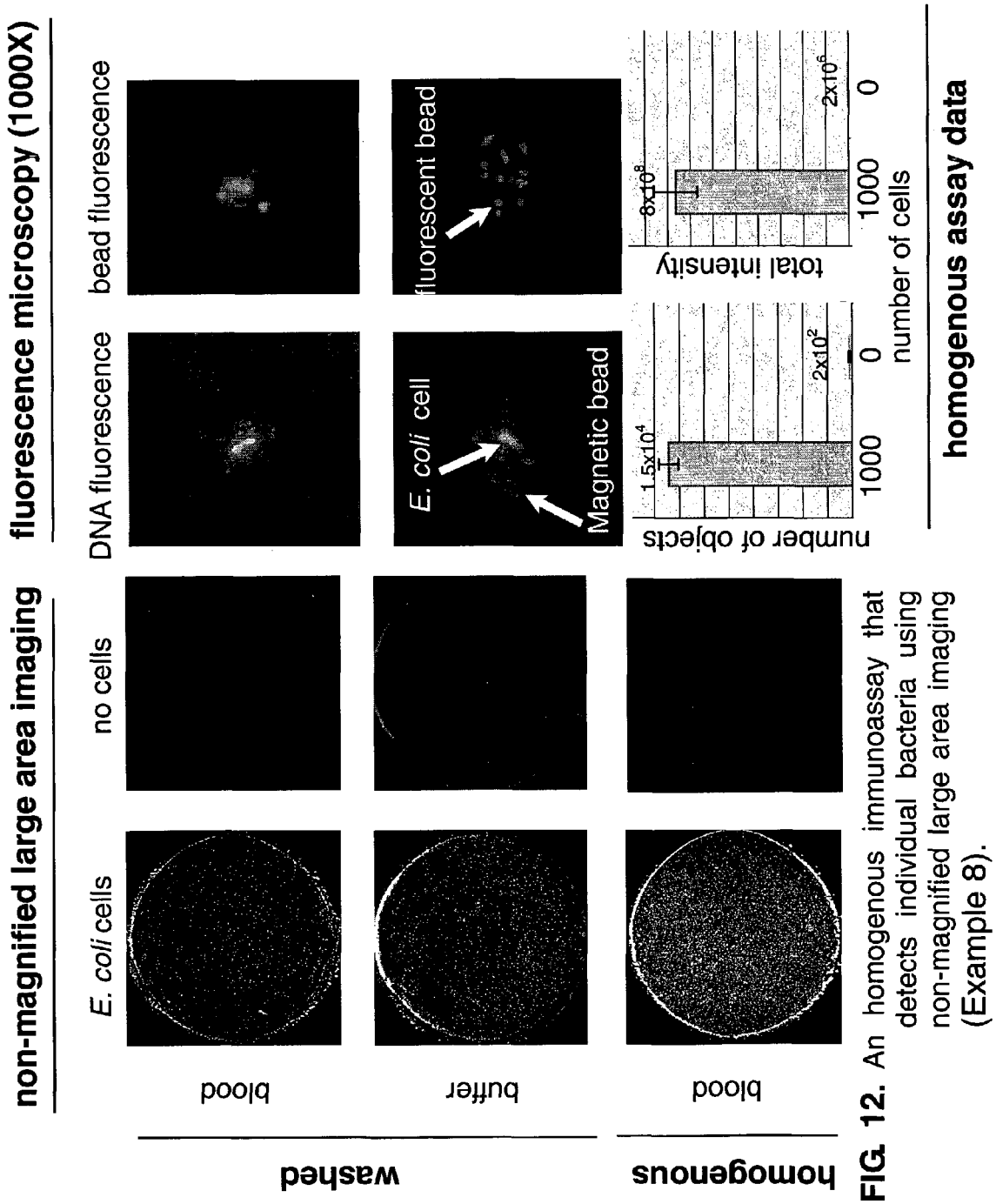
FIG. 12. An homogenous immunoassay that detects individual bacteria using non-magnified large area imaging (Example 8).

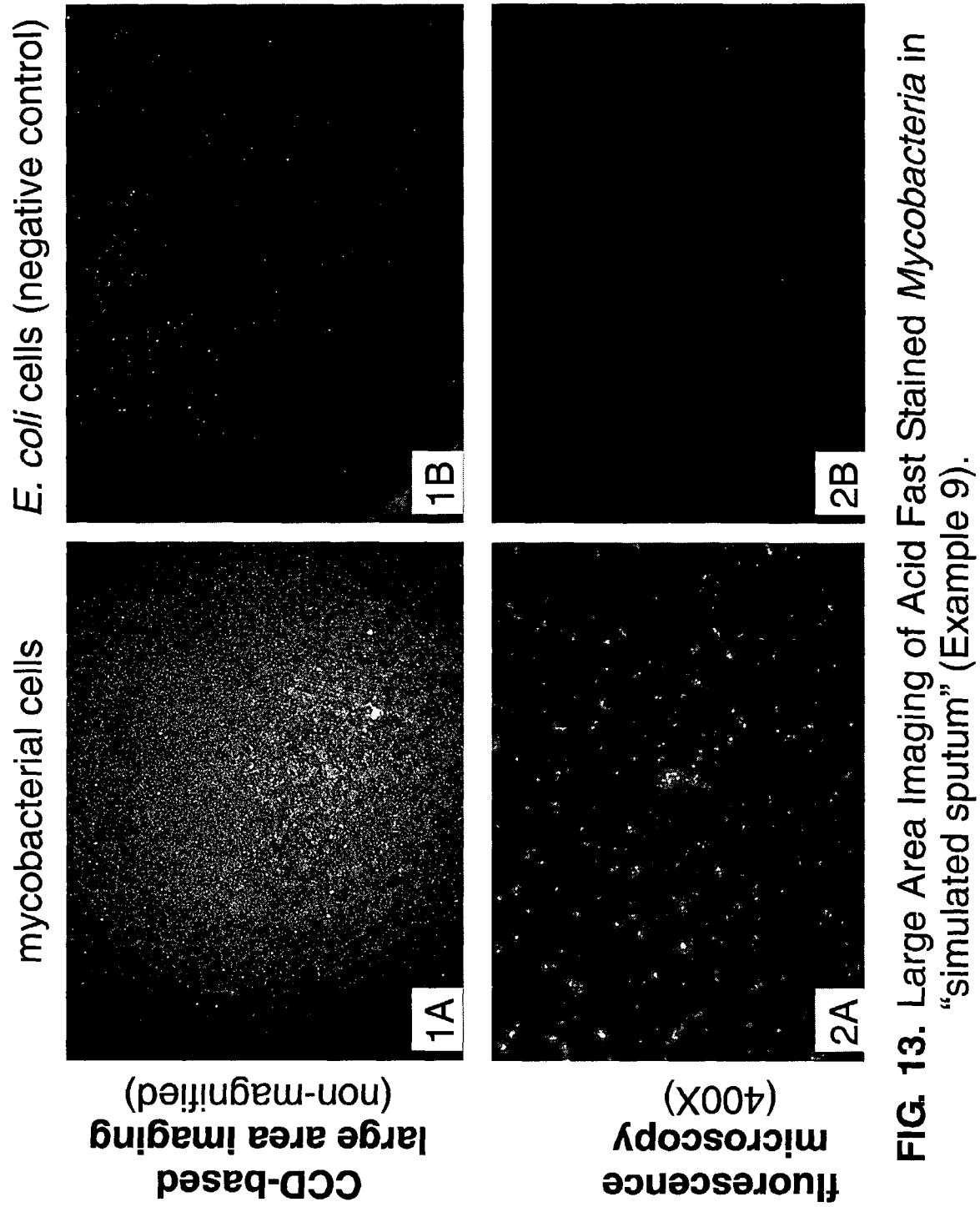
FIG. 13. Large Area Imaging of Acid Fast Stained *Mycobacteria* in "simulated sputum" (Example 9).

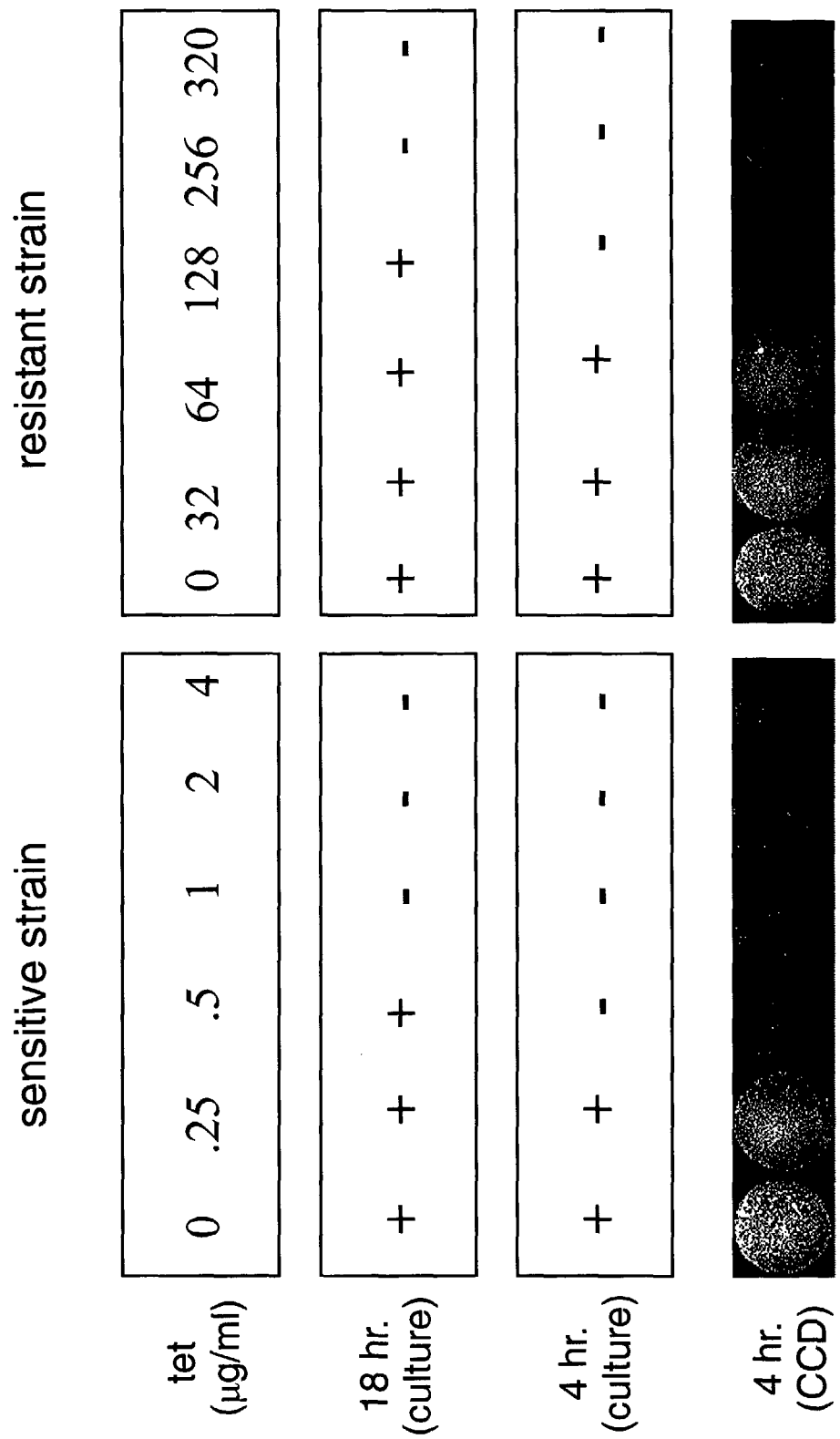
FIG. 14. Rapid antimicrobial susceptibility testing using large area imaging. (Example 10).

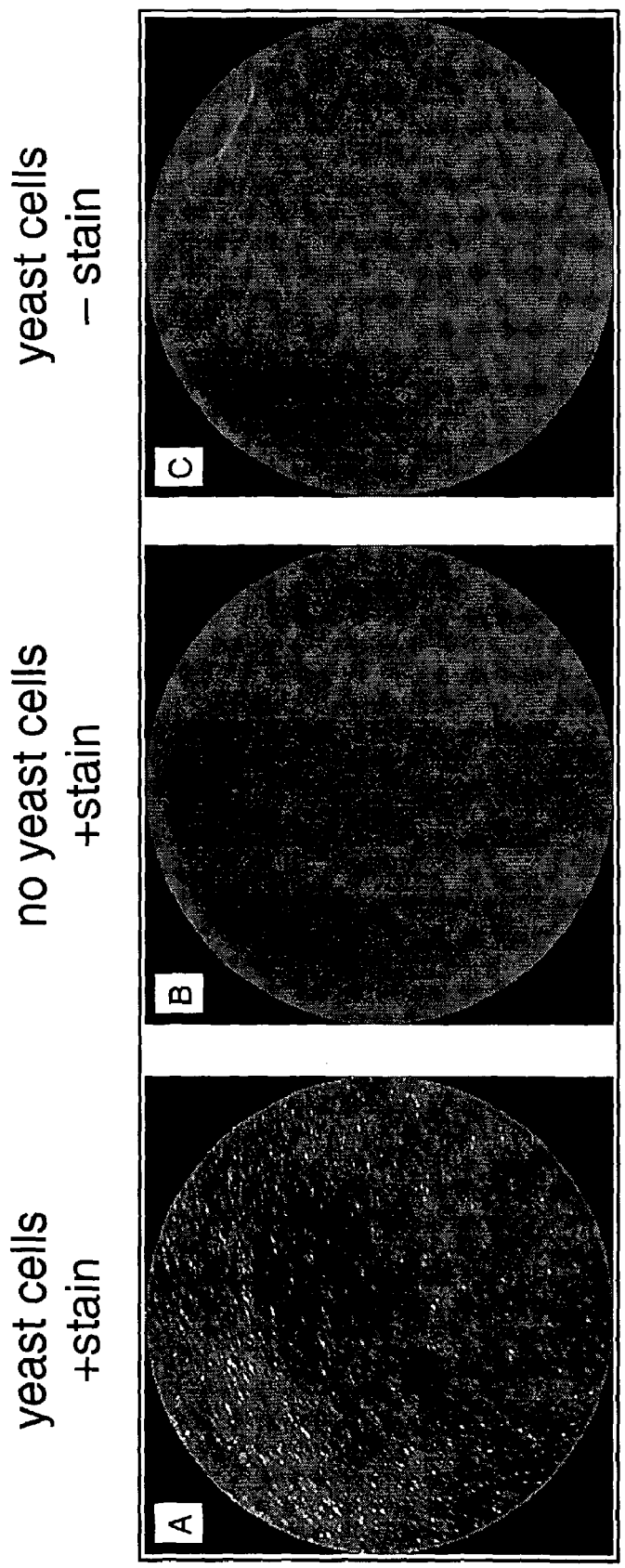
FIG. 15. Large area detection of individual fluorescently labeled *Candida albicans* cells that have been magnetically selected (Example 11).

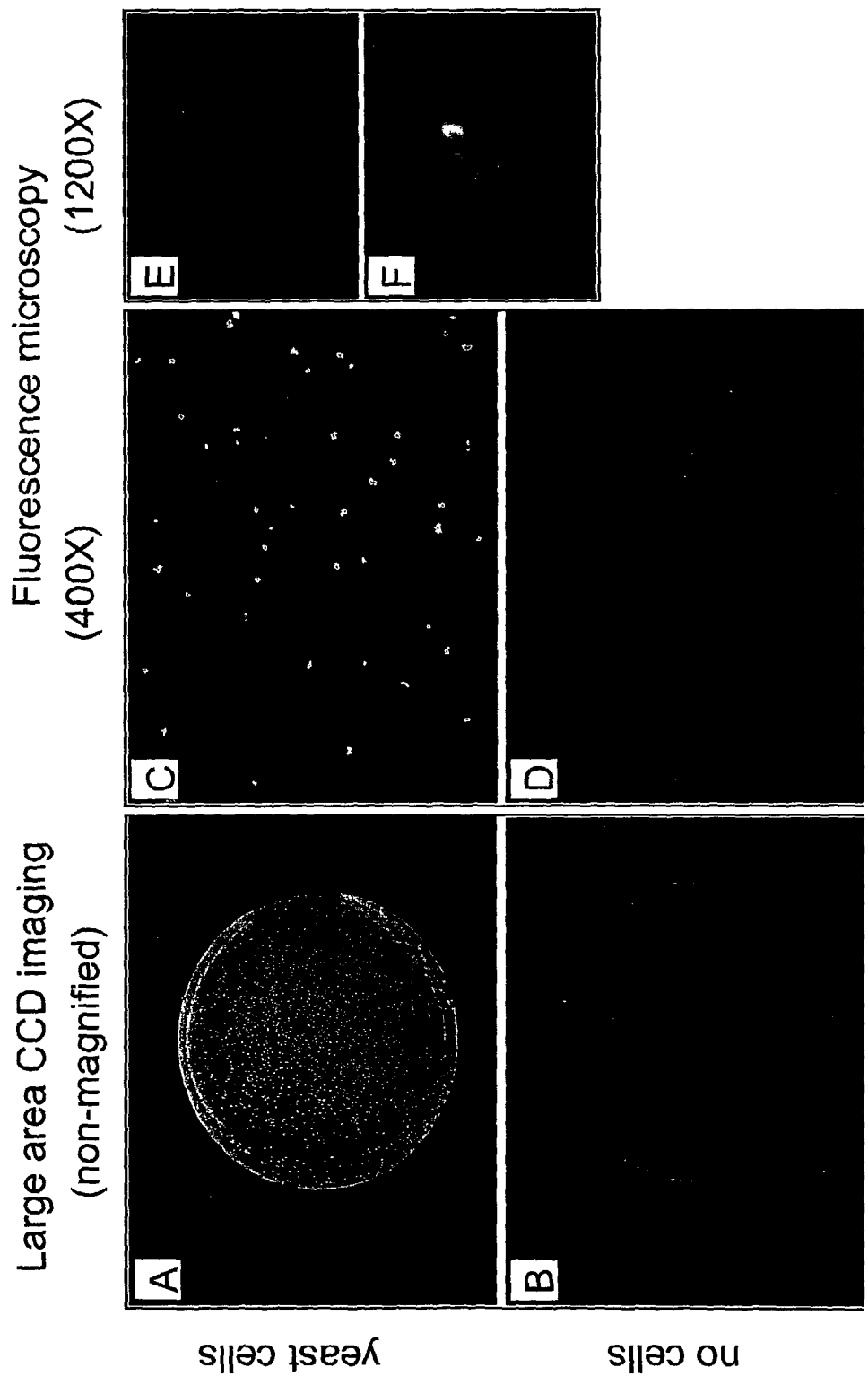
FIG. 16. Large area detection of individual *Candida albicans* cells specifically bound to fluorescent and paramagnetic polystyrene particles (Example 12).

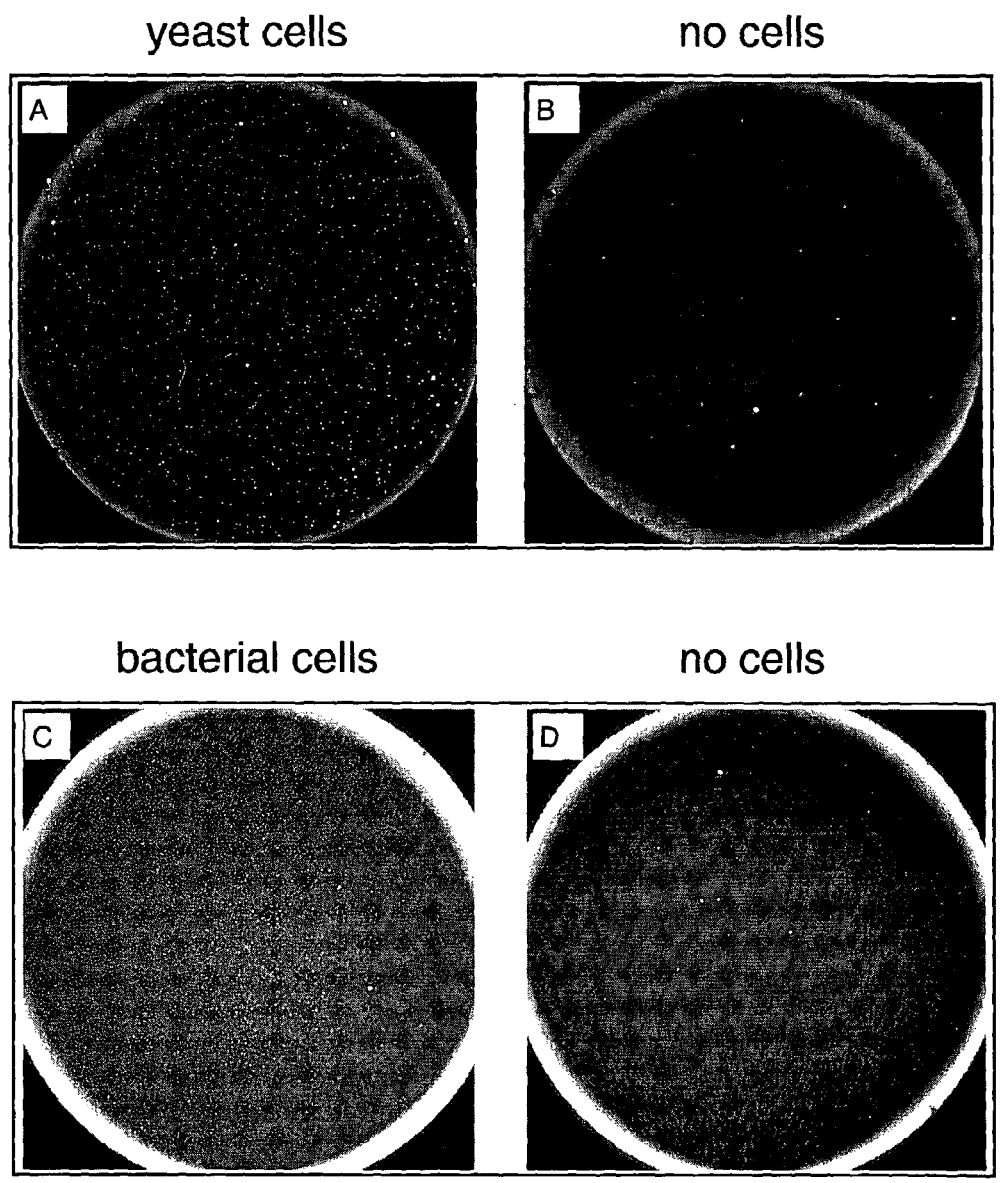
FIG. 17. Large area detection of individual Candida albicans specifically bound to fluorescent antibodies and magnetic particles (Example 13).

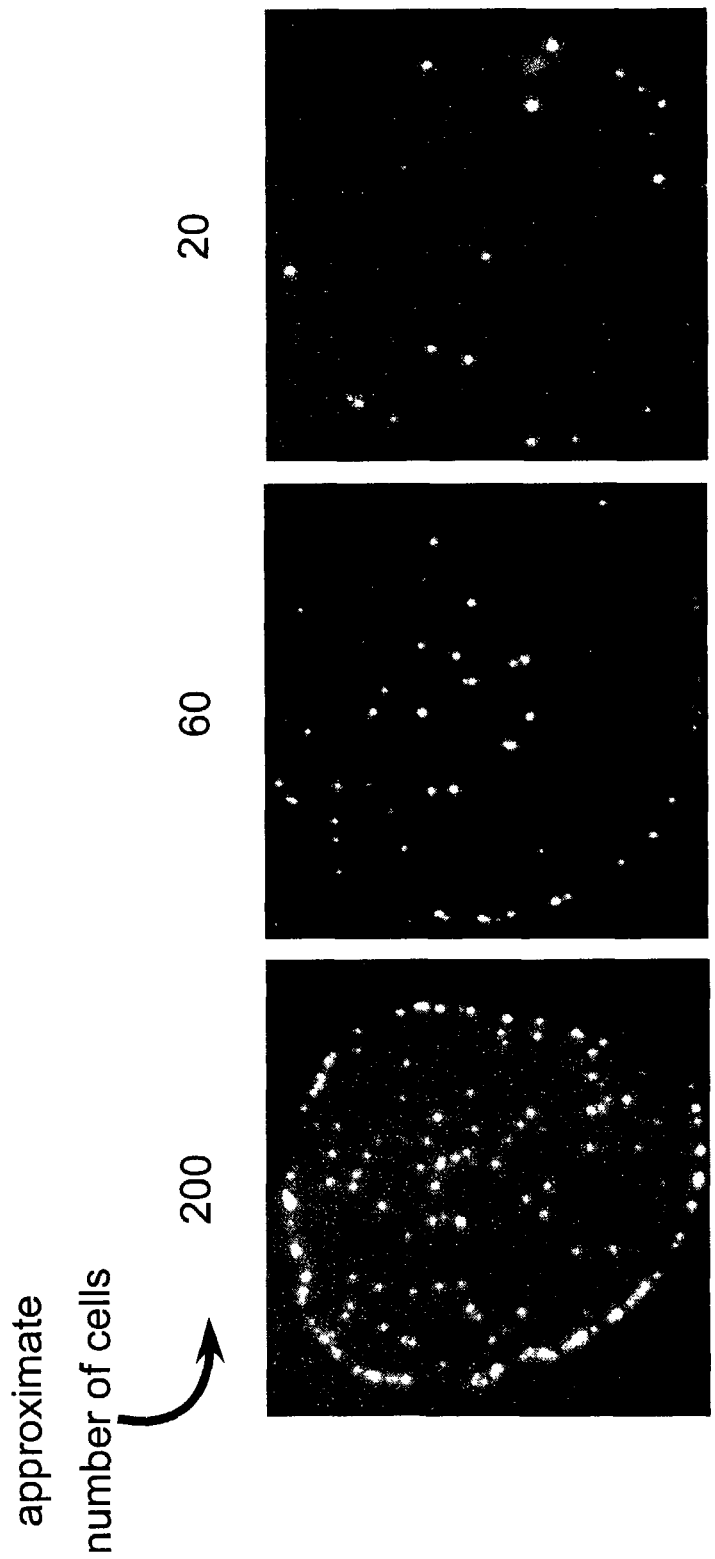
FIG. 18. Non-magnified large area detection of single chemiluminescent yeast cells (*C. albicans*) using a CCD camera (Example 14).

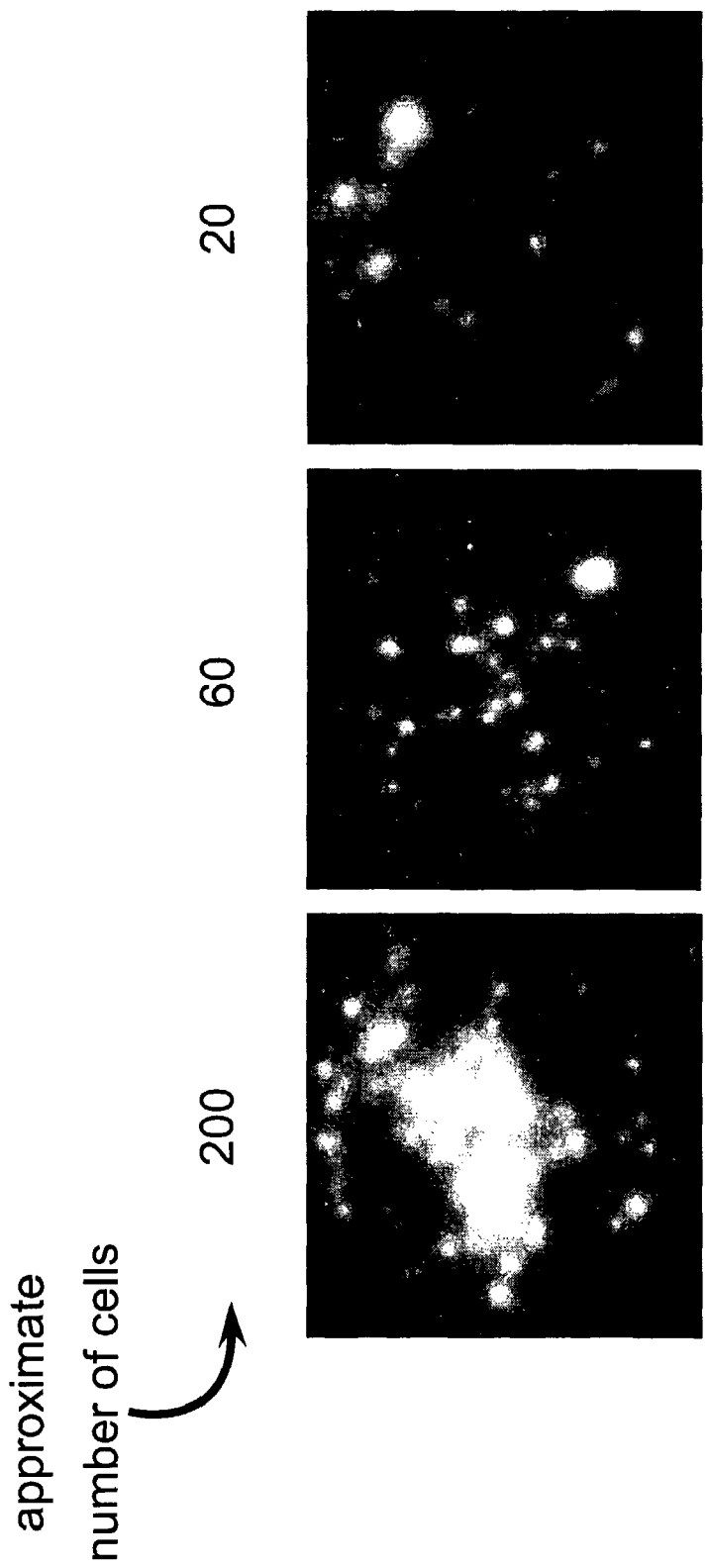
FIG. 19. Non-magnified large area detection of single chemiluminescent yeast cells (*C. albicans*) using direct exposure of instant film. (Example 15).

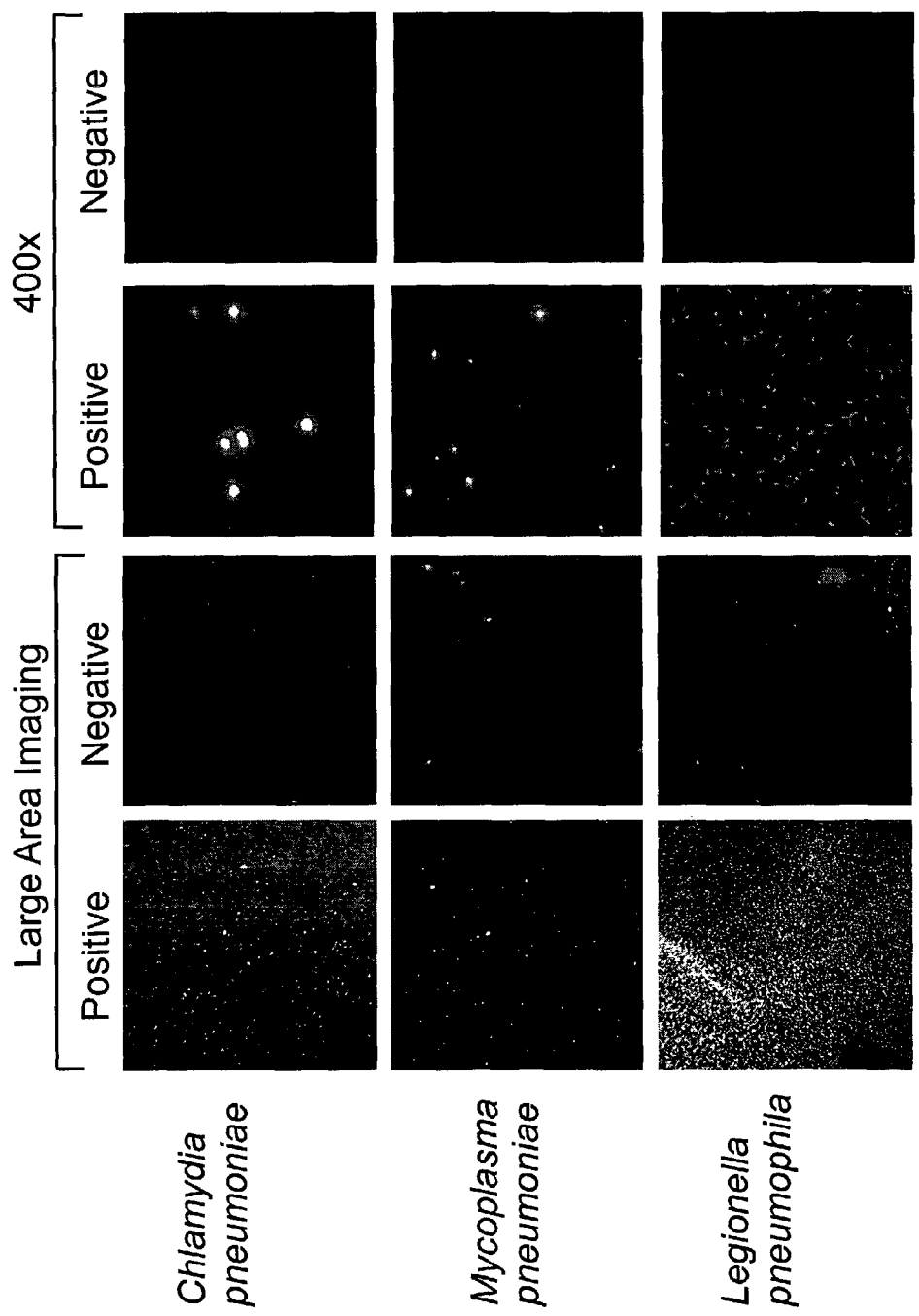
FIG. 20. Detection of organisms involved in lower respiratory tract infections using non-magnified large area imaging (Example 16).

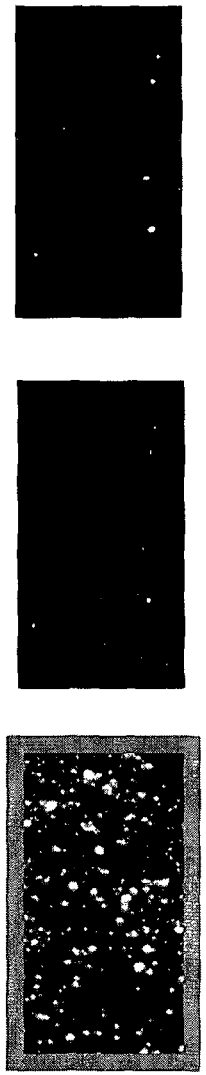
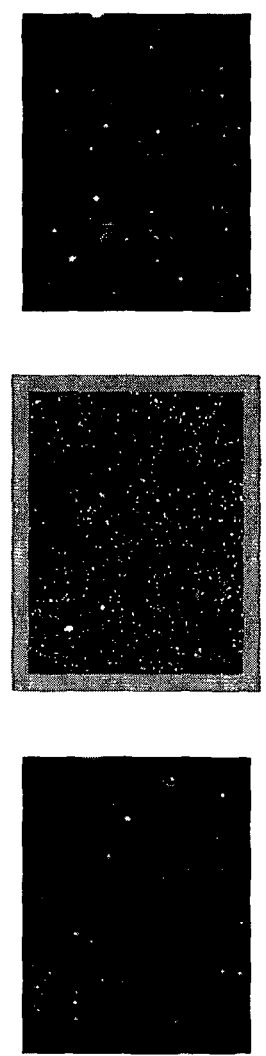
FIG. 21. A mulitiplexed direct fluorescence immunoassay that simultaneously scans a sample for 3 disparate microbes using non-magnified large area imaging (Example 17).

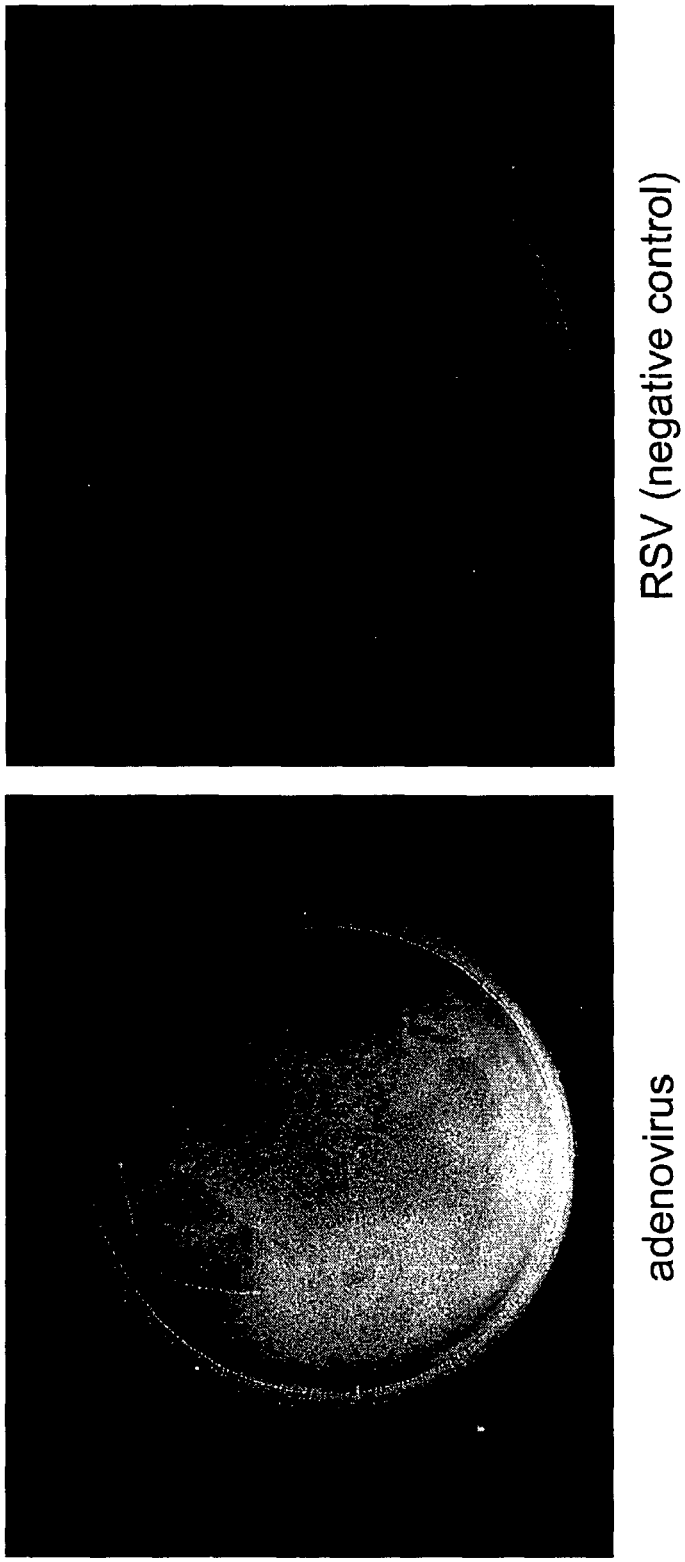
FIG. 22. A viral immunoassay using solid-phase capture and non-magnified large area imaging (Example 18).

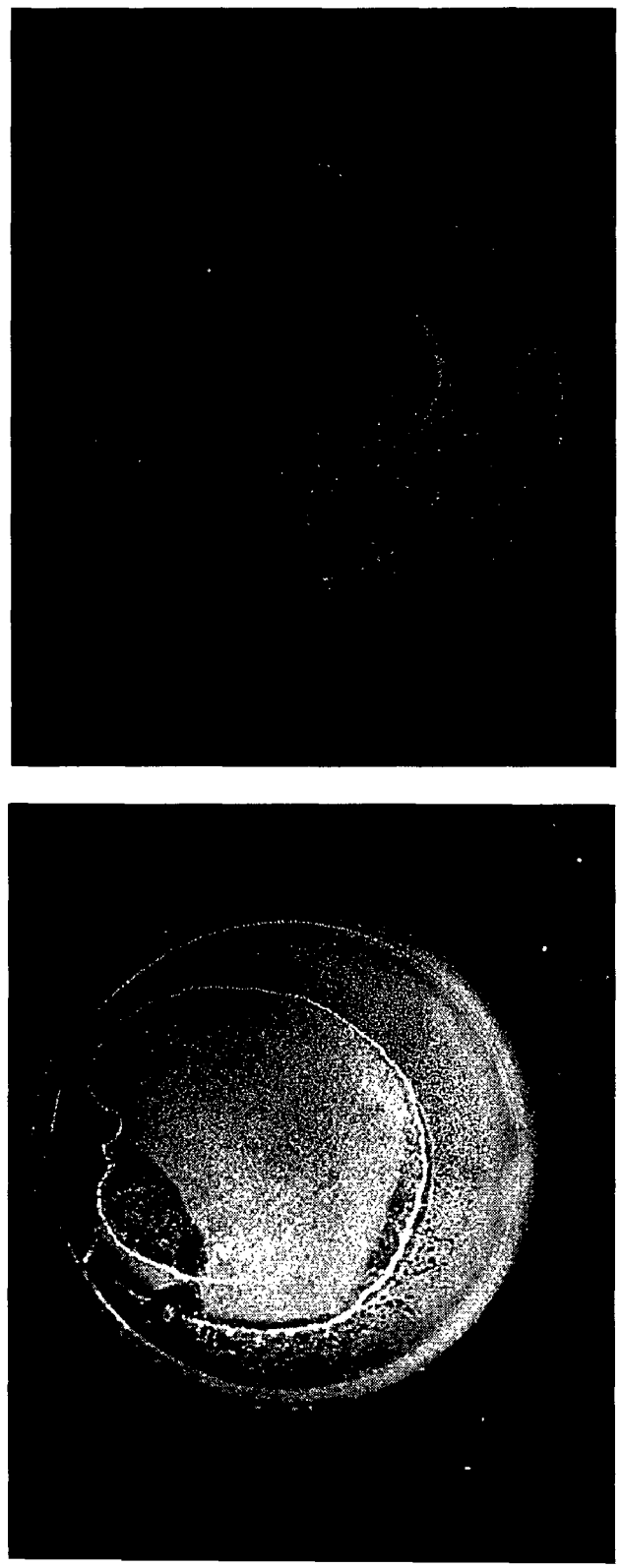
FIG. 23. A viral immunoassay in blood using solid-phase capture and non-magnified large area imaging (Example 19).

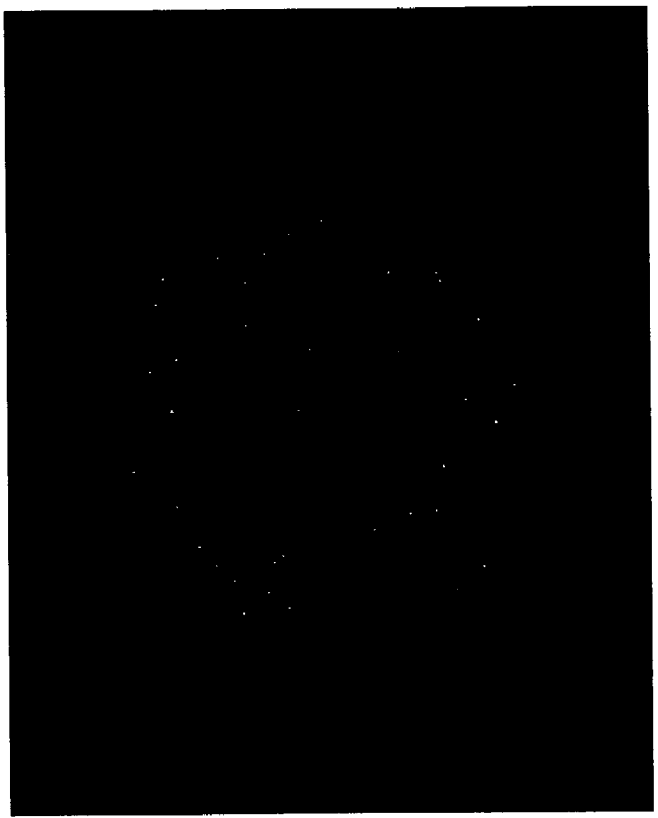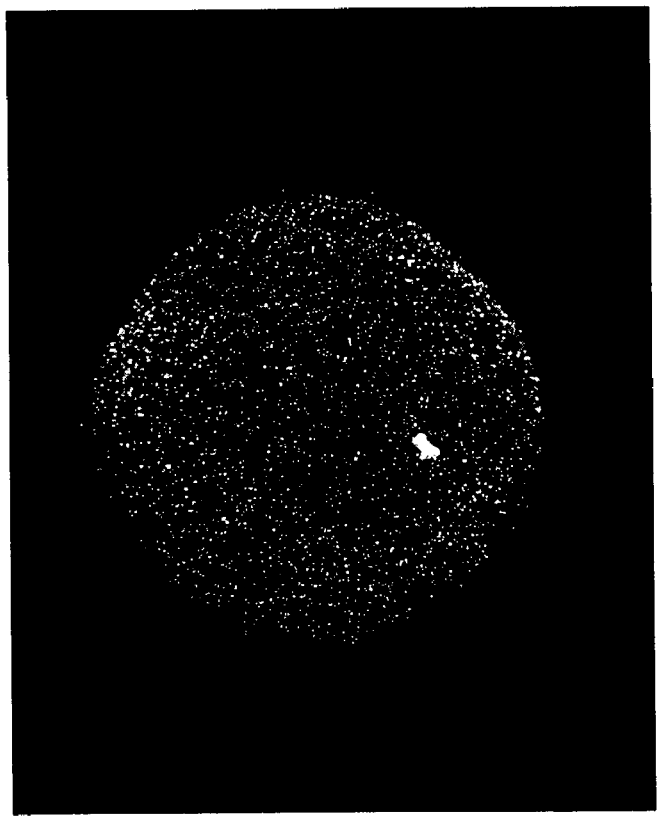
FIG. 24. A viral immunoassay using magnetic and fluorescent beads to form a liquid phase sandwich followed by non-magnified large area imaging (Example 20).

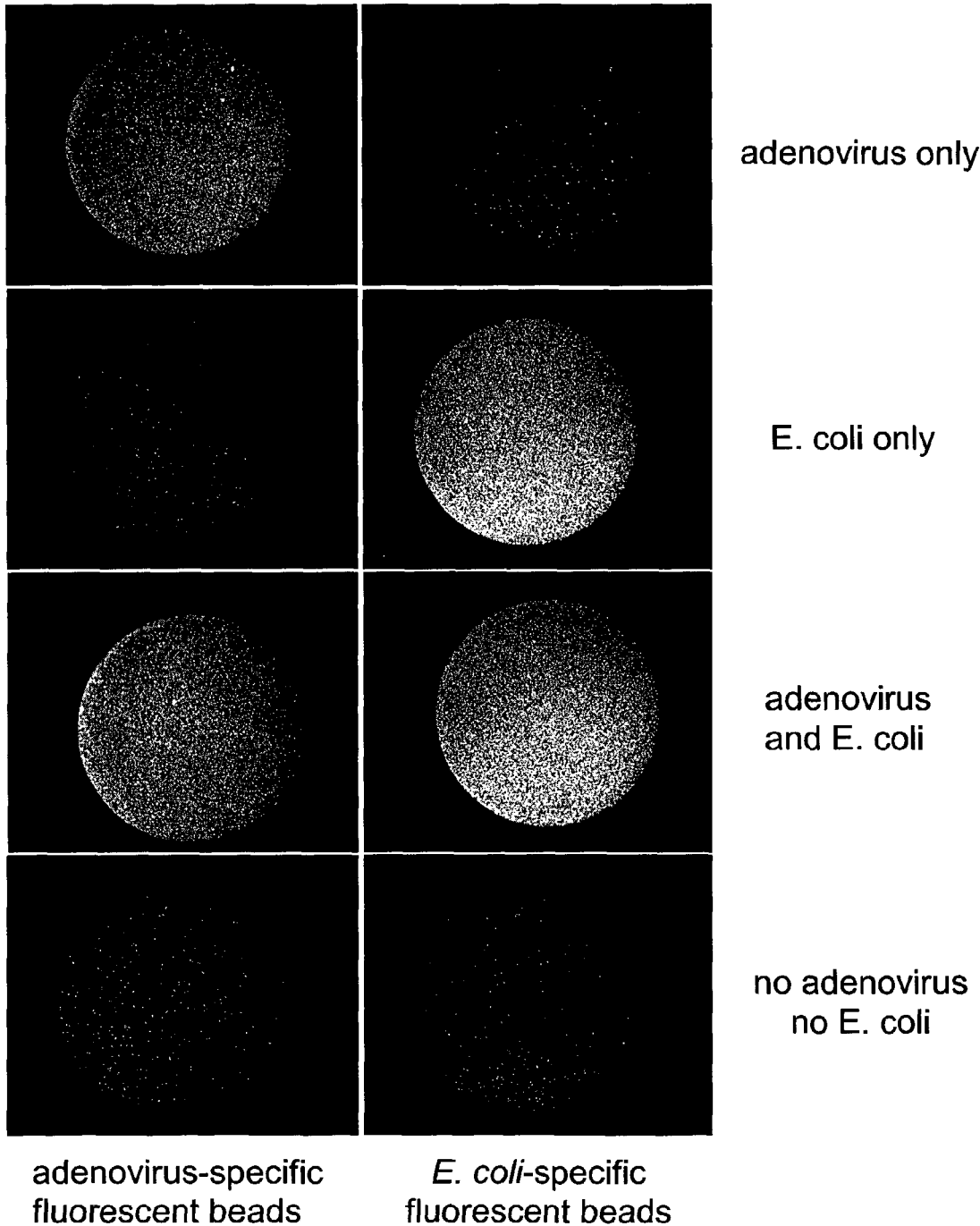
FIG. 25. Multiplex large area imaging immunoassay that simultaneously scans for a bacterium and a virus (Example 22).

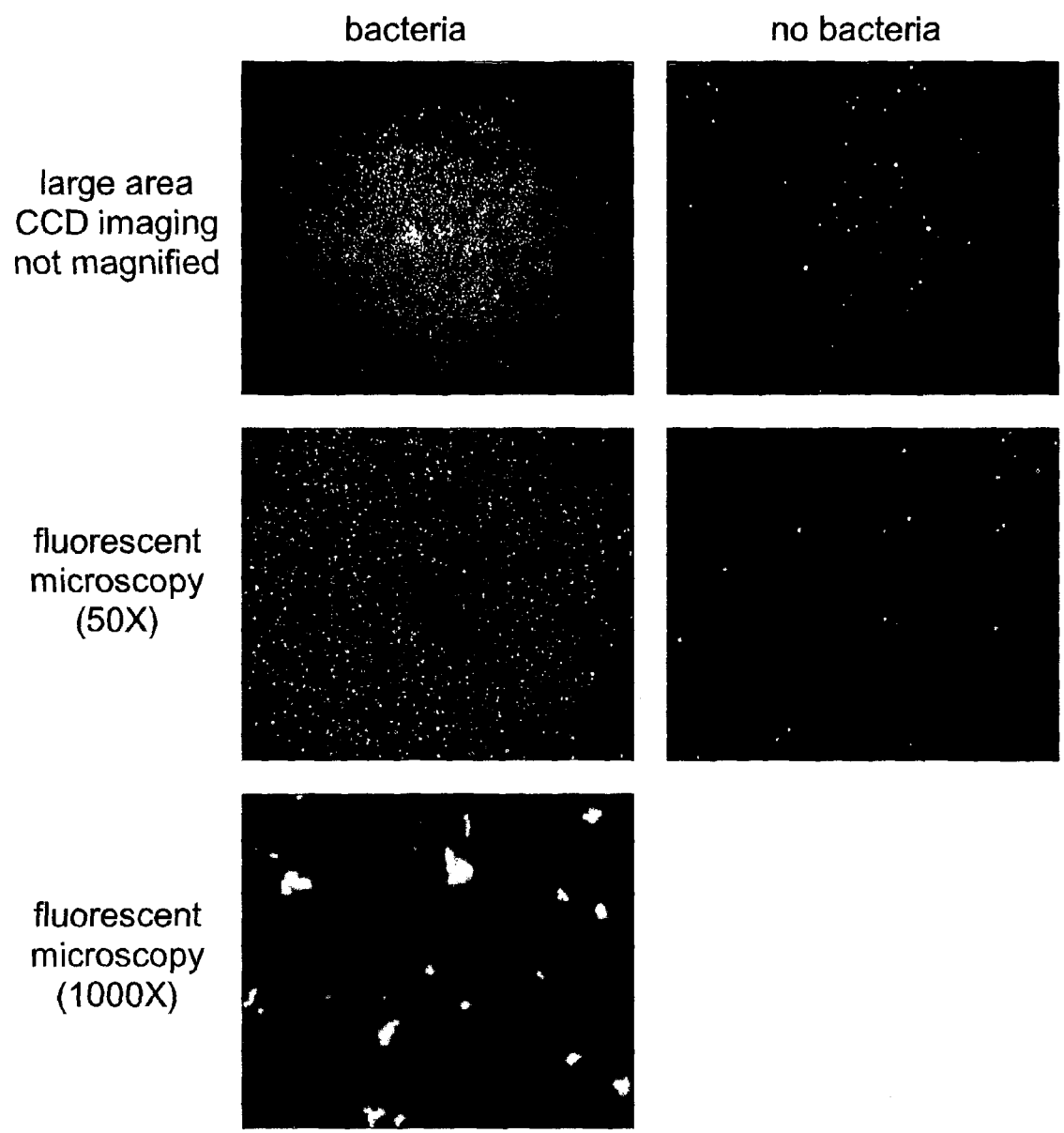
FIG. 26. Filter flow-through assay for detecting single bacteria using non-magnified large area imaging (Example 23).

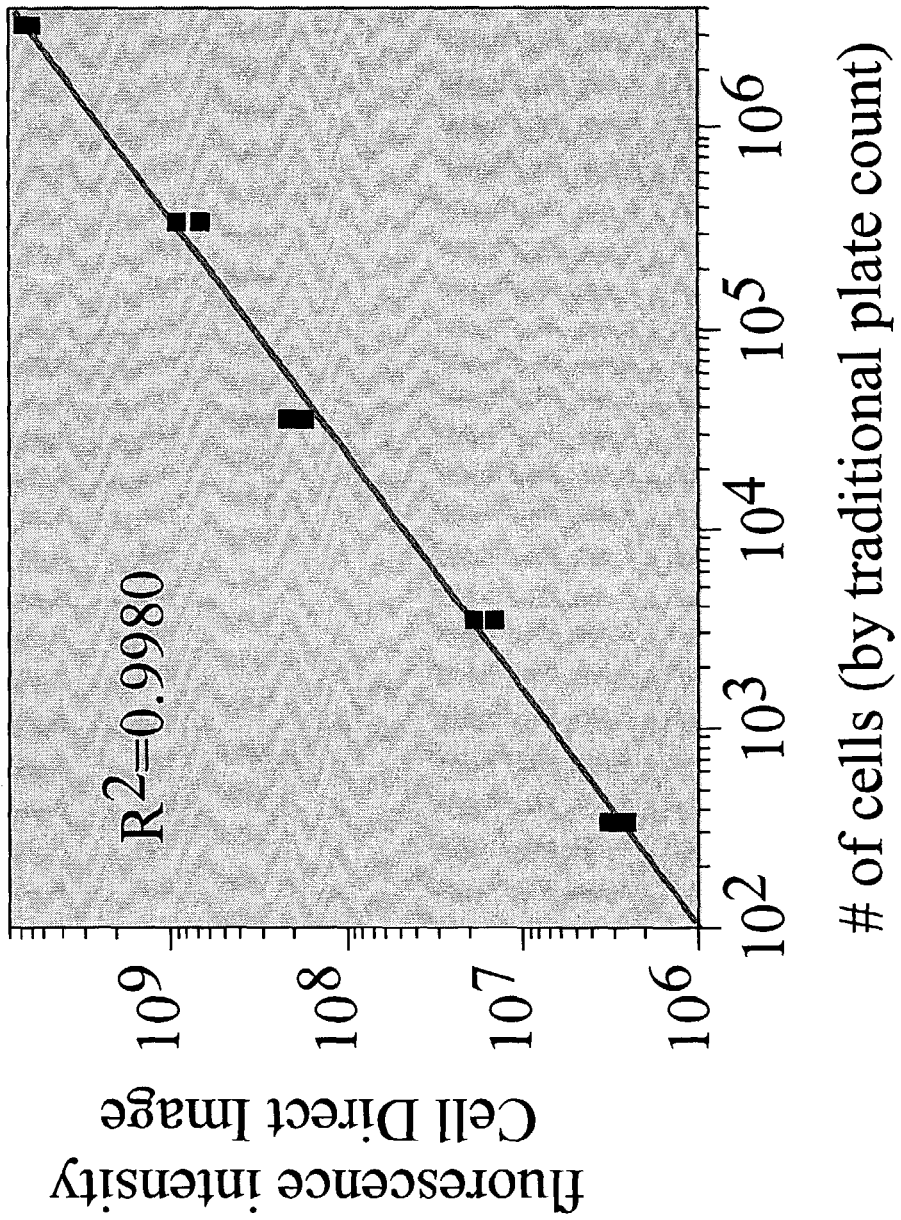
FIG. 27. Quantification of bacteria using large area imaging of cells stained with a fluorogenic esterase substrate (Example 24).

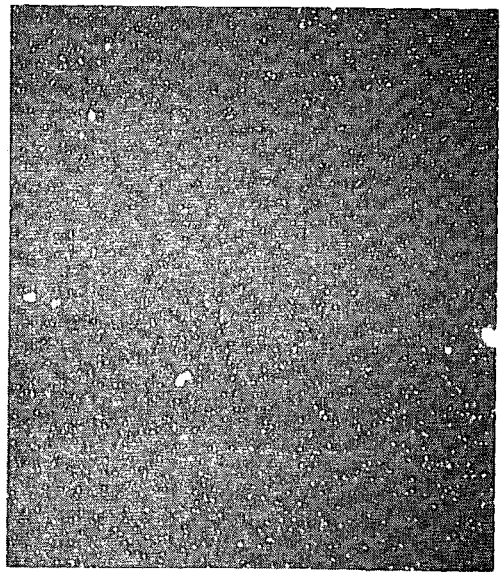 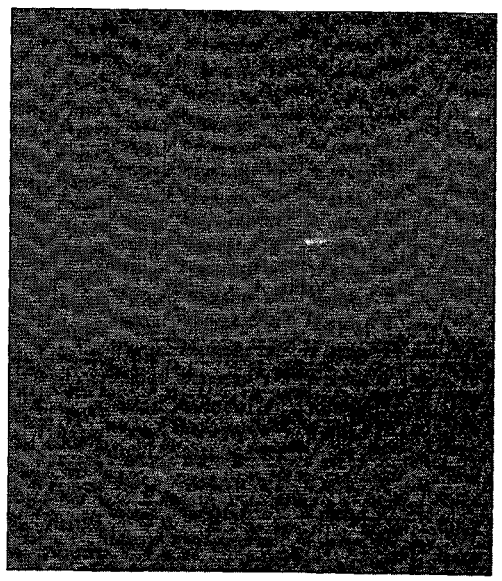
large area CCD imaging (not magnified)
fluorescent microscopy (1000X)
FIG. 28. Detecting individual stained bacteria on a filter using non-magnified large area imaging (Example 25).

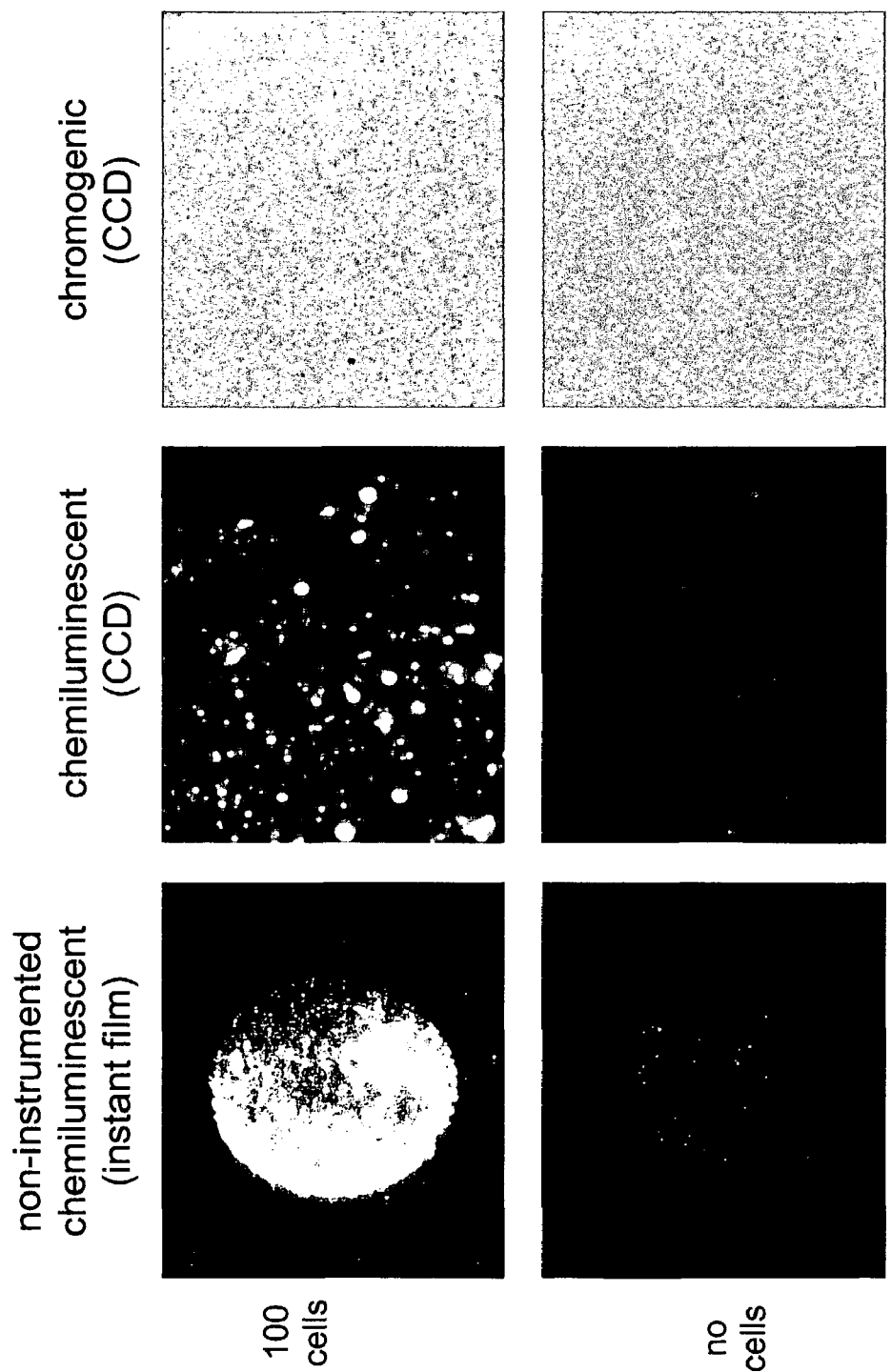
FIG. 29. Non-instrumented detection of small numbers of bacterial cells without magnification using enzyme-coated beads (Example 26).

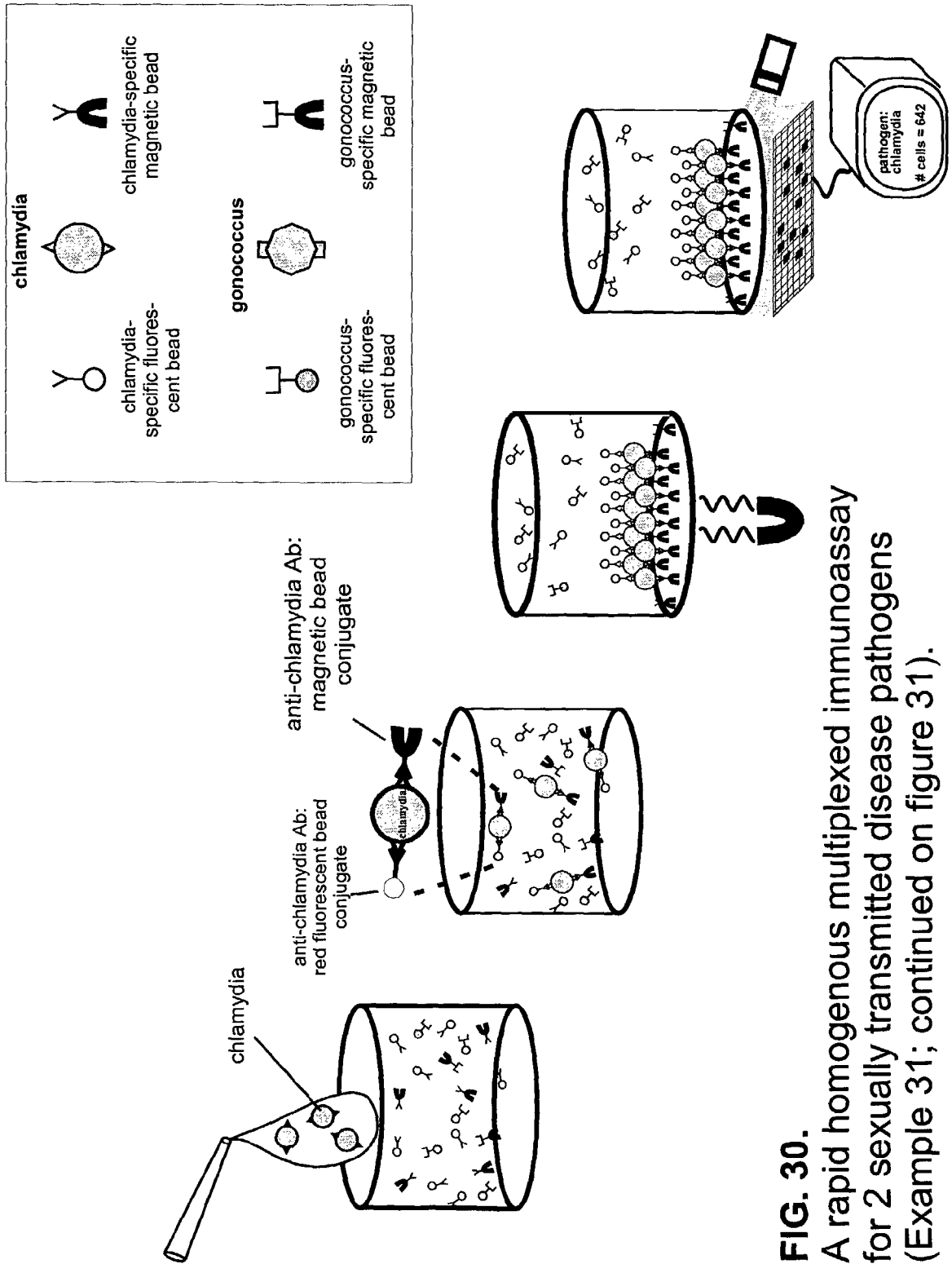
FIG. 30. A rapid homogenous multiplexed immunoassay for 2 sexually transmitted disease pathogens (Example 31; continued on figure 31).

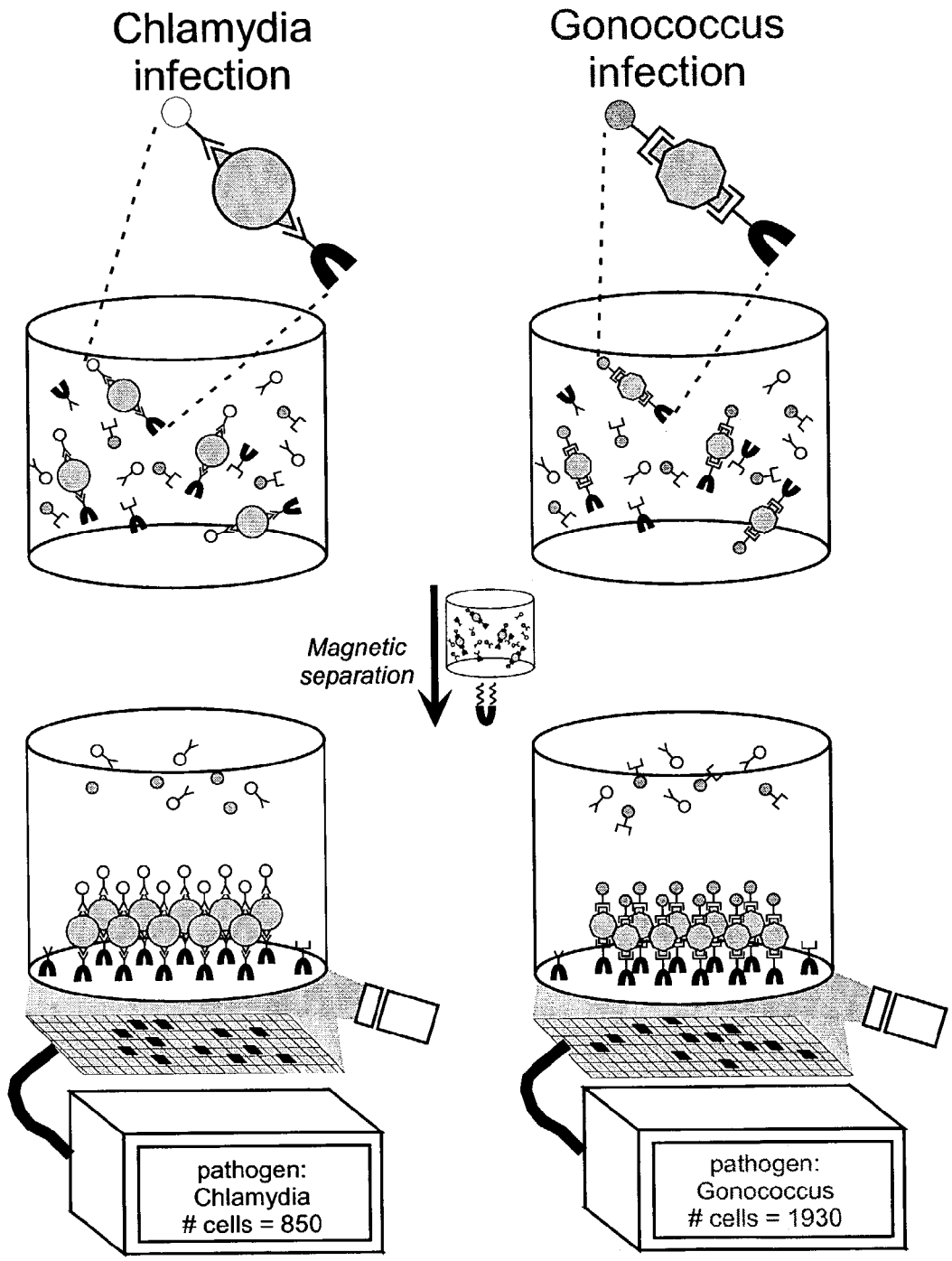
FIG. 31. A rapid homogenous multiplexed immunoassay for 2 sexually transmitted disease pathogens (Example 31; continued from figure 30).

A rapid homogenous multiplexed immunoassay for numerous pathogens using non-magnified large area imaging (Example 32).

An immunoassay that scans in parallel for numerous lower respiratory pathogens using non-magnified large area imaging (Example 33).

Multiplexed immunoassay for urinary tract infection that detects single cells using non-magnified large area imaging (Example 34).

Multiplexed immunoassay for bloodborne viruses using non-magnified large area imaging (Example 35).

FIG. 36. Ultra sensitive lateral flow assay for detecting low levels of virus using non-magnified large area imaging (Example 36).

FIG. 37. Rapid lateral flow test for *M. tuberculosis* using visual detection (Example 37).

FIG. 38.
Rapid lateral flow test for detecting numerous disparate biowarfare agents using non-magnified large area imaging (Example 38).

A. Phylogeny

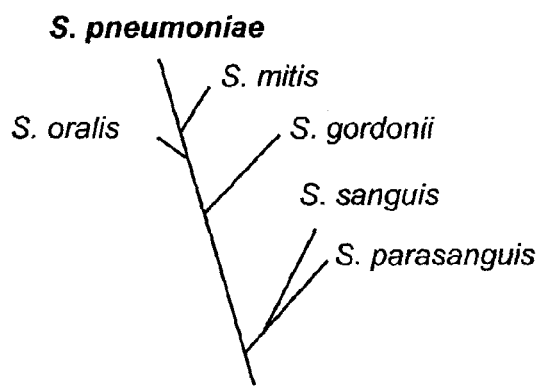

B. Isolate *S. pneumonae-specific* sequences using genomic subtraction

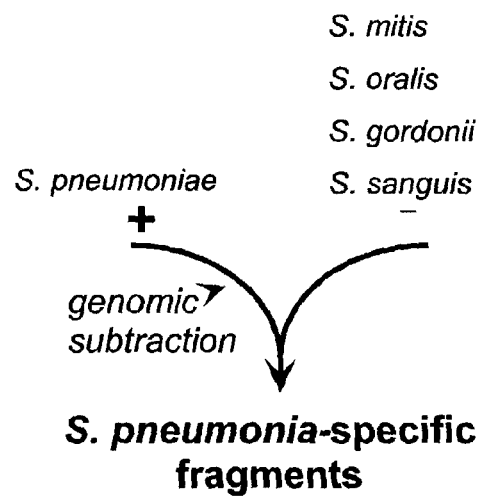

C. Screen for group-specific ID sequences

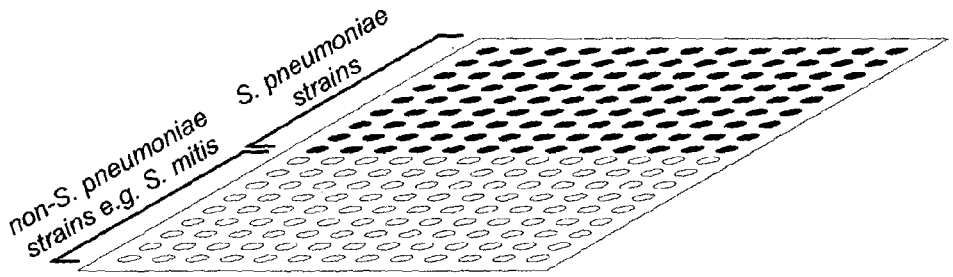

a. probe dot blots containing *Streptococcus* genomic DNA with oligonucleotides corresponding to genomic subtraction products b. choose oligonucleotide probes that are group-specific, *i.e.* that hybridize to *all S. pneumoniae* strains, but to *no* related species

FIG. 39. Isolating a family of *S. pneumonia*-specific sequences using genomic subtraction (Example 39).

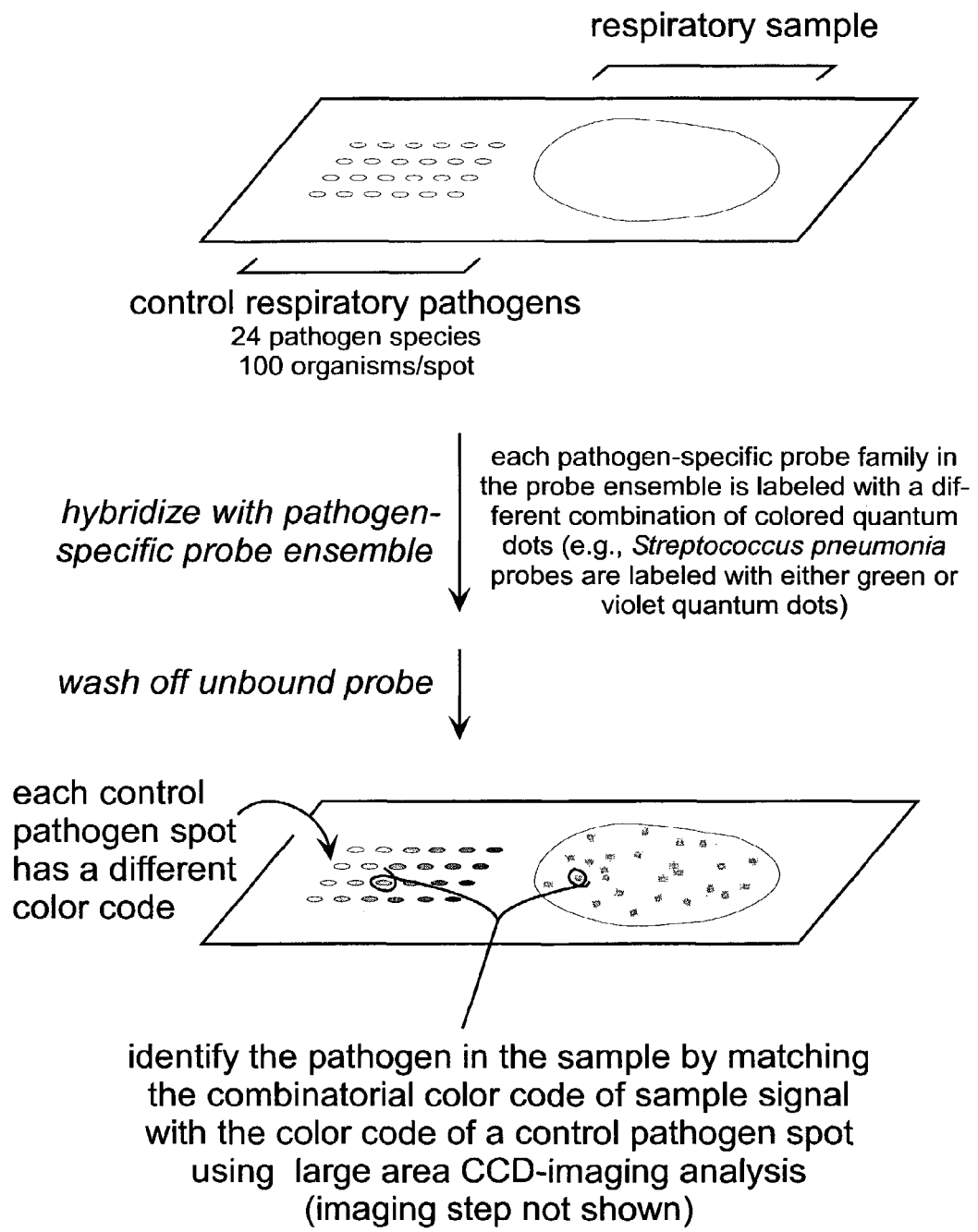
FIG. 40. Scanning a respiratory sample for 24 different pathogens simultaneously using large area imaging (Example 39).

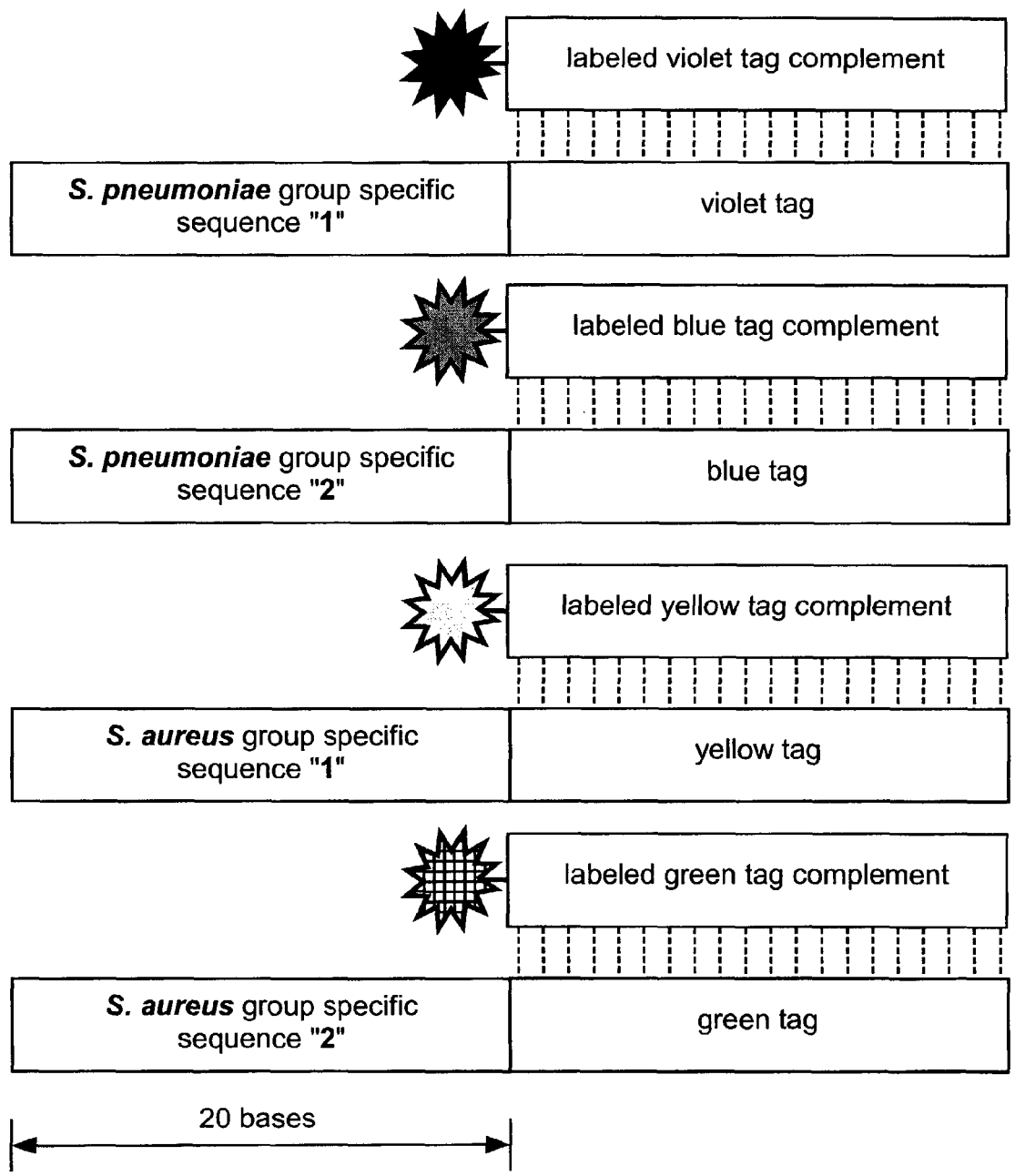
FIG. 41. Indirect combinatorial labeling of group-specific sequences (Example 40).

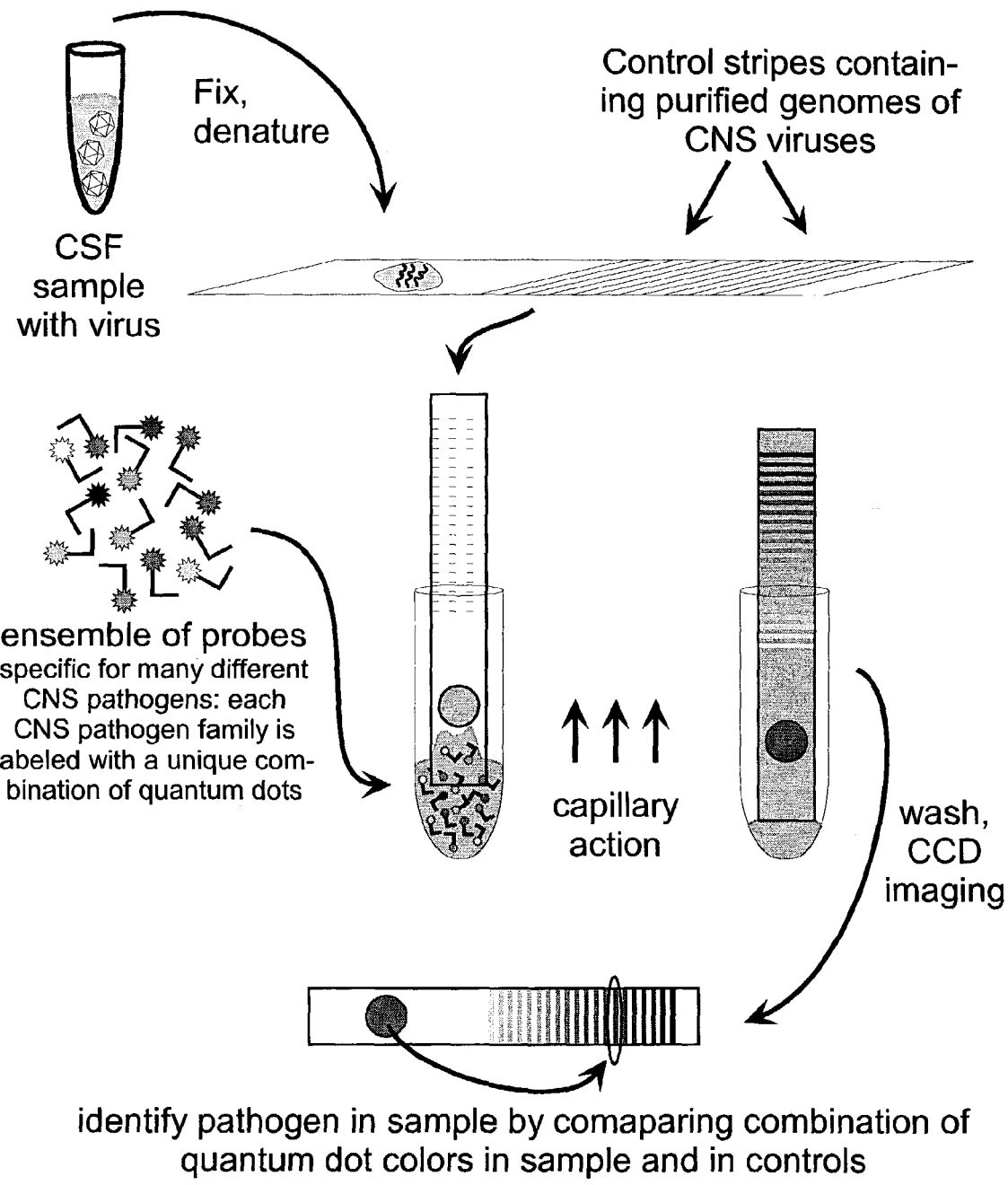
FIG. 42. Scanning for numerous CNS viral pathogens simultaneously using a rapid hybridization chromatography assay (Example 41).

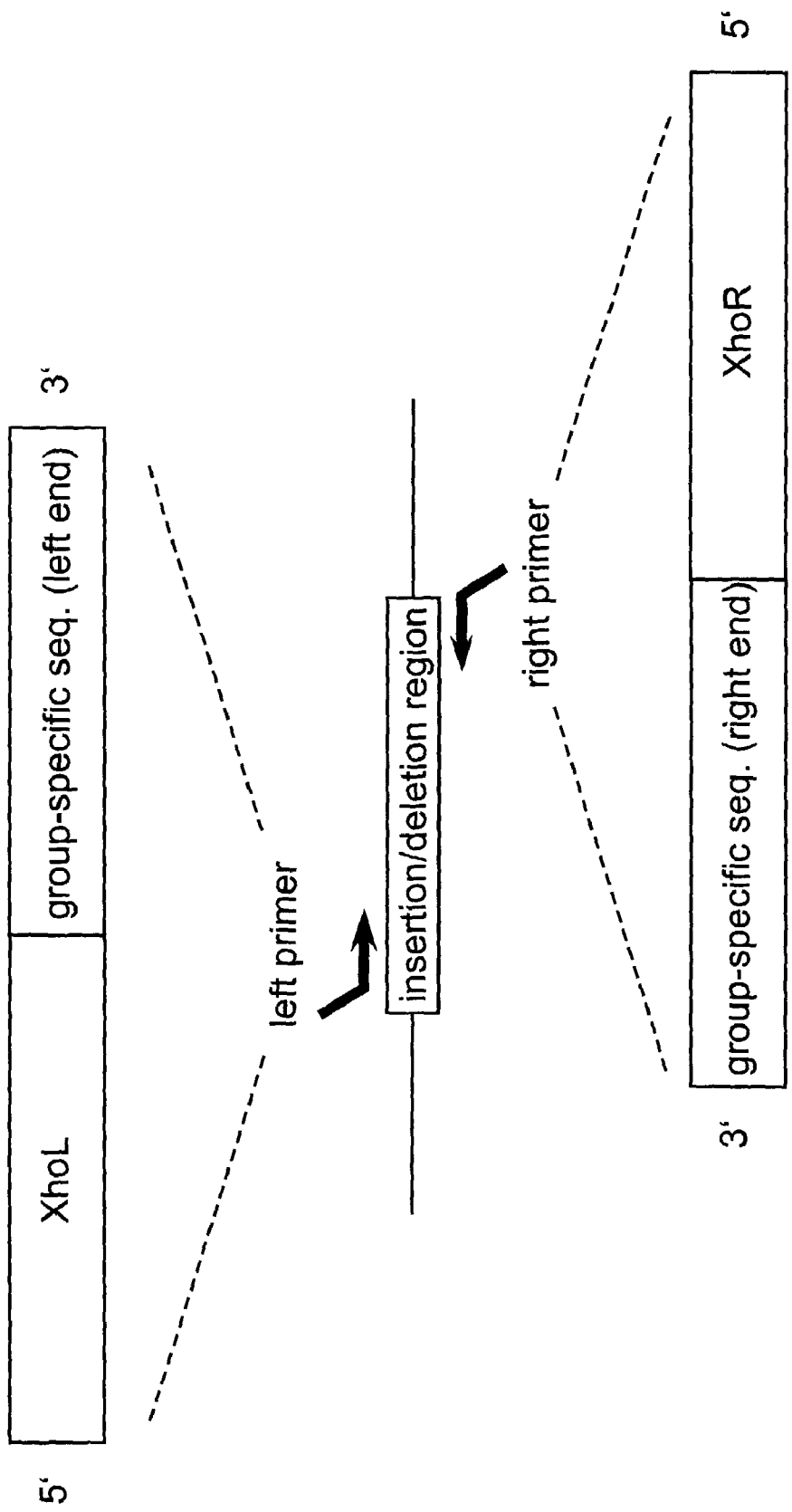
FIG. 43. Bipartite primers for PCR amplification of the products of "virtual subtraction" (Example 43).

RAPID AND SENSITIVE DETECTION OF CELLS AND VIRUSES

CROSS-REFERENCE TO RELATED APPLICATIONS

This application claims priority from U.S. Provisional Application No. 60/317,658, filed Sep. 6, 2001, hereby incorporated by reference.

BACKGROUND OF THE INVENTION

The invention relates to the identification of cells and viruses in medical, industrial, or environmental samples.

Overview

Detecting, enumerating, and identifying low levels of specific cells and viruses are a cornerstone of routine medical, industrial, and environmental diagnostics. For example, samples are analyzed to detect infectious agents, cancer cells, food pathogens, microbial contaminants of pharmaceutical and cosmetic products, and microbes in water and the environment.

For simplicity, the discussion that follows focuses on routine medical diagnostics; similar methods are used for industrial and environmental applications.

Microbiological Methods

Microbial culture allows simple visual detection of microbes, (e.g., bacteria, viruses, and fungi) by exploiting their propensity to reproduce rapidly in large numbers. For example, a individual bacterial cell, which is much too small to see by eye (about one millionth of a meter), when placed in nutrient broth, can cause the broth to become visibly cloudy in less than 24 hours.

A related microbial culture technique, called microbial enumeration or colony counting, quantifies the number of microbial cells in a sample. The microbial enumeration method, which is based on in situ microbial replication, generally yields one visually detectable "colony" for each microbial cell in the sample. Thus, counting the visible colonies allows microbiologists to determine the number of microbial cells in a sample accurately. To perform microbial enumeration, bacterial cells can be dispersed on the surface of nutrient agar in petri dishes ("agar plates") and incubated under conditions that permit in situ bacterial replication. The individual, visually undetectable, microbe replicates repeatedly to create a large number of identical daughter microbes at the physical site where the progenitor microbial cell was deposited. The daughter cells remain co-localized (essentially contiguous) with the original cell, so that the cohort of daughter cells (which may grow to tens or hundreds of millions of cells) eventually form a visible colony on the plate.

Microbial culture is a remarkably successful method, as evidenced by the fact that even after more than a century the method still dominates medical microbiology and quality control testing in industrial microbiology (e.g., pharmaceutical, food, and beverage manufacturing). The method is inexpensive, relatively simple, and ultra-sensitive. The sensitivity of microbial culture can be seen in the common test for foodborne pathogens in ground beef. A individual microscopic bacterial pathogen cell can be detected in 25 grams of ground beef using microbial culture. Another advantage of microbial culture is its ability to detect a large range of microbes of medical and industrial significance.

Some viruses can be grown in culture. Viral culture has been especially useful for fast growing bacteriophage (viruses that infect bacteria) in research applications. Viral culture is sometimes used to diagnose clinical infections although methods such as nucleic acid amplification are increasingly used instead.

Traditional microbial culture is slow—it takes time to generate the number of cells or viruses required for visual detection. The long growth period required for microbial culture is a significant problem in both healthcare and industry. For example, because it requires days to culture and identify the microbe causing a patient's blood infection, a patient with a fungal blood infection could die before anti-fungal therapy is even begun. Some infectious agents, such as the bacterium that causes tuberculosis, generally require weeks to grow in culture. The long time required for detecting $M.\ tuberculosis$ can result in a patient with tuberculosis infecting many others with the highly contagious disease or the costly quarantine of patients who do not have tuberculosis. In the manufacture of food, long testing cycles can increase food spoilage. Slow microbial culture also adversely impacts the production of biopharmaceuticals and vaccines.

A number of microbial culture methods for more rapid microbial enumeration have been developed. One rapid method deposits bacterial cells on microscope slides coated with nutrient medium. Using microscopic examination, microbial growth can be detected much earlier than with the naked eye, since microscopes can detect microcolonies resulting from a small number of cell divisions. A commercialized system, the Colifast Rapid Microcolony Counter (Colifast), can detect small fluorescently labeled colonies of coliform bacteria hours before they can be seen by eye. The Colifast system achieves enhanced detection by using a fluorogenic compound (a substance that is not fluorescent until metabolized by coliform bacteria) is included in the nutrient agar media. A system for rapid enumeration of microbial colonies using bioluminescent labeling has recently been commercialized. The MicroStar system (Millipore) uses the cellular ATP in microcolonies to generate light via the action of applied luciferase enzyme and substrates. The method reduces time to detection substantially. The MicroStar imaging system has also been used in conjunction with labeled probes to identify specific bacteria (Stender, H., et al. (2001). J Microbiol Methods 46: 69-75).

Immunological Methods

Immunological tests, or immunoassays, are frequently used to identify specific cells and viruses in medical diagnostics. Immunoassays can detect the specific binding of antibodies to sites on the molecular components of targets and viruses. Serological tests are immunological assays that, rather than testing directly for antigens, test for a host immunological response to previous exposure to the antigen—for example they can test for the presence of host antibodies to particular cells and viruses. Numerous immunoassay systems are available for ranging from large automated central lab systems to over-the-counter pregnancy tests. The tests cover a broad range of formats including agglutination assays, precipitin assays, enzyme-linked immunoassays, direct fluorescence assays, immuno-histological tests, complement-fixation assays, serological tests, immuno-electrophoretic assays, and rapid "strip" tests (e.g., lateral flow and flow through tests). Immunological tests can be extremely simple and rapid. Thus, many of the most desirable tests, those that can be conducted in a physician's office or at home by the patient, are immunological tests.

Genetic Methods

Genetic methods are general and powerful tools for detecting and identifying nucleic acid molecules from cells and viruses. Revolutionary new methods for ultra-sensitively detecting and distinguishing the nucleic acid content of cells and viruses based on nucleic acid amplification have recently been developed. For example, commercial tests can detect the nucleic acids from a small number of sub-microscopic HIV virus particles (e.g., 50 particles/ml). Amplification technologies include the polymerase chain reaction (PCR), ligase chain reaction (LCR), nucleic acid sequence-based amplification (NASBA), Transcription Mediated Amplification (TMA), and rolling circle amplification (RCA). Amplification methods can deliver impressive analytical sensitivity and can be moderately rapid, for example, the Smart Cycler (Cepheid) can deliver results in an hour (Belanger, S. D., et al. (2002). Journal of Clinical Microbiology 40: 1436-40).

Microscopic Imaging Methods

Microscopic imaging is one of the most common methods for detecting cells and viruses. Targets can be visualized microscopically by labeling with stains, antibodies, or nucleic acid probes, for example. The sensitivity of microscopic analysis can be enhance using methods such as catalyzed reporter deposition (CARD), which has been used to detect single copy level viral genomes in human cells (Huang, C. C., et al., Modern Pathology 11: 971-7, 1998). Other methods for increasing the sensitivity of in situ hybridization rely on in situ amplification or replication, or signal amplification using, for example, branched DNA or dendrimer technology (e.g., Orentas, R. J., et al., Journal of Virological Methods 77: 153-63, 1999).

Multiple fluorescent labels can be used to detect several pathogens at once using in situ analysis. For example, antibodies to different category-specific antigens can be labeled with different fluorescent tags. Combinatorial labeling strategies have been also used in conjunction with microscopy to identify several bacterial pathogens simultaneously (Amann, R., et al., Journal Of Bacteriology 178: 3496-500, 1996; U.S. Pat. No. 6,007,994).

Several commercial systems have been developed that achieve high throughput in situ microscopic analysis of microscopic targets (e.g., WO 98/22618 and WO 93/21511). Typically, microbes or cells are deposited on a slide or on the bottom of the wells of a multiwell plate. Labeled targets in the wells are then imaged microscopically.

Non-Microscopic Imaging Methods

Non-microscopic imaging allows larger areas to be surveyed for the presence of cells. For example, researchers at Hamamatsu Corporation (Masuko, M., et al., FEMS Microbiol Lett 67: 231-8, 1991; Masuko, M., et al., FEMS Microbiol Lett 65: 287-90, 1991; Yasui, T., et al., Appl Environ Microbiol 63: 4528-33, 1997) developed a system that can image individual bacterial cells without magnification. The system uses an ultrasensitive photon-counting CCD camera coupled to a fiber optic system, image intensifier, and image-processor. The Elisa spot test method is a specialized technique for enumerating single cells that produce a particular antibody (or other abundantly secreted product; Logtenberg, T., et al., Immunol Lett 9: 343-7, 1985). The method's sensitivity derives from the fact that large numbers of targets (the secreted protein molecules) are localized around the secreting cell.

Flow Cytometric Methods

Flow cytometry is an important tool for characterizing cells in clinical diagnostic laboratories. Flow cytometric methods are used for quantitatively detecting particular cell types on the basis of their physical properties and their ability to bind labeled probes (e.g., stains, antibodies, or nucleic acids). Individual cells or particles are forced to flow through a narrow channel, one at a time, past a laser beam. Fluorescence emission and size/shape information is gathered by analyzing the spectrum and light scattering caused by the organism/particle. Thousands of individual cells or particles can be analyzed per minute. For example, flow cytometry is used to quantify the population sizes of classes of lymphocytes in patients with AIDS. A highly multiplexed flow cytometric method that can detect and identify non-cellular molecules such as proteins or nucleic acids has been commercialized by Luminex (U.S. U.S. Pat. No. 5,981,180).

Laser Scanning Methods

Laser scanning is a powerful and sensitive method for detecting cells and viruses deposited on surfaces. Typically, a microscopic laser beam (e.g., 20 µm in diameter) is traced over a two dimensional sample containing fluorescently labeled targets on a solid surface in a large number of successive linear passes, each slightly offset from the previous, so that the entire sample area is eventually scanned. When a fluorescently labeled target falls under the beam, a flash of emitted fluorescence is detected by a detection device such as a photomultiplier. The number and position of the microscopic targets can be obtained by laser microbeam scanning.

A number of systems for laser scanning have been developed. The ScanRDI® system (Chemunex) uses a non-specific fluorescent dye to label microbial cells on a filter (U.S. Pat. No. 5,663,057; Mignon-Godefroy, K., et al., Cytometry 27: 336-44, 1997). The fluorimetric microvolume assay technology (FMAT; PE Biosystems and Biometric Imaging; Miraglia, S., et al., J Biomol Screen 4: 193-204, 1999) has also been used to detect cells in microtiter wells. A sophisticated laser scanning system has been developed and commercialized by CompuCyte Corporation (Kamentsky, L., 2001, *Laser Scanning Cytometry*. In Cytometry, Z. Darzynkiewicz, H. Crissman and J. Robinsnon, eds. Methods in Cell Biology Vol. 63, Part A, 3rd ed, Series Eds. L. Wilson and P. Matsudaira. (San Diego: Academic Press)). A microbeam laser scanning system that detects individual microscopic targets in a liquid sample (e.g., whole blood) has been developed by Immunicon Corporation and collaborators at Twente University (Tibbe, A. G., et al., Nat Biotechnol 17: 1210-3, 1999).

Biochemical, Chemical, and Physical Methods

Other technologies for sensitive detection of the cells and viruses, or their molecular components, molecular components of cells and viruses include flow cytometry, mass spectroscopy, biosensors, absorbance spectroscopy, fluorescence polarization, fluorescence fluctuation spectroscopy, electrophoresis, chromatography, among many others.

Biosensor technologies also hold promise for sensitive detection of cells and viruses. Biosensors use physical methods to convert a biological event, for example binding of an antibody to an antigen, to a detectable signal. One popular biosensor used for molecular detection uses surface plasmon resonance (Mullett, W. M., et al. (2000). Methods 22: 77-91). Thermo BioStar's optical immunoassay (Schultze, D., et al. (2001). Eur J Clin Microbiol Infect Dis 20: 280-3) uses the principle of optical interference to detect binding of antigens to antibodies. The BARC biosensor technology uses magnetoresistive detection (as used for hard disk storage) of analytes tagged with single magnetic microparticles (Edelstein, R. L., et al., Biosens Bioelectron 14: 805-13, 2000).

Unmet Needs for Detection of Cells and Viruses

Although numerous disparate and powerful methods for routine detection of low levels of cells and viruses have been commercialized there are still gaps in the testing repertoire. In particular, there is a need for tests to detect very low levels of cells and viruses that are rapid, do not require laboratory growth, are user-friendly, and are cost-effective.

SUMMARY OF THE INVENTION

The invention provides efficient methods for rapidly and sensitively identifying cellular and viral targets in medical, industrial, and environmental samples. The invention labels targets and then detects them using large area imaging. Diagnostic tests based on the invention can be rapid, ultrasensitive, quantitative, multiplexed, and automated. The tests minimize sample preparation and do not require nucleic acid amplification or cell culture. A broad range of cells and viruses can be detected by the tests. Tests based on the invention can deliver the high level sensitivity of nucleic acid amplification tests, the user-friendliness, and speed of immunoassays, as well as the cost effectiveness and quantification offered by microbiological tests. The invention embodies the best attributes of the current diagnostic technologies, while addressing gaps in the diagnostic repertoire.

The ability of the invention to detect low levels of targets and viruses rapidly and cost-effectively results from the advantages of combining high intensity labeling, formats that facilitate rapid reaction kinetics, and large area imaging based using either instrumentation made from off-the-shelf commercial components or no instrumentation at all. Table 1 lists some of some of the advantages of the invention.

TABLE 1

Selected advantages of the invention

Rapid results
Ultra-sensitive
Easy-to-use
Cost-effective
Multiple targets analyzed simultaneously
Scans for all types of cells and viruses
Analyzes large or small volumes
Automated quantitative analysis
Minimal sample preparation The invention detects low levels of cells and viruses by specifically labeling them to generate high-intensity signals. A variety of signal generating complexes can be used including fluorescently dyed, light-scattering, quantum dot, phosphor, and enzyme-coated particles. These particles, in turn, can generate a variety of types of signals including fluorescent, chemiluminescent, and calorimetric. Similarly, a variety of molecules can be used for achieving specific binding of the signal generating labels including antibodies, nucleic acids, ligands, and aptamers.

Detecting small numbers of targets and viruses in large volumes is a requirement when testing some clinical, environmental, and manufacturing samples. The invention's ability to survey large samples for low levels of targets rests, in part, on its ability detect individual cells and viruses without magnification. Non-magnified detection allows a large area to be surveyed for small numbers of the particles in a single image. Imaging a large area, in turn, is a key to the invention's ability to analyze large sample volumes efficiently. Detecting labeled particles in large volumes using high power microscopy or microfluidics can require challenging concentration steps or analysis of thousands of images. Methods that scan for small numbers of particles using microscopic beams become very time consuming and expensive when applied to large areas.

Enumerating individual microscopic labels adds robustness to the results of tests based on the invention. In contrast to many large area imaging methods for analyzing cellular and viral targets, the invention generally compares individual signals directly to small neighboring regions. This comparison improves the signal to background ratio for samples containing few labeled targets compared to methods that integrate the total signal and background in a large area.

Another advantage of detecting individual cells or viruses is that the sensitivity of the tests can be increased without sacrificing speed by increasing the sample volume with a proportionate increase in the size of the detection zone.

Enumerating individual signals in a large area image also decreases the chance of false positive results. (False positive results are positive test results that occur when the actual target is not present). This enumerating method is an advantage compared with methods that detect a single integrated signal, such as methods that measure the total amount of a molecule (e.g., ATP, antigens, or nucleic acids) in the sample. Any artifact that causes a signal can generate a false positive when using methods that rely on signal integration. Consider a sample that contains 482 positive signals, each of which generates 100 fluorescent units. The result of an integrative method is a single number (48, 200 fluorescent units). Artifacts that generate a similar number of fluorescent units, for example, a large fluorescent dust particle may be indistinguishable. In contrast, the present invention can easily distinguish between a single large fluorescent dust particle and 482 positive signals.

Tests constructed using the invention can detect targets and viruses over a broad range of concentrations, from very low levels to high levels. This property of the invention, its large dynamic range, allows users to forgo the sample preparation steps (e.g., multiple dilutions) that are often required by technologies that have small dynamic ranges.

Tests based on the invention can exploit a variety of useful formats ranging from single-use strip tests that are simple, non-instrumented, and cost-effective, to sophisticated automated benchtop systems.

Various detection methods can be used by the invention including visual, film-based, and electronic detection. The range of detection methods is an advantage for addressing a broad spectrum of diagnostic problems and testing venues.

Other features and advantages of the present invention will be apparent from the following description and the claims.

By target is meant a cell or virus that is potentially present in a sample and whose presence is tested for by the invention.

By category of target is meant multiple targets that have in common one or more features and that are considered identical for the purposes of a test constructed using the invention. For example, for a test designed to detect all HIV viruses, the category would simply be HIV. Such a test would detect all HIV viruses, without differentiating the HIV-1 and HIV-2 variants. In this case, the category of the target includes both HIV-1 and HIV-2. The goal of another test might be to distinguish HIV-1 from HIV-2. In this case, each type of HIV would be considered a different category.

By non-overlapping categories of targets is meant categories of targets whose union is the null set the category of all *E. coli* bacteria, the category of all bacteria in the genus Pseudomonas, the category of all fungi, and the category of all HIV viruses are non-overlapping categories. That is, no member of any of the categories is a member of any of the other sets. In contrast, the category of HIV-1 viruses and the category of HIV viruses are overlapping categories of targets, since each member of the HIV-1 category is also a member of the category of all HIV viruses.

Tests that detect and identify multiple categories generally detect multiple non-overlapping categories of targets. For example, consider a test designed to identify HIV, HCV, and HBV viruses in blood. Such a test would differentiate three non-overlapping categories of targets, one for each of the three types of viruses. Note that each type of virus is in only one of the three categories (e.g., there is no HIV virus that is in the HCV category).

By the categorical complexity of a test is meant the number of non-overlapping categories of targets that are detected in the test.

By a category-specific binding site is meant a site on a target that specifically binds to a category-binding molecule under specific-binding conditions (see definitions of terms in italics) and that distinguishes targets that are members of a particular category to be identified in a test from targets that are not members of that category but might also be present in the test sample. That is, the site is present typically on all members of one category, and typically not on any members of non-overlapping categories. Category-specific binding sites specifically bind to category-specific binding molecules.

A category-specific binding site is always physically associated with the target. Consider an ELISA spot assay in which a single antibody secreting hybridoma cell is identified by detecting a large number of antibody proteins that bind fluorescent antigen and that are immobilized near the secreting cell of origin. In this case, the secreted antibody molecules, which contain binding sites for the antigen, are not physically associated with the hybridoma cell. Therefore the antigen binding sites on the free antibodies are not category-specific binding sites.

If a test scans a sample for a category of targets that constitutes a taxonomic group, a category-specific binding site is one that is present in essentially all members of that taxonomic group, but is not present in essentially all members of other taxonomic groups that might be present in the test sample. An example is a site on an HIV membrane protein that binds to a particular monoclonal antibody.

Alternatively, a test might scan a sample for category-specific binding sites that are shared by members of different taxonomic groups. Examples of this type of category-specific binding sites include various macromolecules (e.g., DNA) and genes, mRNAs, and proteins that confer antibiotic resistance, confer virulence, or indicate viability. A category-specific binding site is often a part of a larger molecule or complex. For example, a category-specific genomic sequence can be used as a category-specific binding site in a test. Such a category-specific binding site is part of a much larger genome that may contain: (1) sections that are not category-specific; (2) sections that are category-specific binding sites but for which the test does not scan; and (3) other sections that are distinct category-specific sequences for which the test does scan.

Binding sites that are present, e.g., in 80%, 90%, 95%, or more than 99% of the target that are members of a category but that are absent, e.g., in 80%, 90%, 95%, or more than 99% of the targets that are members of all other categories of the same class, are considered category-specific binding sites. Note that a category-specific binding site can be trivially or exceptionally absent from a target that is a member of the category. Similarly, a category-specific binding site can be trivially or exceptionally present in a target that is not a member of a category. For example, consider a protein site that occurs in essentially all *E. coli* bacteria but in no other bacterial species. If, as might be the case in less than one cell out of millions of bacteria, a mutation causes the protein not to be produced, the marker will not be present in that strain of *E. coli*. However, this protein site is still considered a category-specific binding site. Alternatively, the gene for the same protein is transferred to a strain of a different species of bacteria by recombinant DNA technology or by natural means (e.g., by viral transduction). In this case, a bacterial strain that is not a member of the category *E. coli* would express what would still be considered an *E. coli*-specific binding site.

By category-binding molecule is meant a molecule or molecular complex that specifically binds to a category-specific binding site. Examples of category-binding molecules are nucleic acid probes that hybridize to genomic DNA; nucleic acid aptamers that have been selected or "evolved" in vitro to bind specifically to sites on proteins; antibodies that bind to cellular antigens or serum proteins; and ligands such as epidermal growth factor or biotin that bind specifically to hormone receptors or to binding molecules, such as avidin. Two category-binding molecules are said to be distinct if they bind to distinct and non-overlapping category-specific binding sites. Category-binding molecules may be referred to according to their molecular composition, e.g., a category binding oligonucleotide, probe, antibody, ligand, etc.

By capture molecule is meant a category-binding molecule that is stably bound to a surface, membrane, or other matrix that is not a particle.

By a category-binding molecule that specifically binds to a category of targets is meant a category-binding molecule that binds under defined binding conditions to essentially all targets that are members of a category scanned for by a test, but to essentially no other species that are not members of the category but that are likely to be present in the sample. The number of category-binding molecules that are bound by targets in a category scanned for as compared to the number bound by targets not in such a category, are, e.g., two-fold, five-fold, ten-fold, or greater than fifty-fold greater.

By binding conditions is meant the conditions used in a test to achieve specific binding of category-binding molecules to category-specific binding sites. For example, when the category-binding molecules are category-specific DNA probes, the binding conditions for a particular test might be stringent DNA hybridization conditions. The appropriate stringent DNA hybridization conditions depend on the nature of the probes, as is well known by those familiar with the art. For example, for typical DNA probes of length greater than 500 bases, an appropriate binding condition (usually referred to as a "washing condition" in the hybridization vernacular) is 65° C. at 0.2×SSC. For binding an antibody to an antigen, typical binding conditions are room temperature in PBS-TB.

By a family of category-binding molecules is meant a set of category-binding molecules that specifically bind to a particular category of targets.

A polyclonal antibody preparation raised to Hepatitis C virus constitutes a family of category-binding molecules since it comprises multiple distinct antibodies that bind specifically to the same category of target—HCV, in this case. Polyclonal antibodies generally constitute families of category-binding molecules since they generally include multiple distinct category-binding molecules that bind to the same category of target. Note that, unless affinity purification is used, polyclonal antibody preparations typically also contain antibodies that do not bind to the chosen category of target and may contain antibodies that bind to other categories because the antibody repertoire of an animal is determined by the animal's infection history. Therefore, polyclonal antibodies are preferably purified by affinity methods.

Category-binding molecules in a family might bind to some targets in the category but not to others. For example, consider HIV-1-specific antibodies that do not cross-react with HIV-2, and HIV-2-specific antibodies that do not cross-react with HIV-1. If HIV is to be detected as a category in a test without differentiating between HIV-1 or HIV-2, a mixture of the two types of antibodies could be labeled with signaling moieties with the same signal signature. The same signal is obtained whether HIV-1 or HIV-2 is present when this family of category-binding molecules, which is a mixture of the two antibody preparations, is used in a test. (Note that if antibodies are used to capture the HIV targets at a site in the detection zone in this example, a mixture of anti-HIV-1 and anti-HIV-2 capture antibodies is used at the site).

Another example of a family of category-binding molecules is a set of 80 category-specific genomic DNA sequences that occur in all *E. coli* O157:H7 strains, but that do not occur in members of other groups of bacteria. This family of category-binding molecules can hybridize as a group to suitably prepared *E. coli* O157:H7 cells, but does not hybridize to other categories of cells. Families can include different types of category-binding molecules. For example, a monoclonal antibody that specifically binds to the O157 antigen and one that binds to the intimin protein (a virulence factor) could also be included in the above family of category-binding molecules. A family of category-binding molecules can comprise any number of category-binding molecules (i.e., one or more).

By non-overlapping families of category-binding molecules or is meant families of category-binding molecules in which each family binds specifically to one, and only one, category in a set of non-overlapping categories. That is, a set of non-overlapping families of category-binding molecules map to a congruent set of non-overlapping categories. For example, in a test that scans the 4 USP objectionable organisms *E. coli, Salmonella, Pseudomonas* spp., and *Staphylococcus aureus*) there are four non-overlapping categories. Such a test might incorporate four different non-cross-reacting polyclonal antibodies, each specific for one of the test categories. Thus, the test comprises four non-overlapping families of category-binding molecules. The non-overlapping families of category-binding molecules in a test are called an ensemble of category-binding molecules (see definition below).

By an ensemble of category-binding molecules is meant a set of one or more non-overlapping families of category-binding molecules that are combined in a mixture for a particular test. Tests that scan for multiple non-overlapping categories of targets comprise one family of category-binding molecules per category. The entire set of category-binding molecules, that comprise these families, is referred to as an ensemble. For example, consider a test that scans for the presence of five types of upper respiratory viruses (RSV, influenza A, influenza B, parainfluenza, and adenovirus) using five virus-specific monoclonal antibodies. The five monoclonal antibodies constitute five non-overlapping families of category-binding molecules. The combined set of antibodies is an ensemble of category-binding molecules.

By the category-binding molecule complexity of an ensemble is meant the number of distinct category-binding molecules or moieties in an ensemble. For example, if an ensemble of category-binding molecules consisted of 234 oligonucleotide probes, the category-binding molecule complexity of the ensemble would be 234.

By the family complexity of an ensemble is meant the number of non-overlapping families of category-binding molecules in an ensemble. The family complexity is the same as the minimum number of targets required to bind a category-binding molecule from each of the families in an ensemble. The family complexity of a test corresponds to the categorical complexity of a test—i.e., the number of distinct categories for which the sample is scanned. Consider an ensemble of DNA probes consisting of three families of probes. One family consists of a set of 12 *E. coli* category binding DNA sequences, another family consists of a set of 10 rotavirus category binding DNA sequences, and another family consists of a set of 15 Giardia category binding DNA sequences. The family complexity of this probe ensemble is three since the genomes of no fewer than three types of targets (*E. coli*, rotavirus, and Giardia) are required to bind to all of the probes in the ensemble.

By signal element is meant a molecule or particle that directly generates a detectable signal. The phrase "directly generates" refers to the fact that signal elements are the immediate source or critical modulator of the detectable signal. Thus, if the signal is photons that arise from a fluorophore, the fluorophore is the immediate source of the photons and, therefore, is a signal element. If the signal is photons scattered by an RLS particle, the RLS particle is a signal element. Alternatively, if the signal is the light transmitted or scattered from a chromogenic precipitated product of the enzyme horseradish peroxidase, the chromogenic product is the signal element.

A characteristic of a signal element is that such an element cannot be divided into parts such that each part generates a signal that is comparable (in character, not necessarily in intensity) to the whole. Thus, a 2 nM diameter quantum dot is a signal element, as dividing it changes the character (emission spectrum) of the resulting nanocrystals. A 5 μm particle impregnated with a fluorescent dye such as fluorescein, is not a signaling element, since it could be divided into parts such that each part has signaling characteristics comparable to the intact particle. The molecule fluorescein, in contrast, is a signaling element. The detectable products of signal generating enzymes (e.g., luciferase, alkaline phosphatase, horseradish peroxidase) are also considered signal elements. Such signal elements (or their precursors when there is a chemical conversion of a precursor to a signal element) may be diffusible substances, insoluble products, and/or unstable intermediates. For example, the enzyme alkaline phosphatase converts the chemiluminescent substrate CDP-Star (NEN; catalog number NEL-601) to an activated product, which is a photon-emitting signal element.

By signaling moiety is meant a molecule, particle, or substance comprising or producing (in the case of enzymes) one or more signal elements and that is or can be conjugated to a category-binding molecule. The signaling moiety can be attached to the category-binding molecule either covalently or non-covalently and either directly or indirectly (e.g., via one or more adaptor or "chemical linker" moieties or by both moieties being conjugated to the same particle). Examples of signaling moieties include carboxylated quantum dots; a fluorophore such as Texas Red that is modified for binding to a nucleic acid probe or an antibody probe; streptavidin-coated fluorescent polystyrene particles (which can be conjugated to biotinylated category-specific binding proteins); a rolling-circle replication product containing repeated nucleic acid sequences each of which can hybridized to several oligonucleotides tailed with fluorescently modified nucleotides and which contains a category-specific binding oligonucleotide at the 5' end. A signaling moiety can comprise physically distinct elements. For example, in some cases the signaling moiety is an enzyme (e.g., alkaline phosphatase) that is conjugated to a category-binding molecule (an antibody, for example). Signal is generated when a substrate of alkaline phosphatase (e.g., CDP-Star, or BM purple from NEN and Roche, respectively) is converted to products that are signal elements (e.g., an unstable intermediate that emits a photon, or a precipitable chromogenic product). It is not unusual for the category-binding molecules, enzymatic signaling moieties, and substrate to be applied to the reaction at distinct times.

By signaling moiety complex is meant a physical entity that comprises more than one signaling moiety and more than one category-binding molecule. The physical association of the signaling moieties and category-binding molecules in a signaling moiety complex must be stable (e.g., the signaling moieties and category-binding molecules should have mean half-lives of association with the complex of at least one day in PBS at 4° C.). As an example of a signaling moiety complex, consider a polystyrene microparticle that is coated with thousands of molecules of two types: a target-specific antibody and alkaline phosphatase. Such a signaling moiety complex binds to the target via the conjugated antibody category-binding molecule. When incubated with a chromogenic alkaline phosphatase substrate (the signal element; e.g., BM purple, Roche), a colored spot can be generated which can be detected by eye. Alternatively, the same signaling moiety complex, when incubated with either a chemiluminescent or a fluorescent alkaline phosphatase substrate, generates either a chemiluminescent or fluorescent signal. Further examples of signaling moiety complexes include: nanogold particles conjugated to fluorescein-labeled antibodies, and latex particles conjugated to both oligonucleotide category-binding molecules and acridinium esters that chemiluminescence upon addition of hydrogen peroxide.

By particle is meant an object or matrix which is less than 50 microns in size. The size of a population or batch of particles is defined as the mean measurement of the longest pair of orthogonal dimensions for a sample of the particles. The longest pair of orthogonal dimensions is the pair of orthogonal dimensions of a particle the sum of the lengths of which is the maximum for all such sums for the particle. If a sample of two particles has a longest pair of orthogonal dimensions of 1 micron×2 micron and 2 micron×3 micron, respectively, the mean measurement of the longest pair of orthogonal dimensions is 2 microns [(1+2+2+3)/4=2 microns]. The mean measurement of the longest pair of orthogonal dimensions for a sample of particles is, e.g., less than 50 microns, less than 20 microns, or less than 5 microns.

Many particles have some characteristics of a solid. However, molecular scaffolds or complexes, which may not be rigid, are also defined as particles. For example, dendrimers or other branching molecular structures are considered to be particles. Similarly, liposomes, are another type of particle. Particles can be dyed with or conjugated to signal elements. Particles are often referred to with terms that reflect their dimensions or geometries. For example, the terms nanosphere, nanoparticle, or nanobead are used to refer to particles that measures less than 1 micron along any given axis. Similarly, the terms microsphere, microparticle, or microbead are used to refer to particles that measure less than one millimeter along any given axis. Examples of particles include latex particles, polyacrylamide particles, magnetite microparticles, ferrofluids (magnetic nanoparticles), quantum dots, etc.

By labeling particle is meant a particle that can specifically bind to targets and generate a signal. Labeling particles are conjugated or stably associated with both signaling moieties and to category-binding molecules.

By target:labeling particle complex is meant a labeling particle to which one or more targets are specifically bound.

By target:label complex is meant a target that is specifically bound to one or more category-binding molecule and associated with one or more signaling moieties.

By labeling ratio is meant the ratio of targets to labeling particles during the contacting step. For example, if $1\times10^7$ labeling particles are contacted with a sample containing $1\times10^8$ targets the labeling ratio is 10.

By signal character of a signal element or signal moiety is meant the aspect or aspects of a signal generated by the signal element signaling moiety that is useful for distinguishing it from other signal elements or signaling moieties. For example, the signal character of a signaling moiety labeled with fluorescein and rhodamine is fluorescence. The character of a radio transponder is radio frequency. Examples of photonic signaling character are fluorescence, light scattering, phosphorescence, reflectance, absorbance, chemiluminescence, and bioluminescence. All but the latter two examples of photonic signaling character depend on external illumination (e.g., a white light source, a laser light source, or daylight). In contrast, chemiluminescence and bioluminescence are signaling characters that are independent of external light sources.

By the class of a signal element or signaling moiety is meant the distinct quality of the signal that is useful for distinguishing it from other signal elements or signaling moieties. For example, a liposome that is labeled with red dye is distinguished from differently colored liposomes. The color red is its class. For a micro-transmitter that broadcasts a particular radio-frequency signal, the quality of the radio-frequency signal that differentiates the micro-transmitter from other micro-transmitters constitutes the signal element class.

By signal signature is meant the distinctive signaling quality of the combination of signaling moieties that bind to a category of targets in a test. A target that is bound to four types of antibodies, one of which is conjugated to a fluorescein molecule, and three of which are conjugated with rhodamine molecules has a signal signature that is described by the combined weighted absorbance and emission spectra of fluorescein and rhodamine.

By signal complexity of a test or an ensemble of labeled category-binding molecules is meant the number of categories of targets that can be distinctly labeled in the test or by binding to the ensemble. Alternatively, the signal complexity is defined as the number of distinct signal signatures that would be expected to occur if a member of each category of target were present. For some tests, the signal complexity of an ensemble of category-binding molecules is the same as the number of categories for which the test scans. Other tests, which scan for many categories, may only have a signal complexity of one.

By selection force is meant a force that is used to capture, isolate, move, or sequester targets. Examples of selection forces include gravity, magnetism, electrical potential, centrifugal force, centripetal force, buoyant density, and pressure. Targets can be mobilized by a selection force acting on the target alone. Alternatively, selection forces can act specifically on targets that are associated with selection moieties (see definition below).

Examples of the application of selection forces to mobilize targets include centrifugation of targets; magnetic selection of targets bound to magnetic particles; gravitational sedimentation of targets labeled with metallic particles; and deposition of targets on a porous membrane by vacuum filtration. Further instances of the use of selection forces are included in the examples below.

By selection moiety is meant an atom, molecule, particle, or other entity that can be conjugated to a category-binding molecule and that confers on the category-binding molecule the ability to be selectively captured, isolated, moved, or sequestered by a selection force. When a category-binding molecule:selective moiety complex is specifically bound to a target, the target can also generally be selectively captured, isolated, moved, or sequestered by the selection force. Selective, in the sense used here, refers to the preferential conferring of susceptibility to mobilization by the selection force on selection moieties and associated entities over entities not associated with selection moieties.

Paramagnetic particles and ferritin are examples of selection moieties. A dense silica particle that sinks in solution is another type of selection moiety. Such particles, when coated with category-binding molecules and bound to a target will cause the target to sink in aqueous solution, thus enabling separation of the bound target from other sample unbound constituents.

By selective character is meant the aspect or aspects of a selection moiety that is useful for capturing, selecting, or moving the selection moiety. For example, the selective character of a paramagnetic particle is magnetism. The selective character of a silica particle that rapidly sinks in aqueous solution is mass.

By a roughly planar surface or substrate is meant a surface that can be aligned in parallel to an imaginary plane such that when the distance is measured from points in any 1 mm×1 mm square on the surface to the closest points on the imaginary plane, the absolute value of the mean distance is less than 50 micrometers.

By detection surface is meant the surface of a roughly planar substrate onto which targets are deposited. In embodiments using photonic signaling character, if the detection surface is optically clear, detection can be effected via either face of the detection surface. If the detection surface is opaque, detection is effected via the face of the detection surface on which the targets are deposited.

By detection area is meant the area of the detection surface or detection zone that is simultaneously analyzed by the invention. The detection area is typically greater than 1 mm, e.g., greater than 5 mm, greater than 10 mm, or greater than 15 mm in its longest linear dimension. For example, the section of a glass slide that is simultaneously imaged by an optical device that includes a collection lens and a CCD chip might measure 0.8 cm×0.5 cm. The detection area is then 0.4 cm$^2$.

By detection zone is meant the volume in which targets can be detected. The detection zone has the same dimensions as the detection area but has a depth corresponding to the depth in which signaling moieties can be detected and identified. The depth of the detection zone is therefore dependent on the threshold criteria used to score for positive signal. When optical detection is used, the depth of the detection zone is dependent on the optical depth of field.

By the longest dimension of the detection area is meant the line of maximum length that can be drawn between two points on the perimeter of the detection area. For example, if the detection area is a rectangle measuring 0.3 cm×0.4 cm, the longest dimension of the detection area is the diagonal, 0.5 cm. If the detection area is an ellipse with semi-major axis of length 7 mm and semi-minor axis of length 2.5 mm, the longest dimension of the detection area is 14 mm.

By large area detection or large area imaging is meant a method for detecting microscopic targets in which the detection area (the area that is simultaneously analyzed by the detection device) is much larger than the target. The detection area for large area detection has at least one linear dimension that is $\geq$1 mm. In contrast, the microscopic targets are substantially smaller, typically measuring less than 50 μm in at least two orthogonal dimensions. Examples of large area detection include imaging a 9 mm diameter detection area with a CCD camera; imaging a 2 cm×1 cm rectangle by scanning with a CCD line scanner that has a long dimension of 1 cm; imaging a 4 cm×4 cm filter containing microbial targets using direct exposure on photographic film; and visual detection of colored spots corresponding to microscopic targets on a 1 cm×3 cm test area in a rapid lateral flow strip test.

Several technologies scan samples for microscopic targets but do not exploit large area detection. Examples include: flow cytometry; solid phase laser microbeam scanning cytometry; liquid phase scanning (as in Tibbe, et al., Nat Biotechnol 17: 1210-3, 1999); and examining/imaging multiple high power microscopic fields on a slide.

By conjugated or stably associated is meant a physical association between two entities in which the mean half-life of association is least one day in PBS at 4° C. Consider, for example, the complex case of passive protein adsorption to polystyrene particles. There are several different classes of adsorbed proteins. Some proteins are stably associated to the surface with half-lives of many months. Other proteins, such as those that are loosely bound on the outer layer of adsorbed protein, may not be stably associated with the particles and can leach out within hours.

By image intensifier or image tube is meant a device that amplifies a photonic signal, as defined in the glossary of Inoué, Shinya, et al., *Video microscopy: the fundamentals* (Plenum Press, New York, 1997; p. 665): "A device coupled (by fiber optics or lenses) to a video camera tube to increase sensitivity. The intensifier is a vacuum tube with a photocathode on the front end that emits electrons according to the image focused upon it, an electron lens and/or microchannel plate(s) that focuses the electrons onto a phosphor at the back end, and a high voltage accelerator that increases the energy of the electrons. Can be single or multiple stage." A variety of such image intensifiers is described in detail in Chapter 8 of the same reference.

By simultaneously detecting targets in a section of the detection area is meant detection of the signal from a section of a roughly planar detection surface in one step. Large area imaging of targets in a detection area using a CCD chip, visual detection, or photodiode-based signal integration are examples of simultaneous detection.

By targets in the stationary phase is meant targets that are non-mobile. For example, targets fixed on glass slides are in the stationary phase. Targets that are captured by category-binding molecules in fixed positions on the bottom of the well of a microtiter dish are in the stationary phase. Even if such targets are not affixed to a surface, and might be moved by hydrodynamic or other forces, targets are considered to be in the stationary phase if, during detection/imaging, successive images taken with intervals of more than 10 seconds detect essentially the same targets in essentially the same relative positions. Targets in flow cytometry applications are not in the stationary phase. However, targets captured by antibodies bound to the solid-phase test zone of a lateral flow test are in the stationary phase.

By homogenous assay or homogenous immunoassay is meant an assay or immunoassay in which the reactants are not physically removed from the products of the completed assay.

By identification is meant determining the category or categories of which a target is a member. For example, consider a lateral flow test that scans for several categories of targets, each of which is potentially present in a sample. A target belonging to a particular category is captured at the region of the membrane to which the corresponding category-specific antibodies are bound. Since it is known which membrane zones contain which capture antibodies, targets are identified by the zone in which capture occurs.

By sample is meant material that is scanned by the invention for the presence of targets.

By direct visual detection is meant visual detection without the aid of instrumentation other than wearable corrective lenses. For example, direct visual detection can be used to detect the reddish reflective signal of nanogold particles in some rapid lateral flow tests.

By photoelectric detector is meant a man-made device or instrument that transduces photonic signals into electric signals. Examples of photoelectric detectors include CCD detectors, photomultiplier tube detectors, and photodiode detectors, e.g., avalanche photodiodes.

By encircled energy or ensquared energy is meant the percentage of photons from an infinitely small light source that are captured on a pixel of a photodector array.

By thermal radiation is meant black body radiation.

By cellular autofluorescence or autofluorescence is meant the fluorescence exhibited by cells due to the fluorescence of natural intrinsic cellular constituents, such as NADH and oxidized flavoproteins. Cells expressing fluorescence due to recombinant fluorescent proteins such as green fluorescent protein are not considered to be autofluorescent.

By illuminating is meant irradiating with electromagnetic radiation. Electromagnetic radiation of various wavelengths can be used to illuminate. It includes, for example, radiation with wavelengths in the X-ray, UV, visible, or infrared regions of the spectrum. Note that illuminating radiation is not necessarily in the visible range.

By signal elements or signaling moieties with photonic signaling character is meant signal elements or signaling moieties that are detectable through the emission, reflection, scattering, refraction, absorption, capture, or redirection of photons, or any other modulation or combination of photon behavior. Some examples of signal elements or signaling moieties that have photonic signaling character include: the fluorophore Texas Red (fluorescent signaling character); CDP-Star (chemiluminescent signaling character); luciferase (bioluminescent signaling character); resonance light scattering particles (light scattering signaling character); BM purple (light absorption or chromogenic signaling character); and up-converting phosphors (absorption of two long wavelength photons and emission of one shorter wavelength photon).

By 'number'×'solution name' is meant an aqueous solution comprising the constituents of the solution at number times the concentration of the solution (except for water). For example, 10×EE contains 10 mM EDTA/100 mM EPPS (EE, or 1×EE, contains 1 mM EDTA/10 mM EPPS).

EE is a solution that is 1 mM EDTA/10 mM EPPS. Before mixing them together, the conjugate acids of both components are brought to pH 8.0 with NaOH HYB is a solution used for hybridization containing: 1M NaCl, 50 mM EPPS pH 8.0, 2% blocking reagent (Boehringer Mannheim); 0.5% v/v Tween, 20 µg/ml yeast tRNA (Sigma).

UBB (universal binding buffer) is a solution useful for binding mixtures of various types of category-binding molecules (such as antibodies and nucleic acids) containing: 250 mM NaCl, 50 mM EPPS pH 8.0, 2% blocking reagent (Boehringer Mannheim); 0.5% v/v Tween, 20 µg/ml yeast tRNA (Sigma).

BB (blocking buffer) contains 100 mM EPPS pH 8.0/150 mM NaCl/2% blocking reagent (Boehringer Mannheim).

PB is 0.1M sodium phosphate buffer pH 7.4.

PBS is a phosphate-buffered saline solution containing: 120 mM NaCl, 2.7 mM KCl and 10 mM phosphate buffer (sodium salt) pH 7.4.

PBS-B is 0.1% BSA (IgG Free; Sigma Cat. No. A-7638) in PBS.

PBS-T is 0.05% Triton X-100 (Sigma Cat. No. X-100) in PBS

PBS-TB is PBS/0.1%BSA/0.05% Triton X-100

PBT is PBS/0.1% BSA (IgG Free; Sigma Cat. No. A-7638)/0.05% Tween-20 (Sigma Cat. No X-100)

LB is Luria Broth for growing bacteria and is made as described previously (Ausubel 1987, supra).

SSC is 150 mM NaCl/15 mM $Na_3$ citrate adjusted to pH 7.0 with HCl.

MES (2-[N-Morpholino]ethanesulfonic acid)

MESB is 0.05M MES (2-[N-Morpholino]ethanesulfonic acid), pH 6.1

EDAC (1-Ethyl-3-(3-dimethylaminopropyl) carbodiimide

Ligation buffer is 10 mM $MgCl_2$/50 mM Tris-HCl/10 mM dithiothreitol/1 mM ATP/25 µg/µl bovine serum albumin.

Prelysis solution: The solution is prepared according to Graves, L, et al. (1993). *Universal Bacterial DNA isolation procedure*. In Diagnostic molecular microbiology: principles and applications, D. Persing, T. Smith, F. Tenover and T. White, eds. (Washington, D.C.: American Society for Microbiology). The solution, which is freshly prepared and maintained on ice, contains: 0.25 ml of 2M Tris (pH 7.0), 3.1 ml of pancreatic lipase (prepared by dissolving 6.1 mg of pancreatic lipase (Sigma) in 59.8 ml of water and adding 1.2 ml of 0.1M $CaCl_2$; stored at −20° C. in 3.1 ml aliquots), 0.3 ml of 1% sodium taurocholate (Difco), 0.5 ml of 0.1M $CaCl_2$, 5.25 ml of sucrose, and 0.05 g of lysozyme.

Standard PCR protocol: All PCR reactions (unless otherwise noted) are carried out in 50 mM KCl, 1.5 mM $MgCl_2$, 10 mM Tris HCl pH 8.3, 250 µM (each) dNTP, and 10 µM (each) primer, in a Perkin-Elmer Geneamp 9700 thermocycler, for 30 cycles followed by incubation for 10 min at 72° C. A cycle is composed of three steps: 94° C., 30 sec; 550, 30 sec; 72° C. 90 sec.

AP: Alkaline phosphatase
BAL: Bronchioalveolar lavage
BSA: Bovine Serum Albumin
CCD: Charged coupled device
CFTR: Cystic fibrosis transmembrane conductance regulator
cfu: Colony forming unit (a measure of bacterial concentration that corresponds to the number of viable bacterial cells)
CMV: Cytomegalovirus
FITC: Fluorescein isothiocyanate
HBV: Hepatitis B virus
HCV: Hepatitis C virus
HIV: Human Immunodeficiency virus
pfu: Plaque forming unit (a measure of virus concentration that corresponds to the number of infectious virus particles)
PNA: Peptide nucleic acid
RSV: Respiratory syncytial virus
$TCID_{50}$: Tissue culture infectious dose at which 50% of flasks demonstrate infection Oligonucleotide sequences are presented in the 5' to 3' orientation when written as text, unless otherwise noted.

Unless otherwise noted, microbiological strains described in the specifications are obtained from the American Type Culture Collection (ATCC), Manassas, Va.

The figure shows the principle of imaging individual targets using a CCD array detector.

Figure 1:
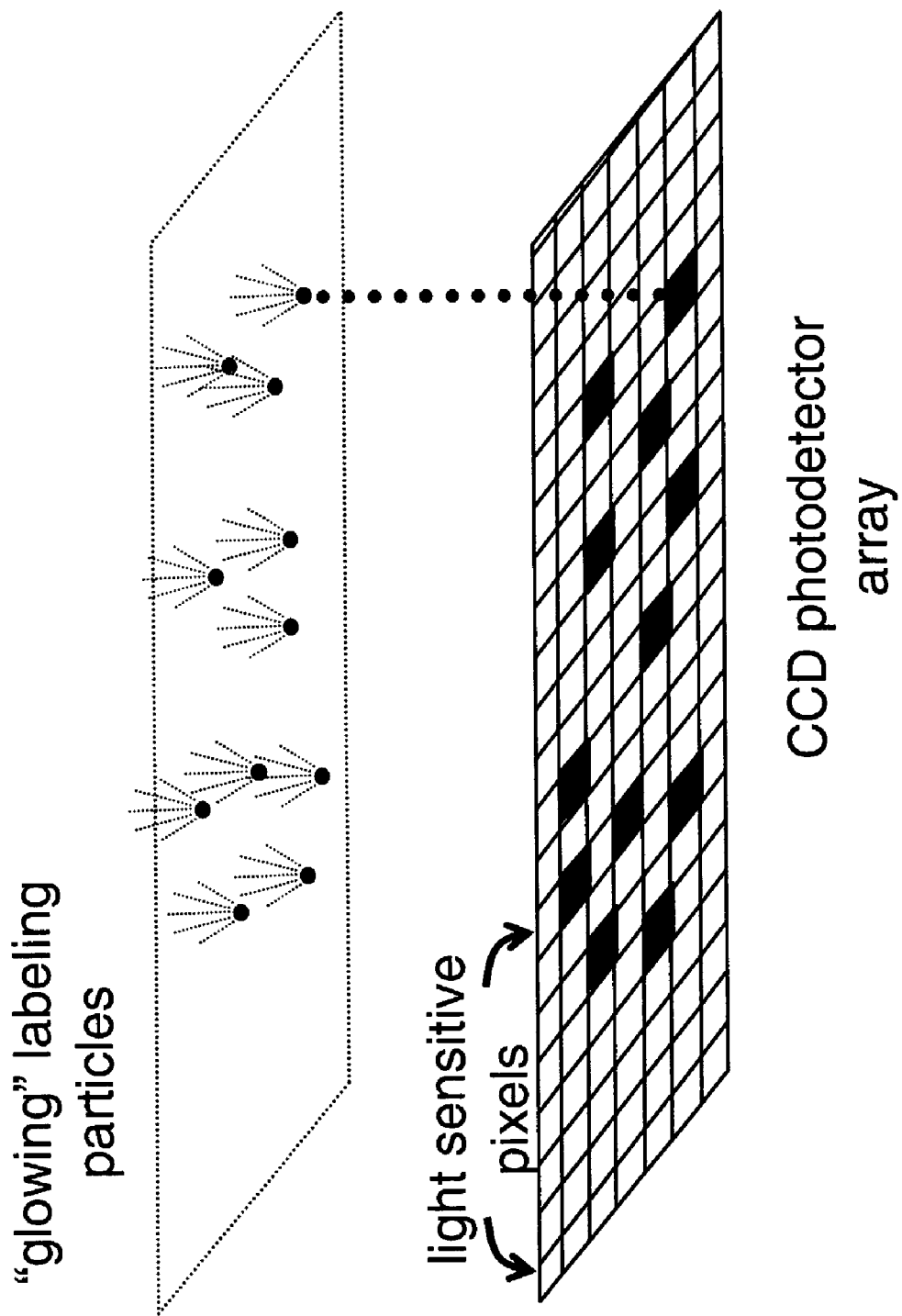
FIG. 1. The principle of non-magnified large-area imaging of individual signal generating particles with a CCD array.
Figure 2:
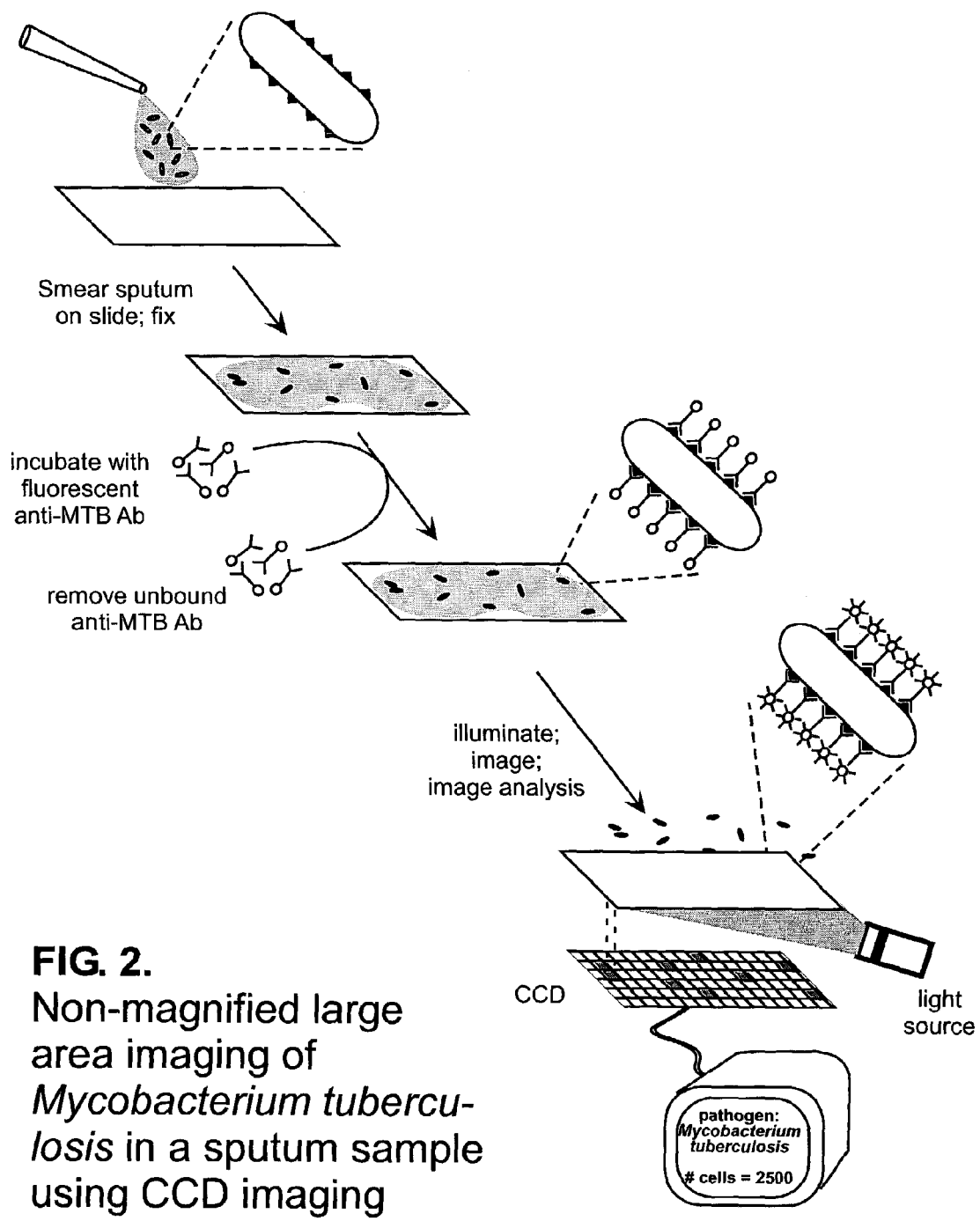

FIG. 2. Detecting *M. tuberculosis* using non-magnified large area imaging.

The figure shows a test based on the invention that scans a sputum sample for the presence of *M. tuberculosis*, the bacterial pathogen that causes tuberculosis. After heat-fixing a sputum sample to a microscope slide, the sample is incubated with labeled antibodies that specifically bind to *M. tuberculosis* (anti-MTB Ab). The unbound antibodies are removed leaving only the antibodies that are bound to *M. tuberculosis* bacteria. The antibodies are labeled with a fluorophore, so that when illuminated with one color of light (the excitation spectrum), they emit a second color (the emission spectrum). Illuminating the slide with the excitation spectrum causes the antibodies, which are localized at the sites where bacteria are fixed to the slide, to emit light in the emission spectrum. The emitted light is focused onto the array of pixels on a CCD chip. Pixels lying beneath a fluorescent bacterium are illuminated and transmit an electronic signal to a computer where it is preserved as an image. Software analyzes the image and the user interface reports the number of bacteria found in the scan.

Figure 3:
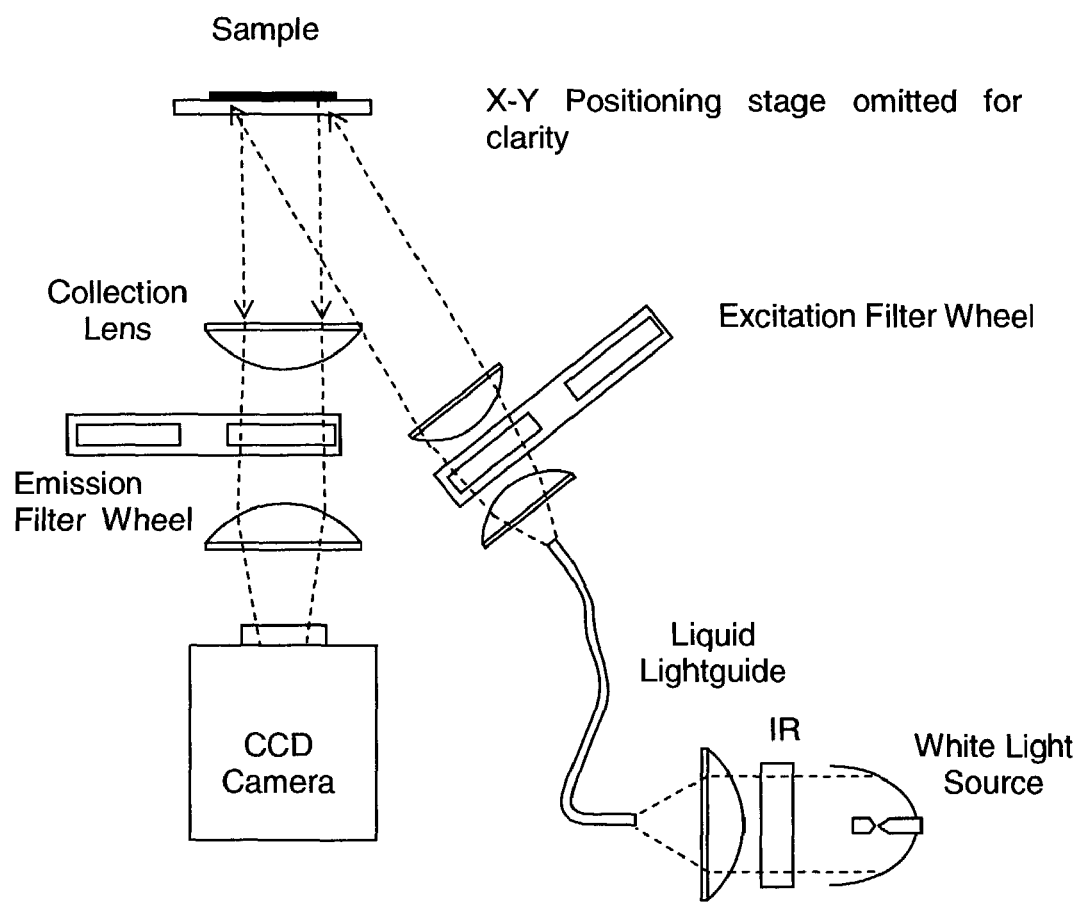

FIG. 3. A CCD imaging device for large area imaging.

The CCD-based imager depicted in the figure was used to collect much of the data described in the examples (see also Step 6 of Detailed Description section). Excitation light is provided by introducing light from a high intensity white light source (1000 Watt Xenon arc lamp, Model A-6000, Photon Technology Incorporated, Monmouth Junction, N.J.) into a liquid light-guide (5 mm core diameter, Model 380, Photon Technology Incorporated, Monmouth Junction, N.J.). The liquid light-guide carries the light to an excitation filter-wheel (BioPoint FW, Ludl Electronics, Hawthorne, N.Y.) and directs the filtered beam (typically 9 mm in diameter) onto the detection surface containing the labeled targets. The apparatus can detect labeled targets on various detection surfaces (e.g., porous membranes, microscope slides, microtiter dishes, coverslips, and tubes with flat, optically clear, bottoms). The incident light strikes the detection surface inducing fluorescence in the signaling moieties that are bound to targets via category-binding molecules and that are deposited on the optically clear surface. A portion of the emitted fluorescent light is collected by a high-collection efficiency lens system and transmitted through an emission filter-wheel (BioPoint FW, Ludl Electronics) to a CCD Camera (Orca II, Hamamatsu, Bridgewater, N.J.).

Figure 4:
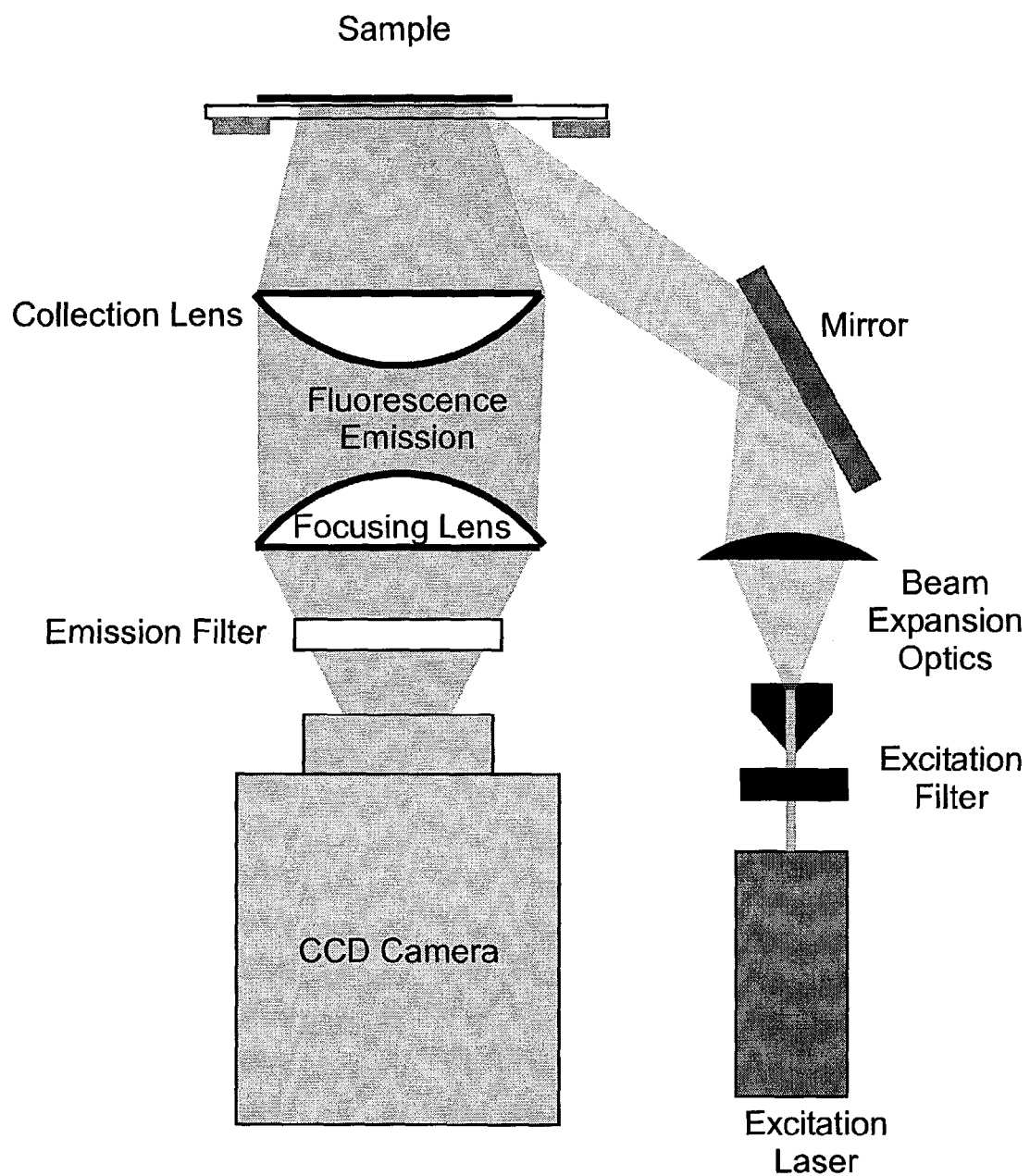

FIG. 4. A CCD imaging system for non-magnified large area imaging.

The figure shows a CCD imager with an angular illumination configuration in which light is introduced onto the detection surface (shown here as the bottom of a well of a microtiter plate) at an angle from the side of the collection optics. The angle is chosen to optimize collection efficiency and to avoid obstruction of the incident beam by the collection lens. The advantage of this configuration is that reflections from the bottom surface of the sample holder are not collected by the collection lens and therefore do not contribute to the fluorescence background noise.

Figure 5:
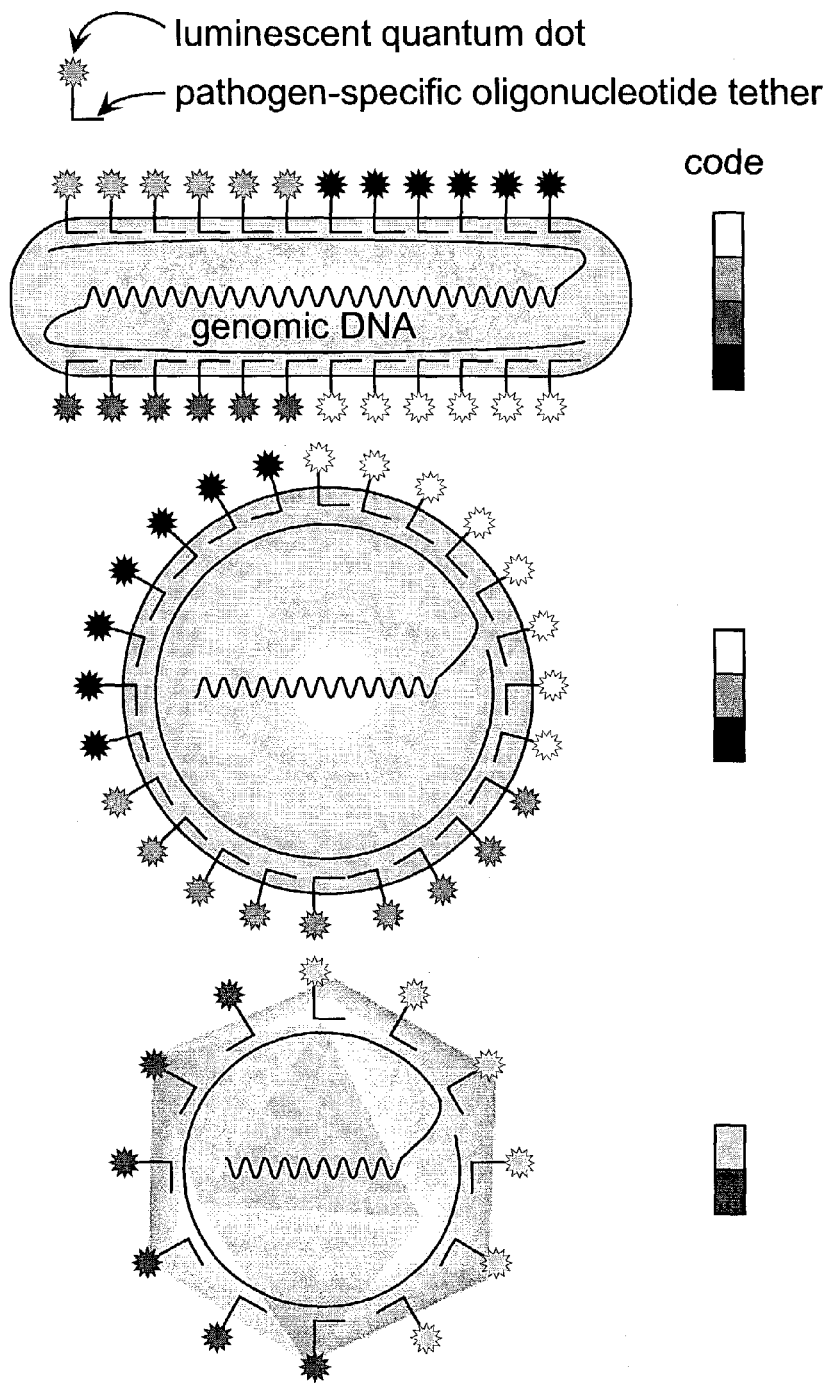

FIG. 5. Detecting different pathogens using combinatorial labeling.

Combinatorial labeling using multiple signaling moieties (labels) can be used to achieve high signal complexity (i.e., a large number of distinct signal signatures; see also discussion in Step 2 in the Detailed Description section). Each of the three pathogens represented in the diagram are labeled with a distinct combination of quantum dots. Thus, each pathogen emits the distinct coded signal (shown as a colored bar code to the right of the pathogen). The category-binding molecules shown are pathogen-specific oligonucleotide probes that hybridize to genomic DNA. Each probe is conjugated to a fluorescent quantum dot. Many types of category-binding molecules (e.g., antibodies, ligands, PNA probes, etc.) can be used for combinatorial labeling as can other types of signaling moieties (e.g., fluorophores, fluorescent particles, RLS light-scattering particles, etc.).

FIG. 6. Using tag complements to conjugate signal moieties.

The illustration depicts a method for indirectly labeling a category-specific oligonucleotide category-binding molecule. A bipartite oligonucleotide is synthesized comprising a category-specific binding moiety and a tag sequence moiety. A signaling moiety is conjugated to a second oligonucleotide, called a tag complement, which is complementary to the tag sequence. Using this system for indirect labeling, families of category-specific oligonucleotides with tags can easily be synthesized encoded with a combination of signaling moieties.

FIG. 7. Large area imaging of individual bacteria labeled with a fluorescent DNA-binding stain The figure shows detection of individual fluorescently stained bacterial cells on a porous membrane support. Cells were stained with the nucleic acid stain Syber Green I, and filtered through a black polycarbonate membrane. The fluorescent signal was imaged with the CCD based non-magnifying large area imager, with an FITC optical filter set. The left panel shows the fluorescent image from about 100 *E. coli* cells. The number of spots correlates with the number of cells added to the membrane. The right panel shows a negative control where no cells were added to the membrane FIG. 8. Large area imaging of individual bacterial cells labeled with various category-binding molecules and signaling moieties.

The figure shows the results of experiments in which *E. coli* cells on glass coverslips were labeled with four types of signaling moieties (Syber Green I, Example 2); fluorophore-labeled oligonucleotide probes, Example 3; fluorophore-labeled PNA probes, Example 4; fluorophore-labeled antibodies, Example 5). Individual cells were detected by non-magnified large area imaging using the apparatus shown in FIG. 3. Dilutions of the labeled cells were spotted onto coverslips coated with poly-l-lysine. After imaging the labeled cells using the CCD imager, the imaged objects were confirmed to comprise single cells or occasional groups of several cells by fluorescence microscopy. The upper panels of images show labeled cells as detected by CCD imaging. Bright spots correspond to labeled cells. The lower panels show the same labeled cells as viewed in a fluorescent microscope (1000× magnification).

FIG. 9. Detecting individual viable bacterial cells using non-magnified large area imaging The figure shows that the invention can detect live bacteria using a fluorogenic viability stain. Live *E. coli* cells (left panel) were detected as bright fluorescent spots, while dead *E. coli* cells (right panel) do not have a detectable fluorescent signal. Approximately 400 live *E. coli* cells are present in the imaged area of the left panel, and approximately 400 dead *E. coli* are in the right panel.

FIG. 10. Large area non-magnified imaging of individual bacteria labeled with highly fluorescent particles The figure shows the results of an experiment (Example 7) in which pathogenic *E. coli* cells were bound to the optically clear surface of a microtiter dish well, labeled with fluorescent particles, and imaged using non-magnified large area imaging. *E. coli* O157 cells (stained with Syber Green I) were fixed to the bottom of a 96-well plate using heat, and labeled by binding to fluorescent particles coated with anti-*E. coli* O157 antibodies. The left panel shows the cell:particle complexes as seen in the CCD imager. The middle panel shows the same sample as seen by low power fluorescence microscopy (50× magnification). The stained *E. coli* O157 cells are surrounded by numerous fluorescent particles as shown by high power fluorescence microscopy (right panels; 1000× magnification).

Figure 11:
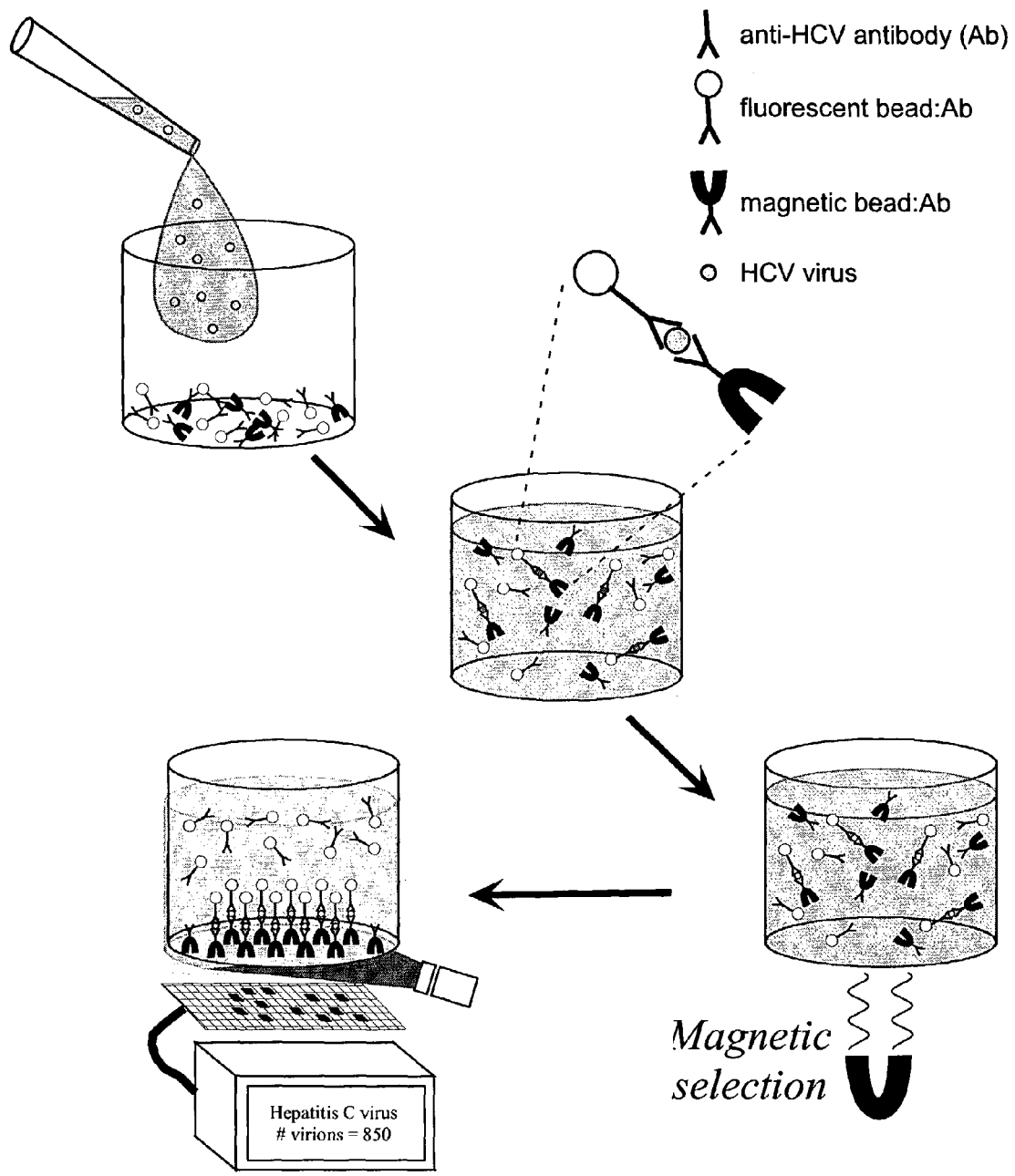

FIG. 11. Homogenous immunoassay for a virus (HCV) using liquid-phase magnetic selection of fluorescent particle: virus:magnetic particle complexes followed by non-magnified large area imaging.

The figure diagrams a useful method for scanning for microscopic targets—in this case Hepatitis C virus (HCV)—in a liquid-phase sample. Magnetic and fluorescent particles, coated with antibodies that bind specifically to the virus, are mixed in a well of a microtiter dish with a sample that potentially contains the virus. Viruses in the sample then bind to the particles. Some of the viruses bind to a magnetic particle and to a fluorescent particle as represented in the magnified projection in the figure. This magnetic particle:virus:fluorescent particle complex has the properties of being selectable by magnetic force and of being highly fluorescent. The microtiter dish is placed on a magnet so that the magnetic particles, and HCV viruses and fluorescent particles associated with the magnetic particles, are drawn down to the optically clear bottom surface of the well. Using a CCD imaging apparatus (like the one shown in FIG. 3), the bottom of the well is imaged. The virus complexes appear as bright spots in the image due to the highly fluorescent particles that are bound to the viruses. Software analysis of the image quantifies the number of complexes on the detection surface and integrates the total intensity of signal derived from the labeled complexes (see Example 8 and FIG. 12 for representative results of the homogenous immunoassay method).

FIG. 12. An homogenous immunoassay that detects individual bacteria using non-magnified large area imaging.

The figure shows the results of immunoassays that sensitively detect *E. coli* by non-magnified large area imaging described in Example 8. Magnetic and fluorescent particles coated with category-specific antibodies were first bound to the bacterial cells, the complexes were then drawn to the bottom surface of the optically clear well (the detection area) using magnetic force, and the complexes were detected using non-magnified large area CCD-based imaging. The figure shows the comparison of the results of the homogenous immunoassay in blood (bottom panel) and the non-homogenous (washed) immunoassay in both blood (top panel) and in buffer (middle panel). The simplest format, the homogenous immunoassay, effectively detected cells with excellent signal to background ratios (see quantification of the homogenous assay in the bottom right panels of the figure).

The two leftmost panels show the images obtained using non-magnified, large-area CCD-based imaging. All three assays gave strong signals when *E. coli* were present (left panel) but low background signals when *E. coli* were not added. Further confirmation that the signals obtained using the CCD camera corresponded to *E. coli* cells coated with particles were obtained using high power fluorescence microscopic analysis (1000×; top two rows, rightmost two columns). Images are shown of typical complexes containing *E. coli* cells, magnetic particles, and fluorescent particles. Two images of each complex were made using two filter sets: one for visualizing DNA fluorescence (Syber Green I; second panel from right) and one for visualizing the fluorescent particles (rightmost panel). The figure shows that the complexes consist of an *E. coli* cell surrounded by magnetic and fluorescent particles.

Quantitative analysis of the images was carried out by software that counts the number of fluorescent objects (FIG. 12, bottom panel, left bar graph) and that integrates the intensity of all of the objects (FIG. 12, bottom panel, right bar graph). The data shown represent the analysis of six samples: three samples that contained 1000 *E. coli* cells, and three samples containing no cells. In both measurements, the sample containing *E. coli* (1000 cells) scores significantly higher than the sample containing no *E. coli*. The height of the bars indicates the average values for the three samples. Error bars indicate three standard deviations around the mean values of the three samples.

For further details and discussion refer to Example 8.

FIG. 13. Large Area Imaging of Acid Fast Stained Mycobacteria in "simulated sputum"

The figure shows the results of the test described in Example 9 in which a strain of mycobacteria that is closely related to the pathogen that causes tuberculosis was detected using the acid-fast bacillus (AFB) staining method combined with non-magnified large area imaging. Commercial slides containing either mycobacteria cells (*Mycobacteria scrofulaceum*; left panel: 1A, 2A) or *E. coli* (right panel: 1B, 2B) in "simulated sputum" were stained with auramine-rhodamine and visualized using non-magnified, large-area, CCD-based imaging (top panel: 1A, 1B). Numerous objects were detected in the sample containing mycobacteria cells compared to a much lower number of background spots in the sample containing *E. coli*. Fluorescence microscopic analysis (400×; bottom panel: 2A, 2B) confirmed that the signals captured with the CCD camera without magnification correspond to single mycobacteria cells.

FIG. 14. Rapid antimicrobial susceptibility testing using large area imaging.

The figure shows the results of an experiment designed to determine the minimal inhibitory concentration (MIC) of an antibiotic on the growth of *E. coli* by using non-magnified large area imaging (Example 10). Duplicate aliquots of the cells at various time points were cultured on LB agar and deposited on the optically clear surface of a 96 well microtiter dish well for imaging using a CCD imager (FIG. 3). Growth (displayed qualitatively in the figure with +/− symbols) was measured by colony counts on LB agar plates (not shown in figure) and by object and intensity measurements of the images captured by the CCD camera. The 18 hr culture time point corresponds to the NCCLS standard protocol. Also shown are four hour culture results and four hour CCD imaging results. Comparison of the antibiotic concentration dependence of the growth of the resistant and sensitive strains, as detected by culture and CCD imaging, shows that the two approaches are comparable.

FIG. 15. Large area detection of individual fluorescently labeled *Candida albicans* cells that have been magnetically selected.

The figure shows the results of the experiment described in Example 11. *C. albicans* cells were pre-labeled with a nucleic acid stain (YOYO-1) and a rabbit anti-Candida polyclonal antibody. Labeled cells were added to magnetic particles coated with goat anti-rabbit IgG antibodies in the wells of a glass-bottomed microtiter tray. Cells were caused to align evenly over the bottom of the well by application of a magnetic field. The cells were detected by imaging the entire bottom surface of the well using the CCD imager and appropriate excitation and emission filters for the YOYO-1 fluorescent dye (FITC set, 480/40 nm excitation, 535/50 nm emission).

Non-magnified large area CCD image of a microtiter tray well containing *C. albicans* cells stained with YOYO-1 as described. Fluorescent signals (white spots in figure) were shown to correspond to single or small groups of *C. albicans* cells by examining the microtiter well in a fluorescent microscope under high power magnification (1000×).

Non-magnified large area CCD image of a microtiter tray well with no *C. albicans* cells added (Negative control).

FIG. 16. Large area detection of individual *Candida albicans* cells specifically bound to fluorescent and paramagnetic polystyrene particles.

The figure shows the results of the experiment described in Example 12. Cells were added to a mixture of magnetic and red fluorescent particles coated with anti-Candida antibodies in a microtiter dish. Cells bound to magnets were separated from unbound particles by application of a magnetic field and fluidic washing. The cell-fluorescent particle complexes were detected by imaging the entire bottom surface of the well using the CCD imager (A and B) or fluorescent microscopy (C-E) and appropriate excitation and emission filters for the fluorescent particles.

A. Non-magnified large area CCD image of microtiter well containing *C. albicans* cells labeled with multiple red fluorescent particles.
B. Non-magnified large area CCD image of microtiter well with no *C. albicans* cells added (negative control).
C. Magnified fluorescent microscopic image (100× magnification) of an area of the same well imaged in A. Single or small clumps of *C. albicans* cells (green stain) are surrounded by multiple red fluorescent particles.
D. Magnified fluorescent microscopic image (100× magnification) of an area of the same well imaged in B (negative control with no cells added).
E. and F. High power magnification (1000×) fluorescent microscopic image of an area of the same sample that is shown in A. *C. albicans* cells (approximately 5 μm diameter, green stain) are surrounded by multiple 1 μm diameter red fluorescent particles. Magnetic particles are not visible.

FIG. 17. Large area detection of individual *Candida albicans* specifically bound to fluorescent antibodies and magnetic particles.

The figure shows the results of the experiment described in Example 13. *C. albicans* cells were mixed with magnetic particles coated with anti-*C. albicans* or anti-*E. coli* antibodies in wells of a glass-bottomed microtiter tray. After 30 minutes, a fluorophore-labeled anti-*C. albicans* or anti-*E. coli* antibody was added. Magnetic complexes were washed and then caused to align evenly over the bottom of the well by application of a magnetic field. Cells were detected by imaging the entire bottom surface of the well using the CCD imager of the present invention and appropriate excitation and emission filters for the fluorophore.

A. Non-magnified large area CCD image of reaction well containing *Candida albicans* cells labeled with fluorescent anti-*C. albicans* antibody.
B. Non-magnified large area CCD image of reaction well with no cells added (Negative control).
C. Non-magnified large area CCD image of reaction well containing *E. coli* cells labeled with fluorescent anti-*E. coli* antibody.
D. Non-magnified large area CCD image of reaction well with no cells added (Negative control).
Note: Punctate fluorescent signals were shown to correspond to single or small groups of cells by staining with a red fluorescent nucleic acid-binding dye (YOYO-3) and examining the microtiter well in a fluorescent microscope under high power magnification (1200×)

FIG. 18. Non-magnified large area detection of individual chemiluminescent yeast cells using a CCD camera.

The figure shows the results of the experiment described in Example 14. *C. albicans* cells were labeled with FITC-conjugated anti-*C. albicans* antibodies, which were, in turn, bound to anti-fluorescein antibody:alkaline phosphatase conjugates. Dilutions of the labeled cells were spotted onto slides coated with nylon membrane, and the chemiluminescent substrate CDP-Star was added. The cells were imaged without magnification in the CCD Imager. Positions of single cells were confirmed by fluorescence microscopy.

From left to right, panels represent approximately 200, 60, and 20 individual *C. albicans* cells. Many individual cells are imaged in the middle and right panels. Larger brighter spots represent two or more cells that are close together.

FIG. 19. Non-magnified large area detection of individual chemiluminescent yeast cells using direct exposure of instant film.

The figure shows the results of the experiment described in Example 15. *C. albicans* cells were labeled with FITC-conjugated anti-*C. albicans* antibodies, which were, in turn, bound to anti-fluorescein antibody:alkaline phosphatase conjugates. Dilutions of the labeled cells were spotted onto a nylon membrane and the chemiluminescent substrate CDP-Star was added. The nylon membrane was loaded into a Spot Light camera (Boston Probes) and imaged with ASA2000 Polaroid Film.

From left to right, panels represent approximately 200, 60, and 20 individual *C. albicans* cells, as in FIG. 15. Given the number of cells spotted in each panel, it can be concluded that many of the spots represent individual cells, especially in the right most panel.

FIG. 20. Detection of organisms involved in lower respiratory tract infections using non-magnified large area imaging The figure shows the results of an image captured using non-magnified large area imaging that sensitively detects the signal generated from fluorescently labeled lower respiratory tract organisms described in Example 16. The figure shows the signal generated using non-magnified large area imaging (two left most panels) from various lower respiratory tract pathogens from top to bottom: *Chlamydia pneumoniae*, *Mycoplasma pneumonia* and *Legionella pneumophila*. The two right most panels show the images obtained using fluorescent microscopy.

FIG. 21. A multiplexed direct fluorescence immunoassay that simultaneously scans a sample for 3 disparate microbes using non-magnified large area imaging The figure shows the results of the experiment described in Example 17. Three samples, containing three different microbes (*E. coli*, *C. albicans*, and *S. pyogenes*) were fixed to a glass coverslip and allowed to incubate with an ensemble of category-specific (in this case, species-specific) antibodies. Each family of antibodies in the ensemble was conjugated to a different fluorophore (*E. coli*=green, *C. albicans*=blue, *S. pyogenes*=red). After washing away the unbound antibodies, images of the samples were captured using three different filter sets (green, blue, and red channels). For all three samples, the strongest signal was obtained in the channel that corresponds to the labeled antibody that binds to the microbe in the sample.

FIG. 22. Solid phase capture assay for Adenovirus

The figure shows the results of a test that scans a sample for adenovirus using antibodies bound to the solid-phase to capture the virus (Example 18). The wells of a microtiter plate were coated with anti-adenovirus antibodies. Fixed adenovirus samples or fixed RSV samples were added to the wells along with anti-adenovirus coated fluorescent particles. After incubation for an hour, all unbound particles were washed away and the remaining bound particles were visualized without magnification in the CCD Imager.

The negative control (RSV panel) shows very few particles remain in the well. In the adenovirus panel, thousands of fluorescent particles have been captured in the well due to the interactions of the anti-adenovirus coated wells, the adenovirus, and the anti-adenovirus coated particles.

FIG. 23. Solid phase capture of a virus in blood

The figure shows the results of a test that was used to scan a blood sample for the adenovirus using antibodies bound to the solid-phase to capture the virus (Example 19). The wells of a microtiter plate were coated with anti-adenovirus antibodies. Fixed adenovirus samples or fixed RSV samples were added to the wells in 50% mouse blood. After an hour incubation all unbound particles were washed away and anti-adenovirus coated fluorescent particles were added to the wells. After washing, the bound particles were visualized without magnification in the CCD Imager.

The negative control (RSV panel) shows very few particles remain in the well. In the adenovirus panel, thousands of fluorescent particles have been captured in the well due to the interactions of the anti-adenovirus coated wells, the adenovirus, and the anti-adenovirus coated particles. The presence of blood during the adenovirus capture phase did not interfere with the assay.

FIG. 24. Liquid phase assay for Adenovirus

The figure shows the results of a test that uses a "dual particle" test format to detect adenovirus (Example 20 see also diagram in FIG. 11). Fixed adenovirus or fixed RSV were mixed with anti-adenovirus coated magnetic and fluorescent particles. After incubating four hours, the magnetic particles and any bound particles were separated from the other materials, transferred to a microtiter plate, and visualized without magnification in the CCD Imager.

The adenovirus panel shows thousands of anti-adenovirus coated fluorescent particles captured by the magnetic particles due to their interaction with adenovirus. Very few fluorescent particles have been captured in the RSV panel.

FIG. 25. Multiplex large area imaging immunoassay that simultaneously scans for a bacterium and a virus The figure shows the results of an experiment using a test that simultaneously scans a sample for the presence of *E. coli* and adenovirus (Example 22). Anti-adenovirus coated red fluorescent particles and magnetic particles and anti-*E. coli* coated green fluorescent particles and magnetic particles were mixed in the presence of fixed adenovirus, fixed *E. coli*, both or neither. After an hour of incubation, the magnetic particles and any bound particles were separated from the other materials, transferred to a microtiter plate, and visualized without magnification in the CCD Imager.

Top row: Only adenovirus was added to the particle mixture. Most of the signal can be seen with the Texas Red filter set, which visualizes the red fluorescent anti-adenovirus particles.

Second row: Only *E. coli* was added to the particle mixture. Most of the signal can be seen with the FITC filter set, which visualizes the green fluorescent anti-*E. coli* particles.

Third row: Both adenovirus and *E. coli* were added to the mixture. Signal can be seen with both the Texas Red and FITC filter sets.

FIG. 26. Filter flow-through assay for detecting single bacteria using non-magnified large area imaging.

The figure shows the results of a rapid "flow-through" assay that detects single dispersed bacteria in a liquid sample (Example 23). Two nitrocellulose membranes were soaked in anti-*E. coli* O157 antibodies and allowed to dry. One filter was used to collect *E. coli* cells that had been pre-incubated with fluorescent *E. coli*-specific particles ("*E. coli*"; these particles had been coated with *E. coli* O157:H7-specific antibodies. A sample that contained the *E. coli*-specific particles but no *E. coli* cells was passed over the other filter ("No *E coli*"). Unbound particles were removed by washing the filters. A CCD imaging device was used to detect the fluorescent signal (top panels) using non-magnified large area imaging. Confirmatory microscopic images of the two filters are shown in the middle (50× magnification) and bottom (100× magnification) panels.

FIG. 27. Quantification of bacteria using large area imaging of cells stained with a fluorogenic esterase substrate Objective: In many applications it is useful to have a large dynamic range for quantifying live bacterial cells. An ideal system would be able to accurately count from zero or one bacterial cell up to millions or tens of millions, thus eliminating the serial dilutions and their inherent lack of precision that are necessary for traditional microbiological plating methods. In this example we show how staining live cells with fluorogenic substrates, coupled with CCD-based, non-magnified large area imaging can be used to quantify cells over at least 5 orders of magnitude.

Experimental Methods: *E. coli* ATCC 8739 cells were grown and processed as described in Example Y (Cell Direct example). Serial 10-fold dilutions of the cells were made in PBS and filtered in duplicate samples through black polyester membranes (Chemunex cat. #200-C2010-01) mounted on absorbent pads (Chemunex cat. #200-C3012-02) in a Millipore 1225 manifold and stained as described in Example Y (Cell Direct Example). In addition, 10µλ of the 10-5 dilution was plated in triplicate on TSA (BD catalogue no. 236950) and grown at 37° C. overnight to get a cell titer. The fluorescent signals on the polyester membranes were captured using a CCD Imager (described in step 6 above; FIG. 3) with an FITC optical filter set (Chroma/excitation 470/40 nm, emission 522/40 nm). Image-Pro Plus software, version 4.1 (Media cybernetics) was used to capture and process images from the CCD Imager. The signal generated from each filter was defined as the sum of the pixel intensities of all objects (where objects are defined in this particular example as containing pixel intensities from 350-65301). This method of defining signal eliminates the background from regions of the filter that do not contain any stained cells, but does not mask or undercount intensities from overlapping objects. (Since the cells are small and fairly transparent, signals are additive as long as the layer of cells is thin.)

Results: As shown in FIG. 28, the signal generated from this method is linear over at least 5 orders of magnitude, which is considered a large dynamic range for this test.

Variations. At low object numbers, accurate quantification can be achieved by counting individual objects rather than using the sum of their pixel intensities, since the objects will be unlikely to overlap. This can extend accurate counting down to one or zero cells, especially if multiple stains and multiple excitation and/or emission wavelengths are used to determine which objects represent viable cells. In addition, more sophisticated object finding algorithms can be employed to take into account local background intensities and variations in illumination.

Detecting Individual Stained Bacteria on a Filter Using Non-Magnified Large Area Imaging.

The figure shows that non-magnified large area imaging using a CCD camera detects individual bacterial cells that have been deposited on a membrane (Example 24). *E. coli* cells stained with Syber Green I were filtered through a black polycarbonate filter. The filter was then imaged using a CCD imager (top panel). The bottom panels show fluorescent microscopic confirmation that the luminescent objects in the CCD images are indeed Syber green stained *E. coli* (100×).

FIG. 28. The dynamic range of a test based on the invention

The figure shows the large dynamic range possible when using the invention. *E. coli* cells were diluted from a few million cells to a few hundred, filtered, and stained with fluorogenic esterase substrates. The fluorescent images generated by CCD-based non-magnified large area imaging were analyzed and their signals plotted vs. cell count. The signal is linear over at least 5 orders of magnitude.

FIG. 29. Non-instrumented detection of small numbers of bacterial cells without magnification The figure demonstrates use of a dually coated (alkaline phosphatase/anti-*E. coli* antibody) particle in a liquid capture assay that detects single *E. coli* cells (described in Example 26). The images in each of the three columns of panels were obtained using a different detection method. The upper row of panels shows the assay as applied to a sample containing 100 cells. The bottom row of panels shows the results when the sample contained no cells. Each of the panels labeled "100 cells" has significantly more spots than the corresponding "no cells" control. For chemiluminescent signals, the spots are white on a black background, while for chromogenic signals the spots appear black on a white background. Note that the latter spots were also apparent by inspection of the membranes with the naked eye, without the use of magnification. Thus, the results of this example demonstrate that non-magnified large area imaging using bifunctional beads can be a powerful tool for sensitive detection even without complex instrumentation.

FIG. 30. A rapid homogenous immunoassay for *Chlamydia trachomatis* and *Neisseria gonorrhoeae*; part 1: detecting the presence of *Chlamydia trachomatis*

The figure diagrams the homogenous immunoassay described in Example 31 that scans for the common sexually transmitted disease pathogens *Chlamydia trachomatis* and *Neisseria gonorrhoeae*. The figure shows how the immunoassay detects the presence of *Chlamydia trachomatis* in a sample. To understand how the test differentiates between the two pathogens refer to FIG. 31. The format of the assay corresponds to the one diagrammed in FIG. 11. Experimental details are similar to the multiplexed assay used to detect a bacteria and a virus in Example 22 (FIG. 25).

FIG. 31. A rapid homogenous immunoassay for *Chlamydia trachomatis* and *Neisseria gonorrhoeae*; part 2: the principle of multiplex detection The figure, a continuation of FIG. 30, diagrams the homogenous immunoassay described in Example 31, which scans for the common sexually transmitted disease pathogens *Chlamydia trachomatis* and *Neisseria gonorrhoeae*. Detection of red particles indicates *Chlamydia trachomatis* infection, while detection of green particles indicates *Neisseria gonorrhoeae* infection.

The format of the assay corresponds to the one diagrammed in FIG. 11. Experimental details are similar to the multiplexed assay used to detect a bacteria and a virus in Example 22 (FIG. 25).

Figure 32:
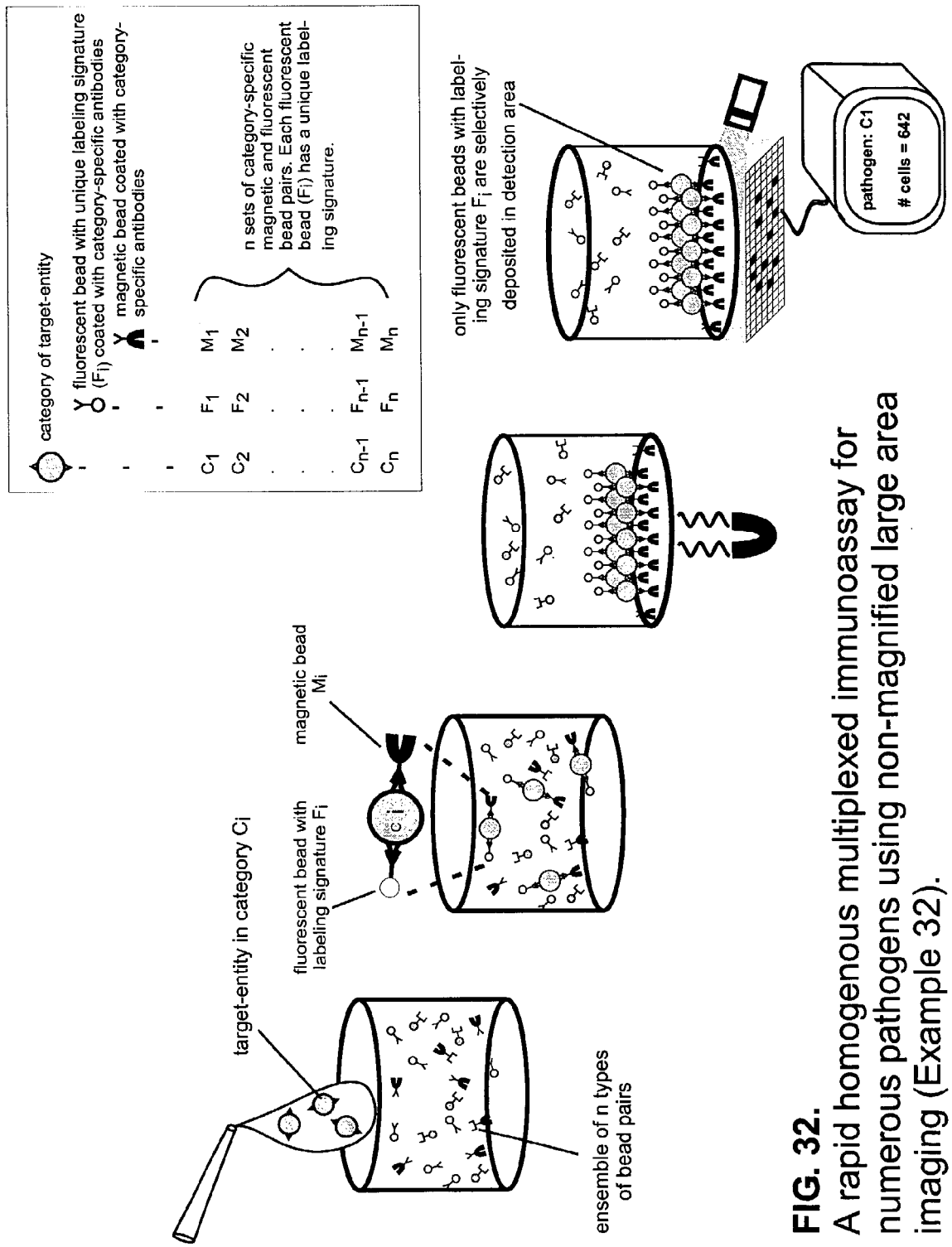

FIG. 32. A multiplexed homogenous immunoassay with high signal complexity using non-magnified large area imaging.

The figure shows the scheme for a highly multiplexed homogenous immunoassay. The principle of the assay is the same as the one diagrammed in FIG. 30 except, that rather than two pairs of analyte-specific fluorescent particles, this assay incorporates many analyte-specific particle pairs to scan for many analytes simultaneously. Methods for achieving the high signal complexity (i.e., the large number of distinct signals) required to identify numerous categories of targets are discussed in Step 6 of the Detailed Description section.

Figure 33:
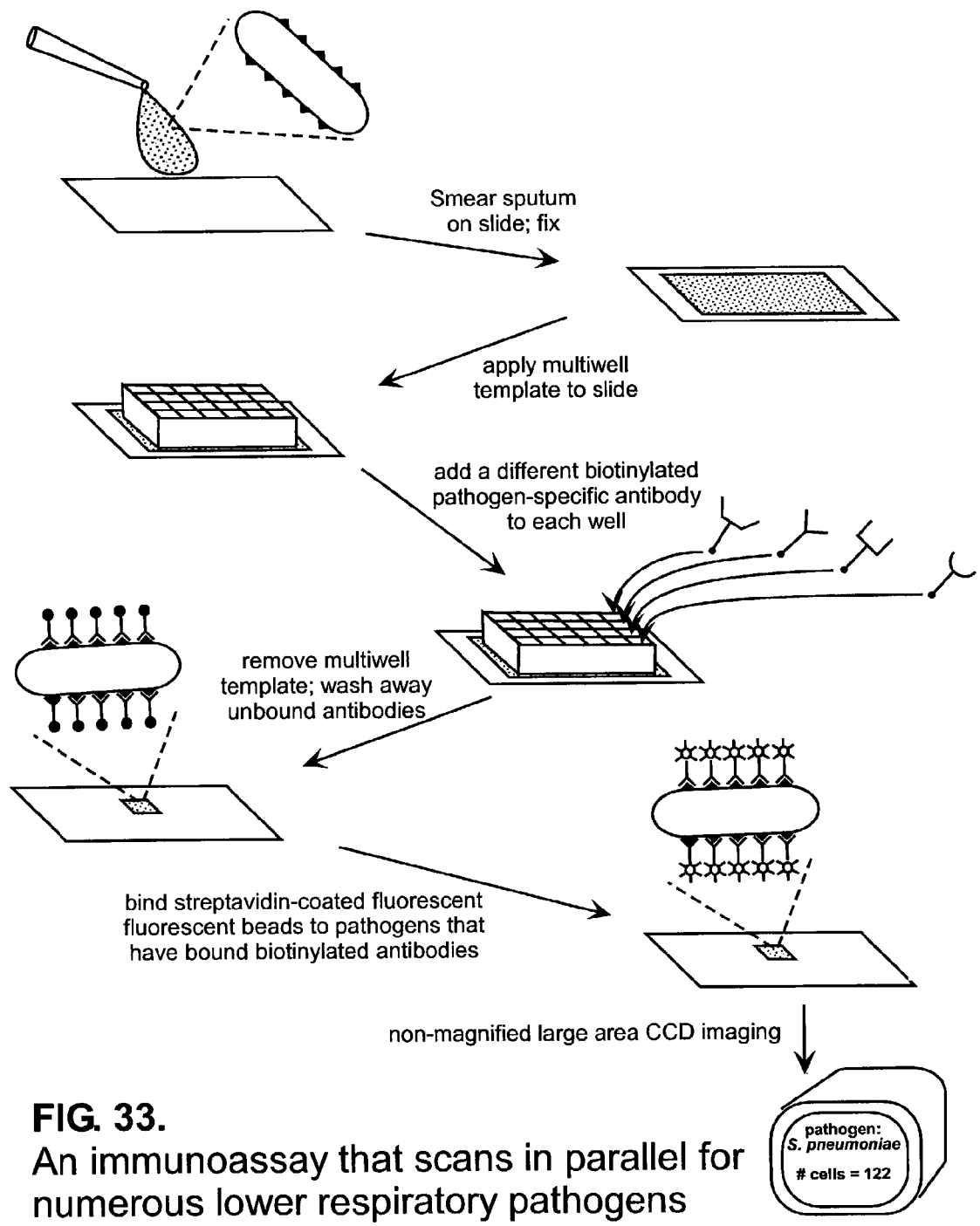

FIG. 33. An immunoassay that scans in parallel for numerous lower respiratory pathogens.

The figure diagrams the immunoassay described in Example 33. A lower respiratory sample (e.g., sputum or BAL) is fixed to a microscope slide. After affixing a multiwell template to the slide, a different family of pathogen-specific biotinylated antibodies is added to each well (e.g., anti-*S. pneumoniae* or anti-*legionella* antibodies are added to separate wells). Unbound antibodies are washed away and fluorescent particles coated with streptavidin are bound to pathogens that have bound to biotinylated antibodies. The location of sectors where fluorescent particles have bound indicates the identity of the pathogen since such sectors corresponds to wells that contained antibodies to a known pathogen. The particle-containing sectors are imaged using CCD detection FIG. 34. Multiplexed identification of urinary tract infections without culture This figure diagrams the test described in Example 34. Capture antibodies for different urinary tract pathogens are affixed in parallel stripes on a glass slide. The slide is immersed in a urine solution that has been treated with a fluorescent stain that binds to the nucleic acids in bacterial cells. Bacterial pathogens, if present, adhere to the corresponding line of capture antibodies on the slide, and are imaged using non-magnified large area imaging.

Figure 35:
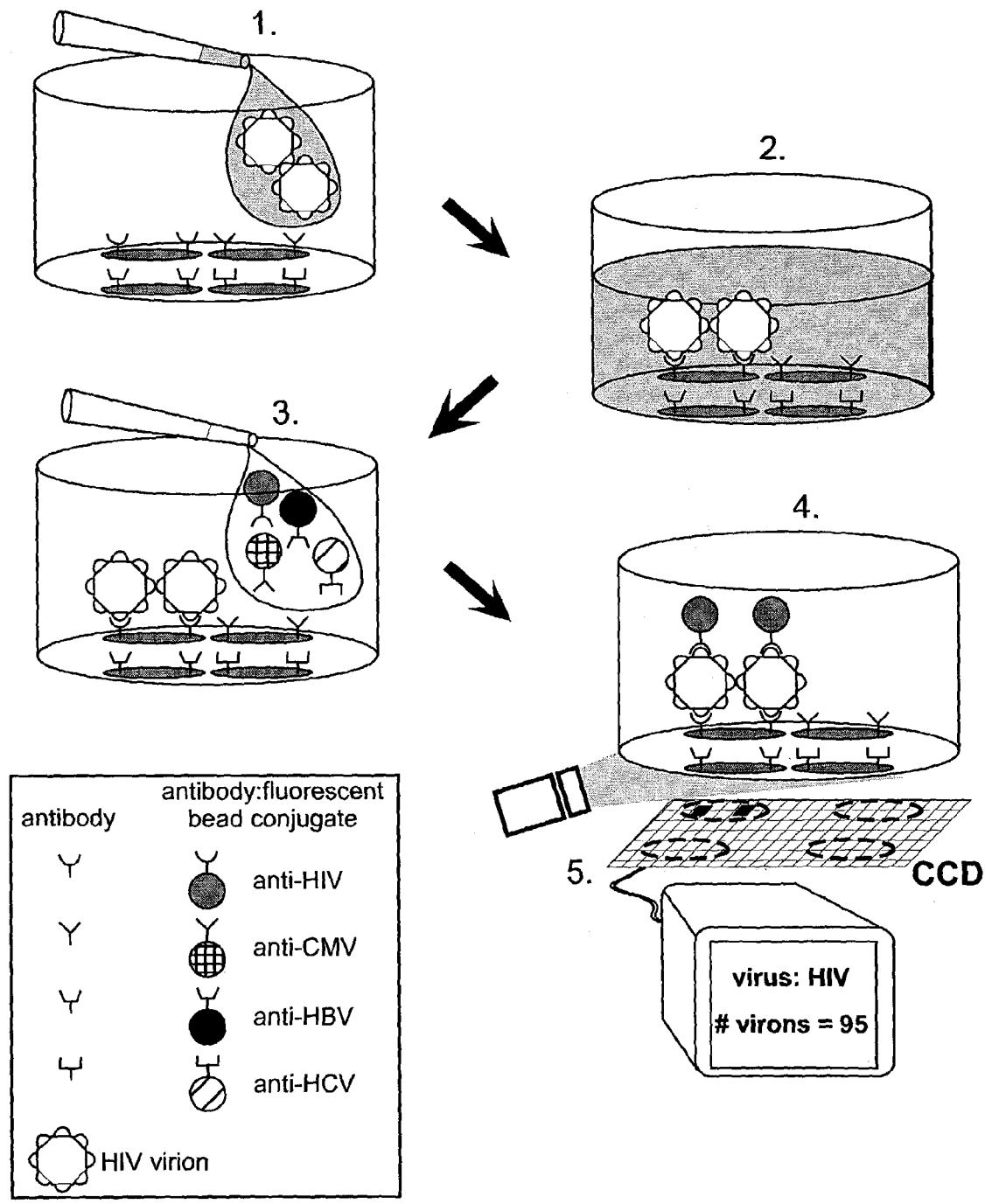

FIG. 35. Rapid, multiplexed, identification of blood-borne viruses: HIV, HCV, HBV, and CMV This figure diagrams the test described in Example 35. Adsorbed to the optically clear bottom of a microtiter dish are four distinct spots containing 4 different capture antibodies that are specific for four different viruses (HIV, HBV, HCV, and CMV). Blood (containing HIV in the figure) is added to the well and viruses are allowed to bind to the capture antibodies. After removing the blood, a mixture of four types of virus-specific fluorescent particles is added to the well. Each type of particle is dyed with a fluorophore with distinct spectral characteristics (signal signature) and is coated with a different viral-specific antibody. Virus particles, which are trapped on the surface of the well, bind to the corresponding fluorescent particles that are detected and quantified by CCD-based non-magnified large area imaging. Both the position and signal signature of the bound particles identify the virus in the blood.

Figure 36:
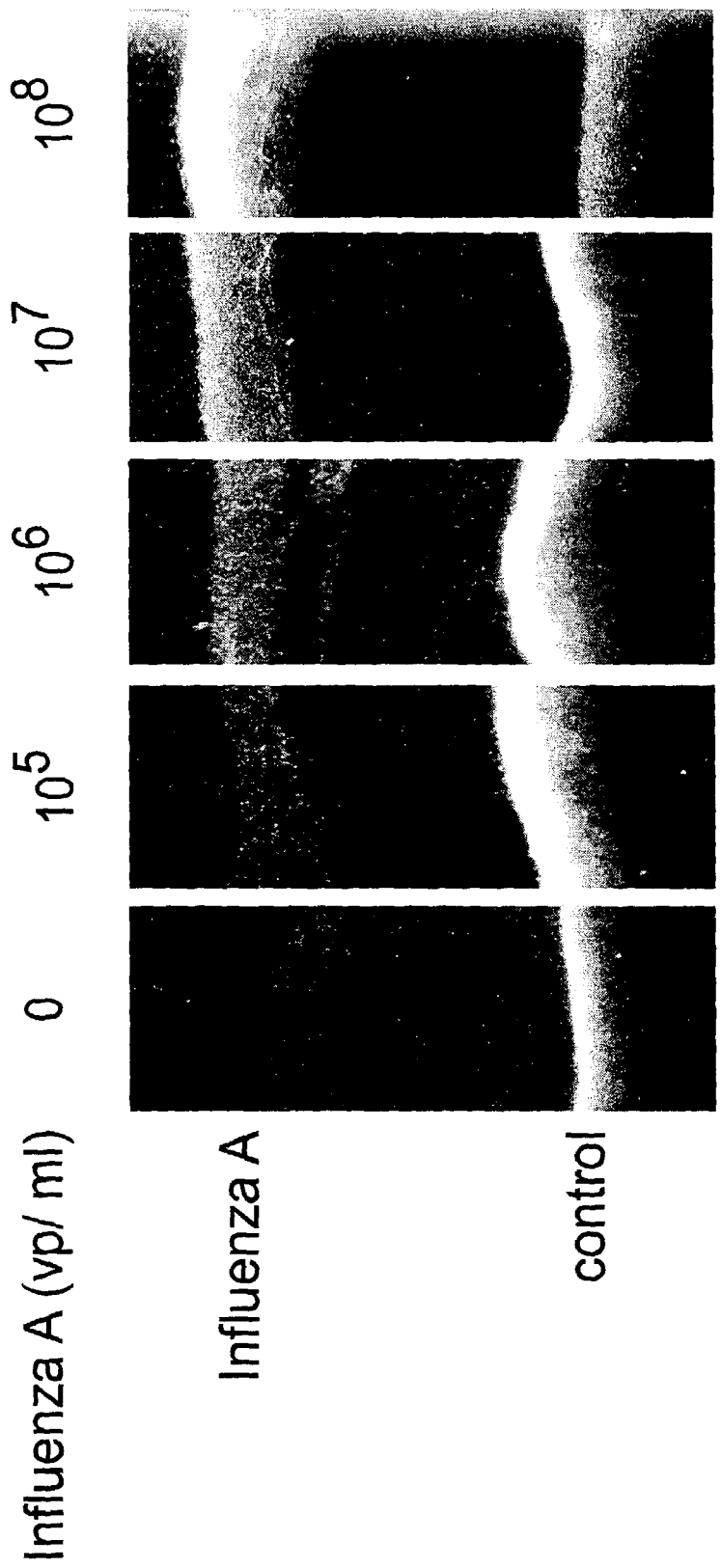

FIG. 36. Ultra-sensitive lateral flow test for Influenza A virus using non-magnified large area imaging The figure shows the results of lateral flow tests for Influenza A virus labeled with fluorescent labeling particles and analyzed using non-magnified large area imaging. The figure shows images of the capture and control lines from test strips onto which were applied samples containing (from left to right) 0, $10^5$, $10^6$, $10^7$ and $10^8$ virion/ml. The fluorescent signal increases with increasing concentration of Influenza A virions. The data shown shows the test can detect concentrations at least as low as $10^5$ virions/ml. This experiment therefore demonstrates the sensitivity of lateral flow tests based on the invention.

Figure 37:
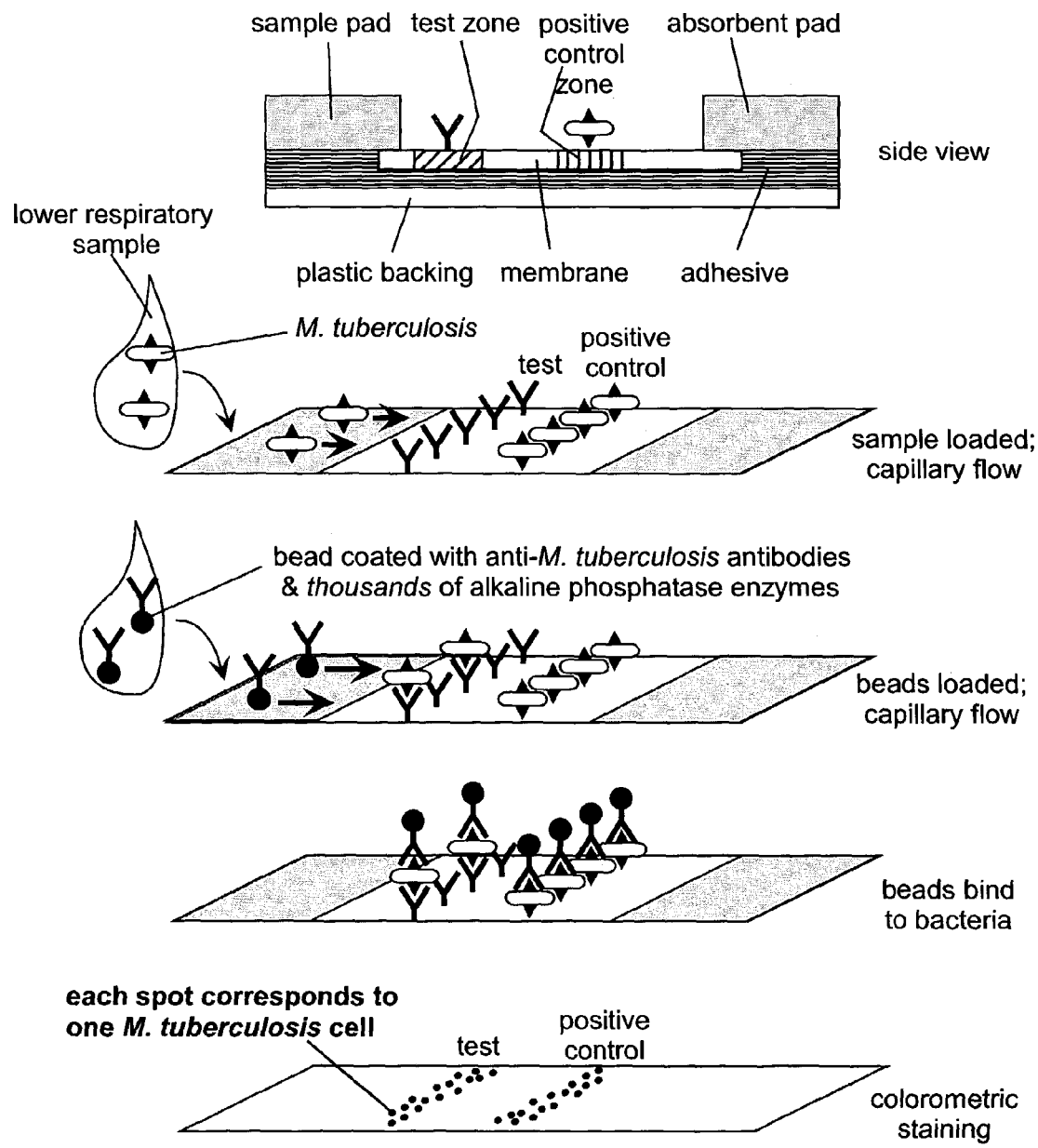

FIG. 37. A rapid lateral flow test for *M. tuberculosis* using visual detection

This figure diagrams the test described in Example 36. The top panel shows a side view of the lateral flow test configuration. The test zone contains a line of anti-*M. tuberculosis* capture antibodies that are bound the bibulous membrane. The positive control zone contains *M. tuberculosis* bacteria bound to the membrane. A sample (containing *M. tuberculosis* in the figure) is applied to the sample pad. Capillary flow draws the pathogen cells along the membrane so that they encounter and are trapped by the capture antibodies in the test zone. Particles, conjugated to anti-*M. tuberculosis* antibodies and alkaline phosphatase, are applied to the sample pad. In the course of migrating towards the absorbent pad via capillary flow, the conjugates bind to captured *M. tuberculosis* cells in the test zone and to the filter-bound *M. tuberculosis* in the control zone. These bound conjugates are directly visualized after chromogenic staining with an alkaline phosphatase substrate.

FIG. 38. A rapid lateral flow test for detecting numerous disparate biowarfare agents using non-magnified large area imaging This figure diagrams the test described in Example 38. The strategy is similar to the one described in the legend of FIG. 37 with the following exceptions. This test scans a sample for numerous disparate biowarfare agents including bacteria, viruses, and toxins. (Note, that for simplicity, the figure does not depict all of the targets, conjugates, and capture antibodies in the test described in Example 38.) In this example, the sample encounters and mobilizes the conjugates in a conjugate pad. Finally, this test uses a chemiluminescent substrate of alkaline phosphatase and CCD imaging to detect specifically bound conjugate particles.

FIG. 39. Using genomic subtraction to isolate *S. pneumoniae* category-specific sequences.

This figure diagrams the isolation of *S. pneumoniae*-specific sequences as described in Example 39. FIG. 39A shows the phylogenetic relationship between *S. pneumoniae* and its closest relatives (Kawamura, et al., International Journal Of Systematic Bacteriology 45: 406-8, 1995). The strategy for isolating category-specific sequences can be broken down into two steps: a genomic subtraction step (FIG. 39B) and a screening step (FIG. 39C). First, genomic subtraction (Straus, 1995, supra) is carried out using the DNA from the pathogenic strain (in this case *S. pneumoniae*) as the "+" genomic difference sample (FIG. 39B). The "−" genomic difference sample is constructed by pooling several of the closest related strains (strains that do not commonly cause pneumonia). The resulting subtraction products are fragments that hybridize to the pathogen's genome but not to the genomes of the closely related species. After cloning the subtraction products, the subset that are category-specific are isolated (FIG. 39C). These are DNA fragments that hybridize to all *S. pneumoniae* strains but do not hybridize to any strains in other groups. Probes are chosen that hybridize to all *S. pneumoniae* strains tested but to no strains of the genus Streptococcus that are in other species. For details, see Example 39.

FIG. 40. A comprehensive test for respiratory pathogens using nucleic acid probes.

The figure diagrams the test described in Example 39. An ensemble of pathogen-specific probes is hybridized to a slide comprising two sectors: one containing a respiratory sample and one containing an array of spots each of which includes control respiratory pathogens in a different category. Each family of probes in the ensemble is labeled with a distinct signal signature. Comparison of the signal signatures of pathogens in the clinical sample to the signal signatures in the control spots identifies the pathogen in the clinical sample. The number and intensities of objects found by the image analysis software quantifies the number of pathogens in the sample. For details, see Example 39.

FIG. 41. Indirect combinatorial labeling of category-specific sequences.

The figure shows the method used to achieve high signal complexity in Example 40. Each family of category-specific oligonucleotide category-binding molecules is labeled with a particular signal signature using a scheme analogous to the one shown in Table 5. Thus, as shown in the figure, *S. pneumoniae* probes are indirectly labeled with either violet or blue quantum dots while *S. aureus* probes are labeled with either yellow or green quantum dots. For example, probes that are to be labeled with violet quantum dots are synthesized with two adjacent moieties: a category-specific oligonucleotide and a "violet tag." The violet tag sequence can hybridize to a "violet tag complement" that is conjugated to a violet quantum dot.

FIG. 42. CNS strip test.

This figure diagrams the test described in Example 41.

FIG. 43. Bipartite PCR primer for amplifying genomic difference sequences pinpointed by virtual subtraction (Example 43).

The figure shows the PCR primers that are used in Example 43 for amplifying regions (~200-500 bp) that occur in

*Chlamydia trachomatis*, but not in *Chlamydia pneumoniae*. The PCR primers are designed with a bipartite structure. The "left primer" has the XhoL primer sequence (5'-GGG CCC CCC CTC GAT C-3' SEQ ID NO: 1) linked to a 20 bp primer corresponding to the "left" end of an insertion/deletion region in *Chlamydia trachomatis* (5'-XhoL-*Chlamydia trachomatis* left primer-3'). The "right primer" has the XhoR primer sequence (5'-ATC GAT ACC GTC GAC CTC-3' SEQ ID NO: 2) linked to a 20 bp primer corresponding to the "right" end of an insertion/deletion region in *Chlamydia trachomatis* (5'-XhoR-*Chlamydia trachomatis* right primer-3').

DETAILED DESCRIPTION OF THE INVENTION

Overview of the invention. The invention rapidly and cost-effectively scans a minimally processed sample for small numbers of microscopic and submicroscopic targets of many types (e.g., cells, viruses, or protein molecules). The powerful features offered by the invention arise from a novel diagnostic approach that combines modern high-intensity labeling, low-cost imaging technology, and non-magnified large-area detection.

To understand how the invention detects small numbers of microscopic targets in a relatively large sample, it is helpful to first examine a specific embodiment. FIG. 1 shows a simple schematic of one embodiment of the invention that detects small numbers of bacteria spread out over a large area, in this case a part of a microscope slide. The bacteria are labeled so that they emit light, as will be described shortly. The approach that is used to detect the "glowing" bacteria, which is used in many of the examples below, uses a digital camera (CCD chip) to capture an image of an area of a sample that is much larger than the individual bacteria. The CCD chip has an array of photosensitive pixel elements. Light from a "glowing" bacterium at one position in the sample impinges on pixel elements at the corresponding position of the CCD chip. The end-user receives information about the number of bacteria in the sample from a computer that processes the image data (i.e., the number and intensities of the illuminated pixels) acquired from the CCD chip.

Next, consider a specific application of the embodiment (FIG. 1) that scans a respiratory sample for the presence of the important bacterial pathogen, *Mycobacterium tuberculosis*. In this test, depicted in FIG. 2, the bacteria are labeled with a fluorescent chemical, a fluorophore, so that they emit light of a specific color (the emission spectrum) when illuminated by a light of a different color (the excitation spectrum). To develop reagents for labeling the bacteria, a category-binding molecule is first chosen. An ideal category-binding molecule would be a monoclonal antibody that binds to *M. tuberculosis* but to no other type of bacterium or substance that might be present in a respiratory sample. The antibody might, for example, bind specifically to a particular molecular site, a "category-specific binding site," that is found only on the surface of the *M. tuberculosis* bacterium. Next, the *M. tuberculosis*-specific category-binding molecule is labeled by conjugation to a fluorophore, e.g., fluorescein. The fluorescein molecule is called the "signaling moiety," as it provides the signal to be detected in the test. Having prepared the category-binding molecule (the anti-*M. tuberculosis* antibody) labeled with the signaling moiety (fluorescein), diagnostic tests for *M. tuberculosis* can be performed.

FIG. 2 illustrates how the test determines whether a patient is infected with *M. tuberculosis*. A sputum sample is spread on and affixed to a glass slide. After incubating the slide with the fluorophore-labeled antibodies, the unbound antibodies are removed from the sample by washing. Illuminating the sample with light in the excitation range of fluorescein elicits fluorescence emission by the fluorescein-tagged antibodies coating the surface of *M. tuberculosis* cells that are present in the sample. The fluorescent image of the cells is collected, focusing the emitted light on the surface of a CCD chip without magnification. Thus, a large area of the sample smear, typically about 1 to 2 $cm^2$, is scanned concertedly for *M. tuberculosis* cells. Fluorescent light from each cell impinges on a small cluster of pixels causing a localized electronic signal that is relayed from the CCD chip to a computer where it can be stored in the form of an image file. Image analysis software enumerates the *M. tuberculosis* in the sample by counting the number of pixel clusters responding to light from cells and by integrating the total photonic intensity of the responding pixels.

The invention can be used to construct tests using a number of types of formats, labeling methods, category-binding molecules, and detection methods. However, the tests have several key features in common. The steps and processes that are common to many embodiments of the invention are described below.

The general configuration of applications of the invention consists of the following steps:

Step 1: Formulating the test question, choosing category-binding molecules for detecting targets Step 2: Choosing and preparing signaling moieties Step 3: Preparing the biological sample Step 4: Binding targets in the sample to category-binding molecules and signaling moieties Step 5: Selecting targets and bound category-binding molecules Step 6: Identifying and quantifying targets present in the sample by detecting the signaling moieties bound to targets Step 1: Formulating the Test Question, Choosing Category-Binding Molecules for Detecting Targets Choosing the categories of targets to be detected by the test. Categories are defined functionally as a range of related targets that are to be considered identical, for the purposes of a test. Choosing the categories of targets that will be identified by a test is tantamount to defining the goals of the diagnostic test. Choosing the categories is also central to defining the molecular reagents, the category-binding molecules that will be used in the test.

When constructing a new test based on the invention, the first step is to decide which categories of targets the test should identify and distinguish. For example, to construct a test to identify the infectious agents that cause a patient's pneumonia, one selects categories of pathogens that commonly cause pneumonia, such as Respiratory Syncytial Virus and *Streptococcus pneumoniae*; or, to test for foodborne pathogens, one selects categories of bacteria that cause toxicity. The invention can identify a broad range of targets including multicellular organisms, bacteria, and viruses. Furthermore, targets from various categories (e.g., bacteria and viruses) can be tested for in the same assay.

A significant use of the invention is in the identification of pathogens in a human bodily fluid sample, such as blood, urine, cerebrospinal fluid, sputum, or feces. (The method is also important as applied to other types of clinical samples including tissue samples.) Depending on the bodily source of sample and the symptoms of the patient, a decision is made as to the important types of organisms to be identified. For example, in the case of a sputum sample from a patient with lower respiratory symptoms, one can choose to detect viruses, bacteria, and fungi that are common causes of pneumonia.

The choice of categories depends on the diagnostic question that is addressed by a test. Thus, when two tests answer two different diagnostic questions, different categories may be chosen even if the tests both scan the same type of sample for the same targets. When considering a test for screening urine samples for urinary tract infections the operative diagnostic question is often: "Are there a significant number of bacterial cells in the urine?" For such a test, the test category might comprise all bacteria. That is, the test does not distinguish different species of bacteria from each other. So, for example, both *Escherichia coli* and *Enterococcus facacium* fall into the same "pan-bacterial" category for the purposes of this type of screening test. In contrast, the goal of a different type of urinary tract infection test is to identify the pathogen at the species level. For this type of test, each species of bacteria that commonly causes urinary tract infections is defined as a different category (e.g., *Escherichia coli* and *Enterococcus facacium* would be separate test categories).

For some tests, multiple categories of organisms that span multiple kingdoms are chosen. It is frequently clinically important to determine which of a panel of disparate pathogens is the cause of a patient's symptoms. The invention addresses the critical unmet need for cost-effective efficacious tests that simultaneously scan a patient's sample for the presence of various viruses, bacteria, and fungi. The categorical complexity is a measure of the number of categories of targets for which a test scans. (see also the Definition section).

Category-specific binding sites and category-binding molecules. Different categories of targets are distinguished by their distinct molecular constituents. For example, consider the following set of disparate pathogens, each of which causes lower respiratory disease: influenza A virus, RSV, *Haemophilus influenzae, Streptococcus pneumoniae*, and *M. tuberculosis*. Each pathogen category possesses molecular constituents that are characteristic of the category but that do not occur in members of other categories or in other components of respiratory samples. Tests based on the invention detect members of a particular category by scanning for the presence of category-specific molecular constituents.

To detect the presence of a category of targets, the invention deploys molecules that bind specifically to category-specific molecular constituents. The category-specific molecular constituents that occur on targets are called category-specific binding sites and the molecules that bind specifically to them are called category-binding molecules. Note that category-specific binding sites are a property of targets that are potentially present in the sample to be tested. In contrast, category-binding molecules are a reagent provided in the diagnostic test kit.

An advantage of the invention is that a broad spectrum of category-binding molecules can be used. This is important since different types of category-binding molecules are used to ask different types of diagnostic questions (e.g., broad kingdom-level screening vs. narrow subspecies-level identification). Classes of category-binding molecules (also sometimes referred to as probes) comprise: nucleic acids (oligonucleotides, aptamers, cloned sequences, genomic DNA, RNA, etc.), chemical variants related to nucleic acids, such as peptide nucleic acids (PNA); antibodies; enzymes (which can bind target substrates); non-enzymatic proteins such as avidin (which binds the target molecule biotin); molecules that bind cellular constituents specifically (e.g., phalloidin which binds actin or biotin which binds avidin); dyes and stains, such as propidium iodide, auramine-rhodamine, or SYTO 17); ligands (e.g., epidermal growth factor, which binds specifically to the epidermal growth factor receptor); and polypeptide or nucleic acid binding reagents that have been selected using in vitro evolution techniques (e.g., Zhang, et al., Nat. Biotech. 18: 71-74, 2000).

Category-binding molecules can incorporate other functional domains or modifications. For example, category-binding molecules are often covalently or non-covalently associated with signaling moieties (i.e., a labeling domain such as a fluorophore or a dyed microparticle) or selection moieties (e.g., magnetic particles or solid surfaces). Alternatively, a category-binding molecule may be linked to an adaptor moiety that, in turn, facilitates linkage to another functional moiety. Sometimes the category-binding molecule has dual non-separable functions. For example, propidium iodide, a nucleic acid stain, can be used as a category-binding molecule (e.g., the category-specific binding site might be the cellular nucleic acid in a yeast) while, at the same time, the bound dye functions as a signaling moiety (i.e., it can fluoresce when bound to the category-specific binding site). Tests based on the invention can incorporate more than one class of category-binding molecule (e.g., antibodies and nucleic acid stain, or antibodies and oligonucleotides).

The simplest tests incorporate a single type of category-binding molecule to scan for a single category of target. For example, a test for *M. tuberculosis* might use a monoclonal antibody that binds specifically to a category-specific binding site on the surface of *M. tuberculosis*. Alternatively, for example, when screening for urinary tract infections, the single category is "all cells"—or, if human cells are lysed, "all non-human cells"—and the single type of category-binding molecule could be a nucleic acid stain (e.g., propidium iodide).

A family of category-binding molecules is a set of distinct category-binding molecules that bind to members of the same category of target. For example, a polyclonal antibody raised to Hepatitis C virus is a family of antibodies since it comprises multiple category-binding molecules that bind specifically to the same category of target—in this case HCV. Another example of a family of category-binding molecules is a set of 80 category-specific genomic DNA sequences that occur in all *E. coli* O157:H7 strains, but do not occur in members of other groups of bacteria. This family of category-binding molecules can hybridize as a group to suitably prepared *E. coli* O157:H7 cells, but does not hybridize to other types of cells.

To detect multiple categories of targets, a test includes one family of category-binding molecules for each category. A set of families of category-binding molecules is called an ensemble of category-binding molecules. For example, tests for pneumonia or tests for drugs of abuse, must distinguish numerous categories of targets from each other. One family of category-binding molecule is used for each category of target. For a pneumonia test, an ensemble of antibodies that react to category-specific antigens on the surface of microbes that cause pneumonia might be used. One family in this category-binding molecule ensemble might comprise polyclonal antibodies from the immunoglobulin fraction of antiserum raised in a rabbit host and directed against *Streptococcus pneumoniae*. Another family could comprise a recombinant antibody or a monoclonal antibody directed against a coat protein of adenovirus.

The number of distinct groups or categories of targets tested for by an ensemble, i.e., the categorical complexity, is reflected by the number of families of category-binding molecules in the ensemble. The number of families in an ensemble can, in turn, be accurately defined by a quantity called the "minimum categorical derivation" of an ensemble. The family complexity is the minimum number of distinct targets required to bind members from each of the families of category-binding molecules in the test ensemble. For example, consider an ensemble of category-specific antibodies used to simultaneously test a sputum sample for the presence of *Mycobacterium tuberculosis*, *Legionella* spp, *Coccidoides immitus*, influenza virus, and Respiratory Syncytial Virus. The family complexity of the ensemble would be five, since a minimum of five targets, one from each pathogen category, would be required to bind to members of each family of category-binding molecules in the ensemble. The ability of the invention to identify a broad spectrum of targets in a single test is a consequence of its ability to scan a sample using an ensemble of category-binding molecules that has a large family complexity.

Category-binding molecules used in conjunction with the invention should be specific in that they should bind under assay conditions to the desired target (analyte) but not to other types of targets (meant to be distinguished by the assay) or to other possible constituents of the sample or test. Thus, in a test for upper respiratory bacterial infection, potential category-binding molecules are screened to eliminate those that cross react with normal (commensal) microbial constituents of the upper respiratory tract.

Representative methods for obtaining and characterizing category-binding molecules are included in the examples below.

Step 2: Choosing and Preparing Signaling Moieties

Labeling category-binding molecules with signaling moieties. The invention's ability to detect individual microscopic targets without optical magnification or expensive instrumentation generally depends on specifically labeling the targets at high signal intensity. Labeling is achieved by specifically binding signaling moieties to the targets via an association with category-binding molecules. Note, however, that for certain applications of the invention that use intrinsic properties of the targets as signaling moieties, labeling is not required (e.g., cellular autofluorescence).

The invention discriminates between categories of targets in two general ways. One method, called signal differentiation, labels each category-specific family of category-binding molecules with signaling moieties such that it has a unique signal signature. The ability to generate and detect large numbers of distinct signal signatures (i.e., high signal complexities) enables construction of tests that scan for numerous categories of targets (i.e., highly multiplexed tests). The other method for distinguishing between multiple categories of targets, geometric differentiation, relies on depositing different categories of targets in different regions of the detection area. Geometric differentiation, which can be independent of the signal signature of signaling moieties, is discussed below (Step 5).

The invention can exploit various types of signal character including: fluorescence, scattered light, light polarization, radio waves, particle size, magnetic field, chemiluminescence, and radioactivity. Examples of signaling moieties and detection schemes using various signal characters appear below. There can be multiple signal classes within a signal character. For example, if the signal character is fluorescence, various characteristic emission spectra comprise the signal classes (e.g., red fluorescence, green fluorescence, and blue fluorescence). Alternatively, as another example, consider red fluorescent microparticles that are dyed with different concentrations of the same fluorophore. Fluorescence is again the signaling character; however in this case the different intensities of the particles constitute the classes of signal character, i.e., fluorescence intensity is the quality of the signal character that differentiates one group of particles from another.

A great variety of signaling moieties can be used in conjunction with the invention as demonstrated in the examples below. Signaling moieties can comprise simple fluorophores, up-regulated phosphors, naturally fluorescent proteins (such as green fluorescent protein and its relatives), dyes, enzyme:substrate systems (generating substate:product color changes or chemiluminescence), fluorescent microparticles, light scattering particles, magnetic particles, or radio transmitting microdevices.

Attaining a high signal complexity is useful for developing tests that scan for numerous types of targets (i.e., tests with high categorical complexity).

Achieving high signal complexity. The number of distinguishable labels (or signaling moieties) in a mixture is called the signal complexity. For highly multiplexed tests, it is sometimes advantageous to use signaling moieties with high signal complexity. Three general approaches that can be used with this invention to generate high signal complexity are: (1) distinct labeling, (2) combinatorial labeling, and (3) ratio labeling.

1. For distinct labeling, probes in different probe families are tagged with a single signaling moiety that can be readily detected in the presence of all other signaling moieties in the experiment. Thus far, it has been difficult to achieve distinct labeling at high signal complexities. This is because most labeling methods use optical signals (e.g., chromogenic, fluorescent, chemiluminescent) or radioactive labeling. Due to the spectral bandwidth of optical signals and the limited range of signals detectable by current instruments, the resolvable signal complexity using optical signals is rather small. For example, due to spectral overlap, the resolution of dozens of fluorophores with distinct emission spectra is currently impossible.

2. Another way to achieve the high signal complexity used in the invention is to apply a combinatorial labeling approach. Combinatorial labeling is a technique for achieving high signal complexity using a relatively small number of distinct signaling moieties. With this approach, distinct combinations of signaling moieties are bound to different targets. The concept is illustrated in FIG. 5 (see also Example 1). Currently, fluorophores are a favored class of signal moiety for molecular diagnostics. However, given the complications involved in analyzing multiple distinct fluorophores (arising in large part from overlap of the excitation and emission spectra), it is only currently practical to incorporate about seven or fewer conventional fluorophores. However, used in combination, seven fluorophores can be used to generate 127 distinct signals (N fluorophores generate $2^N-1$ combinations). High signal complexity can also be achieved via combinatorial labeling using other types of signaling moieties. For example, particles impregnated with different dyes, particles that fall into different discrete size classes, or transponders emitting distinct radio signals could be used with this approach. Combinatorial labeling using fluorophores has recently been applied with success for human karyotyping (Speicher et al 1996, supra; Schröck et al 1996, supra). Instrumentation and software for analysis of combinatorial labeling experiments is commercially available.

3. High signal complexity can also be obtained using the ratio labeling approach (Fulton, et al 1997, supra). In ratio labeling, as in combinatorial labeling, many distinct types of signaling moieties are generated using a relatively small number of distinct signaling elements. However, in contrast to combinatorial labeling, the signaling moieties in ratio labeling are distinguished by the ratio of the signaling elements. For example, two fluorophores, X and Y, with different excitation/emission characteristics can be used to dye polystyrene particles. Different relative concentrations of the fluorophores ([X], [Y]) are applied to different sets of particles. For example, eight different concentrations of X and eight different concentrations of Y can be used to dye particles in all combinations ($X_1Y_1$, $X_1Y_2$, $X_8Y_7$, $X_8Y_8$) resulting in 64 classes of distinguishable particles. Ratio labeling simplifies instrumentation, as only a small number of signal types need be used. Signal elements, other than fluorophores and including non-optical signal elements, can also be used to generate high signal complexities using a ratio labeling approach.

Generating strong signals facilitates detection of individual microscopic targets. The level of signal intensity needed is, of course, dependent on the type of signal character (optical, particle size, etc.) and the detection method/instrumentation (see below).

Various approaches for labeling category-binding molecules can be used to achieve the required sensitivity. One method for optimizing the signal strength is to label target molecules with highly fluorescent signaling moieties. For example, quantum dots, fluorescently dyed nanospheres, and polymerized fluorophore molecules generate strong fluorescent signals. Incorporating numerous signal elements can increase the fluorescence intensity of a signaling moiety. For example, fluorescent nanospheres (~20 nm in diameter; Molecular Probes) can generate a signal equivalent to about 180 fluorescein molecules. Fluorescently dyed polystyrene microparticles (e.g., 1 µm in diameter) can incorporate millions of fluorophore signaling elements. A method for incorporating multiple fluorophores in a signal moiety associates with a nucleic acid category-binding molecule is to incorporate fluorophore-dNTP conjugates during PCR amplification of a cloned category-specific sequence. Alternative methods for incorporating multiple fluorophores into nucleic acid category-binding molecules include approaches using: dendrimers, branched DNA, or rolling circle templates bound to multiple signal moieties, or tailing with numerous polymerized fluorophore labeled nucleotides. Conjugating category-binding molecules to multiple signaling moieties also increases signal intensity. For example, signal amplification can also be achieved by conjugating large numbers of signaling enzymes (e.g., alkaline phosphatase or horseradish peroxidase) to a nanoparticle.

Another approach to obtain strong signals is to bind numerous labeled category-binding molecules to each target. This can be done by various means including: using multiple category-binding molecules (recognizing multiple category-specific binding sites in the same target) or by choosing category-binding molecules that bind to target molecules that are highly represented in a target. For example, a labeled microbe-specific polyclonal antibody can achieve high signal intensities by binding to numerous distinct epitopes on a microbial target (e.g., see Example 11). Example 1 also describes using labeled category-binding molecules that bind to many distinct category-specific binding sites in each target organism. The strategy of choosing category-specific binding sites that are present in large numbers in each target has been frequently used previously. Examples of this strategy include the use of nucleic acid probes for ribosomal RNA (which depending on the target organism and cell type can be present in thousands of copies per cell). Similarly, some antigenic target molecules are present in hundreds or thousands of copies in each cell of a target organism. The invention can exploit both of these strategies. As another example, the large number of category-specific binding sites present in a bacterium yield strong signal intensity when using the nucleic acid-binding fluorescent dye Syber Green I as the category-binding molecule/signaling moiety (e.g., see Examples).

Binding numerous signal moieties to a target not only increases signal strength, but it endows the invention with robustness since the chances are small of observing numerous clusters of a large number of signaling moieties with the expected composite signal signature in the absence of the target.

Conjugating signaling moieties to category-binding molecules. The invention can incorporate numerous types of signaling moieties which can be directly conjugated to category-binding molecules using various methods which are known by those familiar with the art (see, for example, Hermanson, G., *Bioconjugate Techniques* (Academic Press, 1996) and specific examples below). For example, antibody or oligonucleotide category-binding molecules can be directly conjugated to a fluorophore or a quantum dot signaling moiety. Alternatively, for example, antibodies or oligonucleotide category-binding molecules can be used to coat fluorescent microparticle-based or light-scattering nanoparticle-based signaling moieties. Signaling moieties can be indirectly conjugated to category-binding molecules. For example, as shown in FIG. 6, a signal moiety can be conjugated directly to a tag complement that is then hybridized to a tag sequence, which is part of an oligonucleotide also containing a category-binding sequence. Alternatively, for example, avidin can be directly conjugated to multiple signal elements to constitute a signaling moiety. The labeled avidin molecule can then be bound to a biotinylated category-specific antibody. Signaling moieties can be conjugated to the category-binding molecules before, during, or after the binding steps. For example, in one embodiment of the invention, digoxygenin-labeled nucleic acid probes are used as the category-binding molecules. After binding the category-binding molecules to the category-specific binding sites in the targets in the sample, the unbound probes are washed away. Anti-digoxygenin antibody:alkaline-phosphatase conjugates (the signaling moieties) are then conjugated to the bound digoxygenin-labeled probes. An alkaline-phosphatase substrate (e.g., the chemiluminescent substrate CDP-Star; NEN)) is then added to the bound alkaline-phosphatase to generate the signal.

Step 3: Preparing the Biological Sample.

Sample preparation. An important attribute of the invention is its compatibility with rapid and simple sample preparation protocols. This represents a major advantage over other sensitive diagnostic methods, such as nucleic acid amplification-based techniques, which require much more demanding sample preparation procedures to eliminate enzyme inhibitors.

Sample preparation can have several functions depending on the nature of the sample and the test format. In some cases, sample preparation concentrates targets and/or deposits them on a substrate. For example, a test for water-borne microbes might concentrate the microbes by filtration, depositing the cells on a paper filter for detection. Other samples are smeared onto a solid substrate (e.g., a glass microscope slide).

Making category-specific binding sites on targets accessible to binding by category-binding molecules is an important function of the sample preparation. In some cases little or no treatment is necessary as, for example, when the category-specific binding site is an epitope on the surface of a microbe in an aqueous sample that is freely accessible to a category-specific antibody (e.g., see Example 8). In other cases, sample preparation is required to make internal category-specific binding sites accessible. This is the case, for example, when category-specific DNA sequences are used to bind to category-specific binding sites on genomic DNA. Target cells must be made permeable to the probes and their genomic DNA must be denatured. When a large number of different types of targets are tested for in the same sample, the sample preparation must be effective for the entire spectrum of targets. Further specific examples of sample preparation methods are detailed in the examples below.

If an assay yields a negative result, it is important to know whether the sample is truly free of target organisms or whether the assay itself failed, i.e., whether or not the result is a false negative. To identify false negative results, one or more positive control targets can be added to the experimental sample. The positive control target contains category-specific binding sites that do not occur in the range of targets being tested. Category-binding molecules corresponding to the positive control targets are included with the other category-binding molecules used in the test. These targets will be detected in all assays, unless one or more of the assay steps is unsuccessful. Failure to detect a signal from a positive control thus can indicate a false negative result.

Step 4: Binding Targets in the Sample to Category-Binding Molecules and Signaling Moieties.

In this step, category-binding molecules and associated signaling moieties are brought into contact with targets in the sample under conditions that facilitate specific binding. For example, an ensemble of category-specific nucleic acid sequences is hybridized to complementary target sequences in the sample in this step. Similarly, category-specific antigens in the sample are allowed to bind to the corresponding category-specific antibodies. There are several possible physical configurations for the binding step. For example, binding can be carried out in the liquid phase (e.g., see Example 8) on a microscope slide (e.g., see Examples) or on a nitrocellulose strip, using lateral flow chromatography (e.g., see Example 38). The concentration of the category-binding molecules is optimized to achieve rapid binding kinetics. The chosen conditions for selecting for specific binding depend on the characteristics of the category-binding molecules and their interactions with target molecules. Specific conditions and procedures are described in the examples below.

Step 5: Selecting Targets Complexed with Category-Binding Molecules and Signaling Moieties.

Physical separation of targets that are bound to signaling moieties from unbound signaling moieties enhances the subsequent detection process. A further purpose of the selection step is to deposit the targets in a detection zone (e.g., an area in the focal plane of an imaging device). The complexes are generally bound to a solid phase while the unbound category-binding molecules and signaling moieties remain in a liquid phase. In some cases the unbound material is washed away. In other test formats (e.g., homogenous liquid phase formats and membrane-based assays), washing is not necessary.

For assays in which the sample is fixed to a solid substrate before the binding step, the unbound category-binding molecules and signaling moieties are generally removed by washing. Representative examples below include those using in situ hybridization and immunocytochemical methods.

Other test formats are carried out in the liquid phase, for example in microtiter wells. In these examples the target/category-binding molecule/signaling moiety complexes are generally deposited on a surface after the binding step (see e.g., Example 8). Methods for depositing the target complexes on a surface include centrifugation, filtration, gravitational settling, magnetic selection, or binding to surface bound category-binding molecules (e.g., capture antibodies, as in Example 18). In some cases (e.g., magnetic separation) a distinct moiety, the selection moiety is used. Magnetic microparticles coated with category-specific antibodies are an example of a selection moiety (see e.g., Example 8). The unbound category-binding molecules and signaling moieties generally remain in the liquid phase and can be removed. If the detection procedure (e.g., optical imaging) selectively analyzes the solid surface with a narrow depth of field, the unbound material (lying outside of the plane of focus) sometimes need not be removed (e.g., see Example 8). Further examples of each of these and other methods are presented below.

Lateral-flow and flow-through formats are arguably the most successful test formats in point-of-care testing. These formats exploit the advantages of capillary flow in bibulous membranes. They generally select the target complex using surface-bound category-binding molecules. Unbound category-binding molecules and signaling moieties flow out of the capture zone by capillary action. Another important advantage of membrane-based assays is the ease of multiplexing by using geometric differentiation (see below).

Geometric differentiation for constructing multiplexed tests. Geometric differentiation is an important method when scanning for multiple categories of targets (i.e., in multiplexed tests). Geometric differentiation has the advantage, when compared to high signal complexity multiplexed tests (see Step 2), of requiring only a single signal signature for multiplexed tests. In a typical immunoassay that uses geometric differentiation, different category-specific capture antibodies are deposited in distinct areas in the detection zone (e.g., different stripes in a lateral flow test or different spots in a flow through or microtiter well-based test). Thus, different categories of targets are captured in different pre-determined areas of the capture zone. Other types of capturing moieties that are analogous to capture antibodies include antigens, ligands, and nucleic acids. Several examples of geometric differentiation appear below (e.g., see Example 38 and Example 34).

Step 6: Detecting, Identifying, and Quantifying Target Organisms Present in the Sample By Detecting the Signaling Moieties Bound to Targets in the Sample Significant advantages of the invention, including its sensitivity and its ability to quantify targets, derive from the ability to use large area imaging to detect individual targets. Detection of the targets labeled with signaling moieties is effected once the complexes are localized in a detection zone. The detection process used depends on the type of signal character of the signaling moieties (e.g., fluorescence, chemiluminescence, or light scattering). For some signal characters (e.g., light scattering and fluorescence), the complexes in the detection zone must be illuminated by a light source. For others (e.g., chemiluminescence, radio transmission, or magnetic fields), illumination is not required. Various detection modes can be used including CCD cameras, film, and direct visualization.

Non-microscopic large area imaging can greatly increase sensitivity. Detecting targets without microscopy is an important aspect of the invention, as it can in many cases achieve more rapid, efficient, and sensitive sample analysis than microscopic methods used in standard in situ analysis methods. The gain in sensitivity of non-microscopic, large area detection over microscopic detection arises from the ability to scan a much larger volume of the sample for target. For example, the invention can image an area on a microscopic slide that is several thousand times larger than the typical area imaged using microscopic imaging. The resulting increase in sensitivity is illustrated by considering a sputum sample that contains 10,000 bacteria per milliliter from a patient with tuberculosis. For in situ analysis, a portion of the sample (e.g., about 10 µl containing about 100 *Mycobacterium tuberculosis* bacteria) is spread over an approximately 1 cm²-sized area on a microscope slide. In this case, the invention, which images the entire 1 cm²-sized field, simultaneously detects the 100 individual cells. In contrast, when using microscopic analysis, due to the small field size examined, there is a high probability that a single field will contain no bacteria at all. Thus, numerous (often hundreds of) fields must be examined carefully when using microscopic analysis. This is a cost-, labor-, and time-intensive process that is circumvented by tests based on the invention.

Detection of single targets is naturally quantitative. During the detection or imaging step, the invention can detect the individual targets in a defined volume of the sample. Quantification can be accomplished manually by counting individual cells in a photographic or digital image or automatically by software analysis in the case of digital images. Integrating signal intensity over the sample can also be used to quantify the targets. Signal integration is particularly useful with samples containing high concentrations of targets or physically linked targets (e.g., filamentous fungi). In these cases, resolving coincident signals may not always be possible. When it is appropriate to use them together (e.g., when the levels of targets are low enough that dispersed targets can be distinguished), automated signal integration and particle counting provide a robust, and therefore preferred, quantification regime.

Decoding the signatures of labeled probe families allows identification of numerous categories of targets. An important goal of this step is to identify the category of targets in the sample by determining the signature of labeled category-binding molecules that have adhered to the sample.

Imaging control standards provides identification references and indicates that the assay is functioning correctly. Robustness and reproducibility are greatly enhanced by the ability to easily incorporate internal standards and controls in the invention. For example, when scanning a lower respiratory sample for 24 pathogens that commonly cause pneumonia, a set of internal standards comprising each of the pathogens can be scanned in parallel (e.g., see Example 1). Besides offering a comprehensive and highly redundant check of all reagents and procedures, the internal standards provide a set of reference signals to which sample signals are compared for identification.

The CCD camera-based imager, shown in FIG. 3, is a useful device for large area imaging using when fluorescence is used as the signal character. This device was used to collect the data for many of the examples below. Excitation light is provided by introducing light from a high intensity white light source (1000W Xenon arc lamp, Model A-6000, Photon Technology Incorporated, Monmouth Junction, N.J.) into a liquid light-guide (5 mm core diameter, Model 380, Photon Technology Incorporated, Monmouth Junction, N.J.). The liquid light-guide carries the light to an excitation filter-wheel (BioPoint FW, Ludl Electronics, Hawthorne, N.Y.) and directs the filtered beam (typically 9 mm in diameter) onto the detection surface containing the labeled targets. The device shown in FIG. 3 can detect labeled targets on various detection surfaces (e.g., microtiter wells, microscope slides, coverslips, and tubes with flat, optically clear, bottoms). The incident light strikes the detection surface inducing fluorescence in the signaling moieties that are bound to targets via category-binding molecules. A portion of the emitted fluorescent light is collected by a high-collection efficiency lens system and transmitted through an emission filter-wheel (BioPoint FW, Ludl Electronics) to a CCD Camera (Orca II, Hamamatsu, Bridgewater, N.J.). The design and construction of the optical train is based on principles and practices known to workers familiar with the art.

Experiments in the examples below use the instrument diagrammed in FIG. 3 equipped with an X-Y positioning Stage (BioPoint XY, Ludl Electronics) to move the sample vessel (e.g., a microtiter plate) over the excitation and collection optics (the stage is not shown in the figure). Image-Pro and Image-Pro add-ins control all instrument components and image acquisition. Filter wheels are managed with the ScopePro add-in (Media Cybernetics, Baltimore Md.), and the StagePro add-in (Media Cybernetics, Baltimore Md.) handles stage positioning, while the camera control is via the Hamamatsu Orca II driver (Hamamatsu, Bridgewater, N.J.). Image-Pro Plus is also used for Image-Processing and analysis as described below.

A low cost camera that captures a medium resolution image of the sample area can be used. For a typical infectious disease application, it is expected that each sample will have on the order of one target to 10,000 targets spread out over a 20×20 mm sample area. A single, non-filamentous, prokaryotic microbe is expected to appear as a point source less than 10 um in diameter. For routine tests carried out in cost conscious medical diagnostics laboratories, medium resolution cameras can be used. For example, inexpensive cameras with excellent sensitivity and noise characteristics (e.g, SenSys CCD from Roper Scientific) are readily available. These systems typically have resolutions of 500×500 or greater pixels. Imaging the 20 mm square sample area with a resolution of 500×500 pixels provide 250,000 pixels, more than sufficient to discriminate the majority of the one target to 10,000 targets expected in a typical assay.

The sensitivity of the imaging system can be increased by choosing a more sensitive camera (e.g., a camera cooled to a lower temperature, or a camera that uses a back-thinned chip). Alternatively, the detection sensitivity and resolution can be increased by implementing a line scanning system (e.g., BT Image Array; Hamamatsu). For line scanning, a linear CCD or photodiode array (e.g. 1×500 or 1×1000 pixels) is used to capture the image. The resolution in one dimension corresponds to the number of array elements, while the second dimension is generally captured by moving the sample slide perpendicularly under the linear array. Since there are fewer elements, similar sensitivity linear arrays are typically less expensive than area format CCD cameras.

Embodiments of the invention using white light illumination utilize spectral filters to provide an optimal excitation peak for each of the fluorophores. The white light spectrum is large, allowing a wide variety of fluorophores to be selected to eliminate emission spectrum overlaps. Typically spot sizes achievable with white light illuminators, e.g., 2 mm to 5 mm, are appropriate for large area imaging. Since filter changes are relatively simple, and can be automated, white light systems are very adaptable, allowing the same apparatus to be used for tests that use distinct sets of fluorophores.

The collection efficiency of the system shown in FIG. 3 is maximized by incorporating a custom designed collection optic consisting of two components: a collection objective and a focusing element. The collection objective has high collection efficiency ($\geq f\#/1.2$) and outputs a relatively collimated beam. The focusing lens captures the light output from the collection objective and focuses it onto the detection surface of the CCD. The optics are designed in two parts to allow a filter wheel to be inserted in the path of the collection lens. For certain embodiments of the invention, e.g. for some embodiments that do not require filter changes, it may be desirable to include a tapered optical fiber bundle for achieving high collection efficiency. The fiberoptic bundle contains fibers that collect light proximally to the sample and channel the light directly to a CCD chip. Alternatively, the invention can detect signals very sensitively using direct proximal detection in which the sample is applied directly or in close proximity to the CCD chip (for highest sensitivity to the back of a back-thinned CCD chip).

In addition to the white-light, multi-spectral system described above, we have also developed a simpler single-color fluorescence imaging system for non-magnified large area imaging. In this system, excitation light is provided by a 532 nm Frequency-Doubled Diode Laser (50 mW, Model#BWT-50E, B&W Tek, Newark, Del.). The system using angular illumination is shown in FIG. 3.

Since the detection systems shown in FIG. 3 are single color, filter wheels are not necessary. A single excitation filter removes harmonic spectra from the laser output (Model HQ532/1 Ox, Chroma Technology, Brattleboro, Vt.) and a single emission filter (Model HQ620/60m, Chroma Technology, Brattleboro, Vt.) allows only the specific fluorescent signals to pass to the CCD camera. These systems also use a less-expensive CCD camera (Model KX-2E, Apogee CCD, Auburn, Calif.) than the one described previously, to capture images. The instruments shown in these figures can easily be adapted to multicolor analysis by incorporating multiple lasers and filter sets.

Means for depositing targets on the detection surface can be incorporated in the detection system. For example, a magnetic station can be integrated into the instrument. A magnet (Dexter Laboratories) can be configured to deposit magnetic beads onto the bottom face of a 96-well format microtiter dish. Using a automated stage, the microtiter dish is moved into position over the magnet for a period of time sufficient to deposit the magnetic beads and associated targets onto the bottom face of the wells (generally several minutes is sufficient). The microtiter dish is then moved off the magnetic station and the wells are imaged individually.

Other means for selection can also be incorporated in the system containing the detection instrumentation. For example, a filtration station can be used to deposit targets onto filters that can then be imaged automatically. Similarly, targets can be deposited on the detection surface by centrifugation in an onboard centrifuge. Gravity selection of targets labeled with dense particles simply requires incubation within the detection instrument.

Other modules can be interfaced with or incorporated in the instrument system that includes the detection device. An automation module for handling sample vessels such as microtiter dishes are one example.

The CCD cameras incorporated in the invention are generally cooled to a temperature between $-5°$ C. and $-20°$ C., sufficient for integration times from ten seconds to about two minutes (depending on the camera sensitivity) with minimal camera noise build-up. Longer integration times generally give higher sensitivity by allowing the collection of the photons emitted from the fluorophores for an extended period. Long integration times are inappropriate for line scanning; however, there are back-thinned linear arrays available that have very high quantum efficiencies, increasing sensitivity.

The invention can also use interferometer-based spectral imaging for the detection and decoding of signals (Schrock, E., 1997, supra). Using this technique, light emitted or scattered by signaling moieties is split into two paths, passed thorough prisms (so that different wavelengths travel different distances), and allowed to recombine to create an interference pattern. Fourier analysis of the interference pattern generates a spectrograph for each point in the image.

Alternatively, photographic film can be used to inexpensively record images of the targets in a sample. When the signaling character is chemiluminescence, this approach is most easily implemented (e.g., see Example 15).

For embodiments of the invention that use imaging detectors, computer software identifies and quantifies the targets. In general the software: (1) corrects for illumination non-uniformity; (2) if necessary, corrects for fluorescence cross-talk through a deconvolution matrix; (3) if necessary, aligns images using registration marks imprinted on the substrate; (4) performs algorithms to distinguish targets from other signals; (5) assigns an identity to each imaged target in the sample; (6) calculates the total number of targets in each category; (7) images and records the sample bar code for sample identification; and (8) automatically saves the output data (including internal standard and sample data), images, and bar code to a database that can be queried via a web browser interface. Commercially available image analysis packages can be used to provide these functions. Software packages for multicolor image analysis can be used (e.g., Image-Pro, Media Cybernetics; MetaMorph, Universal Imaging, MatLab, The Mathworks).

Although the invention can enumerate individual dispersed targets, the targets may be physically linked (as in the case of filamentous fungi, for example) or may be overlapping, or coincident (as will occur frequently at high densities). Therefore, software analysis packages used with the invention preferably include modules that quantify targets by integrating the signal intensities for the signal signatures over the imaged area. The number of targets in the sample can often be determined by comparing the integrated signal intensity of the sample image to the average signal intensity of individual targets in the internal standard control. The software quantification module is preferably "tuned" for each type of target by comparing the output for numerous samples to "gold standard" methods. For example, samples containing a filamentous fungus are preferably quantified using a software module that has been calibrated by comparison to microscopic quantification. Or, for certain bacteria, quantification by microbiological culture or microscopic examination of stained bacteria can be used to calibrate the software. The examples below provide specific examples of software analysis of images obtained using the invention.

It is useful to outline here the software packages and methods that were used to analyze the fluorescence data collected in many of the examples that follow. The detection surface is imaged to determine the number of fluorescence-labeled complexes and/or the total fluorescent signal. The fluorescence was captured from the bottom of the assay container by a CCD camera and stored as a TIFF (Tagged Image File Format) image file that contains records of pixel locations and intensities. Three approaches were used to quantify the assay results. The total integrated signal of the imaged detection zone was determined by summing the fluorescent signal from all of the pixels. The integrated signal from the sample was compared to that of negative controls. Measuring the total integrated signal is especially useful for samples containing numerous targets. A second approach was to count the objects in the detection area. A third approach was to integrate the intensity of all of the pixels contained within the fluorescent objects (as opposed to summing the intensity of all of the pixels in the image). All image analysis was performed using Image-Pro v 4.0 (Media Cybernetics, Silver Springs, Md.).

Obtaining the total integrated signal was achieved by initially defining an area on the image (the area of interest) that represents the bottom of the container. Image-Pro allows the area of interest to be converted into a single object and other Image-Pro tools permit the total signal of the pixels represented in this object to be summed. A similar image from an assay container to which no target was added was then analyzed in the same way and used as a negative control. The negative control values were subtracted from the values of target containing samples. This removed both assay and electronic noise.

The second and third quantification methods used Image-Pro's object-finding utility. This utility joins contiguous pixels that have a value (signal) above an automatic or user-defined threshold. This establishes a contour line around the perimeter of the object. The perimeter pixels and those inside are defined as the object, and summing these pixel values results in the object integration value. The analysis software was then used to automatically count all the objects in an area of interest that represents the bottom of the sample container and, in addition, can calculate the integrated signal intensity of all objects found.

Using the IPP Image-Pro macro language, the above utilities can be automated to allow batch processing of several images at one time. In addition, the data can be manipulated with other user-defined IPP scripts. For example, objects below or above a certain size (area) or intensity can be included or excluded, which can be a useful tool for dust exclusion.

EXAMPLES

The examples below provide technical details for implementing various embodiments of the invention for use in conjunction with a range of applications and are not intended to be limiting.

Example 1

Large Area Imaging of Individual Bacteria Labeled with a Fluorescent DNA-Binding Stain Overview: This example demonstrates the use of the invention to detect individual bacterial cells on a porous membrane without magnification. $E.\ coli$ bacterial cell targets were labeled with a fluorescent nucleic acid stain, filtered through a membrane, and the fluorescent image captured with a CCD camera using large area imaging Experimental Methods:. A culture of $Escherichia\ Coli$ ATCC 8739 was grown in Trypticase Soy Broth (TSB, BD cat. #211822) for 18 hours at 37 C. A 1 ml aliquot of cells was spun down in a microcentrifuge and resuspended in an equal volume of water. The cells were killed by heating the 1 ml aliquot to 100° C. for 5 minutes. The nucleic acid stain Syber Green I (Molecular Probes; catalogue no. S-7563) was added to the killed cells to a final concentration of "10×". (The Syber Green I stock is defined as 10,000×). The stained $E.\ coli$ cells were serially diluted in water and filtered through 0.22 µm black polycarbonate filtration membranes (Osmonics catalogue no. K02BP04700) using a vacuum filtration device and a plastic funnel cup (Millipore Microfil V User Guide, PF07114, Rev A 3/00). Fluorescence was detected using the large area non-magnifying CCD Imager (described in step 6 above; FIG. 3) with an FITC optical filter set (Chroma/excitation 470/40 nm, emission 522/40 nm). Image-Pro Plus software, version 4.1 (Media cybernetics) was used to capture and process images from the CCD Imager.

Results: The left panel of FIG. 7 shows individual $E.\ coli$ cells stained with Syber Green I and imaged using large area non-magnified imaging. The number of fluorescent signals, visible as white spots, correlates well with the expected number of about 100 $E.\ coli$ cells, based on the dilution used and the area of the field of view. The right panel shows a negative control where "no cells" were filtered through the membrane and imaged in an identical manner.

Example 2

Large Area Imaging of Single Bacteria Stained with a DNA-Binding Fluorescent Dye Overview. In this example, large area imaging on a glass coverslip was used to detect single $E.\ coli$ bacterial cell targets that were labeled with a fluorescent nucleic acid stain. The stained cells were illuminated with white light and imaged with a CCD camera.

Experimental design. A culture of $Escherichia\ Coli$ MG1655 was grown in LB broth (BD; Sparks, Md.) for 18 hours at 37 C. The cells were fixed by heating a 1 ml aliquot of an 18-hour culture to 95 C for five minutes in a heat block. The nucleic acid stain, Syber Green I, (Molecular probes; cat. num.S-7563) was added to the fixed culture to achieve a 1:1000 dilution of the stain stock. (1 µl Syber Green I stock (10,000×) to 999 µl of heat fixed culture). The $E.\ coli$ cells were stained for 10 minutes. Then the cells were spun down in a microcentrifuge at 11700 g for 10 minutes. The supernatant was discarded and the pellet of cells was resuspended in an equal volume of $H_2O$ (type 1 quality). Stained cells were serially diluted to achieve concentrations ranging from of $10^8$ to $10^4$ cells per ml. Corning No. 1½ cover slips were coated with Poly-L-lysine by submerging slides in a 1:10 dilution (5 ml Poly-L-lysine in 45 ml type 1 $H_2O$) of Poly-L-lysine solution (Sigma Diagnostics; cat. num. P-8920). Once coated the cover slips were washed in $H_2O$ (type 1 quality) and were allowed to air-dry. A 5 µl aliquot of diluted stained cells was pipetted onto a Poly-L-lysine cover slip and dried at room temp (about 20 min). Fluorescence was detected by imaging using a CCD Imager (described in step 6 above; FIG. 3) with an FITC optical filter set (Chroma/excitation 470/40 nm, emission 522/40 nm). Image-Pro Plus software, version 4.1 (Media cybernetics) was used to capture and process images from the CCD Imager. Positive signals detected on the Imager were confirmed to be $E.\ coli$ by using an Axioplan II fluorescent microscope (Carl, Zeiss Inc., Thornwood, N.Y.) equipped with the same filter set.

Results: FIG. 8 shows that cells stained with Syber Green I were detected using large area non-magnified imaging. The fluorescence signals, visible as white spots, were shown to correspond to either single $E.\ coli$ cells or grouped cells by using high magnification fluorescence microscopy (1000×; FIG. 8).

Example 3

Large Area Imaging of Individual Bacteria Labeled by Hybridization to Fluorescently Labeled Oligonucleotide Category-Binding Molecules Overview. In this example, large area imaging was used to detect single $E.\ coli$ bacterial cell targets that were labeled by hybridization of cellular rRNA to a fluorescently labeled oligonucleotide category-binding molecule. The cells were imaged as in Example 2.

Experimental procedure. $E.\ coli$ cells were grown as in Example 2. Cells were fixed in a 2.5% solution of Formaldehyde in PBS for 30 minutes at room temperature. The cells were "washed" by centrifuging in a microcentrifuge for 10 min at 11,700 g followed by resuspending the pellet of cells in an equal volume of PBS. The cells were spun down as before, resuspended in 50% ethanol, placed at 20 C for 14 hours, and were washed as above with PBS. The cells were then spun down as before and resuspended in hybridization buffer (1M NaCl/50 mM EPPS/0.5% Tween 20/0.4 µg/µl yeast t-RNA/ 2% blocking agent, where the blocking agent was 100 mM Maleic acid pH 7.65/150 mM NaCl/10% Blocking Agent (Boehringer Mannheim)). The cells were then incubated at 49 C for 30 minutes (pre-hybridization step). FITC conjugated DNA ribosomal probe (1 µl; Synthetic genetics 5' FITC-GCTGCCTCCCGTAGGAGT SEQ ID NO: 3) was added and the cells were incubated at 49 C for 1 hour (hybridization step). After hybridization, the cells were washed with wash buffer (PBS-TB) and incubated at 49 C for 10 min. The wash step was repeated twice more for a total of three washes. Labeled cells (5 µl) were deposited on a Poly-L-lysine coated cover slip (described in Example 2) and imaged using a CCD imager (described in Step 6 of Detailed description section and shown in FIG. 3). Image-Pro Plus software, version 4.1 (Media cybernetics) was used to capture and process images from the CCD Imager.

Examination of the sample using a fluorescent microscope (1000×; FIG. 8) was used to confirm that the spots in the non-magnified digital image correspond to E. coli cells.

Results. After probing E. coli cells with FITC conjugated E. coli-specific rRNA oligonucleotide probes, individual cells were readily seen (FIG. 8) using the CCD imager. The fluorescence signals, seen as white spots, were shown to correspond to either single E. coli cells or grouped cells by using high magnification fluorescence microscopy (1000×; FIG. 8).

Example 4

Large Area Imaging of Single Bacteria Labeled by Hybridization to Fluorescently Labeled PNA Category-Binding Molecules Overview. In this example, large area imaging was used to detect single E. coli bacterial cell targets that were labeled by hybridization of cellular rRNA to a fluorescently labeled PNA category-binding molecule. The cells were imaged as in Example 2.

Experimental procedure. Cells were grown as in Example 2. The cells were prepared for hybridization and hybridized with PNA probes specific for E. coli as specified by the manufacturer in the PNA micro Dx Fish Reagent kit (Boston Probes; cat. num. KT11000). The labeled cells (5 µl) were spotted on a poly-L-lysine coated cover slip and imaged as in Example 2. Image-Pro Plus software, version 4.1 (Media cybernetics) was used to capture and process images from the CCD Imager.

Results. FIG. 8 shows that single bacterial cells tagged with fluorophore-labeled species-specific PNA probes were detected by large area CCD imaging without magnification. The white spots in the image obtained with the CCD were shown to correspond to either single E. coli cells or groups of several cells by analyzing the same sample using high magnification fluorescence microscopy (1000×; FIG. 8).

Example 5

Large Area Imaging of Single Bacteria Labeled by Binding to a Fluorescently Labeled Antibody Experimental procedure. Cells were grown as in Example 2. FITC labeled rabbit anti-E. coli polyclonal antibody (1:200 dilution; Biodesign; cat. num. C65110M) was added to dilutions of cells ranging from $10^5$ to $10^2$ cells per ml and allowed to incubate for 1 hr at room temperature. The cells were then "washed" twice by spinning down the cells by centrifugation (11,700 g for 10 min) and resuspended in PBT. The washed cells were then spotted on Poly-L-lysine coated cover slips as in Example 2. CCD imaging and microscopic confirmation were performed as described in Example 2. Image-Pro Plus software, version 4.1 (Media cybernetics) was used to capture and process images from the CCD Imager.

Results. FIG. 8 shows that single bacterial cells tagged with fluorophore-labeled category-specific antibody probes were detected by large area CCD imaging without magnification. The white spots in the image obtained with the CCD were shown to correspond to either single E. coli cells or groups of several cells by analyzing the same sample using high magnification fluorescence microscopy (1000×; FIG. 8).

Example 6

Large Area Imaging of Individual Live Bacteria Stained with a Fluorogenic Esterase Substrate Overview and objectives: In this example, large area imaging was used to detect individual live E. coli bacterial cell targets that were stained with a combination of fluorogenic esterase substrates (signaling moieties). The substrates can diffuse through the cell membrane of intact living cells where they become both fluorescent and charged when acted upon by esterase enzymes found in metabolically active cells. These charged fluorescent products can no longer passively diffuse through cell membranes and become trapped in intact cells. This technique can be useful when it is important to distinguish live cells from dead cells, as only cells with active esterases and intact cell membranes will stain properly. In this example, either live or dead E. coli cells were filtered through a black polyester membrane, incubated with the fluorogenic substrates fluorescein diacetate (FDA) and carboxyfluorescein diacetate (CFDA) and imaged using non-magnified large area CCD imaging.

Experimental Methods: E. coli ATCC 8739 was grown overnight in Tryptic Soy Broth (TSB, BD cat. #211822), and washed once by centrifuging a volume of cells, removing the supernatant, and resuspending the pellet in an equal volume of PBS. Dead cells were prepared by heating a 1 ml aliquot of washed cells to 100° C. for 20 minutes. Appropriate dilutions of both live and dead cells were made in PBS. Using a Millipore 1225 manifold, cells were filtered through black polyester membranes (Chemunex cat. #200-C2010-01) mounted on absorbent pads (Chemunex cat. #200-C3012-02). While still in the filtration manifold, the cells were overlayed with 500 µl filtered TSB and incubated for 60 min. at 30° C. The media was suctioned through the membrane, and replaced with 500 µl of a solution of 20 µM CFDA (Molecular Probes cat. #C-195), 10 µM FDA (Polysciences cat. no. 00615) in ChemSolB16 (Chemunex cat. #200-R2023-02) and incubated at 37° C. for 60 minutes. The reagents were suctioned through the membranes. The manifold was disassembled, polyester membranes were mounted on glass slides and allowed to dry. Fluorescent signal on the polyester membranes was captured using a CCD Imager (described in step 6 above; FIG. 3) with an FITC optical filter set (Chroma/excitation 470/40 nm, emission 522/40 nm). Image-Pro Plus software, version 4.1 (Media cybernetics) was used to capture and process images from the CCD Imager.

Results: FIG. 9 shows that live E. coli cells (left panel) are detected as bright fluorescent spots, while dead E. coli cells (right panel) do not have a detectable fluorescent signal. The number of spots in the field of live cells is about 400 and correlates well with the expected number of cells based on the dilution of cells added to the filter and the area of the field of view.

Variations. Other dyes that distinguish live or dead cells can be used. For example, other fluorogenic substrates, or DNA stains that can or cannot cross intact cell membranes can be used instead of or in conjunction with FDA and CFDA. Multiple stains and dyes can be distinguished by using multiple excitation and emission wavelengths for fluorescence detection. The spectrum of fluorescence associated with an object can be use to determine whether a cell is counted as live or dead. In addition, fluorogenic substrates that are specific for the biochemical activity of a particular type of bacteria can be used to determine its presence. For example a fluorogenic β-galactosidase substrate can be cleaved to its fluorescent product by β-galactosidase, which is specific to coliforms.

Example 7

Large Area Non-Magnified Imaging of Individual Bacteria Labeled with Highly Fluorescent Particles Overview. In this example, large area imaging was used to detect individual *E. coli* bacterial cell targets that were labeled with highly fluorescent particles. The individual bacteria: particle complexes were illuminated with light of 3 distinct wavelengths and imaged with a CCD camera as in Example 2.

Experimental procedure. A culture of *Escherichia Coli* MG1655 was grown in LB broth (BD, Sparks, Md.) for 18 hours at 37 C. *E. coli* cells were added to a microtiter plate with an optically clear bottom (Greiner America, Inc.; cat. num. 655896) to a final concentration of $10^5$ cells per well ($10^5$ cells per 50 µl). The microtiter plate was then heated to 95 C on a heat block until the solution-containing the cells had completely dried. The nucleic acid stain, Syber Green I, (Molecular probes; cat. num. S-7563) was added to the fixed culture to achieve a 1:1000 dilution of the stain stock. (1 µl Syber Green I stock (10,000×) to 999 µl of heat fixed culture). After ten minutes of exposure to the stain, the cells were "washed" twice with water (200 µl for each wash, followed by aspiration). Undiluted sheep serum (Fitzgerald; cat. num. 88-NS55) was added to each well and incubated at room temperature for 30 minutes. The wells were aspirated and Rabbit anti-*E. coli* antibodies (Biodesign; cat. num. C65110M), diluted 1:500 in sheep serum, were then added to the appropriate wells and incubated for two hours at 37 C. The wells were then washed three times, twice with wash solution 1 (PBT) and once with wash solution 2 (PBS-B). Next, a biotin labeled Goat anti-rabbit IgG antibody (Jackson; cat. num. 111-005-003) diluted 1:500 in sheep serum was added to appropriate wells. The antibody was allowed to incubate for 2 hours at 37 C. The wells were washed twice with wash solution 1 and once with wash solution 2. Avidin coated Texas Red Fluorescent particles (0.45 µm; Spherotech; cat. num. VFP-0562-5) were added to all wells to a final concentration of $10^5$ particles per well. The plate was incubated at room temperature overnight. The wells were then washed with solution 1 five times followed by two washes with water. Fluorescence was detected by imaging on a CCD imager (described in Step 6 of Detailed description section and shown in FIG. 3) with FITC optical filter set (Chroma/excitation 470/40 nm, emission 522/40 nm) for Syber Green I, Texas Red optical filter (Chroma excitation 560/55, emission 645/75) for the avidin coated Texas red particles and GFP Long Pass filter set (Chroma/excitation 470/40, emission 500LP) for viewing both Syber Green stained cells and Texas Red Particles. Image-Pro Plus software, version 4.1 (Media cybernetics) was used to capture and process images from the CCD Imager. Positive signals detected on the Imager were confirmed to be individual *E. coli* cells by using an Axioplan II fluorescent microscope (Carl, Zeiss Inc., Thornwood, N.Y.) equipped with the same filter sets.

Results. FIG. 10 shows detection of individual *E. coli* cells tagged with category-specific antibodies and fluorescent particle signaling moieties using large area, non-magnified, CCD-based imaging. The fluorescence signals, visible as white spots, were shown to correspond to either individual *E. coli* cells with multiple particles or groups of cells surrounded with particles by using high magnification fluorescence microscopy (1000×; FIG. 10). These were avidin-coated particles. Cells were labeled with group-specific antibodies, then with anti-antibody-biotin, then avidin particles.

Example 8

An Homogenous Immunoassay that Detects Individual Bacteria Using Non-Magnified Large Area Imaging Objective: This example demonstrates immunoassay methods for detecting individual bacterial cells, including a user-friendly homogenous immunoassay for detecting small numbers of pathogenic *E. coli* O157:H7 cells.

FIG. 11 diagrams the homogenous assay approach used here and in subsequent examples. Homogenous immunoassays are favored in diagnostics because they are simple, fast, inexpensive, and easily automatable. (Homogenous, in the sense used here, means that binding of the antibody and analyte is detected after mixing the reagents and sample, but without physically removing—e.g., by aspiration—the unreacted category binding molecules from the category binding molecule:target complexes). However, most homogenous immunoassays are insensitive (compared to methods like nucleic acid amplification), non-quantitative, and non-multiplexed (or very shallowly multiplexed). Here, in contrast, the invention is used to make a homogenous immunoassay that is sensitive, quantitative, and multiplexed.

In the example, a sample containing *E. coli* O157:H7 was mixed with magnetic and fluorescent particles, magnetically selected, and imaged using non-magnified large area CCD imaging. No washing steps were required.

Experimental Methods: Anti-*E. coli* magnetic particles were made by coupling magnetic particles with active tosyl-groups (Dynal, Oslo, Norway, Cat. No. 140.03) to polyclonal antibodies raised against *E. coli* O157:H7 (BioTrace affinity purified; Kirkegaard & Perry Laboratories, Gaithersburg, Md., Cat. No. 01-95-90) Magnetic particles (30 mg/ml; 100 µl; Dynal, Oslo, Norway, Dynaparticles M-280 Tosylactivated Cat. No. 140.03) were washed in PB (three wash repetitions, 1 ml each) in a microcentrifuge tube (1.5 ml) using a magnetic separation of the particles followed by removal of the supernatant (all magnetic separations in this example, except where noted, were carried out using a device from Polysciences Inc.; cat. no. 8 MB4111S). Particles were resuspended in PB (70 µl). Affinity purified polyclonal antibody raised against *Escherichia coli* O157:H7 (60 µg; Kirkegaard & Perry Laboratories, Gaithersburg, Md., Cat. No. 01-95-90) was purified by passing the solution obtained from the manufacturer through a centrifugal filtration device (Millipore Microcon Model No. YM-30; nominal molecular weight limit 30,000 Daltons) according to the manufacturer's instructions. The antibody, which was collected on the filter, was resuspended in PB (30 µl). Antibody (30 µl) was combined with magnetic particles (70 µl) in a microcentrifuge tube (1.5 ml) and vortexed briefly. The reaction was incubated at 37° C. for 20 minutes using rotation (about 30 rpm unless otherwise noted). After 20 minutes BSA (IgG Free) was added to a final concentration of 0.1% and incubated overnight at 37° C. with rotation. The magnetic particles were washed twice (1 ml each; using magnetic separation) with PBS-B. The magnetic particles were resuspended in buffer (0.2M Tris pH 8.5 supplemented with 0.1% (w/v) BSA (IgG free)) and incubated for 4 hours at 37° C. with rotation. Finally, the magnetic particles were washed twice (in PBS-B using magnetic separation) and resuspended (the final concentration was 1% solids in PBS-B).

Anti-*E. coli* fluorescent particles were made by coating fluorescent particles (Fluospheres; Molecular Probes, Sulfate Microspheres, 1 µm, Red fluorescent (580/605) Cat No. F-8851) by passive adsorption of the same antibody used to coat the magnetic particles. Rabbit anti-*Candida albicans* antibody (1.25 nmol type A polyclonal purified IgG; Biodesign Cat. No. B65411 R, Lot No. 3B03200) antibody was purified as described above. To passively adsorb antibodies to surface sulfate groups, particles (62.5 µl; 2% solids; Molecular Probes Cat. No. F8851, 1 um, red fluorescent (580/605)) were washed by repeatedly (3 repetitions) by centrifugation (5 min; 10,200×g; Eppendorf Centrifuge Model 5417C, Eppendorf Swinging Bucket Rotor Model A-12-11) and resuspension of the particle pellet (1 ml PBS/0.15 M NaCl). The particle pellet was resuspended in PBS (125 µl, for a concentration of 1% solids) followed by dropwise addition of purified antibody (1.25 nmol for a ratio of 1 nmol antibody/mg particles) with vortexing. The suspension was incubated with rotation, for 2 hours at 25° C. followed by overnight incubation at 4° C. Particles were washed (3 repetitions as above, but with resuspension after the centrifugations in PBS-TB), resuspended in PBS-TB (200 µl), and incubated (30 minutes, 25° C.) with rotation. Particles were washed twice as above and resuspended in PBS-TB (125 µl for a concentration of 1% solids).

Following particle preparation, an inoculum (200 µl of an overnight culture) of *E. coli* O157:H7 (Strain DEC 3B, Dr. Tom Whittam, Pennsylvania State University) was cultured (200 ml LB; 4 hr; 250 rpm, 37° C.) and titrated by plating serial dilutions as follows. The culture was immediately placed on ice to prevent further growth. A 10 ml aliquot was fixed by addition of formalin (final concentration=2.5%) directly into the media containing the bacteria. Serial dilutions of aliquots (100 µl) of the culture were made (1:10 in PBS) and an aliquot of each dilution was plated to determine the concentration of bacteria in the stock solution of fixed bacteria. This stock solution was diluted to achieve a concentration of $1\times10^6$ bacteria/ml. The stock solution (1 ml) was washed by centrifugation (950×g) and resuspension (1 ml; PBS) followed by resuspension of the bacterial pellet in PBS (1 ml).

A mixture of the anti-*E. coli* magnetic and fluorescent particles ($1\times10^6$ of each type per 10 µl) was sonicated (1 min; setting 8; Fisher Scientific 550 Sonic Dismembrator). Wells of a 96-well glass bottom plate (Whatman Inc., Clifton, N.J., Cat. No. 7706-2370). were treated with Gel Slick (Biowhittaker Molecular Applications, Cat. No. 50640) for 1 minute. The gel slick was removed by aspiration and washed three times by the addition of sterile water to each well followed by aspiration. The wells were allowed to dry for 5 minutes before the sample was added. To the wells were added buffer (PBS-TB; 115 µl in each of 6 wells) or blood (115 µl in each of 6 wells), followed by the addition of the sonicated particle slurry (10 µl in each well). Fixed *E. coli* O157:H7 cells ($1\times10^3$ in 10 µl) were added to three of the wells that contained buffer and three of the wells that contained blood. The wells were sealed using a storage mat (Corning COSTAR, Cat. No. 3080). The samples were incubated with rotation (30 rpm; Dynal Sample Mixer, Oslo, Norway, Cat. No. 947.01) for 1 hour at room temperature. The magnetic particles were captured on the detection surface at the bottom of the wells by using a magnetic separation device (Dexter Magnetics, Silver Spring, Md., LifeSep, Cat. No. 2501008).

To test the efficacy of a homogenous immunoassay to detect individual bacterial cells in blood, the immunoassays performed in mouse blood were imaged using the CCD imager shown in FIG. 3A. Images of the detection area, i.e., the optically clear bottom of the microtiter wells, were captured (20 msec exposures) using a Texas Red filter set (excitation 560/55, emission 645/75) and Image-Pro Plus digital imaging software (Media Cybernetics, Silver Spring, Md.). Next, to test the efficacy of immunoassays incorporating wash steps, all of the samples (i.e., those containing buffer and those containing blood that were previously imaged) were washed with buffer (PBS-TB; 200 µl; 3 washes achieved by pipetting up and down 10 times). During the washing steps, a magnetic separation device (Polysciences, Inc., Warrington, Pa., Cat. No. 8 MB4111S) was used to capture and secure the magnetic particles, and complexes containing magnetic particles, to the surface of the wells. Each wash was followed by magnetic selection (5 min) and aspiration of the supernatant. The samples were resuspended in PBS-TB (200 µl) containing the fluorescent DNA intercalating dye YOYO-1 (10 nm; Molecular Probes, Cat. No. Y-3601) and magnetically selected (using the device by Dexter Magnetics). The 96-well plate was imaged using the CCD imager as described above. Following CCD imaging the plate was inverted and examined using fluorescence microscopy (Axioplan II fluorescent microscope, Carl, Zeiss Inc., Thornwood, N.Y.). The images (in triplicate; 20 msec exposures) obtained in the homogenous assay in blood (i.e., the images obtained before the washing steps) were quantified using software analysis. A macro (Image-Pro Plus) was used to circumscribe a region of interest containing the detection area contained within the perimeter of each well. Object counting and object integrated intensity within the circumscribed area was performed using a series of Visual Basic scripts to analyze the Image-Pro Plus analysis data (as described in Step 6 of the Detailed Description section). Two bar-graphs representing the analysis for the homogenous assay in blood were plotted (FIG. 12; Microsoft Excel; Microsoft Corp.). Identical threshold value settings were used for the samples that were compared in each experiment.

Results: FIG. 12 shows the results of immunoassays that sensitively detect *E. coli* by non-magnified large area imaging. Magnetic and fluorescent particles coated with category-specific antibodies were first bound to the bacterial cells, the complexes were then drawn to the bottom surface of the optically clear well (the detection area) using magnetic force, and the complexes were detected using non-magnified large area CCD-based imaging. FIG. 12 compares the results of the homogenous immunoassay in blood (bottom panel) and the non-homogenous (washed) immunoassay in both blood (top panel) and in buffer (middle panel). The simplest format, the homogenous immunoassay, effectively detected cells with excellent signal to background ratios (see quantification of the homogenous assay in the figure (bar graphs in bottom right panels).

The two leftmost panels show the images obtained using non-magnified, large area CCD-based imaging. All three assays gave strong signals when *E. coli* were present (left panel) but low background signals when *E. coli* were not added. Further confirmation that the signals obtained using the CCD camera corresponded to *E. coli* cells coated with particles were obtained using high power fluorescence microscopic analysis (1000×; top two rows, rightmost two columns). Images are shown of typical complexes containing *E. coli* cells, magnetic particles, and fluorescent particles. Two images of each complex were made using two filter sets: one for visualizing DNA fluorescence (Syber Green I; second panel from right) and one for visualizing the fluorescent particles (rightlmost panel). The figure shows that the complexes consist of an *E. coli* cell surrounded by magnetic and fluorescent particles.

The percentage of *E. coli* cells selected by the immunoassay is consistently greater than 95%, as shown by experiments measuring the unselected material and microscopic comparisons of the sample before and after the immunoassay (not shown here). Microscopic surveys showed that the selected complexes containing *E. coli* cells were associated with an average of 3.33 fluorescent particles per cell. (n=10; minimum=2; maximum=10).

Quantitative analysis of the images was carried out by software that counts the number of fluorescent objects (FIG. 12, bottom panel, left bar graph) and that integrates the intensity of all of the objects (FIG. 12, bottom panel, right bar graph). In both measurements, the sample containing *E. coli* (1000 cells) scores significantly higher than the sample containing no *E. coli*. Note, that the total objects found in the software analysis ($1.5 \times 10^4$ objects) is about 15 times greater than the number of cells in the sample (1000). This observation is consistent with the microscopic analysis of the complexes described in the following paragraph. By software analysis, the sample containing *E. coli* had 75 times more objects and about 400 times the integrated intensity compared to the sample without *E. coli*. Both analyses show that the signal obtained with $1 \times 10^3$ *E. coli* cells in a sample more than three standard deviations above the signal generated from the no cell control.

Although complex formation is strongly dependent on the presence of *E. coli* cells in the immunoassay (as can be seen by comparing the two leftmost columns of the figure), microscopic examination reveals that many of the complexes lack *E. coli* cells. This is a consistent feature of the *E. coli* immunoassay. It is possible that the formation of cell-less complexes is due to the presence of non-cellular structures, such as fragments of *E. coli* flagella that are not visible in the microscope. Alternatively, it is possible that large particle:cell complexes break apart during the assay yielding some fragments with cells and some without cells. Besides complexes containing a single cell and complexes lacking cells, microscopic analysis revealed that some of the complexes comprised more than one cell.

Based on these results, the simple, rapid, and user-friendly homogenous immunoassay, combined with non-magnified large area imaging detects and identifies low numbers of bacteria in blood.

Variations. As shown in subsequent examples, the methods of this example can be applied to detect other targets in numerous sample types (biological and non-biological). For example, by using the appropriate antibodies to coat particles, the methods described in the example can be applied to detecting specific viruses (e.g., HIV), bacteria, fungi, parasites, proteins, small molecules, or human cells (such as cancer cells or infected cells).

Alternative formats can also be used in conjunction with the methods of the example. By appropriate reconfiguration of the magnet and optics modules described for the instrument described in this example, a variety of containers can be accommodated. For example, samples of larger or smaller volume can be used in other types of vessels (e.g., test tubes with optically clear bottoms and/or sides).

Various methods of labeling category-binding molecules are also possible. Particles of various sizes and with various signaling properties can be used. Fluorescent particles can be used that contain one or more fluorescent dyes with various spectral properties or that contain fluorescent cascades (e.g., Transfluorospheres from Molecular Probes). Other types of fluorescent particles, such as quantum dots can also be used. Particles that scatter light (e.g., RLS, PRP, or nanogold particles) can be substituted for the fluorescent particles in this example. Particles labeled with visible dyes (e.g., dyed polystyrene particles or dye-containing liposomes) can be used. Alternatively, antibodies, or other types of category-binding molecules, can be directly labeled with a fluorophore (or other signaling moiety). Such directly labeled antibodies can coat the targets making them detectable. Similarly, category-binding molecules can be directly labeled with selection moieties. For example, antibodies can be coupled to ferritin, a magnetic selection moiety.

Staining of the target can also be used for detection instead of fluorescent particles. In this case, the specificity is conferred by the selection moiety, the category-specific magnetic particles. For example, nucleic acid stain (e.g., propidium iodide, STYO 17, or DAPI) can be used to non-specifically label targets. Targets that bind to pathogen-specific magnetic particles are selectively brought to the bottom of the sample well and visualized by virtue of the non-specific stain. Category-specific staining procedures can also be used (e.g., see Example 9).

Alternative methods for coupling antibodies to particles are also possible. Such methods are known to those familiar with the art and are detailed in numerous references (e.g., Hermanson, *Bioconjugate Techniques* (Academic Press, San Diego, Calif., 1996); and Edwards, ed. (1999). *Immunodiagnostics: A Practical Approach*. Oxford: Oxford University Press).

Other forms of antibodies can also be used (e.g., Fab, Fab', Fv). Different category-specific antibodies can be used in combination. For example, in the application above, antibodies for different *M. tuberculosis* antigens can be bound to separate yellow-green fluorescent particles and then combined. Alternatively, different antibodies can be bound to the same particle. Other types of category-binding molecules (e.g., lectins, polypeptides, or ligands) can be substituted for antibodies.

Example 9

Large Area Imaging of Acid Fast Stained Mycobacteria in "Simulated Sputum"

Background: Tuberculosis caused more than 3 million deaths in 1995, about 3 times the number of AIDS/HIV deaths in that year. About 25% of avoidable deaths in the developing world are caused by *Mycobacterium tuberculosis* infections. Unfortunately, diagnosing *Mycobacterium tuberculosis* infections is problematic. Consequently, there is a great worldwide unmet need for a diagnostic test that is inexpensive, fast, simple, and rapid. The acid-fast bacillus (AFB) testing method that predominates in the developing world, where the majority of tuberculosis cases occur, is insensitive and thus misses a large fraction of infected patients. As a result, untreated tuberculosis patients with false negative test results continue to transmit this very contagious disease in the community. The AFB test is also time consuming and laborious, as many microscopic fields must be examined carefully for the presence of stained cells. Culture, the testing gold standard, is extremely slow—it generally takes weeks to grow colonies of Mycobacterium tuberculosis in the laboratory. New amplification-based molecular tests are rapid and sensitive, but high expense inhibits adoption of the tests even in the wealthiest nations.

Objective: In this example, the invention was used to construct a rapid and sensitive fluorescent acid-fast bacillus test. The test achieves its sensitivity and labor savings by imaging (in less than 1 second) a much larger area than would be examined in the microscopy-based version of the test.

Experimental Methods: Prepared slides (Remel; Cat. No. 40-146) containing a smear of "simulated sputum" and mycobacteria (Mycobacteria scrofulaceum) that are very similar to the agent that causes tuberculosis were stained with auramine O and auramine-rhodamine. Each slide contained a positive (M. scrofulaceum) and a negative control (E. coli) in a simulated sputum smear. Slides were prepared using either the TB Auramine-Rhodamine Stain (Remel Cat. No. 40090) or the TB Auramine O Staining Kit (Remel Cat. No. 40086). Slides were passed briefly four times through a flame. The slides were flooded with either Auramine O Stain or Auramine-Rhodamine Stain and incubated at room temperature for 15 minutes followed by 3 rinses in deionized water. Slides were decolorized with TB decolorizer (Remel Cat. No. 40-107) for 2 minutes followed by 3 rinses in deionized water. Slides were flooded with potassium permanganate counterstain (Cat. No. 40-092) for 3 minutes followed by 3 rinses with deionized water. The slides were then air dried. Auramine-Rhodamine stained slides were imaged using fluorescence microscopy (Axioplan II fluorescent microscope; Carl, Zeiss Inc., Thornwood, N.Y.; Cy3 channel: excitation 546/11, emission 567/15, 400× magnification; 500 msec exposure) and by non-magnified large area imaging using a CCD imager (as described in Step 6 of Detailed description section and shown in FIG. 3A; using a filter set optimized for TRITC: (excitation 545/30, emission 610/75), 1 sec exposure).

Results: FIG. 13 shows that fluorescence-based large-area imaging detects individual Mycobacteria cells stained with the Auramine-Rhodamine reagent. The fluorescent signals in the large area image were shown to correspond to individual Mycobacterium cells or small clusters of cells by using high magnification fluorescence microscopy (1000×; FIG. 13). E. coli subject to the same procedure did not show significant fluorescence.

Variations. Differentiation of M. tuberculosis infection from other mycobacterial species (e.g., M. avium) is frequently important. Example 27 presents a variation of this example that identifies M. tuberculosis specifically using category-specific anti-M. tuberculosis antibodies.

Example 10

Rapid Antimicrobial Susceptibility Testing Using Large Area Imaging

Overview. The goal of antimicrobial susceptibility testing is to determine which of various antimicrobial therapies is most effective at neutralizing a pathogen isolated from a patient. Rapid antimicrobial susceptibility testing is a critical—sometimes life-saving—application in infectious disease diagnostics. Timely and efficacious choice of antimicrobial therapy depends on the results of antimicrobial susceptibility testing.

After identification, infectious agents are generally tested for their ability to withstand various concentrations of several antimicrobial compounds. Drawbacks of entrenched methods are long turnaround time for results (most often 2 to 4 days from sample acquisition time). This is especially problematic for time-critical medical emergencies such as central nervous system and bloodstream infections.

In this example, large area imaging was used to rapidly detect the susceptibility of model E. coli cells to the antibiotic tetracycline. Cells of two strains, one resistant and one sensitive, were tested for their ability to grow in a period of several hours in the antibiotic. Growth was detected by large area imaging of individual cells stained with a fluorescent nucleic acid stain.

Experimental procedure. Tetracycline susceptibility testing was performed on two E. coli strains: MG1655 (sensitive strain) and MG1655/pLAFRI (resistant strain) following the broth dilution method outlined in the NCCLS guidelines for anti-microbial susceptibility (Methods for Dilution Antimicrobial Susceptibility Tests for bacteria That Grow Aerobically, Fifth edition, NCCLS, M7-A5 Vol. 20 No. 2, January 2000). At six time points following inoculation of the test media (0, 1, 2, 4, 6, and 18 hour), 1 ml aliquots were taken of both the resistant and sensitive strain cultures from each tetracycline dilution (0 µg/ml to 320 µg/m 1 and 0 µg/ml to 4 µg/ml for the resistant and sensitive respectfully). Also at these times points both a visible turbidity growth check and a plate count were performed. The turbidity check was performed according to NCCLS broth dilution guidelines. A "+" was recorded for a turbid culture and a "−" for non-turbid culture. The 1 ml aliquots were then stained with Syber Green I as in Example 2. Aliquots (10 µl) of the stained cells were placed in separate wells (with optically clear bottoms) of a 96 well plate (Greiner America, Inc.; cat. num. 655896), which contained 90 µl of water (Type I quality). The plates were spun in a centrifuge (Beckman Allegra) for 10 min at 600 g and then imaged. Fluorescence was detected by imaging using a CCD imager (described in Step 6 of Detailed description section and shown in FIG. 3) with an FITC optical filter set (Chroma/excitation 470/40 nm, emission 522/40 nm). Image-Pro Plus software, version 4.1 (Media cybernetics) was used to capture and process images from the CCD Imager. Positive signals detected by large area imaging were confirmed to be single E. coli cells by using an Axioplan II fluorescent microscope (Carl, Zeiss Inc., Thornwood, N.Y.) equipped with the same filter set.

Results. FIG. 14 shows the results of the antimicrobial susceptibility test using individual cell detection and quantification by non-magnified large area imaging. Comparing the bottom two panels of the figure shows that for determining cell growth, non-magnified large area imaging is comparable to culture. (Quantification by counting colonies on agar plates also gave comparable results). The minimum inhibitory concentration of antibiotic (MIC) as determined by CCD imaging and by culture were comparable, but somewhat lower than the MIC determined after overnight growth (second panel from the top of FIG. 14).

The figure demonstrates that this rapid imaging method easily discriminates an antibiotic resistant strain (right panel of FIG. 14) from an antibiotic sensitive strain (left panel of FIG. 14). After 4-hours of growth, dramatic growth of the resistant strain was evident in an antibiotic concentration (64 µg/ml) that was several hundred times than that that inhibited growth of the antibiotic sensitive strain (0.25 µg/ml). The results were comparable when assayed by CCD imaging (bottom panel), liquid culture (second panel from bottom), or colony counting (not shown).

Thus, after a 4-hour incubation, large area non-magnified imaging provides antimicrobial susceptibility testing results comparable to both the culture assays (scored as turbidity) and plate counts.

Advantages and applications. There are several clinically important advantages to the method described here over traditional antimicrobial susceptibility testing techniques. By labeling with category-specific binding molecules (e.g., see Example 2-Example 6), identification of the bacteria can be achieved at the same time as quantifying bacterial growth in the presence of an antibiotic. The ability to detect and quantify small numbers of identified cells would meet an important unmet diagnostic need: antimicrobial susceptibility testing in clinical samples without bacterial subculture. Achieving this goal would provide great patient benefit by significantly decreasing the time needed to determine the appropriate antimicrobial therapy.

Example 11

Large Area Detection of Individual Fluorescently Labeled *Candida albicans* Cells that Have Been Magnetically Selected Objective. This example demonstrates the utility of non-magnified large area imaging to detect individual cells that have been magnetically selected and deposited in a detection zone at the bottom of a microtiter plate. *Candida albicans* is a common human pathogen that causes diseases including blood-borne infections and vaginal yeast infections. In this example, *C. albicans* cells were stained with a fluorescent nucleic acid stain and labeled with a rabbit IgG anti-*Candida albicans* antibody, then mixed in the well of a microtiter plate with magnetic particles coated with anti-rabbit IgG antibodies. Application of a magnetic field causes the cell:particle complexes to become arranged on the bottom of the well. Cells were then detected using CCD-based non-magnified large area imaging.

Experimental procedure. *Candida albicans* strain 10453 (American type Culture Collection, Manassas Va.) was grown in YM medium (BD, Sparks, Md.) for 18 hours at 22° C. Cells were fixed in 2.5% solution of formaldehyde in PBS for five minutes, washed twice in PBS-B, and then stained and labeled with YOYO-1 (1 µM) nucleic acid stain (Y-3601 Molecular Probes, Eugene, Oreg.) and a rabbit anti-*Candida albicans* polyclonal antibody (B65411R, Biodesign International, Saco, Me.) for 30 minutes. Cells were then washed three times in PBS-TB to remove unbound stain and antibody. An aliquot of cells was mixed with a suspension of magnetic particles with surface-bound goat anti-rabbit IgG antibodies (8430050, Polysciences Inc., Warrington, Pa.) in PBS-TB buffer in the wells of an optically clear, flat, glass-bottomed microtiter tray (Uniview; Cat. #7706-2370, Whatman, Inc. Ann Arbor, Mich.). After 15 minutes, a magnetic field was applied using a magnetic ferrous block (Cortex Biochem, Inc., San Leandro, Calif.) such that the magnetic particles were caused to align substantially evenly over the surface of the bottom of the well. An image of the bottom of the well was captured using the CCD imager (described in Step 6 of Detailed description section and shown in FIG. 3) using the FITC filter set (480/40 nm excitation, 535/50 nm emission; Chroma Technology Corp., Brattleboro, Vt.) and MetaMorph image capture software (Universal Imaging Corp., West Chester, Pa.). Confirmation that discrete signals seen in large area imaging corresponded to single cells was achieved using high magnification microscopy at 1200 times magnification using a Zeiss Axioplan II fluorescent microscope, Carl Zeiss Inc., Thornwood, N.Y.) using the same FITC filter set.

Results. FIG. 15 shows that non-magnified large area imaging of microtiter tray reaction wells containing cells gave punctate fluorescencent signals. These fluorescent signals were shown to correspond to individual *Candida albicans* cells or small groups of cells by using high magnification (1200×) fluorescence microscopy of the same reaction wells. In contrast, wells containing no cells or wells containing unstained cells (negative control wells) presented no (or very few) positive signals. The small number of fluorescent objects in the negative control images was likely to be due to dust particles or other non-biological material.

Example 12

Large Area Detection of Individual *Candida albicans* Cells Specifically Bound to Fluorescent and Paramagnetic Polystyrene Particles Objective. In this example, individual *C. albicans* cells were detected using non-magnified large area imaging following separation with cell-specific paramagnetic particles and labeling with *C. albicans*-specific fluorescent particles.

Experimental procedure. The following mixture was made in wells of an optically clear, flat, glass-bottomed microtiter tray (Uniview 7706-2370, Whatman, Inc., Ann Arbor, Mich.): PBS-TB buffer containing YOYO-1 (50 nM), $5 \times 10^7$ magnetic particles (MEO3N 1 µm diameter; Bangs Labs Inc., Fishers, Ind.) with surface-adsorbed rabbit anti-*Candida albicans* polyclonal antibody (B65411R, Biodesign International, Saco, Me.), as previously described in example 6, and $5 \times 10^7$ fluorescent particles (Fluospheres F-8821, 1 µm diameter, red fluorescent, Molecular Probes, Eugene, Oreg.) with the same antibody covalently coupled to the surface using standard EDAC coupling chemistry. To covalently couple antibodies to particles, fluorescent carboxylated particles (1 µm, 0.25 ml, 2% solids, Red (580/605), polystyrene, Molecular Probes Cat No. F-8821) were washed in MESB (2 ml) by centrifugation (5 min; 11,000×g; Eppendorf Centrifuge Model 5417C, Swinging Bucket Rotor A-12-11) at room temperature and resuspended by vortexing and pipetting. In coupling experiments using magnetic particles, washing was performed using SPHERO™ FlexiMag Separator Jr. device (Spherotech, Cat No. FMJ-1000) which enabled separation of magnetic particles from a suspension in 5 minutes. Particle washing was repeated twice followed by resuspension of the particles in MESB (500 µl; for a concentration of 10 mg/ml). Freshly prepared EDAC (Sigma Cat No. E-6383) was added to a final concentration of 0.2 mg/ml and mixed gently at room temperature for 5 minutes. To this suspension, rabbit anti-*C. albicans* antibody (5 nmol; type A polyclonal; Biodesign Cat No. B65411R, Lot No. 3B03200; purified as described in Example 8) was added dropwise with vortexing and incubated for 2 hours at room temperature with rotation (about 30 rpm). Particles were washed four times in MESB by centrifugation as described above. Particles were resuspended in MESB containing ethanolamine (0.03%; Sigma Cat No. E9508) and incubated for 30 minutes at room temperature with rotation. Particles were washed four times in MESB by centrifugation as described above, followed by three washes in 0.1M sodium acetate pH 4.0. Lastly particles were washed two times in PBT and resuspended to 1% solids in PBT.

*Candida albicans* cells suspended in PBS-TB buffer were added such that the final reaction volume was 200 µl. The mixture was incubated on a shaker for 60 minutes. Any unbound fluorescent particles were separated from the magnetic particle complexes by three 200 μl PBS-TB buffer washes following application of a magnetic field using an array of neodinium-iron-boron magnets arranged to interface with 96-well microtiter trays (8 MB4109S Polysciences Inc., Warrington, Pa.). Fluorescence was detected by non-magnified large area imaging using the CCD imager (described in Step 6 of Detailed description section and shown in FIG. 3) with optical filter sets appropriate for the red fluorescent particles (Texas Red filter set, 560/55 nm excitation, 645/75 nm emission; Chroma Technology Corp., Brattleboro, Vt.) and the nucleic acid-binding dye YOYO-1 (FITC filter set, 480/40 nm excitation, 535/50 nm emission). The presence of fluorescent particles co-purified with the magnetic particles indicates the presence of *Candida albicans* cells. Positive signals detected on the CCD imager were confirmed to be complexes of cells, fluorescent particles, and magnetic particles by using an Axioplan II fluorescent microscope (Carl Zeiss, Inc., Thornwood, N.Y.) equipped with the same Texas Red filter set to view the fluorescent particles and a FITC filter set to view the nucleic acids of YOYO-1-stained cells. Images were captured using Image-Pro Plus image capture software (Media Cybernetics, Silver Spring, Md.) using a 100 ms exposure time.

Results. FIG. 16 shows that non-magnified large-area imaging of reactions containing cells gave punctate fluorescencent signals while reactions without cells gave no such signals. These fluorescent signals were shown to correspond to red fluorescent particles surrounding single YOYO-1 (green)-stained *Candida albicans* cells (or small groups of cells) by using high magnification fluorescence microscopy of the same reaction wells.

Example 13

Large Area Detection of Individual *Candida albicans* Specifically Bound to Fluorescent Antibodies and Magnetic Particles Objective: This example demonstrates the utility of non-magnified large area imaging to detect and identify individual cells using fluorophore-labeled antibodies (signal moieties: category-binding molecules) and antibody-coated paramagnetic particles (selection moieties). In this example, non-magnified large area imaging in a microtiter dish format was used to separately detect *Candida albicans* and *Escherichia coli* cells following binding of paramagnetic particles and fluorophore-labeled antibody to the cells.

Experimental procedure: Wells of an optically clear, flat, glass-bottomed microtiter tray (Uniview 7706-2370, Whatman, Inc., Ann Arbor, Mich.) were blocked using 'BlockAid' (B-10710 Molecular Probes, Eugene, Oreg.) for 30 minutes at room temperature. Approximately $5 \times 10^7$ magnetic particles (MEO3N 1 μm diameter Bangs Labs Inc., Fishers, Ind.) with surface-adsorbed rabbit anti-*C. albicans* (B65411R, Biodesign International, Saco, Me. or anti-*E. coli* polyclonal antibody (B65003R, Biodesign International, Saco, Me.) prepared as described in example 6 were added to a volume of PBS-TB buffer in the well to give a final reaction volume of 200 μl. *C. albicans* or *E. coli* cells were fixed in 2.5% solution of formaldehyde in PBS for five minutes and washed twice in PBS-B. Cells were added to the suspension of paramagnetic particles and the mixture was incubated at room temperature on a shaker for 30 minutes. FITC-labeled anti-*Candida albicans* polyclonal antibody (5 μg) (CR2155RF, Cortex Biochem, San Leandro, Calif.) or anti-*E. coli* antibodies (1 mg; Biodesign, Saco, Me. B65001R) labeled with Alexa Flour 488 (Molecular Probes, Eugene, Oreg., Cat#A10235) that were labeled according to the manufacturers instructions, were added and the mixture was incubated for a further 15 minutes. Unbound antibody was separated from the magnetic particle:cell complexes by repeated washing and application of a magnetic field using a magnetic ferrous block (CD2001, Cortex Biochem, Inc., San Leandro, Calif.) such that the magnetic particles were caused to align substantially evenly over the surface of the bottom of the well. Fluorescence was detected by imaging using the CCD imager (described in Step 6 of Detailed description section and shown in FIG. 3) using the FITC filter set (480/40 nm excitation, 535/50 nm emission filters for detection of the FITC and Alexa488 fluorophores. Fluorescent signals co-purified with the magnetic particles indicate the presence of *C. albicans* or *E. coli* cells. Positive signals detected on the imager were confirmed to be cell:fluorescent antibody complexes by high magnification fluorescence microscopy (1200×) using an Axioplan II fluorescent microscope (Carl Zeiss Inc., Thornwood, N.Y.) after staining cellular nucleic acid with the red fluorescent nucleic acid-binding dye YOYO-3 (1 μM) (Y-3606, Molecular Probes, Eugene, Oreg.).

Results. FIG. 17 shows that wells containing *Candida albicans* or *E. coli* cells gave numerous punctate fluorescent spots. These fluorescent signals were shown to correspond to individual cells (or small clusters of cells) by using high magnification fluorescence microscopy (1200×) and staining cells for nucleic acid using the red fluorescent dye YOYO-3 (Molecular Probes, Eugene, Oreg.). Wells containing no cells gave no (or very few) such signals. The small number of fluorescent objects in the negative control images was likely to be due to dust particles or other non-biological material.

Example 14

Non-Magnified Large Area Detection of Individual Chemiluminescent Yeast Cells Using a CCD Camera Objective: The goal of this example was to use non-magnified large area imaging to visualize individual cells labeled with chemiluminescent signaling moieties. In this embodiment, the surface of *C. albicans* cells were coated with fluorescein-conjugated antibodies, followed by alkaline phosphatase-conjugated anti-fluorescein antibodies and reacted with CDP Star substrate to generate light. The presence of individual cells in the chemiluminescence image was confirmed by fluorescence microscopy. An image intensifier was not required for detecting the individual cells.

Materials and Methods: *C. albicans* 90028 (American Type Culture Collection) were grown in YM medium (VWR cat #DF0711-17) for 48 hours at 25 C. The cells were fixed in 2.5% formaldehyde in PBS for 5 minutes followed by a wash in PBS, and stored at 4 C. Ten volumes of blocking buffer (0.5% NEN Blocking Reagent cat #FP329, 0.1M Tris-HCl pH 8, 0.15 M NaCl) were added to an aliquot of cells and the suspension was incubated for 30 minutes. Polyclonal rabbit anti-*C. albicans*, fluorescein isothiocyanate conjugated antibodies (BioDesign cat #B65411F) were added at a 1/100 dilution. The cell suspension was incubated with gentle mixing for 60 minutes. The cells were spun down and washed twice with blocking buffer, followed by resuspension in a 1/25 dilution of anti-fluorescein, alkaline phosphatase conjugated antibodies (NEN cat #NEF-709) in blocking buffer. Again the cells were incubated with gentle mixing for 60 minutes. The cells were spun down and washed 3 times in 0.1M Tris-HCl pH 8, 0.15 M NaCl, followed by a wash in 0.1M Tris-HCl pH 9.5, 0.1M NaCl. The final suspension of cells was in the pH 9.5 buffer.

For large area imaging, dilutions of the cells were spotted on CAST nylon coated glass slides (Schleicher and Schuell cat #10484181) that were pre-moistened with the pH 9.5 buffer and overlayed with CDP Star reagent (NEN NEL-601). Chemiluminscence was visualized with 10 minute exposures using a CCD imager (described in Step 6 of Detailed description section and shown in FIG. 3) with no emission filter. After the chemiluminescent image was captured, Slow Fade reagent (Molecular Probes cat #S-2828) was spotted onto the slide and a coverslip was added. The slide was viewed via fluorescence microscopy with an FITC filter cube (Chroma #SP101) at 400× magnification to identify individual cells.

Results: Individual C. albicans cells labeled with chemiluminescent signaling moieties could be detected without magnification as seen in FIG. 18, The three different dilutions represent about 200, 60, and 20 cells respectively, from left to right. At the lowest dilution each spot on the chemiluminescent image could be correlated with a cell or a small group of cells when viewed by fluorescence microscopy. Spatial orientation was aided by the presence of penciled-in grid lines and the relative positions of cells. Larger, brighter spots, seen especially in the left panel, represent more than one cell.

Example 15

Non-Magnified Large Area Detection of Individual Chemiluminescent Yeast Cells Using Direct Exposure of Instant Film Objective: The goal of this example was to use instant photographic film to achieve non-magnified large area detection of individual cells labeled with chemiluminescent signaling moieties. In this embodiment, the surface of C. albicans cells was coated with fluorescein conjugated antibody category-binding molecules, bound to alkaline phosphatase: antibody conjugates, and reacted with CDP Star substrate to generate light.

Materials and Methods: C. albicans 90028 (American Type Culture Collection) were grown and labeled as in Example 14. For imaging on Polaroid film, a piece of Hybond-N membrane (Amersham-Pharmacia RPN1782B) was placed on a piece of absorbent filter paper and pre-wet with 0.1M Tris-HCl pH 9.5, 0.1M NaCl. Dilutions of cells were spotted on the membrane, followed by the addition of CDP Star reagent (NEN NEL-601). The membrane was mounted in a SpotLight camera (Boston Probes DT10000) according to the manufacturer's instructions and exposed to ASA 2000 film (Boston Probes DT20000) for 30 minutes.

Results: Individual C. albicans cells labeled with chemiluminescent signaling moieties could be detected directly on instant film as shown in FIG. 19. The figure shows images of three different dilutions of labeled cells. The sample dilutions shown in FIG. 19 are the same as those imaged in Example 14 (FIG. 18) and represent about 200, 60, and 20 cells (from left to right, respectively in the figure). Large, bright spots, seen especially in the left panel, correspond to clusters containing numerous cells. The spots in the right panel of the figure represent either individual cells or clusters of several cells.

Example 16

Detection of Organisms Involved in Lower Respiratory Tract Infections Using Non-Magnified Large Area Imaging Objective: To identify organisms involved in lower respiratory tract infections: Chlamydia pneumoniae, Mycoplasma pneumoniae and Legionella pneumophila using non-magnified large area imaging.

Overview: Pneumonia is a major cause of death worldwide and is the sixth leading cause of death in the United States. Trends indicate that this figure is rising do an increase in the proportion of individuals >65 years of age as well as other factors. Currently diagnosis is often empirical, though a definitive diagnosis is thought to improve patient outcomes by prescribing the appropriate antibiotic. Detection of specific organisms (some of which are difficult to culture) by direct fluorescence staining of sputum combined with the power of non-magnified large area imaging would assist in diagnosis thereby decreasing the incidence of fatalities due to pneumonia as well as health care expenditures.

Experimental Methods: Chlamydia pneumoniae and Mycoplasma pneumoniae control slides were obtained (Bion, Park Ridge, Ill.; Cat. CP-4212 and MP-1212 respectively). The slides were allowed to warm to room temperature and incubated in blocking solution (PBS/1% BSA, 15 minutes, 25° C.). The blocking solution was removed via aspiration and a dilution of primary antibody (anti-Chlamydia pneumoniae; DAKO Corporation, Carpinteria, Calif., Code NM660, Clone RR402, diluted ⅕, and anti-Mycoplasma pneumoniae; Fitzgerald International Industries, Inc., Concord, Mass., Cat. No. 10-M40, diluted 1/1000) in blocking solution was added to individual wells of the Chlamydia pneumoniae control slide and the Mycoplasma pneumoniae control slide. The slides were incubated (30 minutes, 25° C.) followed by a washing procedure (PBS-BT, 4×5 minutes each) and incubation with a secondary Cy3 conjugated antibody (15 minutes, 25° C., goat anti-mouse IgG-Cy3, Jackson ImmunoResearch Laboratories, West Grove, Pa., Cat. No. 111-165-144). Slides were washed with PBS-BT and sterile type 1 water by flooding the wells (4×5 minutes each and 2×5 minutes each respectively). For demonstration of large area imaging detection of Legionella pneumophila FITC-conjugated antibodies against L. pneumophila serogroup 1 (Cat. No. 92-103-FL) as well as heat fixed Legionella pneumophila serogroups 1 (Philadelphia 1, Cat. No. 92-103-H) and 6 (Chicago 2, Cat. No. 92-110-H) were obtained (mTECH™ Monoclonal Technologies, Alpharetta, Ga.). A smear of cells from the two heat killed Legionella pneumophila serogroups (1 and 6) was prepared on a poly-lysine coated slides (Sigma, Cat. No. P0425). Blocking solution was flooded onto the slide and allowed to incubate (15 minutes, 25° C.) followed by aspiration. A FITC-conjugated primary antibody directed against Legionella pneumophila serogroup 1 was flooded onto the slide (30 minutes, 25° C.) followed by aspiration and washing with PBS and type 1 water (2×5 minutes each and 2×5 minutes each respectively). All slides were air dried followed by image capture using non-magnified large area imaging (TRITC filter set, Chroma Id. No. 41002b, excitation 545/30 nm, emission 610/75 nm for Cy3 conjugates and FITC filter set, Chroma Id. No. SP101, 470/40 nm, emission 522/40 nm for FITC conjugates). Slides were mounted (Pro Long Antifade Reagent, Molecular Probes, Eugene, Oreg., Cat. No. P-4781) and fluorescence microscopy (Axioplan II fluorescent microscope, Carl, Zeiss Inc., Thornwood, N.Y.; Cy3.5 filter set, Chroma Id. No. 41002b, excitation 545/30 nm, emission 610/75 nm for Cy3 conjugates or FITC filter set, Chroma Id. No. SP101 excitation 470/40 nm, emission 522/40 nm) was performed to observe detail (400×).

Results: This example demonstrates that organisms involved in lower respiratory tract infections can be detected using non-magnified large area imaging in conjunction with the direct fluorescent antibody staining technique. Large area imaging of positive and negative controls indicates that the detection is specific (FIG. 20). That the signal seen using large area imaging is specific to that generated by labeled bacterial cells was confirmed by microscopic analysis.

Variations: The power of non-magnified large area imaging can be applied to the detection of other bacteria, yeasts and molds as well as other categories of disease including: urinary tract infection, sepsis, and sexually transmitted diseases.

Example 17

A Mulitiplexed Direct Fluorescence Immunoassay that Simultaneously Scans a Sample for 3 Disparate Microbes Using Non-Magnified Large Area Imaging Overview. In this example, non-magnified large area imaging was used in a multiplex test that detects and identifies 3 types of microbes. The cells were incubated with a mixture of 3 category-specific (in this case, species-specific) antibodies, each of which was labeled with a distinct fluorescent dye. Individual cells were detected using a CCD imager.

Experimental procedure. *E. coli* and *Candida albicans* were grown and fixed according to Example 2 and Example 11 respectively. Streptococcus pyogenes was grow overnight at 37° C. in Brain Heart Infusion (Difco Cat#237500) and fixed and washed according to Example 2. All 3 types of cells were individually diluted in water until 20-50 cells per high power field (×40) could be seen by phase contrast microscopy. Aliquots (3 µl) of these dilutions were placed on poly-L-lysine coated coverslips and spread over an area approximately 5 mm in diameter and allowed to dry.

Anti-*E. coli* antibodies (1 mg; Biodesign, Saco, Me. B65001R), anti-*C. albicans* antibodies (1 mg; Biodesign, Saco, Me. B65411 R), and anti-Streptococcus Grp A antibodies (1 mg; Biodesign, Saco, Me. B10601R) were labeled with Alexa Flour 488 (Cat#A10235), Alexa Flour 350 (Cat#A10170), and Alexa Flour 546 (Cat#A10237), protein labeling kits respectively, according to manufacturers instructions (Molecular Probes, Eugene, Oreg.).

A mixture of the labeled antibodies was prepared in normal rabbit serum (Cat#88-NR50; Fitzgerald, Concord, Mass.) each at 20 µg/ml. The cells, spotted on coverslips, were covered with the antibody mixture and incubated for one hour at room temperature in a humid plastic pipette box lid containing water-saturated paper towels and covered with Saran Wrap. Coverslips were then washed once in PBS containing 1% normal rabbit serum and then twice in PBS (10 minutes per wash). The coverslips were removed from the wash and any residual liquid was blown off using compressed air. The relevant area of each coverslip was imaged for 1 sec in a CCD imager (described in Step 6 of Detailed description section and shown in FIG. 3) in the FITC (Ex 480 nm/40 nm and Em535 nm/50 nm) (Alexa488 specific), Texas Red (Ex 560 nm/55 nm and Em645 nm/75 nm) (Alexa 546 specific) and DAPI (Ex 360 nm/40 nm and Em460 nm/50 nm) (Alexa 350 specific) channels.

Results. The result of the multiplex bacterial assay is shown in FIG. 21. For each distinct bacterial sample, the numbers and intensities of objects were greatest in the expected fluorescence channel. Thus, the numbers and intensities of the objects seen in the FITC (Alexa 488) channel were greatest for the *E. coli* samples. Similarly, *C. albicans* samples, and *S. pyogenes* samples had the strongest intensities and the most numerous objects in the DAPI and Texas Red channels, respectively. Thus, the assay can differentiate the 3 categories of cells with a mixture of antibody category-binding molecules using non-magnified large area imaging.

Example 18

Solid Phase Capture Assay for Adenovirus

Objective: This example shows that small numbers of viruses captured on a solid support can be labeled with fluorescent particles and visualized by non-magnified large area imaging. The wells of a 96 well plate were first coated with anti-adenovirus antibodies. Next adenovirus and particles coated with anti-adenovirus antibodies were added to the well, and the viruses and particles were captured by the antibody-coated surface. Unbound particles were removed and the captured particles, representing the captured virus, were detected by large area fluorescence image analysis.

Materials and Methods: The wells of a 96 well Greiner plate (Greiner Labortechnik cat#655097) were coated with biotinylated-BSA (Sigma cat#A-8549) by adding 50 µl of a 0.2 mg/ml solution in 100 mM sodium bicarbonate pH10 and incubating overnight at room temperature. Wells were washed once with 100 µl PBS. The biotinylated-BSA layer was then coated with 50 µl 0.1 mg/ml streptavidin (Jackson Immunoresearch Laboratories cat#016-000-113) in PBS for two hours at room temperature, followed by a wash of PBS, then coated with 50 µl biotinylated-anti-adenovirus antibodies (Chemicon cat#MAB8052 antibodies biotinylated with Molecular Probes kit cat#F-6347) at 0.1 mg/ml in PBS for two hours at room temperature. The wells were washed three times in 100 µl PBS-TB and stored at 4 C.

Adenovirus type 2 (ATCC VR-846) and Respiratory Syncitial Virus (RSV) (ATCC VR-1302) were fixed by reconstituting in 4% formaldehyde/PBS (final concentration) for 30 minutes at room temperature. Glycerol was added to a final concentration of 16% and aliquots were frozen at −80 C. Virus particle titer was estimated based on the titers provided by the manufacturer expressed as $TCID_{50}$ and converted to pfu (plaque forming units) by multiplying by a factor of 0.7 as recommended by the manufacturer (ATCC). The assumption was made that the pfu is approximately equal to the number of virus particles in the preparation. Before use, aliquots were thawed on ice. After thawing, unused portions were stored at 4 C for further experiments.

Particles were coated with anti-adenovirus antibodies (Chemicon cat#MAB8052) as described in Example 8 except that 0.2 µm diameter fluorescent particles at 1% solids (Molecular Probes cat#F-8848) were used.

To perform the assay, the storage buffer was removed from the well. About 10,000 virus particles and $3 \times 10^8$ particles were added to a well at a final volume of 100 µl in Block Aid buffer (Molecular Probes cat#10701). The microtiter tray was incubated for one hour at room temperature on a shaking platform. The wells were washed 3 times in PBS-TB, and then once in water. After the water was removed the wells were imaged using the CCD Imager (described in Step 6 of Detailed description section and shown in FIG. 3) using the FITC excitation (470 nm/40 nm) and emission filter (522 nm/40 nm) set. Images were processed and analyzed using Image-Pro Plus software (Media Cybernetics). The object counting utility was used to estimate the number of particles in the wells.

Results: This example shows viral particles captured on a solid phase can be labeled with fluorescent particle signaling moieties and detected without magnification as seen in FIG. 22. Analysis of the image (bottom panel) using Image-Pro Plus software indicates the number of objects (particles) is about 13,000, which roughly matches the approximate number of adenovirus particles added (~10,000). However, it should be noted that the number of virions in the preparation were not precisely determined. Also it was not known how many infected tissue culture cells or fragments of such cells were present in the preparation. The object count in the RSV negative control (top panel) was about 800, and represents the non-specific background.

Example 19

Solid Phase Capture of a Virus in Blood

Objective: This example shows that small numbers of viruses in a blood sample can be captured on a solid support, labeled with fluorescent particles, and visualized by non-magnified large area imaging. Blood spiked with Adenovirus was added to anti-adenovirus antibody-coated wells in a 96 well plate. After capturing the virus, fluorescent particles coated with anti-adenovirus antibodies were added. Unbound particles were removed and the captured particles, representing captured virus, were detected by CCD-based fluorescence imaging.

Materials and Methods: The wells of a 96 well plate (Greiner Labortechnik cat#655097) were coated with biotinylated-anti-adenovirus antibodies. Adenovirus type 2 (ATCC VR-846) and RSV (ATCC VR-1302) were reconstituted and fixed as described in Example 18. Particles were coated with anti-adenovirus antibodies (Chemicon cat#MAB8052) as described in Example 8, except that 0.2 μm diameter fluorescent particles (Molecular Probes cat#F-8848) at 1% solids were used. To perform the assay, the storage buffer was removed from the wells. About 10,000 virus particles were added to a well in 50% Block Aid buffer (Molecular Probes cat#10701), 50% mouse blood, in a final volume of 100 μl. The microtiter tray was incubated for one hour at room temperature on a shaking platform. The wells were washed two times in PBS-TB, followed by the addition of $3\times10^8$ particles in 100 ul Block Aid buffer. After an hour of incubation with shaking, the wells were washed three times with PBS-TB, once with water, and visualized using a CCD imager (described in Step 6 of Detailed description section and shown in FIG. 3) using the FITC excitation (470 nm/40 nm) and emission filter set (522 nm/40 nm).

Results: This example shows specific viral particles (in this case, adenovirus) can be captured on a solid phase in the presence of 50% blood, labeled with fluorescent particle signaling moieties and detected without magnification as seen in FIG. 23. Analysis of the image (bottom panel) using Image-Pro Plus software indicates the number of objects (particles) is 13,489, which roughly matches the approximate number of adenovirus particles added (10,000). The object count in the RSV negative control (top panel) was 2,173, and represents the non-specific background. The results of this assay are similar to the results in Example 18 indicating that the presence of blood does not interfere with the capture of viral particles onto the solid phase, their labeling with fluorescent particles, or their detection without magnification.

Example 20

Liquid Phase Assay for Adenovirus

Objective: This example shows that the invention can scan for small numbers of viruses using a liquid-phase sandwich-forming method. A sample containing adenovirus was incubated with a combination of magnetic and fluorescent particles that are coated with anti-viral antibodies. Complexes of magnetic and fluorescent particles were induced to form in the presence of adenovirus (but not a control virus). These fluorescent complexes were magnetically selected, deposited on an optically clear surface and imaged using non-magnified large area imaging.

Materials and Methods: Adenovirus and RSV were reconstituted and fixed as described in Example 18. Antibody coated fluorescent and magnetic particles were prepared as described in Example 8 with anti-adenovirus antibodies (Chemicon cat#MAB8052) used on 1 μm diameter red fluorescent particles (Molecular Probes cat#F-8851) and 2.8 μm diameter magnetic particles (Dynal; cat#142.03). In this example, $5\times10^5$ red fluorescent particles were mixed with $5\times10^6$ magnetic particles in Block Aid buffer (Molecular Probes cat#B-10710) to a final volume of 250 μl. Adenovirus or RSV was added to the assay at a titer of about 1000 virus particles per sample. After four hours at room temperature with mixing, the magnetic particles and any bound particles were separated using a Polysciences BioMag magnetic separator for microcentrifuge tubes and washed three times in PBS-TB. The washed magnetic particles were transferred to microtiter wells (Greiner Labortechnik cat#655097) and visualized in a CCD imager (described in Step 6 of Detailed description section and shown in FIG. 3) with the Texas Red excitation (560 nm/55 nm)/emission (645 nm/75 nm) filter sets. Images were captured and analyzed with Image-Pro Plus software (Media Cybernetics) as in Example 18.

Results: This example shows specific viral particles can be captured using a liquid-phase sandwich-forming method with magnetic and fluorescent particles and detected without magnification as seen in FIG. 24. Roughly 1000 virus particles were added to the assay. In the bottom panel of the figure, analysis with the Image-Pro Plus object counting utility detects 2324 adenovirus particles, while in the negative RSV control (top panel), only 46 particles which represent non-specific background binding, were detected.

Example 21

Homogenous Assay for Adenovirus in Blood

Overview of the example. Efficient and cost-effective viral load testing—determining the concentration of viruses in human samples—represents a major unmet need in medical diagnostics. This example demonstrates how the invention can rapidly enumerate viruses in a sample. The example tests for Adenovirus, an important human pathogen. Technically, the example is similar to Example 8.

Coating particles with antibodies. Particles are coated with antibodies as in Example 8 and resuspended at a concentration of 2% solids. In this example, anti-Adenovirus monoclonal antibodies (anti-hexon; catalogue number MAB8052; Chemicon) is used to coat yellow-green fluorescent particles (TransFluoSpheres; catalogue number T-8871; Molecular Probes) and magnetic nanoparticles (carboxy polymer-coated ferrofluid; Immunicon; catalogue number F3000). Equal volumes of the fluorescent and magnetic particles are mixed so that the final concentration of each type of particle in the mixture is 1% solids. The particle mixture is dispersed using sonication as in Example 8.

Detecting and quantifying Adenovirus in blood. The test described in this example detects adenovirus virions in blood. Samples (10 μl in PBS-B) containing various amounts (0, $10^3$, $10^4$, $10^5$ pfu) of purified adenovirus virions (CsCl gradient purified; Frank Graham, McMaster University) are added to whole blood and to the particle mixture and the reaction is processed as in Example 8. The number of fluorescent particle clusters minus in the experimental sample minus the average number of clusters in the negative control samples indicates the number of Adenovirus particles in the sample.

Example 22

Multiplex Large Area Imaging Immunoassay that Simultaneously Scans for a Bacterium and a Virus Objective: This example demonstrates that the invention can be used to construct tests that simultaneously scan a sample for multiple diverse analytes—here, a bacterium and a virus. Paired antibody-coated microparticles—one fluorescent and one paramagnetic—were used to bind to targets, as in several previous examples (e.g., Example 8). Here, however, two such pairs of particles were used, one set coated with anti-$E. coli$ antibodies and one set coated with anti-adenovirus antibodies. To distinguish the two types of particle:analyte complexes from each other, distinctive fluorescent particles were used for each analyte. The $E. coli$-specific particles had green fluorescent character while the adenovirus-specific particles had red fluorescent character. After mixing the sample and the analyte-specific particles, the resulting particle:analyte complexes were magnetically selected to the detection zone and imaged using non-magnified large area imaging. The viral and bacterial targets were identified and quantified by analysis of two CCD images that were acquired while using optical filter sets tuned for either the red or green particles.

Materials and Methods: $E. coli$ cells were grown and fixed as described in Example 8 and adenovirus was reconstituted and fixed as described in Example 18. Antibody coated fluorescent and magnetic particles were prepared as described in Example 8. Anti-adenovirus antibodies (Chemicon cat#MAB8052) were used to coat red fluorescent particles (Molecular Probes cat#F-8851) and anti-$E. coli$ antibodies (KPL cat#01-95-90) were used with green fluorescent particles (Molecular Probes cat#8852) while batches of magnetic particles (Dynal.cat#142.03) were made with each of the antibodies. For the assay, particles were mixed in a final volume of 250 ul Block Aid buffer (Molecular Probes cat#B-10710) in the following amounts: $2.5 \times 10^7$ particles for each fluorescent particle and $5 \times 10^6$ particles for each magnetic particle. Adenovirus and/or $E. coli$ were added to the assay at about 1000 virus particles/cells each. After one hour at room temperature with mixing, the magnetic particles and any bound particles were separated in a magnetic field and washed three times in PBS-TB. The washed magnetic particles were visualized in Greiner microtiter wells (Greiner Labortechnik cat#655097) using a CCD imager (described in Step 6 of Detailed description section and shown in FIG. 3) with both the FITC and Texas Red excitation/emission filter sets (see Example 18 and Example 20 for filter specifications).

Results: This example demonstrates that a bacterium and a virus can be scanned for in the same sample and detected using non-magnified large area imaging. As seen in FIG. 25, when roughly 1000 adenovirus are added to the mixture, the majority of particles detected are the anti-adenovirus red fluorescent particles (Texas Red filter sets) (top row). When roughly 1000 $E. coli$ are added, anti-$E. coli$ green fluorescent particles are detected using FITC filter sets (second row), while when both adenovirus and $E. coli$ were added, particles are detected in both channels (third row). When neither pathogen is added, an order of magnitude fewer particles were detected, representing the non-specific background (bottom row).

Example 23

Filter Flow-Through Assay for Detecting Individual Bacteria Using Non-Magnified Large Area Imaging Overview. In this example, a rapid flow-through assay is combined with non-magnified large area imaging to detect small numbers of bacteria that are labeled with highly fluorescent particles. After incubating the bacteria and beads together, the resulting solution containing bacteria:bead complexes is passed through a filter, that had been coated with anti-bacterial antibody. The complexes that are captured by the filter are then detected using non-magnified large area imaging as in Example 1.

Experimental design. A nitrocellulose membrane (Pall Biodyne A; 5 μm pore; cat. num.BNCF810S) was cut into two 1 cm by 1 cm squares. The squares were soaked in a solution containing anti-$E. coli$ O157 (200 μg/ml in PBS). After drying at room temperature, the membranes were blocked (200 ml; 30 min; room temperature; 1% casein (Hammerston grade; EM sciences; cat. num.CX0525-1) and 0.1% Tween 20 (Sigma; cat. num. P1379) in PBS). The membranes were then blotted dry on absorbent paper. The membranes were transferred to parafilm and the membrane was saturated with PBS (300 μl). A solution of $E. coli$ O157 ($10^5$ cells) and red fluorescent beads ($10^6$ beads/Molecular Probes; 1 μm; sulfate; 580/605 nm; cat. num.F-8851) that had been coated with anti-$E. coli$ O157 antibodies (Kirkegaurd and Perry Laboratories; cat. num. 01-95-90; antibodies passively adsorbed as described in Example 8) were mixed together in a tube, allowed to incubate for 15 minutes and then added to one of the nitrocellulose squares. On the other square, just the antibody coated fluorescent beads were added (this filter was the "no bacteria" negative control). After an additional 15 minute incubation, the membranes were put on a piece of filter paper (Whatman 50 μm pore) and the excess liquid was absorbed. The membranes were then washed (PBS-T; 50 ml; 20 min). Fluorescence was detected by imaging using a CCD imager with an FITC optical filter set (excitation 560/55 nm, emission 645/75 nm) for red fluorescent beads. Image-Pro Plus software, version 4.1 (Media cybernetics) was used to capture and process images from the CCD imager. Positive signals detected on the imager were confirmed to be beads bound to $E. coli$ by using an Axioplan II fluorescent microscope (Carl, Zeiss Inc., Thornwood, N.Y.) equipped with the same filter sets.

Results. FIG. 26 shows the results of using a flow through assay to detect bacteria that were decorated with specifically bound highly fluorescent beads. The CCD image of the experimental filter through which the bacteria-containing sample was passed contained numerous white spots, while the control filter through which a sample lacking bacteria was passed contains few beads. High power microscopy confirmed that the experimental filter contained numerous complexes consisting of bacteria surrounded with beads, while the control filter contained none of the complexes but rather only dispersed single beads.

Example 24

Quantification of Bacteria Using Large Area Imaging of Cells Stained with a Fluorogenic Esterase Substrate Objective: In many applications it is useful to have a large dynamic range for quantifying live bacterial cells. An ideal system would be able to accurately count from zero or one bacterial cell up to millions or tens of millions, thus eliminating the serial dilutions and their inherent lack of precision that are necessary for traditional microbiological plating methods. In this example we show how staining live cells with fluorogenic substrates, coupled with CCD-based, non-magnified large area imaging can be used to quantify cells over at least 5 orders of magnitude.

Experimental Methods: *E. coli* ATCC 8739 cells were grown and processed as described in Example Y (Cell Direct example). Serial 10-fold dilutions of the cells were made in PBS and filtered in duplicate samples through black polyester membranes (Chemunex cat. #200-C2010-01) mounted on absorbent pads (Chemunex cat. #200-C3012-02) in a Millipore 1225 manifold and stained as described in Example Y (Cell Direct Example). In addition, 10 µl of the $10^{-5}$ dilution was plated in triplicate on TSA (BD catalogue no. 236950) and grown at 37° C. overnight to get a cell titer. The fluorescent signals on the polyester membranes were captured using a CCD Imager (described in step 6 above; FIG. 3) with an FITC optical filter set (Chroma/excitation 470/40 nm, emission 522/40 nm). Image-Pro Plus software, version 4.1 (Media cybernetics) was used to capture and process images from the CCD Imager. The signal generated from each filter was defined as the sum of the pixel intensities of all objects (where objects are defined in this particular example as containing pixel intensities from 350-65301). This method of defining signal eliminates the background from regions of the filter that do not contain any stained cells, but does not mask or undercount intensities from overlapping objects. (Since the cells are small and fairly transparent, signals are additive as long as the layer of cells is thin.)

Results: As shown in FIG. 28, the signal generated from this method is linear over at least 5 orders of magnitude, which is considered a large dynamic range for this test.

Variations. At low object numbers, accurate quantification can be achieved by counting individual objects rather than using the sum of their pixel intensities, since the objects will be unlikely to overlap. This can extend accurate counting down to one or zero cells, especially if multiple stains and multiple excitation and/or emission wavelengths are used to determine which objects represent viable cells. In addition, more sophisticated object finding algorithms can be employed to take into account local background intensities and variations in illumination.

Example 25

Detecting Individual Stained Bacteria on a Filter Using Non-Magnified Large Area Imaging Overview. In this example, large area imaging is used to detect individual *E. coli* bacterial cell targets that are stained with a fluorescent dye that binds to nucleic acids. The stained cells are filtered through a black polycarbonate filter, illuminated with white light, and imaged with a CCD camera.

Experimental design. A culture of *E. coli* MG1655 was stained with Syber Green I as in Example 2. The culture was diluted and approximately $10^5$ cells were filtered through a black polycarbonate filter using a vacuum pump and a plastic funnel cup (Millipore Microfil V User Guide, PF07114, Rev A 3/00). The filters were then washed with water (50 ml; type 1 quality). Fluorescence was detected using a large area CCD-based imager (FIG. 3) and a FITC optical filter set (excitation 470/40 nm, emission 522/40 nm) which is appropriate for detecting Syber green I. Image-Pro Plus software, version 4.1 (Media cybernetics) was used to capture and process images from the CCD Imager. Positive signals detected on the Imager were confirmed to be cells by using an Axioplan II fluorescent microscope (Carl, Zeiss Inc., Thornwood, N.Y.) equipped with the same filter sets.

Results. FIG. 27 shows the capture and detection of bacteria on a filter. Syber green I stained cells on the surface of the filter are seen as white spots. When viewed under high power magnification the spots are seen as stained cells.

Example 26

Non-Instrumented Detection of Small Numbers of Bacterial Cells Without Magnification Overview. In this example, particles, which were coated with both alkaline phosphatase and anti-*E. coli* antibodies, were used to detect *E. coli* O157 bacteria in a liquid capture assay. Bacteria were bound to both the dually coated particles and antibody-coated magnetic particles in liquid and the particle: analyte complexes were separated and washed using magnetic force to separate the particle complexes from the unbound particles. The complexes were deposited on a 0.2 µm pore nitrocellulose membrane using filtration and then visualized using both chemiluminescent and calorimetric substrates.

Experimental procedure. The dually coated particles were made by adding both biotinylated alkaline phosphatase (5 µl of a 2.9 mg/ml stock; Pierce; cat. num. 29339) and biotinylated donkey anti-goat IgG antibody (5 µl of a 1.6 mg/ml stock; Jackson; cat. num. 705-065-147) to streptavidin-coated particles ($10^8$ particles; Bangs; 0.95 um, non-fluorescent; cat. num. CPO1N). The reaction level was brought up to 100 µl with PBS. After a 30-minute incubation, the particles were washed twice. A wash consisted of spinning the particles down in a microcentrifuge at 3000 g for 5 minutes, then discarding the supernatant and resuspended the particles in PBS (100 µl). After washing, goat anti-*E. coli* O157 antibody (5 ul of a 1 mg/ml stock; Kirkegaurd and Perry Laboratories; cat. num. 01-95-90) was added to the particles. The particles were allowed to incubate for 30 minutes at room temperature and then washed twice as mentioned above. After making the dually coated particles, an *E. coli* O157 culture was fixed in 2.5% formaldehyde (see example 1, Large area imaging of individual bacteria stained with a DNA-binding fluorescent dye) and serially diluted in ten fold increments to achieve $10^7$ through $10^3$ cells/ml. In separate 1.5 ml tubes, 10 µl of each dilution (done in duplicate) were combined with both goat anti-*E. coli* O157 antibody coated magnetic particles ($10^6$ particles; Dynal; 2.8 um; tosylated; cat. num. M-280; prepared as in Example 8) and the dually coated particles ($10^6$ particles). The particle: bacteria suspension was brought up to 100 µl with PBS-TB and incubated with mixing for one hour at room temp. After incubation the tubes were washed four times in PBS-TB. A wash consisted of magnetic separation to draw the magnetic particle: bacteria:particle sandwich to one side of the tube followed by aspiration to remove the supernatant and resuspension in PBS-TB (100 µl). Both replicates of each dilution of the washed particle: bacteria sandwiches were filtered separately. Each replicate was added to PBS (50 ml) and filtered through a 0.2 µm pore nitrocellulose membrane using a vacuum pump and a plastic funnel cup (Millipore Microfil V User Guide, PF07114, Rev A 3/00). BM Purple AP substrate (500 ul; Roche; cat. num. 1442074) was added to one set of filters. The other filter set had CDP-star (500 ul; NEN; cat. num. NEL-601) added to them. After a 1-hour incubation the BM purple membranes were washed in water to remove left over BM Purple and the membranes were allowed to air dry. The CDP-star membranes were mounted in a SpotLight camera (Boston Probes; cat. num. DT10000) according to the manufacturer's instructions and exposed to ASA 2000 film (Boston Probes; cat. num. DT20000) for two seconds. The same filters were then exposed using non-magnified large area imaging. Image-Pro Plus software, version 4.1 (Media cybernetics) was used to capture and process images from the CCD Imager.

Results. FIG. 29 shows that the bi-functional particle, that was conjugated to a category-specific binding molecule and an enzymatic signaling moiety, can be detected using either chromogenic or chemiluminescent signal elements. The assay described here using the dually labeled particles is sensitive, detecting low numbers of bacteria (approximately 100 cells). The ability to see with the naked eye, E. coli:bead complexes—which are normally only visible under a high power microscope—is due to the enormous signaling power of these particles that contain large numbers of enzyme molecules. In fact, single dispersed microscopic beads were detectable with the naked eye when prepared, deposited on filters, and treated with chromogenic substrate as in this example. The approach used in this example demonstrates the potential for the invention to provide simple, inexpensive, and non-instrumented point-of-care tests that are, in contrast to current rapid tests, extremely sensitive.

Example 27

A Rapid, Homogenous, Sensitive, and Quantitative Immunoassay for *Mycobacterium tuberculosis* in Clinical Samples Overview. The medical significance of diagnostic testing for *M. tuberculosis* is discussed in the overview of Example 9. In this example, the invention is used to construct a homogenous immunoassay (see Example 8 and FIG. 11) using category-specific anti-*M. tuberculosis* antibodies. This type of test is rapid, sensitive, inexpensive, and easy-to-use. The assay described here complements the acid-fast bacillus approach demonstrated in Example 9 as it differentiates *M. tuberculosis* from other mycobacterial species.

*M. tuberculosis*-specific antibodies. The category-binding molecules in this example are antibodies that specifically bind to *M. tuberculosis*. This example makes use of a monoclonal antibody (MPB64-ICA) that is specific for species in the *M. tuberculosis* complex (Abe, et al., J. Clin. Microbiol. 37:3693-2881, 1999). Alternatively, polyclonal antibodies can be used. For example, for the present application one could use a rabbit polyclonal antibody that reacts with *M. tuberculosis* (BioDesign catalogue number B65601 R).

Category-specific polyclonal antibodies are preferably purified by immunoaffinity chromatography using methods that are familiar to those skilled in the art. In this example, *M. tuberculosis*-specific antibodies are purified using columns containing the target pathogens immobilized on activated particles (e.g., Affigel 10; BioRad) (Harlow, et al., *Using Antibodies: A Laboratory Manual* (Cold Spring Harbor Laboratory Press, Cold Spring Harbor, N.Y., 1999)). After positive selection of the desired antibodies in this way, the antibodies are checked for cross-reaction with other lower respiratory tract pathogens and commensal flora typical of the respiratory tract (e.g., see Chapter 3, Table 1 in Murray, et al., eds. (1999). Manual of Clinical Microbiology. 7th ed. Washington, D.C.: American Society for Microbiology) including mycobacterial species that do not cause tuberculosis (e.g., *M. avium*. Pathogens are fixed (Amann, et al., Appl Environ Microbiol 56: 1919-25, 1990), spotted onto poly-lysine coated glass slides (Sigma; cat. num. P-0425) and treated with the anti-*M. tuberculosis* antibody (1:500 dilution in PBS-B; 20 min; RT), washed 4 times with PBS-TB (50 ml), and then similarly treated with fluorescein-labeled goat-anti-rabbit IgG. Organisms that cross-react with the antibodies are then used to remove the cross-reacting antibodies from the specifically reacting antibodies. The cross-reacting organisms are attached to particles and used to absorb the cross reacting antibodies by immunoaffinity chromatography as described above for positive selection of *M. tuberculosis*-specific antibodies. However, for removing cross-reactive antibodies, the unbound antibodies are collected and the bound antibodies discarded. The resulting antibodies are specific for *M. tuberculosis*.

Alternatively, non-commercial antibodies (polyclonal or monoclonal) or recombinant antibodies can be produced by using standard methods known to those familiar with the art that are described in various works and references therein (e.g., Coligan, J, et al., eds. (1994). *Current Protocols in Immunology*. New York: John Wiley & Sons; Knott, C, et al. (1997). Development of Antibodies for Diagnostic Assays. In Principles and Practice of Immunoassay, C. Price and D. Newman, eds.: Stockton Press; George, A. (1997). Antibody Engineering: Potential Applications for Immunoassays. In Principles and Practice of Immunoassay, C. Price and D. Newman, eds.: Stockton Press).

Coating magnetic and fluorescent microparticles with category-specific antibodies. The category-specific antibodies are used to coat magnetic particles and fluorescently-dyed polystyrene particles as described in Example 8.

Binding *M. tuberculosis*-specific particles to a lower respiratory sample. In the next step, the fluorescent and magnetic *M. tuberculosis*-specific particles are allowed to bind to the *M. tuberculosis* cells in a lower respiratory sample. Liquefied lower respiratory samples (200 µl) are mixed with the *M. tuberculosis*-specific particle mixture ($1\times10^6$ particles of each type) in a well of a 96-well microtiter dish with an optically clear bottom (Greiner Labs; catalogue number 665097). BAL lower respiratory samples are used without prior treatment. Sputum samples are prepared using the NALC-NaOH method (Isenberg, ed. (1992). Clinical microbiology procedures handbook. Washington, D.C.: American Society of Microbiology). Section 3.4).

Detecting and quantifying *M. tuberculosis* in the sample. Samples are processed, imaged and analyzed as described in Example 8.

Controls. Positive and negative control experiments are preferably processed in parallel to clinical samples. Positive control samples, which are treated identically to the clinical samples, preferably contain a known amount (about 1000 cells) *M. tuberculosis* in PBS. Detection of the correct amount of cells in the positive control indicates that the biochemical and image analysis procedures are working correctly. Negative control samples contain PBS, but no cells. No positive signals should be seen in the negative control experiment if all procedures are working properly.

Variations. Staining of the target can also be used for detection instead of or in addition to using fluorescent particles (see variations in Example 8. Specific staining procedures for *M. tuberculosis*, such as auramine O or auramine-rhodamine staining can also be used (see Example 9).

Example 28

Rapid Homogenous Antimicrobial Susceptibility Testing of *Mycobacterium tuberculosis* in Clinical Samples Using Fluorescent Staining Overview. There is great medical importance attached to the rapid identification (see Example 9) and rapid susceptibility testing of *M. tuberculosis*. This example combines rapid growth of *M. tuberculosis* directly in a clinical sample with a simple but sensitive acid-fast smear technique (Example 9, FIG. 13) a to cut weeks off of the time currently required to provide susceptibility data for patients with tuberculosis.

For *M. tuberculosis*, the turnaround time for susceptibility testing ranges from weeks to months, during which time a patient being treated with a sub-optimal antimicrobial therapy can be spreading the disease to many other people. Existing susceptibility tests start from a cultured sample. Thus, whereas for most organisms, the start of susceptibility testing is generally 24 to 48 hr after sample collection, for *M. tuberculosis*, the start of testing is generally delayed for several weeks. Current rapid testing regimes generally require 7-12 days of drug-free growth before antibiotic susceptibility testing. A more rapid susceptibility test for *Mycobacterium tuberculosis* is critically needed because of the growing worldwide epidemic of multi-drug resistant *Mycobacterium tuberculosis*.

The antimicrobial susceptibility assay described here offers clinically valuable features including: minimal growth requirements (several generations), simplicity, cost-effectiveness, parallel analysis of numerous antimicrobial regimes, the ability to directly test biologically complex clinical samples containing low titers of bacteria. The unique features of the test are consequences of the invention's ability to identify and enumerate small numbers of microbes in a sample without using microscopy. The invention cuts several weeks from the classical susceptibility testing turnaround time by bypassing the otherwise obligatory drug-free culture step, and by shortening the incubation with antibiotics to 4 days. The turnaround time for testing using the invention is less than half that of the fastest of the emerging rapid tests (e.g., Norden et al., J. Clin. Micro. 33:1231-1237, 1995). The invention requires much less expensive instrumentation than that required by other rapid susceptibility testing methods (e.g., BACTEC-460, and flow cytometry).

The approach used in this example can also be used for monitoring patients undergoing antimicrobial therapy—another important unmet clinical need. Monitoring viable cell counts in patients receiving antibiotics is important for determining therapeutic efficacy. Current rapid tests for *M. tuberculosis*, based on nucleic acid amplification, cannot be used for patient monitoring. This is because non-viable *Mycobacterium tuberculosis*, containing amplifiable nucleic acid, persist in patients for long periods of time even when therapy is effective. The number of viable organisms can be determined by assessing the number of cells in a sample before and after incubation for several generations of growth (in the absence of antibiotics in this application).

Identifying *M. tuberculosis*. Sputum samples are prepared and stained using the auramine-rhodamine acid-fast bacillus method (Isenberg, ed., 1992, supra) and tested for *M. tuberculosis* as described in Example 9. If *M. tuberculosis* is present, aliquots of sputum are used to analyze the antimicrobial susceptibility of the pathogens.

Direct growth of *M. tuberculosis* in the clinical sample with various antibiotics. Antibiotic susceptibility testing is performed on samples that contain *Mycobacterium tuberculosis* using the broth microdilution method. Aliquots of liquefied sputum (100 μl; prepared as on Example 27) are added to test tubes (2 ml polypropylene screw-cap tubes; Sarstedt) containing concentrated 7H9 broth (100 μl; prepared at three times the normal concentration; DIFCO #211417) and inoculated with various concentrations of ethambutol, isoniazid, and rifampin (100 μl antibiotic added to each tube; Sigma) as described previously (Moore, et al., J Clin Microbiol 37: 479-83, 1999). Two tubes are inoculated with PBS (100 μl) rather than antibiotic. One of these tubes is incubated in parallel with the susceptibility test samples to measure drug free growth of the bacteria (positive control). The other tube is incubated at 4° C. to prevent growth (negative control). All tubes are incubated for 4 days and then killed by treatment with 1% paraformaldehyde as described previously (Moore et al., 1999, supra).

Ascertaining antimicrobial susceptibility using a fluorescent acid-fast bacillus test. The samples that have been grown in the presence or absence of antibiotics are next enumerated using the fluorescent acid-fast bacillus described in Example 9. Aliquots (e.g., 100 μl) of the samples are smeared on slides, imaged using non-magnified large area imaging, and analyzed as before (Example 9). For each antibiotic tested, 2 curves are plotted using sample enumeration data. One curve is based on the total integrated intensity of the images and the other is based on the total number of objects found using the imaging software. Minimum inhibitory concentrations (MICs) of the various antibiotics are determined by examination of these curves (see Example 10).

Variation using a homogenous immunoassay format. Other embodiments of the invention can be applied to this application, such as the homogenous immunoassay format used in Example 27 (see also FIG. 11). When using the liquid-phase format, aliquots (100 μl) of the samples grown in various antibiotic concentrations are added to a mixture of *M. tuberculosis*-specific fluorescent and magnetic particles and processed as described in Example 27.

Example 29

Rapid, Homogenous, Quantitative Testing for Human Immunodeficiency Virus in Blood Overview. Detecting and measuring HIV levels in blood is critically important at all stages of HIV infection. Early diagnosis of HIV infection depends on the ability to detect low levels of virus in plasma. Quantifying levels of virus in plasma is the key strategy for monitoring the health of AIDS patients and is essential for following the effectiveness of anti-viral treatments. The sensitivity required of HIV detection methods is less than 100 virions/ml. Currently ultrasensitive methods are based on nucleic acid detection (e.g., PCR, TMA, and bDNA). However, these methods are expensive and slow relative to immunoassays. Current immunoassays, however, are not sensitive enough to measure low levels of viruses in plasma.

This example demonstrates the power of the invention to offer the ultra-sensitivity of a nucleic acid amplification test in a simple, rapid, and economical homogenous immunoassay format. Key features of the invention, detecting and identifying individual targets in a non-microscopic sample, are essential for achieving the combination of sensitivity and simplicity.

Coating particles with antibodies. To make HIV-specific particles, yellow-green fluorescent particles (FluoSpheres; catalogue number T-8803; Molecular Probes) and magnetic particles (carboxy polymer-coated ferrofluid; Immunicon; catalogue number F3000) are coated with antibodies as in Example 8, except that anti-HIV gp160/120 (Chemicon; catalogue number MAB8836) is used.

Control particles. This example incorporates both positive and negative internal controls. If all procedures and reagents are working correctly the positive control particles will be evident, but an insignificant number of negative control particles will be detected. The positive control particles consist of orange fluorescent particles (TransFluoSpheres; 100 nm catalogue number T-8872) and magnetic nanoparticles (ferrofluid). The positive control particles are coated with anti-bacteriophage Fd antibody (Accurate; catalogue number BYA-3163-1). A known number (~1000) of bacteriophage Fd virions are added to each experimental sample. If the procedure is working correctly, all of the Fd virions will bind to both the Fd-specific orange fluorescent nanoparticles and to the Fd-specific magnetic nanoparticles.

The negative control particles are dark red fluorescent particles (TransFluoSpheres; 100 nm catalogue number T-8876) that are coated with anti-digoxygenin antibody (Roche; catalogue number 1 333 062). The dark red fluorescent particles that are detected in the assay indicate the background level (i.e., the number of particles that are detected independent of association with a magnetically labeled target).

Making the particle ensemble. HIV-specific particles and control particles are mixed so that the total combined particle concentration is 2% solids. The particles are dispersed by sonication as in Example 8.

Preparing plasma. Blood is collected in sterile tubes (e.g., Bection-Dickinson; catalogue number 6454) using EDTA as an anticoagulant. Plasma is separated from whole blood (1.5 ml) by centrifugation in a screw-cap microcentrifuge tube (e.g., Sarstedt; catalogue number 782.694.006) at 900 RPM for 10 min at room temperature. Plasma can be stored frozen for several weeks at −20° C. or used within a day if not refrigerated. Approximately 1000 Fd bacteriophage (10 μl of 100 pfu/μl stock in PBS; ATCC catalogue number 15669-B2) are added to each plasma sample (200 μl).

Immunoassay and HIV detection. The particle mixture (100 μl) and samples are then mixed together in the well of a microtiter dish, incubated, magnetically selected, and imaged as in Example 22 except that 3 images are collected using filter sets appropriate for the 3 types of particles comprising a single excitation filter (Chroma HQ480/40x) and three different emission filters, Chroma HQ522/40m for yellow-green particles, Chroma HQ567/15m for orange particles, and Chroma HQ667/30m for dark red particles.). The number of yellow-green particles (HIV-specific) minus the number of dark red particles (negative control) indicates the number of viruses in the sample. The ratio of the number of dark red particles to the number of input Fd bacteriophage particles indicates the efficiency of the test.

Example 30

Analysis of Human Cells by Immunophenotyping: Quantifying CD4+ Cells in AIDS Patients Human disease diagnostics, including cancer and immunodeficiency diagnostics, depend on identification of human cells based on their distinct molecular constituencies. Immunophenotyping, an important tool identifying specific cell types, uses antibodies to tag and stain target cells. Common technical formats for immunophenotyping include flow cytometry and high magnification microscopy (immunohistochemistry). However, flow cytometry requires expensive instrumentation and high magnification microscopy can be insensitive. In contrast, immunophenotyping assays using the invention can be both sensitive and relatively inexpensive. This example uses the invention for a test that is key to determining the immune status, and thus the health, of patients with AIDS. The assay determines the concentration of CD4+ T cells in blood. The example is technically similar to Example 8 except that in this example the target cells are human cells and that the sample is blood.

Preparing magnetic and fluorescent particles. CD4+-specific fluorescent and magnetic particles are prepared as in Example 8 except that CD4-specific antibody (Biodesign; cat #P54400M) is used here. The coated particles are mixed as in Example 8, and added (25 μl of the 1% suspension) to each of 6 wells of a 96-well microtiter dish with an optically clear bottom (e.g., Greiner; catalogue #655896) containing PBS-TB (175 μl).

Quantifying CD4+ cells in whole blood. Whole blood (5 μl) from a patient with AIDS is added to the particle mixture in each of 2 of the 6 microtiter dish wells (constituting duplicate experimental sample wells). Whole blood (5 μl) from a healthy donor (with known CD4+ cell concentration) is added to each of two wells (constituting duplicate positive control wells). Human serum (depleted of cells; Biochemed; cat. num. 758AB) is added to the third pair of wells containing the particle mixture (constituting duplicate negative control wells). Cells and particles are incubated at room temperature for 20 min. CD4+ cells that have associated with CD4+-specific magnetic particles are drawn to the bottom face of the wells using a magnet as in Example 8. The unbound material is removed by washing (3 washes; 200 μl PBS-TB each wash) while maintaining the magnetic field. The CD4+ cells are imaged and quantified as in Example 8. The efficiency of the test is determined by comparing the CD4+ cell count in the positive control to the known concentration. The background level of the assay is determined from the negative control wells.

Example 31

A Rapid Homogenous Immunoassay for *Chlamydia trachomatis* and *Neisseria gonorrhoeae*

Overview. The diagnostic assay developed in this example tests for two sexually transmitted pathogens, *Chlamydia trachomatis* and *Neisseria gonorrhoeae*, which commonly cause urethritis. The infections have serious sequelae including pelvic inflammatory disease, infertility, and increased susceptibility to HIV infection. It has been estimated that about 150 million people were newly infected with one of these two pathogens in 1995 (almost 1 million people in the U.S. were infected in 1998). Almost 1 billion dollars per year is spent on testing for *C. trachomatis* and *N. gonorrhoeae*. Current testing uses methods range in complexity from Gram staining (for *N. gonorrhoeae*) to DNA amplification. Unfortunately, the tests tend to be either inexpensive and insensitive (e.g., Gram staining, direct fluorescence assays) or sensitive and expensive (e.g., nucleic acid amplification tests).

This example uses the invention to construct a test that inexpensively and sensitively detects, identifies, and enumerates *C. trachomatis* and *N. gonorrhoeae* in a urine sample.

Making pathogen-specific and control particles. The pathogen-specific particles are made using the procedures described in Example 8. Green fluorescent particles (FluoSpheres; catalogue number T-8803; Molecular Probes) and magnetic particles are coated with anti-*Chlamydia* antibodies (BioDesign; catalogue number C65641M). Red fluorescent particles (Molecular Probes TransFluoSpheres, cat#T-8861) and magnetic particles are coated with anti-*N. gonorrhoeae* antibodies (BioDesign; catalogue number C65618M). The positive and negative control particles are made as in Example 29.

Detecting and quantifying *N. gonorrhoeae* and *C. trachomatis* in urine. Urine samples (10 ml) collected using a commercial kit (B-D Urine Collection Kit (Becton-Dickinson, BD Vacutainer™ Brand urine collection cups). The urine is spun at 4000×g for 10 minutes to and the supernatant removed. The pellet is resuspended in 400 µl PBS-B. Samples are mixed with particles, incubated, magnetically selected, imaged and analyzed as in Example 29. However, in this example 4 images are taken of the sample, three with the filter sets described in Example 29, and one with filters appropriate for imaging the red fluorescent particles (Chroma HQ617/40m). The number of yellow-green fluorescent particles indicates the number of *C. trachomatis* in the sample. The number of red fluorescent particles indicates the number of *N. gonorrhoeae* in the sample.

Variations. The test in this example can be extended to include scanning for other pathogens that can cause urethritis (e.g., *Trichomonas vaginalis, Ueraplasma urealyticum* and *Mycoplasma genitalium*). Additional targets can be detected and identified by using additional distinct signaling moieties (i.e., particles with distinguishable fluorescence character) or a combinatorial labeling strategy. Quantitative testing for the presence of polymorphonuclear leukocytes, which is helpful in diagnosing urethritis, can be incorporated into the test by using particles coated with antibodies specific for these cells.

Example 32

A Rapid, Multiplexed, Homogenous, Cytometry Test for Lower Respiratory Pathogens Pneumonia. Pneumonia is the most common cause of death from infectious disease in the United States. The etiology of the disease is dependent on age and immune status. Viruses cause most childhood pneumonia, while bacterial pathogens are the most common pathogens causing adult pneumonia. The spectrum of pathogens that cause pneumonia in immunocompromised hosts varies greatly and differs for patients with cancers affecting the immune system or protective surfaces (mucosal or skin), transplant recipients, and HIV-infected patients.

For successful treatment of pneumonia, it is essential to rapidly identify the pathogen. However, current diagnostic practices are incapable of efficient pathogen identification. More than half of diagnostic efforts to determine the cause of pneumonia fail to identify the etiologic agent. (This does not include the large fraction of cases in which no attempt is made to identify the pathogen). Many bacterial and all viral and fungal pathogens that cause lower respiratory tract infections cannot be identified by routine microbiological culture methods. For example, special methods are required to identify the pathogens that cause tuberculosis, whooping cough, legionnaire's disease, and pneumonia caused by mycoplasma. Lower respiratory diagnostics are complicated by the difficulty in obtaining a lower respiratory sample that is uncontaminated with normal upper respiratory flora. Furthermore, normal flora that are harmless in the upper respiratory tract can cause pneumonia when aspirated by a patient. Discerning whether a strain identified by diagnostics is an upper respiratory contaminant or the etiologic agent requires careful sample quality control measures and microbiological quantification.

Pneumonia cases are generally considered in two classes: community acquired pneumonia and hospital acquired pneumonia. Community acquired pneumonia is a condition that causes about 20,000 deaths and that incurs more than $8 billion treatment costs annually in the United States. Hospital-acquired pneumonia is the most serious and the second most common type of hospital-acquired infection. More than 10% of patients in intensive care units get pneumonia while in the hospital. The fatality rate is high: about ⅓ of nosocomial pneumonia patients die of the disease. Rapid and accurate diagnostics is critical since the optimum life-saving antibiotic therapy depends on which of numerous potential pathogens are causing the disease. The broad range of potential pathogens, some of which are listed in Table 2 contributes to the challenge of lower respiratory diagnostics.

Patients with lower respiratory infections account for 75% of oral antibiotics prescribed in the United States. Nearly $1 billion a year is wasted on useless antibiotics, due to the failure of current diagnostics to identify the pathogen in most lower respiratory tract infections. Incorrect application of antibiotic therapy to viral infections is in large part responsible for the overuse of antibiotics and the current world-wide epidemic of antibiotic resistant pathogens. Thus, there is a great need for a single diagnostic assay that tests for a comprehensive set of lower respiratory pathogens.

Advantages of the test. In this example, the invention is used to make a homogenous immunoassay that is ultra-sensitive, quantitative, and highly multiplexed. By simultaneously testing for common bacterial, viral, and fungal pathogens, the method described here offers a substantial improvement over current practices. The sensitive immunoassay, with no culture, amplification, or enzymatic steps is user-friendly, cost effective, fast, and amenable to commercialization (see Example 8 for advantages of homogenous immunoassays). The test offers major improvements in diagnostic effectiveness leading to appropriate and timely antimicrobial therapy, ultimately saving many lives.

Technical overview of the example. FIG. 32 diagrams the scheme used in this example. A lower respiratory sample (e.g., BAL or liquefied sputum) from a patient with lower respiratory infection symptoms is mixed with an ensemble of particles each of which is coated with antibodies that bind to a particular target pathogen. Each pathogen-specific particle is uniquely color coded by ratio labeling. An approach analogous to that used in Example 31 is used in this more highly multiplexed test.

TABLE 2

| Common lower respiratory pathogens | | |
|---|---|---|
| *Streptococcus pneumoniae* | *Haemophilus influenzae* | *Mycoplasma pneumoniae* |
| *Moraxella catarrhalis* | *Chlamydia pneumoniae* | *Acinetobacter* spp. |
| *Legionella* spp. | *Staphylococcus aureus* | *E. coli* |
| *Klebsiella* spp. | *Serratia marcescens* | *Pseudomonas aeruginosa* |
| *Proteus* spp. | *Enterobacter* spp. | Respiratory Syncytial Virus |
| Adenovirus | Influenza A virus | Influenza B virus |
| Parainfluenza virus | Cytomegalovirus | *Candida albicans* |
| *Aspergillus* spp. | *Cryptococcus neofomans* | *Pneumocystis carinii* |

Pathogen-specific antibodies. The category-binding molecules in this example are antibodies that specifically bind to the lower respiratory pathogens listed in Table 2. Antibodies for each pathogen are obtained, when possible, from commercial sources (e.g., BioDesign, Biotrend Gmbh, Cologne, Germany, Fitzgerald Industries International, Inc., Concord, Mass., and Accurate Chemical and Scientific Corporation, Westbury, N.Y.)). Alternatively, antibodies can be obtained, affinity purified, and tested as described in Example 27.

Antibodies are tested for binding specificity and ability to label target pathogens. For obtaining optimal labeling, several antibodies specific for a particular pathogen are preferably compared to each other. The target pathogen (about $10^5$ pathogens cells or virally infected cells in 10 µl PBS-T) are mixed with the category-specific antibody (about 10 µg in 10 µl PBS-T) and an excess (e.g., 20 µg) of fluorescent labeled (e.g., fluorescein) secondary antibody (e.g., goat anti-mouse or goat anti-rabbit, depending on the source of the category-specific primary antibody) and incubated at room temperature for 20 minutes. Unbound antibodies are removed by washing 2 times in PBS-T (1 ml). Washing is accomplished by spinning the diluted organisms in a microcentrifuge (12,000×g; 1 min). The fluorescently labeled target organisms are then imaged in a fluorescent microscope (Zeiss Axioplan 2) and recorded using imaging software (Image-Pro Plus, Media Cybernetics, Silver Spring, Md.).

Using an analogous assay, antibodies that provide optimal labeling of target pathogens are tested for specificity by binding them to a panel of respiratory pathogens and commensal flora commonly found in the lower respiratory tract. Similarly, to insure that the antibodies do not react with endogenous components of the respiratory tract, each antibody is also tested for binding to panels of upper and lower respiratory samples from normal patients and patients with lower respiratory disease (that is known not to be caused by the target pathogen).

Using these tests, antibodies are chosen that efficiently bind to the target pathogen, but not any other microorganism or component found in respiratory samples.

Constructing an ensemble of category-binding molecule-coated particles. The category-specific antibodies for each of the lower respiratory pathogens listed in Table 2 are used to coat two kinds of particles: polystyrene-coated magnetic particles and fluorescently-dyed polystyrene particles as in Example 8. In this example, however, each family of pathogen-specific antibodies is conjugated to fluorescent particles that are uniquely ratio-labeled. Thus, for each pathogen category, a paired set of category-specific particles is made that comprises magnetic particles and a coded set of fluorescent particles. The fluorescent particles used in this example are custom-made ratio-labeled sulfate-derivatized beads (Bangs Laboratories; combinations of 5 different concentrations of fluorescein (505/515) and Texas Red (595/615). The beads are labeled The particle ensemble is combined so that the final particle concentration is 2% solids (in PBS-TB). Positive and negative control particles are prepared and included in the particle ensemble as in Example 29, except that the control particles in this example are constructed using ratio-labeled particles, with color codings that are distinct from the pathogen-specific particles.

Detection, identification, and quantitation of the pathogens in the sample. Liquefied lower respiratory samples (200 µl BAL samples to which 1000 control phage have been added as in Example 29) are mixed with the particle ensemble (100 µl) in a microtiter dish. The samples are incubated, magnetically selected as in Example 8. Two images are collected using two filter sets appropriate for the two dyes used for ratio-labeling (for fluorescein: excitation Chroma HQ480/40x and emission Chroma HQ535/50m; for Texas Red: excitation Chroma HQ560/55x and emission (Chroma HQ645/75m). The images are aligned using Image-Pro Plus software. The fluorescent signature (i.e., the ratio of the two dyes used for ratio-labeling) of each object found by the software is scored and compared to a look-up table (created empirically using the different classes of ratio-labeled fluorescent particles) that correlates fluorescent signature and pathogen-specificity. The number and classification of objects is tabulated using a customized software module created with the ImagePro Plus software package. The efficiency of the test is monitored by enumeration of the objects corresponding to the positive and negative control particles. The test background is estimated by analysis of a test run in parallel in which PBS (200 µl) is substituted for the BAL sample.

Chroma HQ560/55x) and emission (Chroma HQ645/75m) Chroma excitation 560/55, emission 645/75

Example 33

An Immunoassay that Scans in Parallel for Numerous Lower Respiratory Pathogens Using Non-Magnified Large Area Imaging Overview. The medical goals and significance of this example are identical to those of Example 32. Here, as in that example, category-specific antibodies are used to simultaneously scan a lower respiratory sample for numerous diverse pathogens that cause pneumonia (including viruses, bacteria, and fungi). However, in this example, the sample is affixed to a glass slide. The identity of the lower respiratory pathogen is determined by parallel immunohistochemical analyses followed by imaging individual targets by non-magnified large area imaging. FIG. 33 shows the scheme used in this example.

Indirect fluorescent assay of a lower respiratory sample. Smears of lower respiratory samples are prepared on glass slides and fixed as described previously (e.g., Isenberg, ed., 1992, supra; section 9.5). To bind the different antibodies to different sections of the glass slides, adhesive wells (e.g., adhesive silicone flexiPerm cell culture chambers, custom manufactured with 30 wells; IVSS; Sartorius) are affixed to the slides. The category-specific antibodies used in this example are described in Example 32. Each type of category-specific antibody (200 µl; 10 µg/ml in PBS) is added to a different well. As a negative controls, purified IgG from rabbit pre-immune serum (200 µl; 10 µg/ml in PBS; Rabbit IgG Reagent Grade, Sigma, Cat. No., 15006) and purified IgG from mouse pre-immune serum (Mouse IgG Reagent Grade Sigma, Cat. No., 5381) are added to separate wells. Slides are incubated at room temperature for 30 min. Wells are washed with PBS (200 µl; 4 washes). The adhesive wells are then removed so that the entire slide can be efficiently processed as a single unit. After immersing the slide in PBS (in a Coplin jar) and then in distilled water, the slide is allowed to air dry. The sample is completely overlain with a mixture of goat-anit rabbit and goat anti-mouse biotinylated polyclonal secondary antibodies (5 µg/µl each polyclonal antibody in PBS) and allowed to incubate for 30 min at room temperature in a humidified slide chamber (Boekel). After rinsing (2 times in PBS; 1 time in distilled water; in a Coplin jar), the sample is completely overlain with streptavidin-coated fluorescent particles (Molecular Probes; cat. num. F-8780; 0.5% solids), incubated, and washed as in the previous step.

Imaging and analysis. The sample is imaged using a CCD-based imager as before (described in Step 6 of Detailed description section and shown in FIG. 3). The imager acquires an image of each section of the slide corresponding to a well containing a pathogen-specific antibody or control antibody. Image analysis software (Image-Pro Plus) then calculates the total fluorescence and the number of fluorescently stained objects in each image. A well with significantly more fluorescent objects and fluorescent intensity than the negative control wells indicates the possibility of an infection caused by the corresponding pathogen.

Variations and related embodiments. It may be useful bundle tests in this compound assay (in additional wells) that test for commensal species normally found in the oral/pharyngeal region that typically contaminate lower respiratory samples. It may also be useful to include antibodies specific for squamous epithelial cells (which can indicate the quality of the lower respiratory sample) and/or cells of the immune system (which can be informative about the likelihood of infection).

Other types of signaling moieties with the potential for attaining high signal complexity can be used in place of the ratio-labeled particles. For example, fluorophore labeled antibodies can be used analogously. Labeling two pools of each pathogen-specific antibody with two or more fluorophores can generate high signal complexities. The final antibody family used in the assay is created by mixing a unique ratio of the differentially labeled pathogen-specific antibodies. For example, the antibody family that is specific for pathogen X might have one part red fluorescent antibodies, one part yellow antibodies, and one part blue antibodies. The antibody family that is specific for pathogen Y might have two parts yellow antibodies, and one part blue antibodies, and so on. Note that the signal intensity of targets labeled with fluorescent antibodies will, in general be much reduced compared to the highly fluorescent particles used in the example. The signal intensity depends also on the number of antigens on the targets. Thus, for small targets, and other targets with relatively low numbers of category-specific binding sites, this method may require more sensitive signal detection instrumentation.

An approach analogous to the one in this example can also be used for an in situ nucleic acid hybridization-based test. In this case, cells would be prepared, fixed, and hybridized as described in Example 1 except that each family of category-specific probes would be labeled with biotin (using standard methods; e.g., incorporation during PCR). After hybridization and washing the slides would be processed and imaged as in this example (i.e., the steps that occur after removing unbound biotinylated secondary antibody).

Example 34

Multiplexed Identification of Urinary Tract Infections Without Culture

Figure 34:
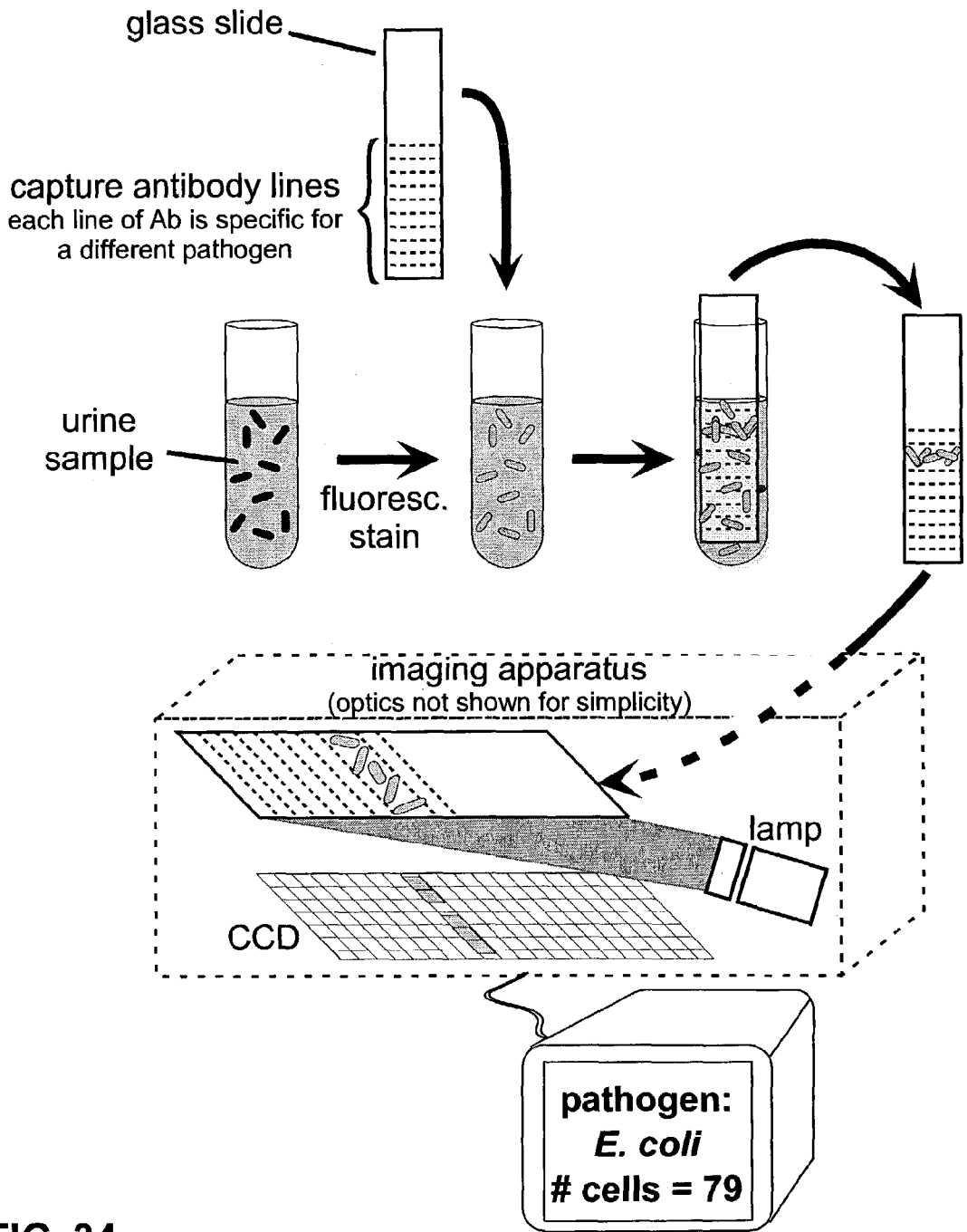

Urinary tract infections (UTIs) are common—about 150 million cases per year—and represent healthcare costs in the billions of dollars. Confirmed diagnosis of UTI generally requires a urine culture which is time-consuming and, for some pathogens, not possible using standard microbiological methods and media (e.g., *Chlamydia trachomatis*). This example describes the use of the invention to construct a simple and sensitive UTI test that is highly multiplexed and does not require bacterial culture. The scheme of the test method is shown in FIG. 34.

Antibodies that bind to common UTI pathogens. Table 3 indicates the cellular pathogens that commonly cause UTI. Antibodies that specifically bind to each pathogen are obtained and selected analogously to those in Example 27 and Example 32. In addition to the species-specific antibodies, antibodies that react to broad groups of bacteria are used in this example. Antibodies that bind to most gram-negative bacteria (e.g., cat. #15306, QED Bioscience, Inc., San Diego, Calif.) and to most gram-positive bacteria (cat #15711, QED Bioscience, Inc., San Diego, Calif.) are included for detection of less common organisms for which species-specific antibodies are not included.

TABLE 3

Bacterial pathogens that cause urinary tract infections (UTI).

| | |
|---|---|
| *Escherichia coil* | Morganella spp. |
| *Staphylococcus saprophyticus* | Citrobacter spp. |
| Klebsiella spp. | Group B streptococcus |
| Enterobacter spp. | Group D streptococcus |
| Proteus spp. | Enterococci |
| *Chlamydia trachomatis* | *Pseudomonas aeruginosa* |
| *Neisseria gonorrhoeae* | Acinetobacter spp. |
| *Corynebacterium urealyticum* | Serratia spp. |

Attaching capture antibodies to a glass slide. Antibodies are covalently bound to aldehyde-containing glass slides (TeleChem International; SuperAldehyde Substrates). To bind the different antibodies to different sections of the glass slides, adhesive wells (e.g., adhesive silicone flexiPerm cell culture chambers, custom manufactured with 24 wells; IVSS/Sartorius) are affixed to the slides. Each type of category-specific antibody (100 µg/ml in PBS; ~2.5 mm deep) is added to a different well and then processed as described previously (MacBeath, G., et al., Science 289: 1760-3, 2000). The silicone wells are removed after the free antibody is removed from the wells by washing and before the subsequent processing steps.

Direct binding of UTI pathogens in urine samples to immobilized capture antibodies. Urine samples are collected according to standard procedures (Isenberg, ed., 1992, supra). Samples (28 ml in 50 ml disposable polypropylene tube; Falcon) are neutralized by addition of 1M EPPS pH 8.0 (4 ml; sodium salt), 100 mM NaEDTA pH 8.0 (4 ml; sodium salt), and 10XPBS-TB (4 ml; see definitions). A microscope slide with bound capture antibodies is submerged in the urine sample and incubated at room temperature for 2 hr with gentle agitation (Bambino rotator; Boekel). During the incubation, bacteria contact and adhere to the section of the slide containing the corresponding capture antibodies. The feasibility of this assay is made possible by the fact that bacterial UTI infections generally occur at high pathogen titers (e.g., $10^3$–$10^5$ cells/ml).

Staining captured cells and imaging. The slide is removed from the urine sample, washed (3×; 50 ml PBS-TB; 5 min; with gentle agitation; followed by a 50 ml EE wash; 15 seconds with gentle agitation), air dried, and heat fixed (5 min on the surface of a heat block heated to 100° C.). The slide is then covered with a solution containing Syber Green I (1:1000 dilution of 10,000× stock solution; Molecular Probes; #S7563), incubated (10 minutes at room temperature), and washed (two 50 ml washes in EE; 1 min each; with gentle agitation).

Each sector of the slide is analyzed by non-magnified large area fluorescent imaging using the imager shown in FIG. 3A and described in Step 6 of the Detailed Description section above.

Alternative tests, methods, and formats. The test described in this example has numerous applications including, for example, identifying pathogens in respiratory, infected surgical wound, food, or environmental samples. Analogous assays could be constructed using alternative labeling techniques (e.g., fluorescent particles, alkaline-phosphatase/antibody-coated particles, horseradish-peroxidase:antibody conjugates, fluorescent antibodies, RLS particles, magnetic particles), formats (e.g., microfluidic or lateral flow and flow through formats, in which the capture antibodies are attached to bibulous membranes), and imaging methods (et e.g., visual or reflectometer detection of chromogenic assays and film luminography of chemiluminescent and bioluminescent assays) many of which are described elsewhere in this application.

Example 35

Rapid, Multiplexed, Identification of Blood-Borne Viruses: HIV, HCV HBV, and CMV Detection of blood-borne viruses is an essential for testing individual patient samples and samples in blood banking applications. Serological tests (testing for antibodies that are specific for the target viruses) are commonly used. However, methods that directly test for the target virus have the advantage of detecting infected samples earlier in the infection process than serological methods. This is because antibodies specific for the pathogen generally do not appear in the blood of an infected individual (sero-conversion) for three to four weeks. Unfortunately, direct tests for viruses are either insensitive (most antigen tests) or expensive (most nucleic acid tests).

This example describes use of the invention to construct a rapid, multiplexed test that can detect individual free virus particles in blood samples without using microscopy. The scheme of the test is displayed in FIG. 35.

Coating fluorescent particles and wells with anti-viral antibodies. Antibodies specific for the target viruses can be purchased from numerous commercial sources. For example, the following antibodies are obtained from the indicated distributors: anti-HIV (anti-gp120; monoclonal; Biodesign; cat. #C65199M); anti-HCV (Biodesign; cat. #C8A024M); anti-HBV (anti-Hepatitis B Surface Antigen; monoclonal; Biodesign; cat. #C86132M); and anti-CMV ((anti-glycoprotein B; monoclonal; Biodesign; cat. #C8A024M).

Antibodies are bound to microtiter dish wells in four adjacent distinct spots per well (1 spot per antibody) by passive absorption. Each anti-viral antibody is spotted (1 µl; 1 µg/µl) in a well of a 96-well microtiter plate (Greiner America; cat. num. 55896) and incubated for 2 hrs at room temperature in a humidified chamber (Boekel Slide Moat; model 240000). Wells are then washed and blocked as described.

Color-coded virus specific fluorescent particles are made by coating fluorescently dyed polystyrene particles with distinct emission spectra with the anti-viral antibodies using methods described in Example 8. Fluorescent particles (Molecular Probes) are coded as follows: HIV-specific particles (Yellow-Green; cat #F8823); HCV-specific particles (Orange; cat #F8820); HBV-specific particles (Crimson; cat #F8816); and CMV-specific particles (Infrared; cat #F8818). The 4 types of antibody-coated particles are mixed at equal concentrations ($10^7$ particles/ml in PBS-T). Before use, the antibodies are sonicated and washed (Example 8). Note that, as the various antibodies are segregated in spots in the well, it is also possible to use the same type of fluorescent particle for each virus. However, use of distinct signaling moieties increases the robustness of the test.

Detecting viruses in blood samples. Blood samples are collected from various sources including, for example, from patients using standard methods including treatment with the anti-coagulant EDTA as described in e.g., (Isenberg, ed., 1992, supra); from units of donated blood; or from blood fractions (e.g., plasma). Whole blood (200 µl) is added to a microtiter dish wells containing spots of each capture antibody. The sample is allowed to incubate at 37° for 2 hours to insure that viruses can adhere to capture antibodies on the well surface. The blood sample is removed from the well which are washed thoroughly (4×; 200 µl PBS-TB used for each wash). The mixture of virus-specific particles (200 µl) is added to the well and spun briefly (Beckman Allegra 6; GH-3.8 rotor; 1200 g) to coat the bottom of the well with particles. After a brief incubation (10 min at room temperature) unbound particles are removed by washing with agitation (4×200 µl PBS-TB with vortexing; 1 min each wash). Finally, the wells are rinsed with EE (200 µl) and allowed to dry. The wells are then imaged and analyzed using a CCD imager as in Example 8 except that multiple images are acquired using the appropriate filter sets (yellow green: excitation Chroma HQ480/40x and emission Chroma HQ535/50m; orange: excitation Chroma HQ535/50X and emission Chroma HG610/75m; crimson: excitation Chroma HQ560/55x and emission Chroma HQ645/75m; and infrared: excitation Chroma HQ710/75x and emission Chroma HQ810/90m). Viruses are identified by the spots to which bound particles adhere. Additional diagnostic robustness is provided by the fact that only particles of the expected color adhere to a particular spot if the assay is successful.

Example 36

Ultra-Sensitive Lateral Flow Test for Influenza A Virus Using Non-Magnified Large Area Imaging Objective: This example demonstrates the use of the invention to rapidly detect low levels of virus with a user-friendly lateral flow assay format and non-magnified large area imaging. In the experiment described below, dilutions of Influenza A particles were applied to porous membrane strips, contacted with labeling particles in a conjugate pad, and moved by capillary action past capture antibodies for selecting virus: labeling particle complexes. These captured complexes were then visualized using large area non-magnified imaging.

Experimental Methods: The lateral flow test strips were assembled as described. Antibody lines were made by stripping both a Influenza A specific capture line (QED, cat. no. 1302) and control line (Jackson Immuno Research Laboratories, Inc.; biotin anti-mouse IgG, cat. no. 115-165-146) onto the membrane (5-10 mm from wicking pad). The lines were allowed to dry (at least 15 min) before use. Streptavidin labeled fluorescent beads (Bangs Laboratories Inc.; cat. no. CP01 F-5121) were labeled with biotin anti-Influenza A antibody (Virostat; cat. no. 1307) by combining the beads (10 µl of $1.23 \times 10^{11}$ stock), antibody (10 µl of 1.0 µg/ml stock) and PBS (80 µl) and mixing (1.5 hours/room temp). The beads were then spun down (5000 g, 10 min) and resuspended in PBS-B (100 µl). The anti-Influenza A coated fluorescent beads (2 µl) were added to the conjugate pad of each strip. A stock of purified Influenza A (Advanced Biotechnologies Inc: Influenza A/PR/8/34 (H1N1), cat. no. 10-210-000) was serially diluted using PBS-B. Test samples (100 µl of an IL-2 dilution) were combined with PBS-TB (50 µl) and added to the sample pad of the test strip. After running the assay (~15 minutes) the strips were imaging using non-magnified large area imaging.

Results: FIG. 36 shows the results of lateral flow tests for Influenza A virus labeled with fluorescent labeling particles and analyzed using non-magnified large area imaging. The figure shows images of the capture and control lines from test strips onto which were applied samples containing (from left to right) 0, $10^5$, $10^6$, $10^7$ and $10^8$ virion/ml. The fluorescent signal increases with increasing concentration of Influenza A virions. The data shown shows the test can detect concentrations at least as low as $10^5$ virions/ml. This experiment therefore demonstrates the sensitivity of lateral flow tests based on the invention.

Example 37

A Rapid Lateral Flow Test for *M. tuberculosis* Using Visual Detection

Overview. Rapid lateral flow, or "strip", test formats are becoming increasingly important for offering point-of-care diagnostics (e.g., in doctors' offices, emergency rooms, and home testing). However, lateral flow tests are often too insensitive to be used to detect infections caused by pathogens that may be present at low levels in clinical samples. For example, detecting *M. tuberculosis* infection in sputum requires detecting several thousand cells/ml of sputum—below the sensitivity threshold of current strip tests. There is a critical unmet public health need in the developing world for simple non-instrumented tests for *M. tuberculosis*. Although nucleic acid amplification tests can detect low titers of *M. tuberculosis*, these tests are too expensive and complex to be of use in most clinical settings.

This example describes an inexpensive, simple, fast, and highly sensitive lateral flow test for *M. tuberculosis*. The user interprets the test visually—without the use of an instrument.

Binding anti-*M. tuberculosis* antibodies and alkaline phosphatase to nanoparticles. Monoclonal anti-*M. tuberculosis* antibodies (MPB64-ICA; Abe, et al., 1999, supra) and alkaline phosphatase (Pierce; 31391) in equimolar concentrations are bound to gold conjugate particles (30 nm; Nanoprobes; CG3054) by passive adsorption according to the manufacturer's recommendations and resuspended at $10^{11}$ particles/ml.

The lateral flow unit is designed and constructed using specifications, materials, and procedures that are understood by those skilled in the art of lateral flow testing. The design and construction issues are described in technical notes provided by manufacturer's of lateral flow tests (e.g., *Millipore's Short Guide for Developing Immunochromatographic Test Strips*, 2nd ed., Millipore, technical note #TB500, 1999; *Lateral Flow Tests*, 1st ed., Bangs Laboratories, technical note #303, 1999) and other literature (e.g., Chandler, J, et al., IVD Technology 6: 37-49, 2000; Weiss, Alan, IVD Technology 5: 48-57, 1999; Wild, D, ed. (2001). *The Immunoassay Handbook.* 2nd ed. New York, N.Y.: Nature Publishing Group, 2001)).

Lateral flow components are assembled from a kit (Millipore; catalog number HFMIDAK015; Hi-Flow Plus Membrane Assortment Assembly Kit) according to the manufacturer's instructions. The antibodies in the test zone and the agents in the control zone are applied as stripes using a reagent dispensing apparatus (matrix 1600; Kinematics) according to the manufacturer's recommendations.

Liquefied sputum or BAL samples (200 µl; Example 27) are spotted onto the sample pad. The sample moves via capillary action through the membrane. After a brief period (3 min) PBS-T (200 µl) is applied to the sample pad to allow the sample to proceed through the membrane via capillary action. This PBS-T wash step is repeated after another brief period (3 min). After another 3 minutes, gold conjugates (10 µl; $10^9$ particles coated with anti-*M. tuberculosis*/alkaline phosphatase) are then applied to the sample pad followed by two PBS-T washes (as before). Alkaline-phosphatase substrate (1 ml; BM purple; Boehringer Mannheim) is applied directly to the membrane and allowed to develop until spots are visible in the positive control zone (30 min-1 hr) after which time the residual calorimetric detection reagent is poured off and water (1 ml) is applied directly to the membrane. After 3 min the water is poured off. If the test works correctly, there are about 1000 spots visible in the positive control zone. The number of spots in the test zone indicates the number of *M. tuberculosis* in the sample.

Various alternative immunochromatographic configurations are also possible including "flow through" arrangements (see Example 23).

Example 38

A Rapid Lateral Flow Test for Detecting Numerous Disparate Biowarfare Agents Using Non-Magnified Large Area Imaging Diagnosing infection due to agents of biowarfare presents several challenges beyond those encountered in routine infectious disease diagnostics. The agents that are likely to be employed in bioterrorism or biowarfare are expected to be different than those seen in normal medical practice and therefore may be difficult to recognize using standard diagnostic protocols. Diagnosing use of unconventional agents in the field requires scanning for disparate agents (including toxins, viruses, and bacteria) using portable user-friendly systems that can detect infection at early stages when titers are very low.

This example describes a lateral flow immunoassay that is rapid, portable, and user-friendly, and that can scan a sample for a broad range of agents present in low numbers in a clinical or environmental sample. Technically, the example resembles Example 36 except that numerous pathogens are detected in one assay and that chemiluminescent signals are detected electronically.

TABLE 4

| Unconventional agents likely to be used in biowarfare or bioterrorism | | |
|---|---|---|
| *Bacillus anthracis* | Shigella spp. | Variola virus |
| *Yersinia pestis* | Salmonella spp. | Marburg virus |
| *Francisella tularensis* | *Vibrio cholerae* | Ebola virus |
| *Brucella suis* | Ricin toxin | |
| *Coxiella burnetii* | Botulinum toxin | |

Nanogold-antibody conjugates specific for agents likely to be used in biowarfare or bioterrorism. The example scans a sample (e.g., blood) for the agents listed in Table 4, some of which are bacteria, viruses, and protein toxins. Antibodies specific to each agent in Table 4 are obtained, affinity purified, and tested for specificity as described in Example 32 and Example 27. Note that for the protein toxins, monoclonal antibodies with distinct and non-overlapping epitopes are used for conjugation to nanogold particles and for the test zone (or capture zone) on the lateral flow membrane (see below).

Nanogold conjugates, specific for the agents in Table 4, are made by passive adsorption of each type of affinity purified antibody and equimolar alkaline phosphatase as described in Example 26. The resultant agent-specific conjugates in PBS-TB are mixed together in equimolar concentrations so that the final total conjugate concentration is solids in PBS-TB.

Lateral flow device. The lateral flow test in this example is constructed and implemented as is the assay in Example 36, except for the larger number of analytes tested, the different signal character (chemiluminescence in this example, calorimetric in Example 36), and the use of a conjugate pad in this example. FIG. 38 shows the configuration of the lateral flow test. The figure has been simplified for clarity (e.g., the test depicts an assay for only three of the agents in Table 4 and the three conjugates shown on the conjugate pad at the top of the figure represent a population of agent-specific conjugates). The disposable lateral flow device has a test zone and a control zone as in Example 36, but in this case the test zone contains parallel stripes of affixed agent-specific antibodies—one stripe for each agent-specific antibody. The control zone contains parallel stripes of affixed unconventional agents—one stripe for each target agent. The mixture of agent-specific conjugates are embedded in the conjugate pad as described in various references (e.g., Millipore, technical note #TB500, 1999, supra; Bangs Laboratories, technical note #303, 1999, supra; Chandler, J, et al., 2000, supra; Weiss, A., 1999, supra; Wild, 2001, supra).

Lateral flow assay. A liquefied sample (200 µl of e.g., saliva, liquefied sputum, serum) is applied to the sample pad, followed by 3 applications of 200 µl PBS-TB to the sample pad (waiting 60 seconds between applications to the sample pad). The liquefied sample mobilizes the conjugates as it moves from the sample pad through the conjugate pad via capillary action (FIG. 38). Any target agents that may be present in the sample bind to the corresponding nanogold: antibody:AP conjugates. The agent:nanogod complexes continue to move by capillary action until they encounter the corresponding agent-specific antibodies in the test zone stripe corresponding to the particular agent whereupon the agent: nanogold complexes become immobilized. Nanogold conjugates that have not bound to agents proceed to the control zone and bind to the corresponding stripe of control antigens.

The test strip is covered with CDP-Star (PE Biosystems) and allowed to incubate for 5 minutes. The strip is then imaged using a CCD imager (Orca II; Hamamatsu) as depicted in FIG. 38. Individual agents (organisms, viruses, or proteins) are detected by virtue of the chemiluminescence emitted by the alkaline phosphatase coated particles to which the agent is bound. If the assay works correctly, all of the control stripes are coated with chemiluminescent particles. If one (or more) agents are present in the sample, the corresponding stripes will contain immobilized chemiluminescent particles. The identity of the agents are determined by the distance of the positive test stripe from the control stripes (the distances of each agent's test stripe from the control stripes is known). Imaging software (Image-Pro Plus) processes the image collected by the CCD camera using macros that quantify the number of spots in the test stripes and assign identity to the agent by measuring the distance from the control stripes.

Example 39

A Comprehensive Test for Respiratory Pathogens Using Nucleic Acid Probes

Objectives and Advantages. In this example, a single assay comprehensively tests for the presence of a disparate array of common respiratory pathogens in a sample from a patient with symptoms of lower respiratory disease. The medical goals and significance of this example are identical to those of Example 32. This example, however, uses genomic DNA probes and an in situ hybridization format rather than antibody category-binding molecules and an immunoassay format.

Technical overview of the example. Category-specific sequences are isolated from various lower respiratory tract pathogens using genomic subtraction (bacteria and fungi), or computer analysis (viruses). A family of oligonucleotide probes is synthesized corresponding to the Category-specific sequences specific to each pathogenic group. Each family of category-specific probes is labeled with a distinct combination of fluorescent quantum dot labels. The entire probe ensemble (i.e., all of the probe families) is hybridized to the sample, which is fixed to a slide and then the unbound probes are washed away. Using a CCD camera, the identity of a pathogen in a clinical sample is determined by ascertaining which family of pathogen-specific probes—i.e. which combination of quantum dot labels—hybridizes to the microbes in the sample.

Isolating Category-specific sequences from pathogens that cause lower respiratory disease. Table 2 lists common pathogens that cause lower respiratory infections. The genomic subtraction method (Straus 1995, supra) is used to isolate category-specific sequences from the bacterial and fungal (i.e., non-viral) pathogens. The following section illustrates the subtraction strategy by describing the process for purifying and identifying diagnostic markers specific to Streptococcus pneumoniae. S. pneumoniae is by far the most common cause of pneumonia; it is responsible for about 30-50% of all cases of community acquired pneumonia (500,000 per year in the U.S.).

Using genomic subtraction to isolate a set of DNA fragments including S. pneumoniae category-specific sequences. FIG. 39A shows the phylogenetic relationship between S. pneumoniae and its closest relatives (Kawamura, et al., International Journal Of Systematic Bacteriology 45: 406-8, 1995). The strategy for isolating category-specific sequences can be broken down into two steps: a genomic subtraction step (FIG. 39B) and a screening step (FIG. 39C). First, genomic subtraction (Straus, 1995, supra) is carried out using the DNA from the pathogenic strain (in this case S. pneumoniae) as the "+" genomic difference sample (FIG. 39B). The "−" genomic difference sample is constructed by pooling several of the closest related strains—these strains do not commonly cause pneumonia. The resulting subtraction products are fragments that hybridize to the pathogen's genome but not to the genomes of the closely related species. These fragments are then cloned into the Xhol site of pBluescript I vector using the partial fill-in method (Corrette-Bennett, et al., Nucleic Acids Res 26: 1812-8, 1998).

Identifying subtraction products that are category-specific sequences. The next step is to isolate a subset of the S. pneumoniae-specific subtraction products that are category-specific, that is, that hybridize to all S. pneumoniae strains but that do not hybridize to any strains in other groups. Note that not all of the subtraction products are category-specific sequences. The set of subtraction products does contain all of the desired category-specific sequences fragments, but also contains some non-category-specific fragments. This is because the genomic subtraction experiment (see previous paragraph) selected for fragments that hybridize to a single S. pneumoniae strain (the "+" strain in the genomic subtraction) and that do not hybridize to single strains of several related species. Thus, for example, some of the subtraction products do not hybridize to some other S. pneumoniae strains and some do hybridize to different strains of S. mitis than were used in the subtraction.

To identify the subset of subtraction products that are category-specific sequences, the cloned fragments are screened by hybridization to the genomic DNA of many different Streptococcus isolates. Because it is impossible to test a probe for hybridization to all S. pneumoniae strains, the best approximation is made by testing the probes for hybridization to hundreds of *S. pneumoniae* strains isolated from all over the world and that have been isolated over a period of several decades (for *S. pneumoniae* strains are obtained from collections archived at the American Type Culture Center, and the Center for Disease Control). Similarly, each probe is tested for hybridization to many non-*S. pneumoniae* strains of Streptococcus. FIG. 39C shows a convenient method for testing whether a probe is a category-specific sequence. Genomic DNA is prepared from disparate isolates of *S. pneumoniae* and related *Streptococcus* species (using the method of Graves and Swaminathan Graves, et al. (1993). Universal Bacterial DNA isolation procedure. In Diagnostic molecular microbiology: principles and applications, D. Persing, T. Smith, F. Tenover and T. White, eds. (Washington, D.C.: American Society for Microbiology), pp. 617-621.), denatured, and spotted on a positively charged nylon filter (e.g., GeneScreen Plus, NEN) in the form of a dot blot array (Ausubel 1987, supra). (For species that are amenable to colony hybridization, rather than "dot blotting", strains can be grown and lysed in situ on nylon filters, thus avoiding purifying DNA from a large number of strains).

To test whether a cloned subtraction product is a category-specific sequence, it is hybridized to the arrayed genomic DNA. A clone is classified as a category-specific sequence if it hybridizes to genomic DNA from all of the *S. pneumoniae* strains but to none of the genomic DNA from related *Streptococcus* species (FIG. 39C). The cloned subtraction products are labeled by incorporating digoxygenin during PCR amplification of the cloned recombinant plasmids. The standard PCR conditions are used (see definitions) with XhoL and XhoR primers (which directly flank the cloned subtraction products in the Bluescript vector) except that reactions are supplemented with digoxygenin-dUTP (100 PM; Boehringer Mannheim). Individual labeled probes are then hybridized to the dot blot arrays of genomic DNA using standard methods for high stringency hybridization (Ausubel 1987, supra) followed by detection using an alkaline-phosphatase:anti-digoxygenin antibody conjugate (Genius; Boehringer Mannheim) and CDP-Star (NEN) following the manufacturer's recommended protocol (Boehringer Mannheim). Chemiluminescent images are obtained using a CCD camera (ORCA II; Hamamatsu) housed in a light-tight enclosure (Alpha Innotech Corp., MultiImage II cabinet, Cat #DE-500-110) and analyzed using Image-Pro imaging software package (Media Cybernetics, Silverspring, Md.).

Synthesizing a family of category-specific oligonucleotides. Next, oligonucleotide probes are synthesized that correspond to 30 of the category-specific clones identified by the dot blot analysis described above. First each of the 30 chosen *S. pneumoniae* category-specific sequences is sequenced. All DNA sequencing is carried out using an ABI 377 automatic sequencer from Perkin Elmer and using methods recommended by the manufacturer. For synthesizing oligonucleotide probes, 2 subsequences approximately 20 bases long from each of the 30 category-specific sequences are chosen using the program "Primer3" (S. Rozen, H. Skaletsky (1998)) using the default parameter settings for internal hybridization oligonucleotide picking except that the minimum melting temperature is set to 59° and the maximum melting temperature is set to 61°.

Each oligonucleotide is synthesized with an amino group modification at the 5' terminus (Midland Certified Scientific Reagent Co.). The amino-modified oligonucleotides is capable of being covalently attached to highly fluorescent quantum dots (see below).

TABLE 5

Combinatorial labeling using quantum dots. By combining 5 types of distinctly colored quantum dots, 31 ($2^5$ - 1) different combinations of colors are possible. For each of the 24 pathogens listed in top row of Table 2, a subset of the pathogen-specific oligonucleotides are bound to each type of quantum dot marked with a diamond in the column. Thus, a family of probes with a distinct signal signature is constructed for each pathogen. Note that 7 of the 31 possible combinations of the 5 label colors are not shown in the table (i.e., the combinations corresponding to no colors, 1 color, and 5 colors).

|  | *Streptococcus pneumoniae* | *Haemophilus influenzae* | *Mycoplasma pneumoniae* | *Moraella catarrhalis* | *Chlamydia pneumoniae* | Acinetobacter spp. | Legionella spp. | *Staphylococcus aureus* |
|---|---|---|---|---|---|---|---|---|
| violet | ♦ | ♦ | ♦ | ♦ |  |  |  |  |
| blue | ♦ |  |  |  | ♦ | ♦ | ♦ |  |
| green |  | ♦ |  |  | ♦ |  |  | ♦ |
| yellow |  |  | ♦ |  |  | ♦ |  | ♦ |
| red |  |  |  | ♦ |  |  | ♦ |  |

|  | Klebsiella spp. | *Serratia marcescens* | *Pseudomonas aeruginosa* | *Pseudomonas aeruginosa* | Proteus spp. | Enterobacter spp. | Respiratory Syncytial Virus | Adenovirus |
|---|---|---|---|---|---|---|---|---|
| violet |  | ♦ | ♦ | ♦ | ♦ | ♦ | ♦ | ♦ |
| blue |  | ♦ | ♦ | ♦ | ♦ |  |  |  |
| green |  | ♦ |  |  |  |  | ♦ | ♦ |
| yellow | ♦ |  | ♦ | ♦ |  | ♦ |  | ♦ |
| red | ♦ |  |  |  | ♦ |  | ♦ | ♦ |

|  | *E. coli* | Influenza A virus | Influenza B virus | Parainfluenza virus | Cytomegalovirus | *Candida albicans* | Aspergillus spp. | *Cryptococcus neoformans* |
|---|---|---|---|---|---|---|---|---|
| violet |  |  |  |  |  | ♦ |  | ♦ |
| blue |  | ♦ | ♦ | ♦ |  | ♦ | ♦ |  |
| green | ♦ |  | ♦ |  | ♦ | ♦ | ♦ | ♦ |

TABLE 5-continued

Combinatorial labeling using quantum dots. By combining 5 types of distinctly colored quantum dots, 31 ($2^5 - 1$) different combinations of colors are possible. For each of the 24 pathogens listed in top row of Table 2, a subset of the pathogen-specific oligonucleotides are bound to each type of quantum dot marked with a diamond in the column. Thus, a family of probes with a distinct signal signature is constructed for each pathogen. Note that 7 of the 31 possible combinations of the 5 label colors are not shown in the table (i.e., the combinations corresponding to no colors, 1 color, and 5 colors).

| | | | | | | | | |
|---|---|---|---|---|---|---|---|---|
| yellow | | ♦ | | ♦ | ♦ | ♦ | ♦ | ♦ |
| red | ♦ | | ♦ | ♦ | ♦ | | ♦ | ♦ |

| | *Pneumocustis carinii* |
|---|---|
| violet | ♦ |
| blue | ♦ |
| green | |
| yellow | ♦ |
| red | ♦ |

Combinatorial labeling of category-specific oligonucleotide probe family with quantum dots. To achieve the goal of a comprehensive lower respiratory infection test, the *S. pneumoniae* probe family must be labeled in a way that distinguishes it from probe families corresponding to the other pathogens in Table 2. In this example, each probe family is labeled with a distinct combination of quantum dot labels. The principle of combinatorial labeling is shown in FIG. 5. Quantum dots are nanometer-sized semi-conductor crystals that fluoresce brightly enough to be detected easily as single particles with simple and inexpensive instrumentation (Bruchez, et al., Science 281: 2013-6,1998; Chan, et a., Science 281: 2016-8,1998; Service, Science 281: 1930-1, 1998). In sum, the properties of quantum dots that are very useful for the invention include the fact that the emission spectrum is very narrow; the emission spectrum is determined by the size of the nanocrystal—by varying size, quantum dot labeling reagents with numerous distinct emission spectra are generated (important for this multicolor application); the luminescence is very high, so that single particles can be imaged; the size of the particles is small, comparable to that of a small protein (enhancing accessibility of probes to targets in fixed cells during in situ analysis); quantum dots can be covalently modified with biologically important molecules (e.g., nucleic acids, proteins, biotin); and a single wavelength of light causes emission from quantum dots with different emission spectra.

To distinctly label each of the 24 category-specific oligonucleotide probe families (corresponding to the respiratory pathogen listed in Table 2) different combinations of quantum dots are used. By combining 5 types of distinctly colored quantum dots, 31 ($2^5-1$) different combinations of colors are possible (Table 2). From each set of pathogen-specific oligonucleotides, 100 oligonucleotides are conjugated to each type of quantum dot marked with a diamond in the pathogen's column in Table 2. Thus, for *S. pneumoniae,* 100 different *S. pneumoniae* category-specific oligonucleotides are labeled with violet quantum dots. Similarly, 100 other *S. pneumoniae* category-specific oligonucleotides are labeled with blue quantum dots. The 200 quantum dot-labeled *S. pneumoniae* category-specific oligonucleotides constitute a *S. pneumoniae* category-specific probe family. In situ hybridization of the probe family to individual *S. pneumoniae* cells is detected as clusters of blue and violet quantum dots. Similarly, *Staphylococcus aureus* cells are detected as localized clusters of violet and green quantum dots (as indicated in column 2 of Table 2). Oligonucleotides are covalently bound to quantum dots (Quantum Dot Corp) using the manufacturer's recommended procedures.

An occasional oligonucleotide probe may not behave as a category-specific sequence, even though it is a sub-sequence of a category-specific sequence. This can occur due to patchy sequence divergence within the larger category-specific sequence. Confirmation that the oligonucleotides are category-specific sequences is achieved by hybridizing the quantum dot-labeled oligonucleotides to the dot blots as described above but using hybridization conditions appropriate for oligonucleotides (Ausubel 1987, supra). The dot blots are analyzed using an ORCAII CCD camera (Hamamatsu) with UV epi-illumination in a benchchtop enclosure (Alpha Innotech Corp., MultiImage II cabinet; Cat #DE-500-110) and imaging software (MetaMorph Universal Imaging Corporation, Downingtown, Pa.). Oligonucleotides in the probe set that do not behave as category-specific sequences (hybridizing to all *S. pneumoniae* strains but no other *Streptococcus* strains) are not included in the category-specific oligonucleotide probe family.

Note that other signal generating moieties can be substituted for quantum dots in this example. For example, carboxylate-modified fluorescently labeled particles (40 nanometer diameter TransFluoSpheres, Molecular Probes) can be attached to 5' terminal amino-modified oligonucleotides using EDAC chemistry (according to manufacturer's instructions). Five types of TransFluoSpheres with distinct emission spectra (560, 605, 645, 685, and 720 nm) but all with the same absorbance maximum (488 nm) are then used to label pathogen-specific oligonucleotides in the combinations analogous to the ones using 5 differently types of quantum dots in Table 5.

Alternatively, the larger cloned category-specific sequences can be labeled using a nucleic acid polymerase (e.g., Klenow fragment of DNA polymerase 1, reverse transcriptase, or Taq polymerase) in the presence of modified nucleotides. Examples of useful nucleotide modifications include nucleotides directly conjugated to fluorophores (e.g., the Alexa series from Molecular Probes, or Fluorescein-12-dUTP (NEN Life Sciences; Cat. No., NEL413) nucleotides containing primary amines (which can be conjugated to fluorophores after incorporation into polynucleotides), and hapten modified nucleotides (e.g., digoxygenin-dUTP; Boehringer Mannheim). For hapten-modified polynucleotides, the signaling moiety (e.g., fluorescein-labeled anti-digoxygenin antibody) is often conjugated to the probe after the probe is hybridized to the sample. For combinatorial labeling using polymerase-labeled category-specific sequences, as for oligonucleotides, labeling schemes must use a set of distinguishable signaling moieties.

Isolating category-specific probes for other lower respiratory pathogens. Category-specific probe families for the other bacterial and fungal pathogens in Table 2 are made as described above for S. pneumoniae. However, as indicated above and in Table 5, each category-specific probe family is labeled with a different combination of quantum dots. Pathogens used for developing this test are obtained from the American Type Culture Collection (ATCC; Manassas, Va.).

Viral category-specific probe families are prepared similarly except that the viral category-specific sequences are isolated by comparison of publicly available genomic sequences. First the public databases (e.g, GenBank) are scanned for sequences derived from a viral pathogen, e.g., Influenza A Virus. These sequences are then imported and aligned in the program MegAlign (DNAStar). Category-specific sequences are chosen from regions that are invariant in the genomes and that have been sequenced from more than one isolate of the virus. Oligonucleotides are designed, synthesized, linked to quantum dots, and tested as described above for S. pneumoniae. Viral isolates are obtained for preparing genomic nucleic acid (for dot blots) from culture repositories such as the American Type Culture Collection (ATCC). For example, the ATCC maintains a large collection of Influenza A and Influenza B viruses. Nucleic acid from various isolates of a viral species is prepared for genomic dot blots by standard methods (see e.g., Stephenson, et al., eds. (1998). Diagnostic virology—Laboratory manuals. (Totaowa, N.J.: Humana Press). 307 pp).

The pathogen-specific probe families are combined to create a lower respiratory pathogen probe ensemble. The probe ensemble is assembled in EE buffer (see definitions) so that the concentration of each probe is 10 nM.

Identifying pathogens present in a clinical sample. The pathogen-specific probe ensemble is used to scan a respiratory sample for 24 pathogens simultaneously (FIG. 40). The preferred layout of the sample and controls is indicated in FIG. 40. The microscope slide is etched with registration marks in the sample and control areas to facilitate alignment of images (see below).

A respiratory sample (e.g., a sputum, bronchioalveolar lavage, or protected bronchial brush specimen) along with control targets are applied to a glass microscope slide and air dried. An internal control section on the slide is constructed on each slide, onto which are arrayed spots containing purified respiratory pathogens. The purpose of the control section of the slide is to confirm that hybridization proceeds correctly and to provide internal fluorescently labeled standards with which to compare the signal in the sample. Each of the 24 respiratory pathogens represented in the probe ensemble (listed in Table 2) is spotted (~250 organisms in 0.1 µl PBS) onto the slide and air dried. Samples and controls are then fixed using the method of Braun-Howland et al (Braun-Howland, et al., Biotechniques 13: 928-34, 1992). Before hybridization, the nucleic acid in the fixed sample is denatured by covering the sample with 70% formamide at 750 for 10 min. The excess liquid is poured off, and the slide is rinsed in EE and allowed to air dry.

Next the probe ensemble is hybridized to the sample on the glass slide. Hybridization is carried out in HYB buffer (50 µl; see definitions) containing 5 µl of the probe ensemble (the final concentration of each probe is 1 nM). The hybridization solution is covered with a glass coverslip and incubated in a humidified slide moat (Boekel) at 50° C. for 30 minutes. Slides are washed 5 times (30 seconds each wash) in HYB buffer at 50°. After cooling the slide to room temperature, they are rinsed with EE and air dried.

A CCD imaging apparatus similar to the one in FIG. 3A (but without the automated stage) is used to acquire images of the sample and of the internal standards. The loading tray has 3 positions: open, first imaging position, and second imaging position. The slide, with bound quantum dot-labeled probes is inserted into the loading tray (in the open position) of the imaging apparatus with the internal standards section positioned towards the imager. The loading tray is moved to the first imaging position for viewing the internal standards section of the slide. After imaging the standards, the slide is moved into the second imaging position for analyzing the experimental sample.

Image acquisition is preferably controlled by computer software (Image-Pro Plus). Five images are automatically acquired, one for each fluorophore signaling moiety. For imaging each fluorophore, the software automatically selects the correct excitation and emission filters, and collects the image according to user-defined parameters (e.g., exposure time, intensity value of standards, etc.). The software constructs a composite image by combining information from each of the five images. The images are automatically aligned with the aid of registration marks (the marks are etched in the sample and control areas such that they are visible in each image). Alignment is necessary because successive images are generally offset slightly due to small mechanical perturbations during filter changes. The software then assigns a matrix of values corresponding to the intensity of each of the five images to each pixel in the composite image.

Software-based analysis of the standards has two main functions. First, it confirms that the experimental procedures are working correctly. Each of the 24 "spots" in the standards array contains individual cells or viruses of a target pathogen that have been treated identically to pathogens that might be in the experimental sample. The combination of signal moieties for each pathogen-specific family of category-binding molecules is known. Thus, the software checks whether the cells/viruses in each spot corresponds to the expected combination of signaling moieties. Furthermore, the number of pathogens observed in each spot is compared experimentally to the known number (about 250 organisms). If the correct number pathogens are labeled as expected by the bound probes, the experimental procedures are deemed have worked correctly. The software analysis includes comparing the results to rejection criteria, which can be set by the user. Experiments are rejected for reasons that preferably include failure of one or more pathogens to be labeled correctly or efficiently, excessive background (determined by analysis of sections of the image that have no pathogens), and poor signal to noise ratio. Values for background fluorescence assessed at this stage for each of the 5 images is preferably subtracted from the images of the standards and sample images.

The second function of analysis of the standards is to generate an accurate key for associating signal signatures with known pathogens. For each pathogen a matrix is constructed of expected values for each of the 5 images (i.e., for each image collected with fluorophore-optimized excitation/emission filters). To establish the expected ranges for a pathogen in one of the images, intensity values for each of the ~250 organisms in a spot are tabulated. In preferred embodiments of the invention, threshold values are chosen based on the observed range of intensity values detected in the standards. Thus, for each pathogen, a set of expected ranges for each image is then constructed. A lookup table is also constructed that associates a pseudocolor with sets of values that fall within the ranges expected for a particular pathogen. The process of assigning pseudocolors is similar to that used for karyotyping (Schröck, et al., 1996, supra; Speicher, et al., 1996, supra).

The barcode for sample identification (constructed by applying black bars of various thicknesses) is preferably placed on the slide so that it is imaged simultaneously with the standards. Methods for barcode application and analysis are understood by average workers familiar with the art.

After analysis of the standards, the slide loader is moved to the second position, placing the sample section of the slide in the imaging area. The software drives the collection of 5 images of the sample, (automatically imaged as before for the standards). Using the lookup table constructed during analysis of the standards, pseudocolors are assigned to individual objects that correspond to the sets of color ratio values that fall within the expected ranges for a particular pathogen. The intensities for each type of pseudocolored objects are summed and divided by the average intensity value of a target in the control sample to obtain an estimate of the number of targets present in each sample. This first pass of the image analysis identifies and enumerates pathogens in objects that represent a single category of target. In a second pass, the software tests pixels registering ratios of values that are not consistent with multiples of any single target pathogen to determine if they have ratios that are consistent with registering more than one type of pathogen. Finally, the software displays for the user a diagnosis (i.e., infection or no infection), the identities and numbers of pathogens in the sample, the sample ID number (extracted from the bar coded information on the slide), and composite images (with pseudocolored pixels) of both the standards and the sample.

Example 40

Testing Blood Samples for Numerous Pathogens Simultaneously Using Nucleic Acid Probes Bloodstream infections. Pathogenic invasion of the cardiovascular system is one of the most serious infectious diseases. Of the approximately 200,000 bloodstream infections that occur every year in the United States, between 20 and 50 percent are fatal. Particularly at risk are immunocompromised patients, the very young and very old, those with skin or soft tissue infections and wounds, and the recipients of invasive medical procedures. All major types of pathogens can infect the bloodstream, including bacteria, viruses, fungi, and parasites. Rapid identification of a pathogen in a bloodstream infection is critical for instituting appropriate, potentially life-saving therapy.

The therapy of choice depends on the identity of the pathogen. Many tests and much expense can be required to determine the source of infection. However, promptly initiating the optimal therapy is often a life and death matter. Thus, there is a need for a single assay that rapidly determines the identity of a broad range of common bloodstream pathogens.

Overview of the example. The test described in this example scans for the presence of a broad range of bloodstream pathogens in a blood sample by using indirectly labeled pathogen-specific probes for in situ hybridization. By simultaneously testing for common bacterial, viral, and protozoan pathogens, the method offers a substantial improvement over current practices. The rapidity of the test (which does not require microbiological culture) makes it particularly useful for the critical task of quickly diagnosing bloodstream pathogens and for instituting appropriate and timely therapy.

TABLE 6

Pathogens that cause bloodstream infections.

| Bacteria | Eukaryotes |
| --- | --- |
| Staphylococcus spp. | Plasmodium spp. |
| Staphylococcus aureus | Leishmania donovani |
| Viridans streptococci | Toxoplasma spp. |
| Enterococcus spp. | Microfilariae |
| Streptococcus spp. | Histoplasma capsulatum |
| Streptococcus pneumoniae | Coccidoides immitis |
| Escherichia spp. | Cryptococcus neoformans |
| Klebsiella spp. | Candida spp. |
| Pseudomonas spp. | Viruses |
| Enterbater spp. | HIV |
| Proteus spp. | Herpes simplex virus |
| Bacteroides spp. | Hepatitis C virus |
| Clostridium spp. | Hepatitis B virus |
| Pseudomonas aueruginosa | Cytomegalovirus |
| Cornybacterium spp. | Epstein-Barr virus |

Assembling an ensemble of combinatorially labeled category-specific probes from pathogens that cause bloodstream infections. Table 6 lists some common pathogens that cause bloodstream infections. Category-specific sequences are isolated from the non-viral (i.e., bacterial, fungal, and parasitic) pathogens using the representational difference analysis method, as modified by Tinsley et al. (1996, supra). This method is technically distinct from the one used in Example 39, yet it isolates subtraction products with identical properties. The genomic difference samples are constructed as described in Example 39 and the products are cloned into the Bluescript II vector using standard methods (Ausubel 1987, supra) Pathogen-specific families of category-specific sequences are identified and sequenced as in Example 39.

Oligonucleotide probes are synthesized and tested as in Example 39. Combinatorial labeling using 5 types of spectrally distinct quantum dots is used, as in the previous example, using a scheme analogous to the one shown in Table 5. In this example, however, each oligonucleotide is designed with two moieties: a category-specific sequence and a tag sequence (FIG. 6 and FIG. 41). The tag moiety provides a means for indirect labeling of the oligonucleotide probes. To indirectly label a probe molecule, an anti-tag (or tag complement) sequence is labeled with a signaling moiety and is then hybridized to the bifunctional oligonucleotide probe (FIG. 41). Five distinct tags are used, one for each color class. Suppose, for example, the "color code" for S. aureus is green, violet, and blue. About 100 S. aureus-specific probes are synthesized with the "green tag", 100 others with the "blue tag", and 100 others with the "violet tag". The tag sequences and category-specific sequences are designed so that the melting temperatures ($T_m$; calculated at 1M NaCl using the algorithm of Suggs (Suggs, S. V., et al., Proc Natl Acad Sci USA 78: 6613-7., 1981) are 60° C. (±1°) for each moiety and its complement. The tags are also designed so that they do not cross hybridize with each other, each other's complements, the category-specific oligonucleotides, or the complements of the category-specific oligonucleotides (i.e., all such combinations of oligonucleotides preferably have melting temperatures ($T_{m(mismatch)}$) of 40° C. (i.e., $T_{m(perfect\ match)} - 20°$ C.). Advantages of this strategy are that only 5 labeled anti-tag sequences need be synthesized (and they can be used for numerous applications) and that tags and anti-tags can hybridize to each other during hybridization to the sample. (Note that in alternative embodiments, a single universal tag sequence can be used on all oligonucleotides, or family-specific tags could be used).

Oligonucleotides are checked to make sure they behave as strict category-specific sequences by hybridization to dot blots of genomic DNA, as in Example 39. In this example, however, the probes are indirectly labeled with anti-tags that are coupled to the enzyme, alkaline phosphatase (Synthetic Genetics). Probes are hybridized to dot blots in HYB buffer at 52° C. (a temperature equal to the melting temperature ($T_m$) of the oligonucleotide/genomic DNA (60°) hybrid minus 80C). The blots are washed in the same buffer at the same temperature (3 10 min washes), rinsed briefly in a solution of 150 mM NaCl and 100 mM tris·HCl pH 9.5, and then overlain with CDPStar (NEN). Digital images of the blots are obtained as described in the previous example.

Thus, each set of oligonucleotides corresponding to a pathogen-specific probe family (each probe family hybridizes specifically to one of the 30 pathogens listed in Table 6) is labeled with a unique combination of fluorescent dyes using a combinatorial labeling scheme. The labeled probe families are combined to form a bloodstream pathogen-specific probe ensemble as in Example 39.

In situ hybridization of the ensemble of blood pathogen probes to blood samples. Blood specimens are collected using standard methods (Isenberg, ed. (1992). Clinical microbiology procedures handbook. Washington, D.C.: American Society of Microbiology). Blood samples (0.5 ml) are prepared for in situ hybridization using the method of Lischewski et al (Lischewski, et al., J Clin Microbiol 35: 2943-8, 1997). Adjacent to the blood sample are spotted an array of control spots as in the previous example, except that in this example the spots contain organisms from the bloodstream pathogens listed in Table 6. Slides are also barcoded as in the previous example. Hybridization and washing are carried out as in the previous example, except that in this example both the ensemble of probes (final concentration is 1 nM each probe) and anti-tags (equimolar to the corresponding concentration of the corresponding tag sequences in the ensemble of probes) are included.

The slides are imaged and analyzed as in Example 39.

Example 41

A Rapid Concerted Test for Numerous Central Nervous System Viruses Using Nucleic Acid Probes Overview of the example. Infection of the central nervous system (CNS) is a medical emergency. Rapid diagnosis of the infectious agent is critical for optimum therapeutic outcome. Diagnosis of viral infection is particularly problematic and often expensive. The method described in this example can be used to test a cerebrospinal fluid (CSF) sample simultaneously for the presence of various types of viruses.

This example details a rapid highly multiplexed test that minimizes sample preparation, required instrumentation, and experimental complexity. CSF samples are spotted and fixed to a filter, denatured, and hybridized to an ensemble of viral probes (combinatorially labeled with quantum dots) using a lateral flow chromatographic method. The bound probes are imaged and identified by non-magnified large area CCD imaging.

Assembling ensembles of viral-specific sequences. Category-specific sequences are chosen that are specific for each of the groups of viruses in the panel of viruses listed in Table 7. In some cases, viral-specific category-specific sequences are already described in the literature. In other cases, sequences are chosen from viral genomic sequences in public databases after comparing the sequences to other viruses in the database. Sequence comparisons are made using standard methods (Ausubel et al., 1987, supra). Category-specific oligonucleotides are chosen, synthesized, and labeled with quantum dots as in Example 39. The combinatorial labeling scheme is analogous to that shown in Table 5 except that the category-specific oligonucleotides from the viruses in Table 7 are conjugated to quantum dots. A central nervous system pathogen-specific probe ensemble is constructed by combining the various category-specific oligonucleotides in EE at a concentration of 10 nM (each oligonucleotide).

TABLE 7

| Viruses that cause CNS infections. | |
| --- | --- |
| coxsakievirus A | coxsakievirus B |
| herpes simplex virus | Togavirus |
| St. Louis encephalitis virus | measles virus |
| Epstein-Barr virus | Hepatitis |
| myxovirus | paramyxovirus |
| JC virus | mumps virus |
| Echovirus | equine encephalitis virus |
| Bunyavirus | Lymphocytic choriomeningitis virus |
| Cytomegalovirus | rabies virus |
| Varicella-zoster virus | BK virus |
| HIV | |

Sample preparation. CSF is collected using standard methods (Isenberg, 1992, supra). Samples (1 ml) are spun briefly in a microcentrifuge (12,000×g; 1 min) to remove cells and particulate matter. Viruses in the supernatant (1 ml) are concentrated by spinning at 7,500 g in a Biomax-5 grade Ultrafree-4 centrifugation unit (Cat #UFV4510XB; Millipore, Bedford, Mass.). The retentate (10 µl) is heated at 95° C. for 5 min to denature nucleic acid and spotted on a supported nitrocellulose strip (0.5×2 cm; 5 µm pore; Osmonics). In a region of the strip distinct from the sample, control samples of denatured genomic nucleic acid from each of the viruses in Table 7 ($1\times10^5$ genomes each) laid down in adjacent stripes (as in a bar code) as described previously (Gravitt, et al., Journal Of Clinical Microbiology 36: 3020-7, 1998). Reference stripes of ink are similarly applied Capillary action-mediated hybridization. The quantum dot labeled probe ensemble is contacted with the denatured sample DNA of the sample and controls by using a paper chromatography hybridization assay described by Reinhartz et al (Reinhartz, 1993, supra). FIG. 42 diagrams the procedure used in this example. Probes in a hybridization solution are applied to one end of the strip allowed to flow past the immobilized denatured sample nucleic acid via capillary action. The hybridization solution is that used by Reinhartz et al, supplemented with 1% polyvinyl pyrrolidone, except that the DNA included in the solution is the bloodborne pathogen probe ensemble (the final concentration is 1 nM for each quantum dot oligonucleotide probe). The strips are dipped into the hybridization solution (100 µl) and hybridization chromatography is performed for 25 min at 50°. Samples are washed twice in 0.3% Tween/PBS for 5 min at 37° C. and then allowed to air dry.

Identifying the pathogen by CCD imaging of filter strips. Pathogens are identified by imaging as in Example 39. Viral nucleic acid molecules in the sample hybridize to probes with a characteristic combination quantum dot labels. Each cluster of quantum dots is assigned a pseudocolor. Identification of the virus in the CSF sample is achieved by comparing the pseudocolor of the spots in the sample to the pseudocolors assigned to the control stripes (containing known viral genomes).

Example 42

Rapid Identification and Antimicrobial Susceptibility Testing for *Mycobacterium tuberculosis* Using Genomic DNA Probes Overview. The medical significance of rapid susceptibility testing for *M. tuberculosis* is discussed in the overview of Example 28. This example differs from previous examples (Example 9, Example 27, and Example 28) in that *M. tuberculosis*-specific genomic DNA sequences are used as category-binding molecules rather than using *M. tuberculosis*-specific stains, non-specific stains, or antibodies.

The *M. tuberculosis*-specific genomic DNA sequences obtained by genomic subtraction and are modified by the hapten digoxygenin. Aliquots of a patient's sputum sample are incubated in growth media containing various antibiotics at various concentrations. After arraying samples on a filter, probing with hapten-labeled *M. tuberculosis*-specific sequences, the cells are enumerated using chemiluminescence and non-magnified large area CCD detection.

Preparing hapten-labeled *M. tuberculosis*-specific category-specific sequences. *M. tuberculosis*-specific sequences are isolated by genomic subtraction and dot blot screening as described in Example 39 and shown in FIG. 40. For genomic subtraction, the plus genomic difference sample is *M. tuberculosis* and the minus genomic difference sample is *Mycobacterium avium*. To determine which of the cloned subtraction products are *M. tuberculosis*-specific sequences, the cloned products are used to probe 50 *M. tuberculosis* isolates (from disparate geographical locations) and 50 isolates of related Mycobacterium species in dot blots as in Example 39. The probes are labeled with digoxygenin and the dot blots are imaged as described in Example 39. Digoxygenin-labeled category-specific sequences (n=96) are pooled (final concentration of each probe is 250 µg/µl).

Testing a lower respiratory sample for *M. tuberculosis*. Sputum samples are prepared using the NALC-NaOH method (Isenberg, ed. (1992). The pretreated sputum is then applied (100 µl) to a nylon filter (GeneScreen; NEN) and prepared by placement on a series of filters as follows. The filter is successively laid (for 5 min each at room temperature, except where noted) on a stack several filters saturated with prelysis solution (see solution section) for 45 min at 37° C. (wrapped in plastic wrap to prevent evaporation); a dry filter (Whatman 3MM); a filter saturated with a solution of 1% SDS/100 µg/ml proteinase K (Life Technologies) for 30 min at 37° C. (wrapped in plastic wrap); a dry filter; a filter saturated with 0.5N NaOH; a dry filter; a filter saturated with 1M tris pH 7.5; and a dry filter. As a positive control, *M. tuberculosis* (~1000 organisms in 10 µl) is spotted adjacent to the sputum sample. As a negative control, *E. coli* (~1000 cells) is spotted adjacent to the positive control. In situ hybridization with hapten-labeled probes is carried out as described in Example 39. Anti-digoxygenin antibody conjugated to alkaline phosphatase (Genius kit; Boehringer Mannheim) is then bound to the hybridized probe, the kaline phosphatase (Genius kit; Boehringer Mannheim) is then bound to the hybridized probe, the filter is placed on a glass slide, and incubated with CDP-Star (NEN) according to the manufacturer's recommendations. The slide is imaged and analyzed using a non-microscopic CCD imager (FIG. 3).

Incubating the clinical sample with various antibiotics. Antibiotic susceptibility testing is performed on samples that contain *M. tuberculosis* as in Example 28.

Arraying samples on a filter and preparing for hybridization. Aliquots of the cultured samples (100 µl) are arrayed on a gridded nylon filter using a disposable filtration device (Millipore; Microfil Funnel (100 ml), Cat #MIHAWG072) mounted on a vacuum flask. Samples (100 µl) are pipetted onto alternating grid squares while applying a vacuum (e.g., using a Gast (Model; DOA-P104-AA) vacuum pump at ⅓ maximum vacuum level). The filter is removed and air-dried. The filter is then prepared for hybridization by laying on a series of filters as described earlier in this example Hybridization, chemiluminescent imaging and analysis. *M. tuberculosis*-specific probes (digoxygenin-labeled above) are bound to the arrayed *M. tuberculosis* using high stringency hybridization and washing (Ausubel 1987, supra) followed by binding to an alkaline-phosphatase:anti-digoxygenin antibody conjugate (Genius; Boehringer Mannheim), and incubating with the chemiluminescent alkaline phosphatase substrate, CDP-Star (NEN) according to the manufacturer's recommended protocol (Boehringer Mannheim). Chemiluminescent images are obtained using non-magnified CCD camera-based imaging as above. The number of distinct objects and the integrated intensity in each sample spot are calculated as before in Description of invention, Step 6.

The numbers of targets in the experimental spots are compared to the negative and positive control spots to determine the amount of growth that occurred in the various antibiotic dilutions. A decrease in cell count of 45, 50, or 25% for samples containing ethambutol, isoniazid, and rifampin, respectively, indicates susceptibility to a given antibiotic regime (Moore et al., 1999, supra).

The approach described above can be applied to other bacteria in the same fashion.

Rapid susceptibility testing by monitoring in-situ growth of microcolonies non-microscopically. Growth of microcolonies (e.g., colonies consisting of between 2 and 1000 clonally related cells) on media containing various antibiotics can also be used to assess a strain's antibiotic susceptibility profile. In concept, this approach resembles the classical disk diffusion or agar dilution techniques or the newer fixed gradient method (e.g., E-test). In all of these methods, cells are placed in solid growth media containing different concentrations of several antibiotics. To ascertain the antibiotic susceptibility profile of a strain, the bacterial isolate is scored for growth on the various antibiotics.

The invention can greatly accelerate acquisition of critical antibiotic susceptibility testing data using this approach For example, a disk diffusion susceptibility testing can be performed as recommended by the NCCLS (NCCLS Performance Standards for Antimicrobial Disk Susceptibility Tests; Approved Standard_Seventh Edition M2-A7 Vol. 20 No. 1 January 2000). However, rather than plating the bacteria directly on agar plates, the bacteria are plated on nylon filters which are placed on agar media plates. Small filter disks (2.5 mm diameter) containing various antibiotics are placed on the nylon filters and the bacteria are allowed to grow for about 5 doubling times (usually several hours for fast growing bacteria). The filter is next placed successively (5 min at room temperature on each Whatman 3MM filter) on a dry filter; a filter saturated with 100% methanol; a dry filter; a filter saturated with propidium iodide (10 µg/µl in water); and a dry filter. A non-magnifying fluorescence imager, used in this example, is then used to directly visualize individual cells surrounding the disk. The diameter of the zone of growth inhibition is automatically measured by imaging software (Image-Pro Plus, version 4.1; Media cybernetics) analogously to the process of measuring the zone or halo around disks by eye in classical disk diffusion antibiotic susceptibility testing. Alternatively, cells can be imaged using methods such as pathogen-specific staining or category-binding molecules with light-scattering, or fluorescent, or chemiluminescent signaling moieties as described in this and other examples.

Rapid antiviral susceptibility testing. Many new antiviral compounds are currently being developed. The problem of antiviral resistance has come into prominence due to the rapid evolution of resistance in HIV. Susceptibility testing is thus becoming important. Although genotypic methods for determining resistance are becoming useful, assessing drug resistance by examining combinations of mutations in nucleic acid sequence is extremely complex and does not always correctly predict resistance. Unfortunately, phenotypic susceptibility testing on viral subculture is time consuming. However, using methods to monitor viral replication in cell cultures, analogous to those described for *M. tuberculosis* above, the invention could greatly improve the turnaround time for viral susceptibility testing.

Example 43

A Test for Sexually Transmitted Disease Pathogens Using Nucleic Acid Probes

Overview of example. This example exploits the invention to simultaneously test urine for two major sexually transmitted pathogens: *Chlamydia trachomatis* and *Neisseria gonorrhoeae*. For more on the significance of the test refer to the overview of Example 31. Category-specific sequences from these strains are isolated using genomic subtraction (*Neisseria gonorrhoeae*) computer-based virtual subtraction strategy (*Chlamydia trachomatis*). Category-specific sequences are labeled with the haptens digoxygenin (*Chlamydia trachomatis*) or fluorescein (*Neisseria gonorrhoeae*) and hybridized to fixed cells that have been concentrated and immobilized on a filter. Intense signaling moieties, called resonance light scattering particles (RLS particles), are used to detect and identify the pathogens. The RLS particles, conjugated to anti-digoxygenin antibodies (red-scattering RLS particles) or anti-fluorescein antibodies (green-scattering RLS particles), are bound to pathogens in the sample. Because of the intensity of the signaling moieties, pathogens can be identified by simple visual inspection of illuminated samples. Red spots indicate a *Chlamydia trachomatis* infection and green spots signal a *Neisseria gonorrhoeae* infection.

Isolating *chlamydia trachomatis* category-specific sequences using virtual subtraction. The existence of completed genome sequences for strains of *Chlamydia trachomatis* (Stephens, et al., Science 282: 754-9, 1998), *Chlamydia pneumoniae* (Kalman, et al., Nat Genet 21: 385-9, 1999) allow for computer-based determination of regions from one genome that differ from the other genome. This process is called virtual subtraction, by analogy to genomic subtraction experiments. The genome sequences, which are available in public databases (NCBI) are processed by software that aligns and compares whole genomes (MUMmer; Delcher, et al., Nucleic Acids Res 27: 2369-2376, 1999). MUMer (using 20 bp for the minimum MUM length parameter) produces a detailed file depicting all of the gaps in the alignment. These gaps include insertion/deletions and highly polymorphic regions. Using the program Primer3 (S. Rozen, et al, 1998, supra) PCR primers were chosen for amplifying regions (~200-500 bp) that occur in *Chlamydia trachomatis*, but not in *Chlamydia pneumoniae*. The PCR primers are designed with the bipartite structure shown in FIG. 43. One primer has the XhoL primer sequence linked to a 20 bp primer corresponding to the "left" end of an insertion/deletion region in *Chlamydia trachomatis* (5'-XhoL-*Chlamydia trachomatis* left primer-3'). The other primer has the structure 5'XhoR-*Chlamydia trachomatis* right primer-3', where the *Chlamydia trachomatis* right primer is a 20 bp primer corresponding to the "right" end of the same insertion/deletion region. Using these primers, the virtual subtraction sequences are amplified from *Chlamydia trachomatis* cells (~$10^5$ cells in 10 μl EE; obtained from ATTC) after boiling the cells in EE buffer for 5 min. Amplification, products are labeled with digoxygenin-dUTP and screened for category-specificity using dot blot analysis as in Example 39.

Isolating *Neisseria gonorrhoeae* category-specific sequences using genomic subtraction. Potential *Neisseria gonorrhoeae* are isolated in this example using genomic subtraction as described in Example 39 (Straus, 1995, supra). The plus genomic difference sample is composed of a Sau3a digest of *Neisseria gonorrhoeae* genomic DNA and the minus genomic difference sequence is composed of sheared *Neisseria meningitidis* DNA. *Neisseria gonorrhoeae* and *Neisseria meningitidis* (obtained from ATTC) are grown in the appropriate medium (ATCC; 814 GC medium) and prepared using the CTAB method (Ausubel 1987, supra). The subtraction products are cloned, labeled, and screened against dot blots (containing DNA from various *Neisseria* species) as in Example 39. Fluorescein-labeled category-specific sequences are synthesized by amplifying recombinant plasmids using Fluorescein-12-dUTP (NEN Life Sciences; Cat. No., NEL413) and the primers XhoL and XhoR (see sequences in abbreviation section) according to manufacturer's recommended procedures.

Assembling a *Chlamydia trachomatis/Neisseria gonorrhoeae* probe mixture. Digoxygenin-labeled *Chlamydia trachomatis* category-specific sequences (n=96) are combined with fluorescein-labeled *Neisseria gonorrhoeae* category-specific sequences (n=96) (equal volumes of the amplification reactions are mixed together so that the final concentration of each probe is approximately 250 μg/μl).

Making probe-specific RLS signaling moieties. By binding RLS particles, which are easily visualized due to intense light scattering, to the bound probes individual pathogen cells are detected and identified. Two different types of RLS particles (prepared as described in U.S. Pat. No. 6,214,560) are used to differentially label bound *Chlamydia trachomatis* probes and bound *Neisseria gonorrhoeae* probes. Red scattering RLS particles (160 nm diameter gold particles) are used to bind to the *Chlamydia trachomatis* probes, while green scattering RLS particles (60 nm diameter gold particles) are used to bind to the *Neisseria gonorrhoeae* probes. The red scattering particles are made specific for the *Chlamydia trachomatis* probes by conjugating anti-digoxygenin antibodies, (Roche, Cat. No. 1 333 062) to the particles as described previously (Hermanson, 1996. supra, and references therein). Similarly, the green scattering RLS particles are made specific for the *Neisseria gonorrhoeae* probes by conjugating anti-fluorescein antibodies (Roche, Cat. No. 1 426 320) to the particles. The red and green scattering RLS: antibody conjugates are mixed together at equal concentrations ($3.8\times10^{-11}$ M).

Preparing urine samples for in situ hybridization. Urine samples (10 ml) collected using a commercial kit (B-D Urine Collection Kit (Becton-Dickinson) and are filtered through a black polycarbonate membrane (0.22 μm; Osmonics) to concentrate bacteria that may be present. Bacterial DNA is denatured and made accessible by treating filters essentially as for colony lifts (Ausubel 1987, supra). The filter containing the sample is placed, in succession, on a filter (Whatman 3MM) saturated with 0.5M NaOH (5 min); a dry filter (5 min); a filter saturated with 1M tris pH 7.5 (5 min); and a dry filter (5 min).

Control filters are prepared similarly. *Chlamydia trachomatis* (~1000 elemental bodies; ATTC) in 10 ml PBS are filtered through a filter and prepared as described for the experimental sample. *Neisseria gonorrhoeae* (~1000 cells) in GC media (10 ml) are similarly collected and prepared on a separate filter. Finally, a negative control filter containing *E. coli* (~1000 cells) in LB (10 ml) is prepared in the same fashion.

Note, that in alternative embodiments other substrates can be substituted for nylon filters (e.g., glass slides, poly-lysine treated glass slides, silanized glass slides, nitrocellulose filters etc.). Also, urine samples can be concentrated by centrifugation (e.g., at 12,000×g, for 1 min) rather than by filtration. Alternatively, urine samples, in smaller volumes (e.g., 100 µl), can, be applied to the substrates directly followed by immobilization and treatment to render the genomic DNA accessible.

Binding the hapten-labeled *Chlamydia trachomatis/Neisseria gonorrhoeae* probe ensemble to filtered urine samples and controls. Filters are hybridized in 1 ml HYB solution (see definitions) containing a 1:2 dilution of the probe ensemble mixture described above (final concentration of each probe is approximately 125 ng/µl). The reactions are carried out for 4 hours at 65° C. in a in an incubator (Hybaid). Unbound probe is removed by washing twice (20 min each wash) in 0.2×SSC (100 ml; see definitions) in glass hybridization bottles (Hybaid).

Binding probe-specific RLS signaling moieties to probe-labeled pathogen cells. Filters are "blocked" by incubation in BB (blocking buffer; 100 ml; see definitions) in a plastic tray (RubberMaid) on a rotating platform with gentle shaking (~60 rpm) at room temperature (~22° C.). RLS particles (200 µl of the mixture from above) in 1×BB (1 ml) are added to the filters in a sealed pouch (Seal-A-Meal) and incubated at room temperature with gentle shaking for 1 hr. Unbound RLS: antibody conjugates are removed from the filters by washing twice in BB (100 ml) at room temperature with gentle shaking. Filters are air dried on glass slides prior to visualization.

Visual identification of pathogens in the samples. Light from the Xenon-arc lamp in the CCD imager (described in Step 6 of the Detailed Description) is trained on filters at an oblique angle to the plane of the filters. Two images are processed using excitation and emission filters that correspond to the two classes of RLS particles. The experimental procedures are evaluated by assessing the control filters. The *Chlamydia trachomatis* control filter should have ~1000 red spots, the *Neisseria gonorrhoeae* filter a similar number of green spots, and the negative control filter (containing *E. coli*) should not have green or red spots. Finally, the filter containing cells from the clinical urine sample is evaluated for the presence of *Chlamydia trachomatis* (red spots), *Neisseria gonorrhoeae* (green spots), a mixed infection (red and green spots), or no *Chlamydia trachomatis/Neisseria gonorrhoeae* infection (lack of a statistically significant number of spots over negative controls).

Other related applications. Many related clinically important diagnostic tests are easily developed along the same lines as the one described in this example. Tests for other urinary tract pathogens (e.g., *E. coli*) can be constructed. Such tests can include a large number of pathogens, if combinatorial labeling is used. Tests for *Chlamydia trachomatis* and *Neisseria gonorrhoeae* (and other infectious agents of the urogenital tract) that use samples collected by swabs represent important related applications (Isenberg, 1992, supra). For example, samples collected using urethral (male or female), cervical, and vaginal swabs are important for uro-genital pathogen diagnostics. Samples on swabs can be directly smeared on filters or slides in these examples. Such tests are also valuable for diagnosing important viral pathogens of the urogenital tract (e.g., Human Papilloma Virus, Herpes Simplex 1, and Herpes Simplex 2), fungi (e.g., *Candida*), and parasites (e.g., *Trichomomas vaginalis*). The methods used in this example (in conjunction with the appropriately modified sample collection techniques) are applicable to many different types of clinical samples (e.g., surgical wound, blood, and respiratory samples). Furthermore, in conjunction with various types of category-binding molecules (e.g., antibodies, probes for mRNA), similar methods can be applied to non-pathogen analytes including diseased tissue, serum proteins, and toxins.

Technical variations. Besides the variations in sample collection and substrate mentioned above, the invention can incorporate other useful technical variations. For example, an operationally simpler test can be constructed using fluorescent category-specific antibodies labeled with fluorophores or fluorescent particles. Such a test allows several steps (e.g., hybridization) to be eliminated. Many types of signaling moieties can be incorporated (e.g., fluorescent nanoparticles, quantum dots, and traditional fluorophores) and automated imaging using a CCD camera. Rather than restriction-fragment sized category-specific sequences, labeled oligonucleotides can also be used, as described in some of the other examples. High throughput applications of this example can incorporate microtiter filter plates (for example 384-well plates) in which each well contains a different sample. After the binding step, the labeled cells on each well's filter can be imaged using a microtiter plate reader or CCD imager capable of detecting light scattering.

Other Embodiments

All patents, patent applications, and publications referenced in this application are hereby incorporated by reference. Other embodiments of the invention will be apparent to those skilled in the art from consideration of the specification and practice of the invention disclosed herein. It is intended that the specification and examples be considered as exemplary only, with a true scope and spirit of the invention being indicated by the following claims. Examples of other embodiments that may be adapted to the methods described herein are found in U.S. application Ser. No. 10/236,107, entitled "RAPID AND SENSITIVE DETECTION OF REPLICATING CELLS", filed Sep. 6, 2002 and U.S. application Ser. No. 10/236,105, entitled "RAPID AND SENSITIVE DETECTION OF MOLECULES", filed Sep. 6, 2002, each of which is hereby incorporated by reference.

Other embodiments are in the claims.

What is claimed is:

1. A method for detecting individual target cells or viruses in a liquid sample, wherein said sample is added to a container comprising a detection surface and said targets measure less than 50 microns in at least two orthogonal dimensions,
wherein said method comprises the steps of:
 a. contacting said individual targets with one or more signaling moieties that specifically bind to the targets,
 b. depositing said targets on said detection surface so that they are randomly dispersed in a detection zone comprising a detection area at a density of less than 100 target cells per mm$^2$,
 c. illuminating said individual targets to generate a detectable signal from said one or more signaling moieties, and
 d. simultaneously detecting said individual targets by detecting said signal in a section of said detection area using a photoelectric detector, wherein the longest linear dimension of said section is greater than 1 mm, using magnification of less than or equal to 5 times, wherein said one or more signaling moieties that do not bind to said targets are not removed from said container prior to said detecting.

2. The method of claim 1, wherein in step (a) said targets are contacted with category-binding molecules under conditions that allow for specific binding of said category-binding molecules to category-specific binding sites on said targets to form complexes.

3. The method of claim 2, wherein category-binding molecules are labeled, either directly or indirectly, with said one or more signaling moieties.

4. The method of claim 3, wherein said detecting detects said complexes.

5. The method of claim 1, wherein said signaling moieties associate either directly or indirectly with said targets.

6. The method of claim 2, wherein said complexes are randomly dispersed in said detection zone at a density of less than 10 complexes per mm$^2$ of the detection area.

7. The method of claim 2, wherein said complexes are randomly dispersed in said detection zone at a density of less than 1 complex per mm$^2$ of the detection area.

8. The method of claim 1, wherein said detection does not entail magnification of more than 2×.

9. The method of claim 8, wherein said detection does not entail magnification of more than 1×.

10. The method of claim 9, wherein said detection does not entail magnification of more than 0.2×.

11. The method of claim 1, wherein said detecting detects and identifies more than one non-overlapping category of targets.

12. The method of claim 2, wherein said category-binding molecules are natural or recombinant antibodies or aptamers.

13. The method of claim 2, wherein said category-binding molecules are DNA, RNA, or PNA probes.

14. The method of claim 2, wherein said category-binding molecules bind specifically to sites immediately adjacent to nucleic acid polymorphisms including single nucleotide polymorphisms.

15. The method of claim 1, wherein said sample comprises a fluid or tissue obtained from a multicellular organism.

16. The method of claim 15, wherein said sample comprises the bodily fluids or tissues of an animal.

17. The method of claim 16, wherein said sample is derived from a human.

18. The method of claim 16, wherein said sample is derived from a non-human vertebrate.

19. The method of claim 16, wherein said sample is a member of, or derived from a member of the group consisting of: respiratory, urogenital, reproductive tract, central nervous system, urine, blood, dermal, plasma, serum, saliva, wound tissue, wound exudate, biopsy, feces, and solid tissue samples.

20. The method of claim 1, wherein said sample is derived from a plant.

21. The method of claim 1, wherein said sample is obtained by sampling environmental air or water, or surfaces, objects, or organisms exposed to the environment.

22. The method of claim 1, wherein said sample is chosen from, derived from, or obtained from the group consisting of: raw, finished or in-process material in the manufacture pharmacological, cosmetic, blood, or other products for topical or internal use in humans or animals; raw, in-process or finished material in the manufacture of foods or beverages; raw, in-process or finished material in the manufacture of medical or in vitro diagnostic devices; chemical products; industrial surfaces; instrumentation; and machinery.

23. The method of claim 1, wherein said method detects the effect of one or more substances or treatments on said targets.

24. The method of claim 1, wherein a selection method is used to deposit said targets on said detection surface, and wherein said selection method is from the group consisting of magnetic selection, centrifugation, and settling.

25. The method of claim 24, wherein said method comprises contacting said sample with magnetic particles that are conjugated to category-binding molecules.

26. The method of claim 24, wherein targets are deposited in said detection zone using one of said selection methods without using a selection moiety.

27. The method of claim 24, wherein said targets are contacted in a liquid with target-specific selection moieties that have an average density greater than the average density of said liquid and are subsequently deposited on said detection surface using gravitational, centrifugal, or centripetal force.

28. The method of claim 1, wherein said sample is treated to liquefy and/or homogenize said sample.

29. The method of claim 1, wherein said sample is treated to remove substances or objects other than said targets.

30. The method of claim 2, wherein said targets are immobilized on said detection surface prior to said contacting.

31. The method of claim 1, wherein said targets are specifically bound in the detection zone by category-binding molecules that are bound to the matrix or substrate of the detection zone.

32. The method of claim 1, wherein said targets are specifically bound in the detection zone by forming chemical bonds to matrix or substrate of the detection zone.

33. The method of claim 1, wherein said targets are immobilized in said detection zone by a process selected from the group consisting of air drying, heat fixation, and chemical fixation.

34. The method of claim 3, wherein a colloidal or soluble substance is added to absorb the signal emitted by signaling moieties that are not in said detection zone.

35. The method of claim 1, wherein said sample is subdivided into individual aliquots that are tested, in parallel, for the presence of different non-overlapping categories of targets.

36. The method of claim 35, wherein each of said aliquots is contacted with a population of labeling particles that is conjugated to a different non-overlapping family of category-binding molecules.

37. The method of claim 35, wherein said sample is contacted successively with distinct families of category-binding molecules that specifically bind to non-overlapping categories of target-entities.

38. The method of claim 1, wherein said detection zone comprises material selected from the group consisting of solid glass, solid plastic, the surface of the wells of microtiter plates, bibulous membranes, plastic strips, the surfaces of capillary tubes, the surfaces of microfluidic chambers, and the surfaces of microfluidic channels.

39. The method of claim 1, wherein said method includes lateral flow chromatography.

40. The method of claim 1, wherein said method is automatically repeated on a series of samples.

41. The method of claim 40, wherein said samples are automatically loaded into an instrument that contains the means for said detecting.

42. The method of claim 40, wherein said samples are automatically deposited in a series of detection zones that are physically associated and that are automatically and successively loaded into an instrument that contains the means for said detecting.

43. The method of claim 3, wherein said method detects light emitted, scattered, reflected, or absorbed as a result of said illumination of said complexes.

44. The method of claim 1, wherein said detecting detects fluorescence.

45. The method of claim 1, wherein the means for illuminating comprises one or more lasers.

46. The method of claim 1, wherein the means for illuminating comprises one or more light-emitting diodes.

47. The method of claim 1, wherein the means for illuminating comprises a source of white-light.

48. The method of claim 1, wherein the means for illuminating comprises one or more optical filters adapted for illuminating said sample with light of a wavelength appropriate for detecting said complexes.

49. The method of claim 3, wherein the means for illuminating comprises one or more optical filters adapted for illuminating said sample with light of a wavelength appropriate for detecting said signaling moieties.

50. The method of claim 3, wherein the means for detecting said emitted, scattered, transmitted, or absorbed light comprises optical filters adapted to detect the signals derived from the illumination of said signaling moieties.

51. The method of claim 1, wherein said detecting detects thermal radiation.

52. The method of claim 1, wherein said detecting detects optical absorbance.

53. The method of claim 52, wherein said optical absorbance is in the infrared region.

54. The method of claim 1, wherein said detecting detects cellular autofluorescence.

55. The method of claim 1, wherein said detecting detects fluorescence polarization.

56. The method of claim 1, wherein said detecting detects optical reflectance.

57. The method of claim 1, wherein said detecting detects light scattering.

58. The method of claim 1, wherein said detecting detects Raman scattering.

59. The method of claim 2, wherein said category-binding molecules are conjugated directly or indirectly to labeling particles.

60. The method of claim 59, wherein said labeling particles are less than 20 microns in size.

61. The method of claim 59, wherein said labeling particles are less than 10 microns in size.

62. The method of claim 61, wherein said labeling particles are less than 5 microns in size.

63. The method of claim 62, wherein said labeling particles are less than 1 micron in size.

64. The method of claim 63, wherein said labeling particles are less than 100 nm in size.

65. The method of claim 64, wherein said labeling particles are less than 10 nm in size.

66. The method of claim 59, wherein said labeling particles comprise enzymatic signaling moieties at an average density of greater than or equal to 2 enzymatic signaling moieties per cubic micron of particle volume.

67. The method of claim 59, wherein said labeling particles are particles dyed with or conjugated to signaling moieties that have fluorescent signal character and that are selected from the group consisting of: organic fluorophores, up-regulated phosphors, lanthanides, quantum dots, and enzymes that generate fluorescent product form non-fluorescent substrates.

68. The method of claim 59, wherein said labeling particles are latex particles, silica particles, quantum dots, resonance light scattering particles, up-converting phosphors, or particles composed chiefly of gold or silver.

69. The method of claim 3, wherein said signaling moieties are enzymatic signaling moieties.

70. The method of claim 69, wherein said signaling moieties are alkaline phosphatase or horseradish peroxidase enzymes.

71. The method of claim 3, wherein said signaling moieties are selected from the group consisting of organic fluorophores, up-regulated phosphors, lanthanides, quantum dots, and enzymes that generate fluorescent product from non-fluorescent substrates.

72. The method of claim 3, wherein said signaling moieties have fluorescent signaling character.

73. The method of claim 3, wherein said signaling moieties have chromogenic signaling character.

74. The method of claim 3, wherein said signaling moieties have light-scattering signaling character.

75. The method of claim 2, wherein said category-binding molecules comprise antibodies.

76. The method of claim 2, wherein, wherein said category-binding molecules comprise aptamers.

77. The method of claim 2, wherein, wherein said category-binding molecules comprise nucleic acids or peptide nucleic acids.

78. The method of claim 2, wherein, wherein said category-binding molecules comprise ligands.

79. The method of claim 2, wherein, wherein said category-binding molecules comprise molecules with molecular weights less than 100 kD.

80. The method of claim 79, wherein said category-binding molecules comprise molecules with molecular weights less than 10 kD.

81. The method of claim 80, wherein said category-binding molecules comprise molecules with molecular weights less than 1 kD.

82. The method of claim 1, wherein said container has a bar code or equivalent label for tracking the sample automatically.

83. The method of claim 1, wherein said detecting occurs on a surface with registration marks to facilitate alignment of multiple images of the same surface.

84. The method of claim 1, wherein said method detects control marks or control cells in a specified region of the detection zone.

85. The method of claim 43, wherein the means for detecting said emitted, scattered, transmitted, or absorbed light comprises optical filters adapted to detect the signals derived from the illumination of said complexes.

86. The method of claim 1, wherein said detecting comprises use of a photoelectric array detector.

87. The method of claim 86, wherein said photoelectric detector comprises a CCD or CMOS detector.

88. The method of claim 43, wherein said means for detecting said emitted, scattered, or absorbed light does not include an image intensifier.

89. The method of claim 1, wherein said detecting comprises use of a photomultiplier tube detector.

90. The method of claim 1, wherein said detecting comprises use of a photodiode detector.

91. The method of claim 1, wherein the number of targets is inferred from said detecting by analyzing images acquired by said detecting.

92. The method of claim 2, wherein the category of targets is inferred from said detecting using image analysis software.

93. The method of claim 92, wherein said image analysis software further comprises functions for discerning the signals generated by said complexes from other signals.

94. The method of claim 1, wherein, in step (b), the liquid in said sample is not filtered through the detection surface.

95. The method of claim 1, wherein the targets are cells.

96. The method of claim 1, wherein the targets are viruses.

\* \* \* \* \*

SEQUENCE LISTING

```
<160> NUMBER OF SEQ ID NOS: 3

<210> SEQ ID NO 1
<211> LENGTH: 16
<212> TYPE: DNA
<213> ORGANISM: Artificial Sequence
```

```
<220> FEATURE:
<223> OTHER INFORMATION: primer

<400> SEQUENCE: 1
gggccccccc tcgatc                                                      16

<210> SEQ ID NO 2
<211> LENGTH: 18
<212> TYPE: DNA
<213> ORGANISM: Artificial Sequence
<220> FEATURE:
<223> OTHER INFORMATION: primer

<400> SEQUENCE: 2
atcgataccg tcgacctc                                                    18

<210> SEQ ID NO 3
<211> LENGTH: 18
<212> TYPE: DNA
<213> ORGANISM: Escherichia coli

<400> SEQUENCE: 3
gctgcctccc gtaggagt                                                    18
```